(12) United States Patent
Gupta et al.

(10) Patent No.: US 7,943,650 B2
(45) Date of Patent: May 17, 2011

(54) METHODS OF TREATING CANCER WITH IMIDAZOLYL COMPOUNDS

(75) Inventors: Ajay Gupta, Dollard-des-Ormeaux (CA); Hyman M. Schipper, Montreal (CA); Moulay Alaoui-Jamali, Laval (CA); Walter A. Szarek, Kingston (CA); Kanji Nakatsu, Kingston (CA); Jason Z. Vlahakis, Kingston (CA)

(73) Assignees: Osta Biotechnologies, Dollard-des-Ormeaux (CA); Queen's University at Kingston, Kingston (CA); The Sir Mortimer B. Davis-Jewish General Hospital, Montreal (CA)

( * ) Notice: Subject to any disclaimer, the term of this patent is extended or adjusted under 35 U.S.C. 154(b) by 19 days.

(21) Appl. No.: 12/139,781

(22) Filed: Jun. 16, 2008

(65) Prior Publication Data
US 2009/0176831 A1    Jul. 9, 2009

Related U.S. Application Data

(60) Provisional application No. 60/943,893, filed on Jun. 14, 2007, provisional application No. 60/979,570, filed on Oct. 12, 2007.

(51) Int. Cl.
 *A61K 31/415* (2006.01)
(52) U.S. Cl. ........ 514/399; 514/322; 514/397; 514/383; 514/381
(58) Field of Classification Search .......... 514/399, 514/322, 397, 383, 381
See application file for complete search history.

(56) References Cited

FOREIGN PATENT DOCUMENTS
CA    2058068    6/1992
WO    WO 2008/124132    * 4/2008

OTHER PUBLICATIONS

Sausville et al. (Cancer Research, 2006, vol. 66, pp. 3351-3354).*
Johnson et al. (British J. of Cancer, 2001, 84(10):1424-1431).*
Lens (Br. J. Nurs., 2008, vol. 17, No. 5, pp. 300-305).*
Divers et al. (Cutis. 2004, vol. 73, No. 4, pp. 257-262).*
Millikan et al. (J. Clin. Oncol. 21 (5): 878-883 (2003)).*
Van Belle et al. (Anticancer Res. 13: 2389-2392 (1993)).*
Van Ginckel et al. (Eur. J. Cancer Clin. Oncol. vol. 20 (1): 99-105 (1984)).*

(Continued)

*Primary Examiner* — Kamal A Saeed
*Assistant Examiner* — Valerie Rodriguez-Garcia
(74) *Attorney, Agent, or Firm* — Lowenstein Sandler PC

(57) ABSTRACT

Disclosed in certain embodiments is a method of treating and/or mitigating prostate cancer, ovarian cancer, melanoma, colorectal cancer, breast cancer or lung cancer, comprising administering to an individual in need thereof a pharmaceutical composition comprising a pharmaceutically acceptable carrier and a compound of formula (I):

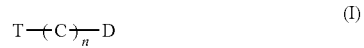

where
T is optionally substituted phenyl;
n is 1 to 6:
C represents optionally substituted carbon; and
D is imidazolyl;
or a pharmaceutically acceptable salt or ester of said compound.

79 Claims, 36 Drawing Sheets

OTHER PUBLICATIONS

Terauchi et al. (Int. J. Clin. Oncol. (2002) 7:356-360).*
Okawa et al. (Breast Cancer (2004) 11 (3):309-312).*
Van Veldhuizen et al. (Cancer 2003, vol. 98 (9); p. 1855-1862).*
Chong et al. (ACS Chemical Biology. (2007), 2 (4); p. 263-270).*
Chou et al. (Food and Chemical Toxicology. 45 (2007) 1356-1367.*
Song, et al., "Over-Expression of Heme Oxygenase-1 Promotes Oxidative Mitochondrial Damage in Rat Astroglia", 2006, Journal of Cellular Physiology, v. 206, p. 655-663.
Vlahakis, et al., "Anti-Plasmodium Activity of Imidazole-Dioxolane Compounds", 2006, Bioorganic and Medicinal Chemistry Letters, v. 16, p. 2396-2406.
Roman, et al., "Heme Oxygenase Inhibition by 2-Oxy-Substituted 1-(1H-Imidazol-1-yl)-4-Phenylbutanes: Effect of Halogen Substitution in the Phenyl Ring", 2007, Bioorganic and Medicinal Chemistry Letters, v. 15, p. 3225-3234.
Kinobe, et al., "Selectivity of Imidazole-Dioxolane Compounds for In Vitro Inhibition of Microsomal Haem Oxygenase Isoforms", 2006, British Journal of Pharmacology, v. 147, p. 307-315.
Vlahakis, et al., "Synthesis and Evaluation of Azalanstat Analogues as Heme Oxygenase Inhibitors", 2005, Bioorganic and Medicinal Chemistry Letters, v. 15, p. 1457-1461.
Vlahkis, et al., "Imidazole-Dioxolane Compounds as Isozyme-Selective Heme Oxygenase Inhibitors", 2006, Journal of Medicinal Chemistry, v. 49, No. 14, p. 4437-4441.
Chong, et al., "Inhibition of Angiogenesis by the Antifungal Drug Itraconazole", 2007, ACS Chemical Biology, v. 2, No. 4, p. 263-270.
Sugishima, et al., "X-Ray Crystallographic and Biochemical Characterization of the Inhibitory Action of an Imidazole-Dioxolane Compound on Heme Oxygenase", 2007, Biochemistry, v. 46, p. 1860-1867.
Kinobe, et al., "Effectiveness of Novel Imidazole-Dioxolane Heme Oxygenase Inhibitors in Renal Proximal Tubule Epithelial Cells", 2007, The Journal of Pharmacology and Experimental Therapeutics, v. 323, No. 3, p. 763-770.
Ebert, et al., "Quantitative Structure Activity Relationships of Fungicidally Active Triazoles: Analogs and Stereoisomers of Propiconazole and Etaconazole", 1989, Z. Naturforsch, v. 44, p. 85-96.
Marinissen, et al., "Inhibition of Heme Oxygenase1- Interferes with Transforming Activity of the Kaposi Sarcoma Herpesvirus-encoded G Protein-coupled Receptor", 2006, The Journal of Biological Chemistry, v. 281, No. 16, p. 11332-11346.
CAS Registry (online), STN International, Columbus, OH, Registry Nos. 64310-41-4 and 76894-56-9 (2 compounds) 1977 and 1981.

* cited by examiner

** P<0.01, compared with sham; # P<0.05, compared with HO-1

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Forward primer containing a HindIII site

<400> SEQUENCE: 1
ttcatacaag cttatggagc gtccgcaacc                                    30

<210> SEQ ID NO 2
<211> LENGTH: 30
<212> TYPE: DNA
<213> ORGANISM: Artificial Sequence
<220> FEATURE:
<223> OTHER INFORMATION: Reverse primer containing a BamHI site

<400> SEQUENCE: 2
tcaatggatc ctcacatggc ataaagccct                                    30

METHODS OF TREATING CANCER WITH IMIDAZOLYL COMPOUNDS

FIELD OF THE INVENTION

This invention is in the field of pharmaceuticals, and relates to compounds and compositions for treating/mitigating cancer and for suppressing tumor growth. The invention also relates to compounds, compositions and methods for the treatment and prevention of diseases of the central nervous system, such as neurological diseases and neurodegenerative disorders.

BACKGROUND OF THE INVENTION

Cancer

Cancer affects millions of adults and children worldwide, and according to the Cancer Statistics 2006 published by the American Cancer Society, is the second leading cause of mortality in the United States today. It is a disease characterized by disorderly division of cells, combined with the malignant behavior of these cells.

Cancer therapy typically involves surgery, chemotherapy and/or radiation treatment. All of these approaches pose significant drawbacks for the patient. Surgery, for example, can pose a significant risk due to the patient's health or may otherwise be unacceptable to the patient. Additionally, surgery might not completely remove the neoplastic tissue. Radiation therapy can often elicit serious side effects. With respect to traditional chemotherapy, there can be many drawbacks. Almost all known chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multi-drug resistance.

For the above reasons, there is a real need for novel compounds and compositions, and methods that are useful for treating cancer with either improved effect or reduced side effects.

CNS Diseases

Neurodegenerative diseases are caused by the deterioration of neurons, which over time lead to neurodegeneration and related physical manifestations. Neurodegenerative diseases can result from stroke, heat stress, head and spinal cord trauma, and bleeding that occurs in the brain, the pressure from which eventually causes the death of one or more neurons. Many times neuronal death begins long before the patient will ever experience any symptoms.

Alzheimer's disease (AD) is one common neurodegenerative disorder related to aging, and is characterized by progressive dementia and personality dysfunction. The abnormal accumulation of amyloid plaques in the vicinity of degenerating neurons and reactive astrocytes is a pathological characteristic of AD. As a leading cause of death in industrialized societies, AD affects a significant portion of the population over the age of 65, and considering the aging populations of Canada and the United States AD will no doubt become an escalating healthcare problem as the geriatric populations grow.

Much work remains in the quest to find an effective treatment for AD, and as such there remains a significant need for novel compounds and compositions, and methods that are useful for treating AD and other neurodegenerative diseases.

SUMMARY OF THE INVENTION

It is an object of the present invention to provide compounds for the treatment and mitigation of cancer, as well as related pharmaceutical compositions and methods of treatment.

It is a further object of the invention to provide compounds for the treatment of neurodegenerative diseases and other diseases of the central nervous system, pharmaceutical compositions and methods of treatment.

According to an aspect of the present invention there are provided compounds of Formula I:

where
T is a hydrophobic moiety;
n is 1 to 6, preferably n is 1 to 4;
each C of $(C)_n$ can be independently substituted or unsubstituted wherein substituents can be further substituted, substituents including alkyl, alkenyl, alkynyl, aryl (including heteroaryl groups), cycloalkyl, cycloakenyl, halo, oxygen (carbonyl), hydroxyl, thiol, sulfur (thio), thio ether, ether, preferably 1,3-dioxolanyl (5-membered), 1,3-dioxanyl (6-membered), 1,3-dithiolanyl, 1,3-dithianyl, or amino;
D is a moiety that binds iron;
and pharmaceutically acceptable salts or esters thereof.

In an embodiment, D may be substituted or unsubstituted wherein substituents may be further substituted. In some embodiments D is a ring structure optionally containing a heteroatom. In certain embodiments D is an unsaturated ring. D may be a five- or six-membered ring, such as, for example, imidazolyl, triazolyl, tetrazolyl. In some embodiments D is an imidazolyl such as, for example, 1,3-imidazolyl.

In an embodiment n is 2. In another embodiment n is 4.

In an embodiment, T is a hydrophobic moiety that has an electron-withdrawing moiety (e.g., F, Cl, Br, I, OH, SH, CN, $NR^8R^9$, $NO_2$, $CO_2R^{10}$, CHO). Preferably, T is 4-chlorophenyl, 3-methoxyphenyl, 2-amino-4-chlorophenyl, hydrogen atom, 4-methoxyphenyl, phenyl, acetoxy, 4-fluorophenyl, 4-bromophenyl, carboxyl, amino, 4-iodophenyl, 2-hydroxyphenyl, trifluoroacetyl, adamantyl, imidazolyl, benzamidyl, acetamido, 4-nitrophenyl, naphthalene-2-yl, naphthalene-1-yl, 4-methylphenyl, biphenyl-4-yl, benzoyl, pyrene-1-yl, indan-1-one-2-yl, 3,4-dichlorophenyl, 4-isopropylphenyl, 4-tert-butylphenyl, 1,3-dioxolan-2-yl, 4-(1H-imidazol-1-yl-methyl)benzyl, 4-hydroxyphenyl, 4-benzoylphenyl, methyl, ethyl, propyl.

In an embodiment at least one C of $(C)_n$ can be substituted appropriately (e.g. as an acetal or thioacetal) so that the C is contained as part of a cyclic ring structure such as a 1,3-dioxolane ring, a 1,3-dioxane ring, a 1,3-dithiolane ring, or a 1,3-dithiane ring. These ring structures may be further substituted.

In an alternate embodiment, at least one C of $(C)_n$ can be replaced with another heteroatom (e.g., S, N, C) which is substituted or unsubstituted, and wherein substituents can be further substituted, substituents including alkyl, alkenyl, alkynyl, aryl (including heteroaryl groups), cycloalkyl, cycloakenyl, halo, oxygen (carbonyl), hydroxyl, thiol, sulfur (thio), thio ether, ether, 1,3-dioxolanyl (5-membered), 1,3-dioxanyl (6-membered), 1,3-dithiolanyl, 1,3-dithianyl, or amino.

Preferably, in Formula I, when n is 2, the carbons are sp$^3$ hybridized.

In an embodiment, D is a five-membered ring as depicted in Formula Ia,

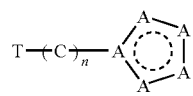

(Ia)

where T and n are as described previously and A is C, N, O, or S; and saturation level of the ring is not intended to be depicted in Formula Ia. In a further embodiment, D can be a substituted or unsubstituted imidazolyl

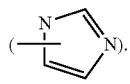

According to a further aspect of the present invention there are provided compounds of Formula II:

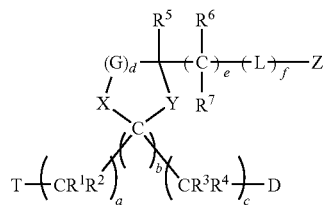

(II)

where D is as described above;
a, b, c, d, e, and f are independently 0, 1, 2, 3, 4, 5, or 6, whereby all of a, b, G, d, e, and f cannot be zero;
$R^{1-7}$ are substituted or unsubstituted and are independently hydrogen, alkyl, perfluoroalkyl, alkyloxy, alkenyl, alkynyl, cycloalkyl, an aryl group, aryloxy, arylalkyl, mercaptoalkyl, or an electron-withdrawing moiety (e.g., F, Cl, Br, I, OH, SH, CN, $NR^8R^9$, $NO_2$, $CO_2R^{10}$, CHO);
G is described by the formula $CR^{11}R^{12}$;
$R^5$ and $R^{11}$ can also together form a saturated or unsaturated 5- or 6-membered ring;
X is O, S, $CR^{13}R^{14}$ or $NR^{15}$;
Y is O, S, $CR^{16}R^7$ or $NR^{18}$;
L is O, S, $CR^{19}R^{20}$, $OSO_2$, SO, OSO, $NR^{21}$, NCO, CON, OCO, COO, CO, OP(O)(OR)O, or OP(OR)O, wherein R is hydrogen, alkyl, aryl, or arylalkyl;
$R^{8-21}$ are the same as $R^1$;
T is independently alkyl, adamantanyl, perfluoroalkyl, an electron-withdrawing moiety, or described by Formula (III) below:

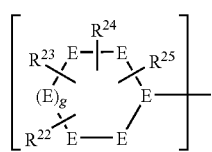

(III)

where
g is 0, 1, 2, 3, or 4;
E is independently an sp$^2$- or sp$^3$-hybridized carbon, nitrogen, oxygen or sulfur atom;
$R^{22-25}$ are the same as $R^1$;
$R^{22}$ and $R^{23}$ can also form a saturated or unsaturated 5- or 6-membered ring, and may be substituted or unsubstituted;
Z is either $R^{26}$ or described by Formula (IV) below:

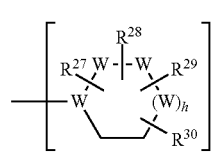

(IV)

where
h is 0, 1, 2, 3, or 4;
$R^{26-30}$ are the same as $R^1$;
W is independently an sp$^2$- or sp$^3$-hybridized carbon or nitrogen atom; and
pharmaceutically acceptable salts or esters thereof.

According to another aspect of the present invention there are provided compounds of Formula (V):

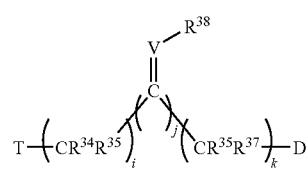

(V)

where
i and k are independently 0, 1, 2, 3, 4, 5, or 6;
j is 0 or 1; whereby all of i, j and k cannot be zero;
V is CH, O, N, or S; when V is CH or nitrogen, $R^{38}$ is hydrogen, alkyl, perfluoroalkyl, hydroxy, alkoxy, aryl, aryloxy, an electron-withdrawing moiety, or benzyl; when V is O or S, $R^{38}$ does not exist;
$R^{34-37}$ are the same as $R^1$ above;
D is as described above;
T is independently alkyl, perfluoroalkyl, an electron-withdrawing moiety, or a hydrophobic moiety that has electron-withdrawing characteristics;
and pharmaceutically acceptable salts or esters thereof.

According to an additional aspect of the present invention there are provided compounds of Formula (VI):

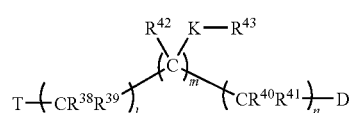

(VI)

where
l, m, and n are independently 0, 1, 2, 3, 4, 5, or 6, whereby all of l, m and n cannot be zero;
$R^{38-42}$ are the same as $R^1$ above;
$R^{43}$ is a hydrogen atom, an alkyl group, a perfluoroalkyl group, a hydroxy group, an alkoxy group, a substituted or unsubstituted aryl group, an aryloxy group, an electron-withdrawing atom, a substituted or unsubstituted benzyl group, or an electron-withdrawing functional group.

K is O, S, $CR^{44}R^{45}$, or $NR^{46}$;

D is as described above;

$R^{40}$ and $R^{41}$ can form a substituted or unsubstituted 5- or 6-membered ring, either saturated or unsaturated, and if $R^{40}$ and $R^{41}$ form a ring D may be absent;

T is as defined above;

and pharmaceutically acceptable salts or esters thereof.

Compounds of the above formulae (I), (Ia), (II), A) and (VI) can be used for the treatment and/or mitigation of cancer, for suppressing tumor growth, as neuroprotectants, or for treatment of diseases of the central nervous system.

In certain embodiments, the compounds may be selected from (2S,4S)-2-[2-(4-chlorophenyl)ethyl]-2-[(1H-imidazol-1-yl)methyl]-4-[{(4-aminophenyl)thio}methyl]-1,3-dioxolane dihydrochloride; (2S,4S)-2-[2-(4-chlorophenyl)ethyl]-2-[(1H-imidazol-1-yl)methyl]-4-[{(2-naphthyl)thio}methyl]-1,3-dioxolane hydrochloride; (2S,4S)-2-[2-(4-chlorophenyl)ethyl]-2-[(1H-imidazol-1-yl)methyl]-4-[{(2-aminophenyl)thio}methyl]-1,3-dioxolane dihydrochloride; (2S,4S)-2-[2-(4-chlorophenyl)ethyl]-2-[(1H-imidazol-1-yl)methyl]-4-[(p-toluenesulfonyloxy)methyl]-1,3-dioxolane hydrochloride; (2R,4S)-2-[2-(4-chlorophenyl)ethyl]-2-[(1H-imidazol-1-yl)methyl]-4-[{(4-aminophenyl)thio}methyl]-1,3-dioxolane hydrochloride; (2S,4S)-2-[2-(4-chlorophenyl)ethyl]-2-[(1H-imidazol-1-yl)methyl]-4-[(p-toluenesulfonyloxy)methyl]-1,3-dioxolane; (2S,4S)-2-[2-(4-chlorophenyl)ethyl]-2-[(1H-imidazol-1-yl)methyl]-4-[{(3-aminophenyl)thio}methyl]-1,3-dioxolane dihydrochloride; (2S,4S)-2-[2-(4-chlorophenyl)ethyl]-2-[(1H-imidazol-1-yl)methyl]-4-[(4-methoxyphenyloxy)methyl]-1,3-dioxolane hydrochloride; 4-(4-chlorophenyl)-1-(1H-imidazol-1-yl)butan-2-one hydrochloride; 4-(4-chlorophenyl)-1-(1H-imidazol-1-yl)butan-2-ol hydrochloride; (2R,4S)-2-[2-(4-chlorophenyl)ethyl]-2-[(1H-imidazol-1-yl)methyl]-4-[{(2-aminophenyl)thio}methyl]-1,3-dioxolane dihydrochloride; (2R,4R)-2-[2-(4-chlorophenyl)ethyl]-2-[(1H-imidazol-1-yl)methyl]-4-methyl-1,3-dioxolane hydrochloride; (2R,4S)-2-[2-(4-chlorophenyl)ethyl]-2-[(1H-imidazol-1-yl)methyl]-4-[{(3-aminophenyl)thio}methyl]-1,3-dioxolane hydrochloride; 2-[2-(4-chlorophenyl)ethyl]-2-[(1H-imidazol-1-yl)methyl]-1,3-dioxolane hydrochloride; (2R,4S)-2-[2-(4-chlorophenyl)ethyl]-2-[(1H-imidazol-1-yl)methyl]-4-[(p-toluenesulfonyloxy)methyl]-1,3-dioxolane; (2S,4R)-2-[2-(4-chlorophenyl)ethyl]-2-[(1H-imidazol-1-yl)methyl]-4-[p-toluenesulfonyloxy)methyl]-1,3-dioxolane; (2S,4R)-2-[2-(4-chlorophenyl)ethyl]-2-[(1H-imidazol-1-yl)methyl]-4-[{(4-aminophenyl)thio}methyl]-1,3-dioxolane hydrochloride; (2S,4R)-2-[2-(4-chlorophenyl)ethyl]-2-[(1H-imidazol-1-yl)methyl]-4-[{(3-aminophenyl)thio}methyl]-1,3-dioxolane hydrochloride; (2R,4R)-2-[2-(4-chlorophenyl)ethyl]-2-[(1H-imidazol-1-yl)methyl]-4-[(p-toluenesulfonyloxy)methyl]-1,3-dioxolane; (2R,4R)-2-[2-(4-chlorophenyl)ethyl]-2-[(1H-imidazol-1-yl)methyl]-4-[{(2-aminophenyl)thio}methyl]-1,3-dioxolane dihydrochloride; (2R,4R)-2-[2-(4-chlorophenyl)ethyl]-2-[(1H-imidazol-1-yl)methyl]-4-[{(3-aminophenyl)thio}methyl]-1,3-dioxolane dihydrochloride; (2R,4R)-2-[2-(4-chlorophenyl)ethyl]-2-[(1H-imidazol-1-yl)methyl]-4-[{(4-aminophenyl)thio}methyl]-1,3-dioxolane dihydrochloride; (2R,4S)-2-[2-(4-chlorophenyl)ethyl]-2-[(1H-imidazol-1-yl)methyl]-4-methyl-1,3-dioxolane hydrochloride; (2S,4S)-2-[2-(4-chlorophenyl)ethyl]-2-[(1H-imidazol-1-yl)methyl]-4-methyl-1,3-dioxolane hydrochloride; (2S,4R)-2-[2-(4-chlorophenyl)ethyl]-2-[(1H-imidazol-1-yl)methyl]-4-methyl-1,3-dioxolane hydrochloride; (2R,4S)-2-[2-(4-chlorophenyl)ethyl]-2-[(1H-imidazol-1-yl)methyl]-4-[(phenylthio)methyl]-1,3-dioxolane hydrochloride; 1-(1H-imidazol-1-yl)butan-2-ol hydrochloride; (2R,4S)-2-[2-(4-chlorophenyl)ethyl]-2-[(1H-imidazol-1-yl)methyl]-4-[{(4-pyridinyl)thio}methyl]-1,3-dioxolane dihydrochloride; 4-(4-methoxyphenyl)-1-(1H-imidazol-1-yl)butan-2-ol hydrochloride; (2R,4S)-2-[2-(4-chlorophenyl)ethyl]-2-[(1H-imidazol-1-yl)methyl]-4-[{(4-hydroxyphenyl)thio}methyl]-1,3-dioxolane; (2R,4R)-2-[2-(4-phenyl)ethyl]-2-[(1H-imidazol-1-yl)methyl]-4-methyl-1,3-dioxolane hydrochloride; 4-(4-chlorophenyl)-2-(4-fluorobenzyloxy)-1-(1H-imidazol-1-yl)butane hydrochloride; (2R,4S)-2-[2-(4-chlorophenyl)ethyl]-2-[(1H-imidazol-1-yl)methyl]-4-(hydroxymethyl)-1,3-dioxolane hydrochloride; (2R,4S)-2-[2-(4-chlorophenyl)ethyl]-2-[(1H-imidazol-1-yl)methyl]-4-[(4-aminophenyloxy)methyl]-1,3-dioxolane dihydrochloride; (2R,4S)-2-[2-(4-chlorophenyl)ethyl]-2-[(1H-imidazol-1-yl)methyl]-4-[(methylthio)methyl]-1,3-dioxolane hydrochloride; (2R,4S)-2-[2-(4-chlorophenyl)ethyl]-2-[(1H-imidazol-1-yl)methyl]-4-[{(4-bromophenyl)thio}methyl]-1,3-dioxolane hydrochloride; 2-[2-(4-chlorophenyl)ethyl]-2-[(1H-imidazol-1-yl)methyl]-1,3-dithiolane hydrochloride; (2R,4S)-2-[2-(4-chlorophenyl)ethyl]-2-[(1H-imidazol-1-yl)methyl]-4-[(4-hydroxyphenyloxy)methyl]-1,3-dioxolane hydrochloride; (2R,4S)-2-[2-(4-chlorophenyl)ethyl]-2-[(1H-imidazol-1-yl)methyl]-4-(fluoromethyl)-1,3-dioxolane hydrochloride; (2R,4S)-2-[2-(4-chlorophenyl)ethyl]-2-[(1H-imidazol-1-yl)methyl]-4-[{(4-methoxyphenyl)thio}methyl]-1,3-dioxolane hydrochloride; (2R,4S)-2-[2-(4-chlorophenyl)ethyl]-2-[(1H-imidazol-1-yl)methyl]-4-[{(4-chlorophenyl)thio}methyl]-1,3-dioxolane hydrochloride; 4-(4-fluorophenyl)-1-(1H-imidazol-1-yl)butan-2-ol hydrochloride; (2R,4R)-2-[2-(4-chlorophenyl)ethyl]-2-[(1H-imidazol-1-yl)methyl]-4-[(1H-imidazol-1-yl)methyl]-1,3-dioxolane dihydrochloride; (2R,4S)-2-[2-(4-chlorophenyl)ethyl]-2-[(1H-imidazol-1-yl)methyl]-4-[{(4-fluorophenyl)thio}methyl]-1,3-dioxolane hydrochloride; 4-(4-bromophenyl)-1-(1H-imidazol-1-yl)butan-2-one hydrochloride; 4-(4-fluorophenyl)-1-(1H-imidazol-1-yl)butan-2-one hydrochloride; 2-[2-(4-fluorophenyl)ethyl]-2-[(1H-imidazol-1-yl)methyl]-1,3-dioxolane hydrochloride; 2-[2-(4-bromophenyl)ethyl]-2-[(1H-imidazol-1-yl)methyl]-1,3-dioxolane hydrochloride; 2-[2-phenylethyl]-2-[(1H-imidazol-1-yl)methyl]-1,3-dioxolane hydrochloride; 1-bromo-4-(4-bromophenyl)butan-2-one; (2R,4S)-2-[2-(4-chlorophenyl)ethyl]-2-[(1H-imidazol-1-yl)methyl]-4-[{(4-nitrophenyl)thio}methyl]-1,3-dioxolane hydrochloride; N-benzyl-2-(1H-imidazol-1-yl)-acetamide hydrochloride; 4-(4-bromophenyl)-1-[1,2,4]triazol-1-yl-butan-2-one hydrochloride; 4-phenyl-1-(1H-imidazol-1-yl)butan-2-one hydrochloride; 2-[2-(4-chlorophenyl)ethyl]-2-[(1H-imidazol-1-yl)methyl]-1,3-dioxane hydrochloride; 1-{2-[2-(4-Chlorophenyl)-ethyl]-hexahydro-benzo[1,3]dioxol-2-ylmethyl}-1H-imidazole; 1-(1H-imidazol-1-yl)-4-(4-methoxyphenyl)-2-butanone hydrochloride; 4-(4-iodophenyl)-1-(1H-imidazol-1-yl)butan-2-one hydrochloride; 4-(4-iodophenyl)-1-(1H-imidazol-1-yl)butan-2-ol hydrochloride; 1-(2-hydroxy-phenyl)-3-imidazol-1-yl-propan-1-one; 4-phenyl-1-(1H-imidazol-1-yl)butan-2-ol hydrochloride; 2-[2-(4-iodophenyl)ethyl]-2-[(1H-imidazol-1-yl)methyl]-1,3-dioxolane hydrochloride; 4-(4-bromophenyl)-1-(1H-imidazol-1-yl)butan-2-ol hydrochloride; (2R,4S)-2-[2-(4-chlorophenyl)ethyl]-2-[(1H-imidazol-1-yl)methyl]-4-[{(5-trifluoromethyl-pyridin-2-yl)thio}methyl]-1,3-dioxolane hydrochloride; 1-adamantan-1-yl-2-imidazol-1-yl-ethanone hydrochloride; 1-(4-chlorophenyl)-3-imidazol-1-yl-propan- 1-one hydrochloride; 4-phenyl-1-[1,2,4]triazol-1-yl-butan-2-one hydrochloride; 4-phenyl-1-(1H-[1,2,3]triazol-1-yl)butan-2-one; 4-(4-chlorophenyl)-3-imidazol-1-yl-butan-2-ol hydrochloride; 2-(2-phenethyl)-2-{(1H-[1,2,4]triazol-1-yl)methyl}-1,3-dioxolane hydrochloride; 4-(4-chlorophenyl)-1-(1H-imidazol-1-yl)butane hydrochloride; 1-{4-Chloromethyl-2-[2-(4-chloro-phenyl)-ethyl]-[1,3]dioxolan-2-ylmethyl}-1H-imidazole hydrochloride; 1-(4,5-Diphenyl-imidazol-1-yl)-4-phenyl-butan-2-one hydrochloride; 1-{4-Azidomethyl-2-[2-(4-chloro-phenyl)-ethyl]-[1,3]dioxolan-2-ylmethyl}-1H-imidazole hydrochloride; 1-{2-[2-(4-Chloro-phenyl)-ethyl]-4-cyclohexylsulfanylmethyl-[1,3]dioxolan-2-ylmethyl}-1H-imidazole hydrochloride; 1-{2-[2-(4-Chloro-phenyl)-ethyl]-4-phenoxymethyl-[1,3]dioxolan-2-ylmethyl}-1H-imidazole hydrochloride; 4-Phenyl-1-tetrazol-2-yl-butan-2-one hydrochloride; 4-Phenyl-1-tetrazol-1-yl-butan-2-one hydrochloride; 1-{4-(4-Bromo-phenoxymethyl)-2-[2-(4-chloro-phenyl)-ethyl]-[1,3]dioxolan-2-ylmethyl}-1H-imidazole hydrochloride; 1-[2-[2-(4-Chloro-phenyl)-ethyl]-4-(4-fluoro-phenylsulfanylmethyl)-[1,3]dioxolan-2-ylmethyl]-1H-imidazole hydrochloride; 1-[2-[2-(4-Chloro-phenyl)-ethyl]-4-(naphthalen-2-ylsulfanylmethyl)-[1,3]dioxolan-2-ylmethyl]-1H-imidazole hydrochloride; 4-Phenyl-1-(4-phenyl-imidazol-1-yl)-butan-2-one hydrochloride; 2-Imidazol-1-yl-1-phenyl-ethanone hydrochloride; 1-(4-Chloro-phenyl)-2-imidazol-1-yl-ethanone hydrochloride; 1-(2-Phenethyl-[1,3]dioxolan-2-ylmethyl)-1H-tetrazole hydrochloride; 2-(2-Phenethyl-[1,3]dioxolan-2-ylmethyl)-2H-tetrazole hydrochloride; 1-Benzyl-1H-imidazole hydrochloride; 1-(1H-Imidazol-1-yl)-butan-2-one hydrochloride; 4-(1H-Imidazol-1-yl)-1,3-diphenyl-butan-2-one hydrochloride; 1-Phenyl-1H-imidazole hydrochloride; 4-Phenyl-1-(4-phenyl-1H-imidazol-1-yl)-butan-2-one hydrochloride; 1-(1H-Imidazol-1-yl)-propan-2-one; 4-(4-(Trifluoromethyl)phenyl)-1-(1H-imidazol-1-yl)-2-butanone hydrochloride; 4-(1H-Imidazol-1-yl)-1,1-diphenyl-butan-2-one hydrochloride; 5-(1H-Imidazol-1-yl)-1-phenyl-pent-1-en-3-one hydrochloride; 1-(5-Bromo-1H-imidazol-1-yl)-4-phenyl-2-butanone; 1-[4-(4-(Trifluoromethyl)phenyl)butyl]-1H-imidazole hydrochloride; 3-[2-(1H-Imidazol-1-yl)-ethyl]-1H-indole hydrochloride; 3-(1H-Imidazol-1-yl)-1-phenyl-propan-1-one hydrochloride; 1-(1H-Imidazol-1-yl)-4-(4-nitro-phenyl)-butan-2-one hydrochloride; Imidazol-1-yl-acetic acid benzyl ester; 1-(2-Phenyl-[1,3]dioxolan-2-ylmethyl)-1H-imidazole hydrochloride; 1-Naphthalen-2-yl-2-[1,2,4]triazol-1-yl-ethanone hydrochloride; 1-(2-Phenyl-[1,3]dioxolan-2-ylmethyl)-1H-[1,2,4]triazole hydrochloride; 1-(4-Bromo-phenyl)-2-[1,2,4]triazol-1-yl-ethanone; 1-(3,4-Dichloro-phenyl)-2-[1,2,4]triazol-1-yl-ethanone hydrochloride; 1-Biphenyl-4-yl-2-[1,2,4]triazol-1-yl-ethanone; 1-(4-Nitro-phenyl)-2-[1,2,4]triazol-1-yl-ethanone hydrochloride; 1-(3-Bromo-phenyl)-2-(1H-imidazol-1-yl)-ethanone hydrochloride; 1-(4-Benzyloxy-phenyl)-2-(1H-imidazol-1-yl)-ethanone; or 1-(2,5-Dichloro-phenyl)-2-[1,2,4]triazol-1-yl-ethanone, as well as analogs and pharmaceutically acceptable salts thereof.

Particularly preferred are the substituted imidazoles: (2R,4S)-2-(2-(4-chlorophenyl)ethyl)-2-((1H-imidazol-1-yl)methyl)-4-(fluoromethyl)-1,3-dioxolane hydrochloride (QC-47); 2-(2-(4-bromophenyl)ethyl)-2-((1H-imidazol-1-yl)methyl)-1,3-dioxolane hydrochloride (QC-56); 1-(adamantan-1-yl)-2-imidazol-1-yl-ethanone hydrochloride (QC-82); 4-(4-chlorophenyl)-1-(1H-imidazol-1-yl)butane hydrochloride (QC-105), their analogs, and pharmaceutically acceptable salts thereof.

All compounds can be provided as a single stereoisomer or as a mixture thereof and/or as a pharmaceutically acceptable salt thereof. Compounds that include carboxyl groups may also be provided as pharmaceutically acceptable esters.

Pharmaceutical compositions for the treatment and/or mitigation of cancer, for suppressing tumor growth, as neuroprotectants, and for treatment of neurodegenerative diseases and other diseases of the central nervous system are also provided comprising one or more compound of formulae (I), (Ia), (TI), (V) or (VI) as defined above together with a pharmaceutically acceptable carrier or excipient.

The above pharmaceutical compositions can also be useful for treating or preventing a non-central nervous system disease such as rheumatoid arthritis, cataract, cystic fibrosis, diabetes, acute respiratory distress syndrome, asthma, atherosclerotic cardiovascular disease, hypertension, post-operative restenosis, pathogenic vascular smooth muscle cell proliferation, pathogenic intra-vascular macrophage adhesion, pathogenic platelet activation, pathogenic lipid peroxidation, myocarditis, multiple organ dysfunction, complication resulting from inflammatory processes, cancer, aging, bacterial infection, sepsis, AIDS, hepatitis C, influenza and other viral diseases, comprising administering one or more compound as defined above to an individual in need thereof.

Methods of treatment and/or mitigation of cancer, suppressing tumor growth, and treating or preventing diseases of the central nervous system are also provided comprising administering one or more compound of formulae (I), (Ia), (II), (V) or (VI) as defined above, or a pharmaceutical composition as defined above comprising one or more compound of formulae (I), (Ia), (II), (V) or (VI), to an individual in need thereof.

Pharmaceutical combinations are also provided which comprise at least one antineoplastic agent and one or more compound of formulae (I), (Ia), (II), (V) or (VI) as defined above, or a pharmaceutically acceptable salt or ester of said compound. In an embodiment, the antineoplastic agent is selected from, but not limited to, signal transduction inhibitors, apoptosis inducers, angiogenesis inhibitors, monoclonal antibodies, cancer vaccines, gene therapy, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products, colony stimulating growth factors, adjuncts, erythropoetin, alkylating antineoplastic agents, anti-metabolites and combinations thereof. In preferred embodiments, the antineoplastic agent may be one or more of dacarbazine, paclitaxel, cisplatin, herceptin and fluorouracil. In other embodiments, the pharmaceutical combination may comprise any one or more of: Epogen (Johnson & Johnson/Chugai), Neupogen (Amgen), Intron-A (Schering-Plough), Lupron (Takeda/TAP), Zofran (GlaxoSmithKtine), Zoladex (AstraZeneca), Taxotere (Aventis), Aredia (Novartis), Camptosar/Campto (Pharmacia/Aventis), Nolvadex (AstraZeneca), Gemzar (Lilly), Rituxan (oche/Genentech), Casodex (AstraZeneca), Sandostatin (Novartis), Methotrexate, Kytril (Roche), Pharmorubicin (Pharmacia), Doxorubicin, mitomycin C, cylcophosphamide, methotrexate, anthracyclines, aromatase inhibitors, leucovorin, Camptosar (fluorodeoxyuridine), Bacillus Calmette-Guerin (BCG), cyclophosphamide, vincristine, nitrosoureas, procarbazine, fluorodeoxyuridine, Neovastat (Aeterna), Aptosyn (Cell Pathways), ISIS 3521 (ISIS Pharma), Rubitecan (SuperGen), Anti-VEGF (Genentech), Theratope (Biomira), Incel (Vertex), Intradose (Matrix Pharma), Genasense (Genta), SMART M195 (Protein Design Labs), Ceplene (Maxim Pharma), PEG-Intron A (Enzon/Schering-Plough), Rituxan (IDEC/NCI), Abarelix depot-M (Praecis/Amgen), ZD 0473 (Anormed/Astra Zeneca), Leuprogel (Atrix labs), Neovastat (Aeterna), Genasense (Genta), Virulizin (Lorus Therapeutics), R115777 (Janssen), ILX 295501 (ILEX Oncology), Mitoextra (SuperGen), MGV vaccine (Progenies Pharmaceuticals), INC 225 (ImClone), SU5416 (Pharmacia), BMS 275291 (Bristol-Myers Squibb), CEAVac (Titan Pharma), P53 and Ras vaccine (National Cancer Institute), Eflornithine (ILEX Oncology), KLH (BCI Immune activator, Intracel), Celecoxib (Pharmacia), Adenoviral p53 (Introgen Therapeutics), Intron-A (Schering Plough), DOTMP Holmium-166 (NeoRx), Neovastat (Aeterna Labs), Onco-TCS (INEX Pharma), Zevalin (IDEC/Schering AG), HLA-DR10 (Techniclone/Schering AG), Lymphocide (Amgen/Immunomedics), Gastrimmune (Aphton/Aventis), ONYX-015 (Onyx/Warner Lambert), OGT 719 (Oxford Glycosciences), Caelyx (Schering-Plough), Gemzar (Eli Lilly), Ethyol (MedImmune/Schering-Plough), MDX-210 (Immuno Designed Molecules), Proleukin (Chiron), SU 101 (Sugen), RMP-7 (Cereport, Alkermes/Alza), XCYTRIN (Pharmacyclics), NBI 3001 (Neurocrine), and Interferon beta (Biogen). Pharmaceutical compositions as described herein that comprise such pharmaceutical combinations preferably comprise the antineoplastic agent and one or more compound of formulae (I), (Ia), (II), (V) or (VI) as defined above in effective amounts, together with at least one pharmaceutically acceptable carrier or excipient.

There are further provided methods of treating and/or mitigating cancer, and for suppressing tumor growth, which comprise administering a pharmaceutical combination as defined above to an individual in need thereof in amounts effective to treat and/or mitigate the cancer or suppress tumor growth. In embodiments of such methods, the antineoplastic agent and one or more compound of formulae (I), (Ia), (II), (V) or (VI) as defined above may be administered in effective amounts either separately or in a combined formulation or combination.

As a further aspect of the invention, there is provided a process for preparing 2-(2-(4-bromophenyl)ethyl)-2-((1H-imidazol-t-yl)methyl)-1,3-dioxolane hydrochloride (QC-56), comprising the steps of:
(a) reacting 4-bromobenzyl bromide with allylmagnesium chloride to produce 4-(4-bromophenyl)-1-butene;
(b) isolating the 4-(4-bromophenyl)-1-butene from (a);
(c) reacting the isolated 4-(4-bromophenyl)-1-butene from (b) with peracetic acid-sodium acetate to produce (±)-4-(4-bromophenyl)-1,2-epoxybutane;
(d) isolating the (±)-4-(4-bromophenyl)-1,2-epoxybutane from (c);
(e) reacting the isolated (±)-4-(4-bromophenyl)-1,2-epoxybutane from (d) with imidazole-sodium hydride to produce (±)-4-(4-bromophenyl)-1-(1H-imidazol-1-yl)-2-butanol;
(f) isolation of the (±)-4-(4-bromophenyl)-1-(1H-imidazol-1-yl)-2-butanol from (e);
(g) reacting the isolated (±)-4-(4-bromophenyl)-1-(1H-imidazol-1-yl)-2-butanol with DMSO-$P_2O_5$ to produce 4-(4-bromophenyl)-1-(1H-imidazol-1-yl)-2-butanone;
(h) isolation of the 4-(4-bromophenyl)-1-(1H-imidazol-1-yl)-2-butanone from (g); and
(i) conversion of the isolated 4-(4-bromophenyl)-1-(1H-imidazol-1-yl)-2-butanone from (h) by an acid-catalyzed ketal formation reaction to form the 2-(2-(4-bromophenyl)ethyl)-2-((1H-imidazol-1-yl)methyl)-1,3-dioxolane hydrochloride (QC-56).

In an embodiment of the above process, the reaction in step (a) is performed in an appropriate ether solvent such as, for example, THF. In a further embodiment, the isolation in step (b) is conducted by extraction in a non-polar aprotic solvent, such as, for example, ethyl acetate.

In yet further embodiments, the reaction in step (c) is conducted using methylene chloride as solvent.

The isolation in step (d) may be conducted in a variety of ways, although in one exemplary embodiment of the process this isolation step is conducted by extraction in a non-polar aprotic solvent, such as, for example, methylene chloride. Similarly, in further exemplary embodiments of the described process, the isolation in step (f) is conducted by precipitation with water followed by filtration, while the isolation in step (h) is conducted by precipitation using an aqueous solution of potassium carbonate, followed by filtration.

The reaction of step (g) can be carried out according to different reaction conditions. However, in one exemplary embodiment the reaction is carried out at room temperature.

As a further embodiment of the invention, the reaction of step (i) above can be carried out with ethylene glycol, toluene, and p-TsOH.$H_2O$ or another equivalent proton source.

In additional aspects of the invention, there are provided (2R,4R)-2-[2-(4-chlorophenyl)ethyl]-2-[(1H-imidazol-1-yl)methyl]-4-[(1H-imidazol-1-yl)methyl]-1,3-dioxolane dihydrochloride (QC-51); (2R,4S)-2-[2-(4-chlorophenyl)ethyl]-2-[(1H-imidazol-1-yl)methyl]-4-[{(4-fluorophenyl)thio}methyl]-1,3-dioxolane hydrochloride (QC-52); (2R,4S)-2-[2-(4-chlorophenyl)ethyl]-2-[(1H-imidazol-1-yl)methyl]-4-[{(4-nitrophenyl)thio}methyl]-1,3-dioxolane hydrochloride (QC-60); (2R,4S)-2-[2-(4-chlorophenyl)ethyl]-2-[(1H-imidazol-1-yl)methyl]-4-[{(5-trifluoromethyl-pyridin-2-yl)thio}methyl]-1,3-dioxolane hydrochloride (QC-80); (2R,4S)-2-[2-(4-chlorophenyl)ethyl]-2-[(1H-imidazol-1-yl)methyl]-4-[(4-adamantan-1-yl-phenoxy)methyl]-1,3-dioxolane hydrochloride (QC-81); 4-(4-chlorophenyl)-1-(1H-imidazol-1-yl)butane hydrochloride (QC-105); 1-{4-Chloromethyl-2-[2-(4-chloro-phenyl)-ethyl]-[1,3]dioxolan-2-ylmethyl}-1H-imidazole hydrochloride (QC-108); 1-{4-Azidomethyl-2-[2-(4-chloro-phenyl)-ethyl]-[1,3]dioxolan-2-ylmethyl}-1H-imidazole hydrochloride (QC-112); 1-{2-[2-(4-Chloro-phenyl)-ethyl]-4-cyclohexylsulfanylmethyl-[1,3]-dioxolan-2-ylmethyl}-1H-imidazole hydrochloride (QC-115); 1-{4-(4-Bromo-phenoxymethyl)-2-[2-(4-chloro-phenyl)-ethyl]-[1,3]dioxolan-2-ylmethyl}-1H-imidazole hydrochloride (QC-119); 1-[2-[2-(4-Chloro-phenyl)-ethyl]-4-(4-fluoro-phenylsulfanylmethyl)-[1,3]dioxolan-2-ylmethyl]-1H-imidazole hydrochloride (QC-120); 1-[2-[2-(4-Chloro-phenyl)-ethyl]-4-(4-iodo-phenoxymethyl)-[1,3]dioxolan-2-ylmethyl]-1H-imidazole hydrochloride (QC-140); 1-{4-(3-Bromo-phenylsulfanylmethyl)-2-[2-(4-chloro-phenyl)-ethyl]-[1,3]dioxolan-2-ylmethyl}-1H-imidazole hydrochloride (QC-164); 1-{4-(2-Bromo-phenylsulfanylmethyl)-2-[2-(4-chloro-phenyl)-ethyl]-[1,3]dioxolan-2-ylmethyl}-1H-imidazole hydrochloride (QC-171); 4-{2-[2-(4-Chloro-phenyl)-ethyl]-2-imidazol-1-ylmethyl-[1,3]dioxolan-4-ylmethoxy}-benzonitrile hydrochloride (QC-173); {2-[2-(phenyl)-ethyl]-2-imidazol-1-ylmethyl-[1,3]dioxolan-4-yl}-methylamine dihydrochloride (QC-190); 1-{2-[2-(4-Chloro-phenyl)-ethyl]-4-thiocyanatomethyl-[1,3]dioxolan-2-ylmethyl}-1H-imidazole hydrochloride (QC-197); 1-[4-(4-Bromo-phenyl)-butyl]-1H-imidazole hydrochloride (QC-199); 1-{2-[2-(4-Chloro-phenyl)-ethyl]-4-methoxymethyl-[1,3]dioxolan-2-ylmethyl}-1H-imidazole hydrochloride (QC-200); 4-(4-(Trifluoromethyl)phenyl)-1-(CH-imidazol-1-yl)-2-butanone hydrochloride (QC-221);

and 1-[4-(4-(Trifluoromethyl)phenyl)butyl]-1H-imidazole hydrochloride (QC-234); as well as free bases or pharmaceutically acceptable salts thereof, and syntheses thereof.

Those skilled in the art will recognize, or be able to ascertain using no more than routine experimentation, numerous equivalents to the specific procedures described herein. Such equivalents are considered to be within the scope of this invention and are covered by the following claims.

BRIEF DESCRIPTION OF THE DRAWINGS

Further details of the invention will become apparent from the following description, taken in combination with the appended figures wherein.

DETAILED DESCRIPTION

Figure 1:
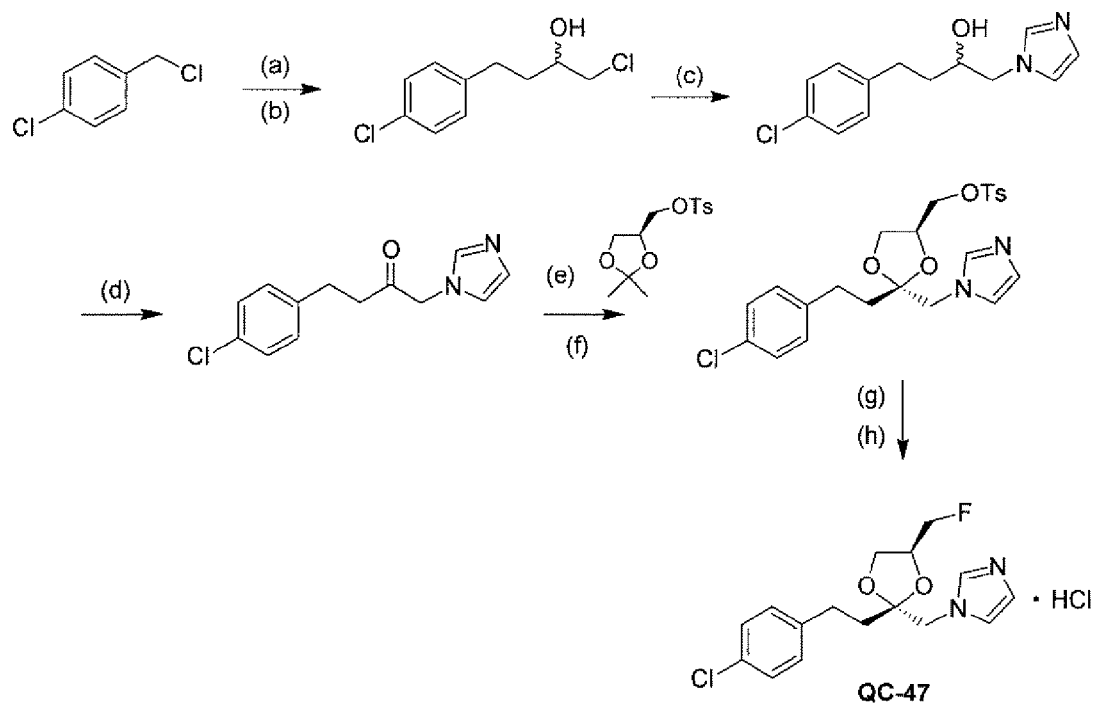
FIG. 1 is a synthetic scheme for the preparation of (2R,4S)-2-(2-(4-chlorophenyl)ethyl)-2-((1H-imidazol-1-yl)methyl)-4-(fluoromethyl)-1,3-dioxolane hydrochloride (QC-47).

Described herein are compounds useful for the prevention and mitigation of cancer and for tumor suppression. The types of cancer include, but are not exclusive to metastatic melanoma, metastatic breast cancer, prostate cancer, colon carcinoma, ovarian cancer and pancreatic cancer. These compounds are also effective as neuroprotectants and for the treatment and prevention of neurological diseases having a pathophysiology that includes, but is not limited to, oxidative damage and/or increased heme oxygenase activity, for instance diseases and disorders of the central nervous system.

The central nervous system diseases include intracerebral hemorrhage (ICH), neurodegenerative diseases such as Alzheimer's disease, Parkinson's disease and other degenerative diseases of the basal ganglia; other neurological causes of memory loss or impairment, including Down's syndrome, Creutzfeldt-Jakob disease, other prion diseases, cerebral ischemia and stroke, and multiple sclerosis; motorneuron disease, such as amyotropic lateral sclerosis; neurological viral disease; post-surgical neurological dysfunction; cancer, spongiform encephalopathy, memory loss and memory impairment.

The described compounds can be provided in pharmaceutical compositions together with an acceptable carrier or excipient, or together with one or more separate active agents or drugs as part of a pharmaceutical combination. In addition, the pharmaceutical compositions may be administered in a treatment regime with other drugs or pharmaceutical compositions, either separately or in a combined formulation or combination.

As an example of a pharmaceutical combination of the present invention, the compounds described herein may be combined with one or more antineoplastic agents or drugs. Antineoplastic drugs are drugs which interfere with cell growth and impede the formation of new tissue, i.e. tumor tissue. These drugs are also known as cytotoxic drugs. Examples of antineoplastic drugs include but are not limited to signal transduction inhibitors, apoptosis inducers, angiogenesis inhibitors, monoclonal antibodies, cancer vaccines, gene therapy, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products such as paclitaxel, colony stimulating growth factors, adjuncts, erythropoetin, alkylating antineoplastic agents such as cisplatin and dacarbazine, anti-metabolites such as fluorouracil and combinations thereof. Particularly preferred are the drugs including trastuzumab, paclitaxel, cisplatin, dacarbazine, and fluorouracil.

Trastuzumab (more commonly known under the trade name Herceptin™) is a humanized monoclonal antibody that acts on the HER2/neu (erbB2) receptor. Trastuzumab's principal use is as an anti-cancer therapy in breast cancer in patients whose tumors over express produce more than the usual amount of) this receptor.

Paclitaxel is a taxoid antineoplastic agent indicated as first-line and subsequent therapy for the treatment of advanced carcinoma of the ovary, and other various cancers including lung cancer, breast cancer, head and neck cancer, and advanced forms of Kaposi's sarcoma. Paclitaxel is an antimicrotubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of microtubules throughout the cell cycle and multiple asters of microtubules during mitosis. Paclitaxel is commercially known under the trademark Taxol™.

Cisplatin, also known as cisplatinum or cis-diaminedichloroplatinum(II) (CDDP), is a platinum-based chemotherapy drug used to treat various types of cancers, including sarcomas, some carcinomas (e.g. small cell lung cancer, and ovarian cancer), lymphomas and germ cell tumors. Cisplatin is classified as an alkylating agent, and is a member of a class which also includes carboplatin and oxaliplatin. Cisplatin is commercially known under the trademarks Platinol™ and Platinol™-AQ Dacarbazine, also known as DIC or 5-(3,3-dimethyl-1-triazenyl)imidazole-4-carboxamide and available under the brand names DTIC and DTIC-Dome™, is an antineoplastic chemotherapy drug used in the treatment of various cancers, among them malignant melanoma and Hodgkin lymphoma. Dacarbazine belongs to the family of chemicals known as the alkylating agents.

Fluorouracil, also known as 5FU, is a chemotherapy drug that is given as a treatment for some types of cancer, including bowel, breast, stomach, and gullet (oesophagus) cancer. It belongs to the family of drugs known as the anti-metabolites.

A composition of the present invention is preferably formulated with a vehicle pharmaceutically acceptable for administration to a subject, preferably a human, in need thereof. Methods of formulation for such compositions are well known in the art and taught in standard reference texts such as *Remington's Pharmaceutical Sciences*, Mack Publishing Co., Easton, Pa., 1985. A composition of the present invention may comprise a single compound, or a combination thereof.

Compositions of the present invention may be administered alone or in combination with a second drug or agent.

Formulations expected to be useful in the present invention, e.g., injectable formulations including intravenous formulations, may include, but are not limited to, sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fingi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including an agent in the composition that delays absorption, for example, aluminum monostearate or gelatin.

Sterile injectable solutions can be prepared by incorporating the composition of the present invention in the required amount in an appropriate solvent with one or a combination of ingredients enumerated above, as required, followed by filter sterilization. Generally, dispersions are prepared by incorporating the composition of the present invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the compound of the invention, optionally plus any additional desired ingredient from a previously sterile-filtered solution thereof.

Solid dosage forms for oral administration of a compound of the present invention include, but are not limited to, ingestible capsules, tablets, pills, lollipops, powders, granules, elixirs, suspensions, syrups, wafers, sublingual or buccal tablets, troches, and the like. In such solid dosage forms the compound is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the compound of the invention in the compositions and preparations may, of course, be varied. The amount of compound in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the compound(s) of the invention only, or preferentially, in a certain part of the intestinal tract, optionally, in a delayed manner. Examples of embedding compositions which can be used include polymeric substances and waxes. The compositions can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the compound of the invention, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurflryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the compound of the invention, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Accordingly, the compositions of the present invention can be administered to a subject, preferably a mammal, more preferably a human, to treat and/or prevent disease. The compositions may be administered by various routes including, but not limited to, orally, intravenously, intramuscularly, intraperitoneally, topically, subcutaneously, rectally, dermally, sublingually, buccally, intranasally or via inhalation. The formulation and route of administration as well as the dose and frequency of administration can be selected routinely by those skilled in the art based upon the severity of the condition being treated, as well as patient-specific factors such as age, weight and the like.

One skilled in the art recognizes that interspecies pharmacokinetic scaling can be used to study the underlining similarities (and differences) in drug disposition among species, to predict drug disposition in an untested species, to define pharmacokinetic equivalence in various species, and to design dosage regimens for experimental animal models, as discussed in Mordenti, Man versus Beast: Pharmacokinetic Scaling in Mammals, 1028, Journal of Pharmaceutical Sciences, Vol. 75, No. 11, November 1986.

Compounds of the invention include compounds of Formula I:

(I)

where
T is a hydrophobic moiety;
n is 1 to 6, preferably n is 1 to 4;
each C of $(C)_n$ can be independently substituted or unsubstituted wherein substituents can be further substituted, substituents including alkyl, alkenyl, alkynyl, aryl (including heteroaryl groups), cycloalkyl, cycloakenyl, halo, oxygen (carbonyl), hydroxyl, thiol, sulfur (thio), thio ether, ether, 1,3-dioxolanyl (5-membered)>1,3-dioxanyl (6-membered), 1,3-dithiolanyl, 1,3-dithianyl or amino;
D is a moiety that binds iron;
or pharmaceutically acceptable salts or esters thereof.

In an embodiment, D may be substituted or unsubstituted wherein substituents may be further substituted. In some embodiments D is a ring structure optionally containing a heteroatom. In certain embodiments D is an unsaturated ring. D may be a five or six-membered ring, such as, for example, imidazolyl, triazolyl, tetrazolyl. In some embodiments D is an imidazolyl such as, for example, 1,3-imidazolyl.

In an embodiment n is 2. In another embodiment n is 4.

In an embodiment, T is a hydrophobic moiety that has an electron-withdrawing moiety (e.g., F, Cl, Br, I, OH, SH, CN, $NR^8R^9$, $NO_2$, $CO_2R^{10}$, CHO). Preferably, T is 4-chlorophenyl, 3-methoxyphenyl, 2-amino-4-chlorophenyl, hydrogen atom, 4-methoxyphenyl, phenyl, acetoxy, 4-fluorophenyl, 4-bromophenyl, carboxyl, amino, 4-iodophenyl, 2-hydroxyphenyl, trifluoroacetyl, adamantyl, imidazolyl, benzamidyl, acetamido, 4-nitrophenyl, naphthalene-2-yl, naphthalene-1-yl, 4-methylphenyl, biphenyl-4-yl, benzoyl, pyrene-1-yl, indan-1-one-2-yl, 3,4-dichlorophenyl, 4-isopropylphenyl, 4-tert-butylphenyl, 1,3-dioxolan-2-yl, 4-(1H-imidazol-1-ylmethyl)benzyl, 4-hydroxyphenyl, 4-benzoylphenyl, methyl, ethyl, propyl.

In an embodiment at least one C of $(C)_n$ can be substituted appropriately (e.g. as an acetal or thioacetal) so that the C is contained as part of a cyclic ring structure such as a 1,3-dioxolane ring, a 1,3-dioxane ring, a 1,3-dithiolane ring, or a 1,3-dithiane ring. These ring structures may be further substituted.

In an alternate embodiment, at least one C of $(C)_n$ can be replaced with another heteroatom (e.g., S, N, C) which is substituted or unsubstituted, and wherein substituents can be further substituted, substituents including alkyl, alkenyl, alkynyl, aryl (including heteroaryl groups), cycloalkyl, cycloakenyl, halo, oxygen (carbonyl), hydroxyl, thiol, sulfur (thio), thio ether, ether, 1,3-dioxolanyl (5-membered), 1,3-dioxanyl (6-membered), 1,3-dithiolanyl, 1,3-dithianyl or amino.

Preferably, in Formula I, when n is 2, the carbons are $sp^3$-hybridized.

In an embodiment, D is a five-membered ring as depicted in Formula Ia,

(Ia)

where T and n are as described previously and A is C, N, O, or S; and saturation level of the ring is not intended to be depicted in Formula Ia. In a further embodiment, D can be a substituted or unsubstituted imidazolyl

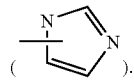
.

In certain embodiments compounds of the invention are of Formula II:

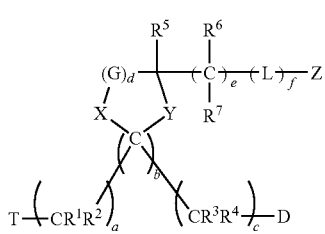

(II)

where D is as described above;
a, b, c, d, e, and f are independently 0, 1, 2, 3, 4, 5, or 6, whereby all of a, b, c, d, e, and f cannot be zero;
$R^{1-7}$ are substituted or unsubstituted and are independently hydrogen, alkyl, perfluoroalkyl, alkyloxy, alkenyl, alkynyl, cycloalkyl, an aryl group, aryloxy, arylalkyl, mercaptoalkyl, or an electron-withdrawing moiety (e.g., F, Cl, Br, I, OH, SH, CN, $NR^8R^9$, $NO_2$, $CO_2R^{10}$, CHO);
G is described by the formula $CR^{11}R^{12}$;
$R^5$ and $R^{11}$ can also together form a saturated or unsaturated 5- or 6-membered ring;
X is O, S, $CR^{13}R^{14}$ or $NR^{15}$;
Y is O, S, $CR^{16}R^{17}$ or $NR^{18}$;
L is O, S, $CR^{19}R^{20}$, $OSO_2$, SO, OSO, $NR^{21}$, NCO, CON, OCO, COO, CO, OP(O)(OR)O, or OP(OR)O, wherein R is hydrogen, alkyl, aryl, or arylalkyl;
$R^{8-21}$ are the same as $R^1$;
T is independently alkyl, adamantanyl, perfluoroalkyl, an electron-withdrawing moiety, or described by Formula (III) below:

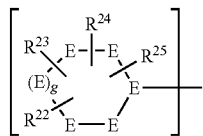

(III)

where
g is 0, 1, 2, 3, or 4;
E is independently an $sp^2$- or $sp^3$-hybridized carbon, nitrogen, oxygen or sulfur atom;
$R^{22-25}$ are the same as $R^1$;
$R^{22}$ and $R^{23}$ can also form a saturated or unsaturated 5- or 6-membered ring, and may be substituted or unsubstituted;
Z is either $R^{26}$ or described by Formula (IV) below:

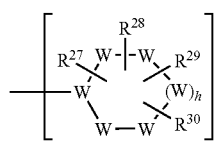

(IV)

where
h is 0, 1, 2, 3, or 4;
$R^{26-30}$ are the same as $R^1$;
W is independently an $sp^2$- or $sp^3$-hybridized carbon or nitrogen atom;

and pharmaceutically acceptable salts or esters thereof.
In another embodiment, the invention pertains, at least in part to compounds Formula (V):

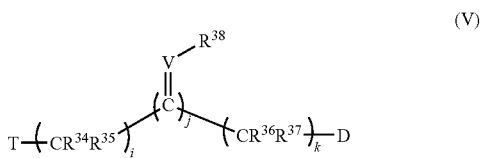

(V)

where
i and k are independently 0, 1, 2, 3, 4, 5, or 6;
j is 0 or 1; whereby all of i, j and k cannot be zero;
V is CH, O, N, or S; when V is CH or nitrogen, $R^{38}$ is hydrogen, alkyl, perfluoroalkyl, hydroxy, alkoxy, aryl, aryloxy, an electron-withdrawing moiety, or benzyl; when V is O or S, $R^{38}$ does not exist;
$R^{34-37}$ are the same as $R^1$ above;
D is as described above;
T is independently alkyl, perfluoroalkyl, an electron-withdrawing moiety, or a hydrophobic moiety that has electron-withdrawing characteristics;
and pharmaceutically acceptable salts or esters thereof.
In yet another embodiment, the invention pertains, at least in part to compounds of Formula (VI):

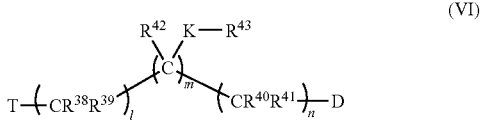

(VI)

where
l, m, and n are independently 0, 1, 2, 3, 4, 5, or 6, whereby all of l, m and n cannot be zero;
$R^{31-42}$ are the same as $R^1$ above;
$R^{43}$ is a hydrogen atom, an alkyl group, a perfluoroalkyl group, a hydroxy group, an alkoxy group, a substituted or unsubstituted aryl group, an aryloxy group, an electron-withdrawing atom, a substituted or unsubstituted benzyl group, or an electron-withdrawing functional group.
K is O, S, $CR^{44}R^{45}$, or $NR^4$;
D is as described above;
$R^{40}$ and $R^{41}$ can form a substituted or unsubstituted 5- or 6-membered ring, either saturated or unsaturated, and if $R^{40}$ and $R^{41}$ form a ring D may be absent;
T is as defined above;
and pharmaceutically acceptable salts or esters thereof.

DEFINITIONS

The term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5.sup.th Edition, Vol 1: Principles and Practice, which is incorporated herein by reference to the extent that it teaches physiologically functional derivatives.

"Bioisosterism" is a lead modification approach used by those skilled in the art of drug design and shown to be useful in attenuating toxicity and modifying activity of a lead compound. Bioisosteric approaches are discussed in detail in standard reference texts such as The Organic Chemistry of Drug Design and Drug Action (Silverman, R B, Academic Press, Inc. 1992 San Diego, Calif., pages 19-23). Classical "bioisosteres" comprise chemical groups with the same number of valence electrons but which may have a different number of atoms. Thus, for example, classical bioisosteres with univalent atoms and groups include, but are not limited to: $CH_3$, $NH_2$, OH, F and Cl; $C_1$, $PH_2$ and SH; Br and i-Pr; and I and t-Bu. Classical bioisosteres with bivalent atoms and groups include, but are not limited to: —$CH_2$— and NH; O, S, and Se; and $COCH_2$, CONHR, $CO_2R$ and COSR. Classical bioisosteres with trivalent atoms and groups include, but are not limited to: CH= and N=; and P= and As=. Classical bioisosteres with tetravalent atoms include, but are not limited to: C and Si; and =$C^+$=, =$N^+$= and =$P^+$=. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown in the following Table.

| Nonclassical Biosteres: |
|---|
| 1. Carbonyl group |

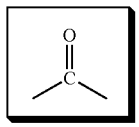

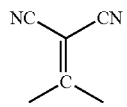

| Nonclassical Biosteres: |
|---|

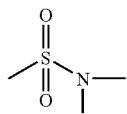

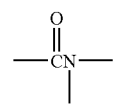

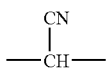

| 2. Carboxylic acid group |
|---|

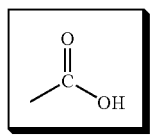

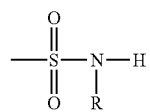

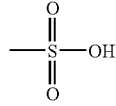

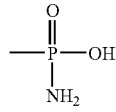

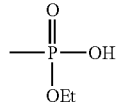

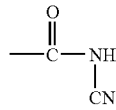

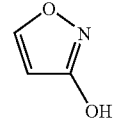

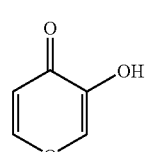

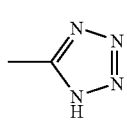

-continued
Nonclassical Biosteres:
3. Hydroxy group
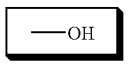
—OH
—NHCR (with =O)
—NHSO$_2$R
—CH$_2$OH
—NHCNH$_2$ (with =O)
—NHCN
—CH(CN)$_2$
4. Catechol
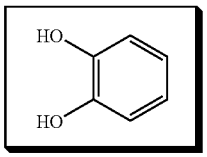
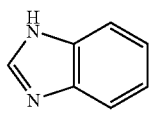
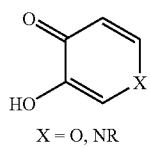
X = O, NR
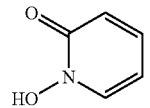
5. Halogen
X
CF$_3$
CN
N(CN)$_2$
C(CN)$_3$
6. Thioether
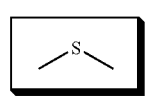
NC   CN
CN
Nonclassical Biosteres:
7. Thiourea
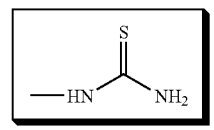
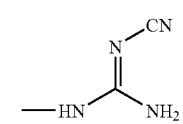
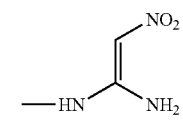
8. Azomethine
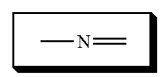
—N=
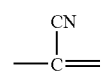
CN
9. Pyridine
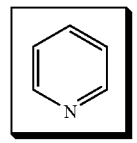
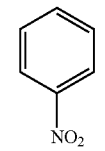
NO$_2$
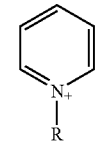
R
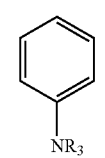
NR$_3$
10. Spacer group
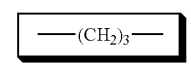
—(CH$_2$)$_3$—
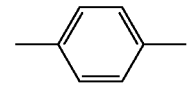

| Nonclassical Biosteres: |
|---|
| 11. Hydrogen |
|  |
| F |

Additional bioisosteric interchanges useful in the design of small organic molecule mimetics of the present invention include ring-chain transformations.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl, Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to seven carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted, where a specific example of a substituted alkyl is 1,1-dimethyl heptyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carboxamide optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

"Hydroxyl" refers to —OH.

"Alcohol" refers to R—OH, wherein R is alkyl, especially lower alkyl (for example in methyl, ethyl or propyl alcohol). An alcohol may be either linear or branched, such as isopropyl alcohol.

"Carboxyl" refers to the radical —COOH, and substituted carboxyl refers to —COR where R is alkyl, lower alkyl or a carboxylic acid or ester.

The term "aryl" or "Ar" refers to a monovalent unsaturated aromatic carbocyclic group having a single ring (e.g. phenyl) or multiple condensed rings (e.g. naphthyl or anthryl), which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of substituted alkoxy groups are: benzyloxy, naphthyloxy, and chlorobenzyloxy.

The term "aryloxy" refers to a group having the structure —O—Ar, where Ar is an aromatic group. A particular aryloxy group is phenoxy.

The term "heterocycle" refers to a monovalent saturated, unsaturated, or aromatic carbocyclic group having a single ring (e.g. morpholino, pyridyl or faryl) or multiple condensed rings (e.g. indolizinyl or benzo[b]thienyl) and having at least one heteroatom, defined as N, O, P, or S, within the ring, which can optionally be unsubstituted or substituted with, e.g. halogen, alkyl alkoxy, alkylthio, trifluoromethyl, acyloxy, hydroxy, mercapto, carboxy, aryloxy, aryl, arylakyl, heteroaryl, amino, alkylamino, dialkylamino, morpholino, piperidino, pyrrolidin-1-yl, piperazin-1-yl, or other functionality.

"Arylalkyl" refers to the groups —R—Ar and —R—HetAr, where Ar is an aryl group. HetAr is a heteroaryl group, and R is a straight-chain or branched chain aliphatic group. Examples of arylaklyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, peperidino, pyrrolidin-1-yl, piperazin-1-yl, or other functionalities.

The term "halo" or "halide" refers to fluoro, bromo, chloro and iodo substituents.

The term "amino" refers to a chemical functionality —NR'R" where R' and R" are independently hydrogen, alkyl, or aryl. The term "quaternary amine" refers to the positively charged group —N$^+$R'R"R'", where R', R" and R'" are independently alkyl or aryl. A particular amino group is —NH$_2$.

A "pharmaceutical agent" or "drug" refers to a chemical compound or composition capable of inducing a desired therapeutic or prophylactic effect when properly administered to a subject.

All chemical compounds include both the (+) and (−) stereoisomers, as well as either the (+) or (−) stereoisomer.

Other chemistry terms herein are used according to conventional usage in the art, as exemplified by The McGraw-Hill Dictionary of Chemical Terms (1985) and The Condensed Chemical Dictionary (1981).

EXAMPLES

I. Synthesis of Representative Compounds

The $^1$H and $^{13}$C NMR spectra were recorded on a Bruker Avance 400 MHz spectrometer in CD$_3$OD or D$_2$O. The signals owing to residual protons in the deuterated solvents were used as internal standards in $^1$H NMR. Chemical shifts (δ) are reported in ppm downfield from tetramethylsilane (Gottlieb, H. E.; Kotlyar, V.; Nudelman, A. *J. Org. Chem.* 1997, 62, 7512-7515). Carbon chemical shifts are given relative to CD)$_3$OD: δ=49.00. High-resolution electrospray mass spectra were recorded on an Applied Biosystems/MDS Sciex QSTAR XL spectrometer with an Agilent HP1100 Cap-LC system. Samples were run in 50% aqueous MeOH at a flow rate of 6 λL/min. Elemental analyses were performed by MHW Laboratories (Phoenix, Ariz., USA). Melting points were determined on a Mel-Temp II melting point apparatus and are uncorrected. Optical rotations were measured using an Autopol™ II automatic polarimeter for solutions in a 1-dm cell at rt. Thin-layer chromatography was performed using glass- or aluminum-backed Silica Gel 60 $F_{254}$ plates (Silicycle, Quebec City, Quebec, Canada). Plates were viewed under UV light or by charring after spraying with phosphomolybdic acid (PMA) in EtOH.

I.I Synthesis of QC-47

(2R,4S)-1-{2-[2-(4-Chlorophenyl)ethyl]-4-fluoromethyl-[1,3]dioxolan-2-ylmethyl}-1H-imidazole hydrochloride (QC-47) was prepared according to the synthetic scheme shown in FIG. 1, wherein the reaction steps (a)-(h) are briefly as follows: (a) Mg, diethyl ether, reflux, 15 min; (b) (±)-epichlorohydrin, diethyl ether, reflux, 2 h; (c) imidazole, NaH, DMF, 70-80° C., 4.5 h; (d) Swern oxidation; (e) p-TsOH.H$_2$O, toluene, n-butanol, reflux 8 h, (f) separate diastereomers (silica gel, EtOAc); (g) Bu$_4$NF, THF, reflux 18.5 h; (h) 37% aq HCl, 2-propanol, rt.

Details of Steps (g)-(h) of Synthesis of QC-47:

To a sample of (2R,4S)-toluene-4-sulfonic acid 2-[2-(4-chloro-phenyl)-ethyl]-2-imidazol-1-ylmethyl-[1,3]dioxolan-4-ylmethyl ester (120 mg, 0.25 mmol) (Vlahakis et al 2005, Walker et al 1997) was added a 1M solution of tetrabutylammonium fluoride in THF (5 mL, 5.0 mmol, 20 equiv) and the mixture was heated at reflux temperature with stirring for 18.5 h. The reaction mixture was cooled to room temperature, diluted with H$_2$O, extracted with EtOAc (3×), and the combined organic extracts were washed sequentially with a saturated aqueous solution of Na$_2$CO$_3$, and water, and then dried (MgSO$_4$). The solution was concentrated and the residue purified by flash column chromatography on silica gel (EtOAc) to give the free base (70 mg, 0.22 mmol) as a golden oil ($R_f$=0.21, EtOAc). To a solution of the free base in warm 2-propanol (2 mL) was added a solution of 37% aqueous HCl (25 mg, 0.25 mmol, 1.1 equiv) in 2-propanol (2 mL). The mixture was concentrated and dried under high vacuum. The residue was dissolved in 2-propanol (1 mL), the solution cooled in the freezer, and then a few drops of Et$_2$O were added and the product allowed to crystallize overnight. The solid was removed by filtration and washed with Et$_2$O. High-vacuum drying left 72 mg (0.20 mmol, 80%) of QC-47 as a white solid: mp 128-129° C.; $[\alpha]_D^{22}$=−6.0° (c=1.0, CD$_3$OD); $^1$H NMR (400 MHz, CD$_3$OD): δ 1.99 (t, J=8.6 Hz, 2H), 2.69-2.84 (m, 2H), 3.86 (t, J=7.8 Hz, 1H), 3.90-4.00 (m, 1H), 4.06 (t, J=6.6 Hz, 1H), 4.35 (~dd, J=10.8, 4.0 Hz, 0.55H), 4.44-4.49 (m, 1H), 4.51 (s, 2H), 4.61 (~dd, J=10.6, 2.6 Hz, 0.5H), 7.20 (d, J=8.4 Hz, 2H), 7.27 (d, J=8.4 Hz, 2H), 7.59 (br s, 1H), 7.64 (br s, 1H), 8.98 (br s, 1H); $^{13}$C NMR (100 MHz, CD$_3$OD): δ 29.7, 38.9, 54.4, 66.7 (d, $^3J_{C-F}$=7.6 Hz), 77.7 (d, $^2J_{C-F}$=19.5H), 82.8 (d, $^1J_{C-F}$=172.71 Hz), 110.1, 120.6, 125.1, 129.6, 131.0, 132.8, 137.8, 141.4; $^{19}$F-$^1$H$_{dec}$ NMR (376 MHz, CD$_3$OD): δ −234.1; HRMS Electrospray Ionization (ES) [M−Cl]$^+$ Calcd. for C$_{16}$H$_{19}$ClFN$_2$O$_2$: 325.1119. Found: 325.1124. Anal. Calcd for C$_{16}$H$_{19}$Cl$_2$FN$_2$O$_2$: C, 53.20; H, 5.30; N, 7.75. Found: C, 53.21; H, 5.23; N, 7.59.

I.I Synthesis of QC-56

1-((2-(2-(4-Bromophenyl)ethyl)-1,3-dioxolan-2-yl)methyl)-1H-imidazole hydrochloride (QC-56) was prepared according to the synthetic scheme shown in FIG. 2, wherein the reaction steps (a)-(e) are briefly as follows: (a) K$_2$CO$_3$, MeOH, reflux, 16 h; (b) Br$_2$, MeOH, rt, 2 h; (c) imidazole, DMF, rt, 1 h; (d) ethylene glycol, p-TsOH.H$_2$O, toluene, reflux, 8 h; (e) 37% aq HCl, 2-propanol, rt.

Step (a). Synthesis of
4-(4-bromophenyl)-2-butanone:

A mixture of 2,4-pentanedione (200 mg, 206 μL, 2 mmol), the 4-bromobenzyl bromide (2 mmol), and anhydrous potassium carbonate (276 mg, 2 mmol) in methanol (10 mL) was heated at reflux temperature for 16 h. The mixture was then cooled to room temperature, methanol was removed under reduced pressure, and the resulting residue was partitioned between ethyl acetate (10 mL) and water (10 mL). The organic layer was separated, and the aqueous layer was extracted further with ethyl acetate (3×10 mL). The combined organic phase was washed with water (10 mL), dried over anhydrous Na$_2$SO$_4$, and then the solvent was removed under pressure. The resulting oil was chromatographed on a silica gel column using hexanes-ethyl acetate as mobile phase to give 4-(4-bromophenyl)-2-butanone as a clear liquid (302 mg, 67%): $R_f$=0.38 (hexanes-ethyl acetate 3:1 v/v); $^1$H NMR (400 MHz, CDCl$_3$): δ 2.15 (s, 3H), 2.75 (t, J=7.2 Hz, 2H), 2.86 (t, J=7.2 Hz, 2H), 7.07 (d, J=8 Hz, 2H), 7.40 (d, J=8.4 Hz, 21; $^{13}$C NMR (100 MHz, CDCl$_3$): δ 29.2, 30.2, 44.9, 120.0, 130.2, 131.7, 140.2, 207.4; HRMS (ESI) Calcd. for C$_{10}$H$_{11}$BrONa: 248.9891 [M+Na$^+$]. Found: 248.9880.

Step (9). Synthesis of
1-Bromo-4-(4-bromophenyl)-2-butanone:

To a solution of 4-(4-bromophenyl)-2-butanone (1 mmol) in methanol (8 mL) stirred at room temperature, a solution of bromine (160 mg, 51.6 μL, 1 mmol) in methanol (1 mL) was added in one portion. The orange reaction mixture was then stirred at room temperature for 2 b, and, after the starting material had been consumed (TLC monitoring, hexanes-ethyl acetate 4:1 v/v), the reaction was quenched by adding a 0.3 M sodium thiosulfate solution (618 μL), and diluted with ethyl acetate (15 mL). The resulting mixture was washed with water (15 mL), the organic layer was separated, and the aqueous layer was extracted further with ethyl acetate (3×15 mL). The combined organic phase was dried over anhydrous Na$_2$SO$_4$, and concentrated under reduced pressure to give a residue that was chromatographed on a silica gel column using hexanes-ethyl acetate (15:1 v/v) as mobile phase to give 1-bromo-4-(4-bromophenyl)-2-butanone as a white solid (193 mg, 63%): mp 63-64° C., $R_f$=0.42 (hexanes-ethyl acetate 4:1 v/v); $^1$H NMR (400 MHz, CDCl$_3$): δ 2.89 (t, J=6.8 Hz, 2H), 2.96 (t, J=6.8 Hz, 2H), 3.84 (s, 2H), 7.07 (d, J=8 Hz, 2H), 7.41 (d, J=8 Hz, 2H); $^{13}$C NMR (100 MHz, CDCl$_3$): δ 29.3, 34.3, 41.2, 120.2, 130.2, 131.7, 139.4, 201.0; HRMS (EI) Calcd. for C$_{10}$H$_{10}$Br$_2$O: 303.9093 (M$^+$). Found: 303.9090.

Step (c). Synthesis of 4-(4-Bromophenyl)-1-(1H-imidazol-1-yl)-2-butanone:

A mixture of 1-bromo-4-(4-bromophenyl)-2-butanone (0.5 mmol) and imidazole (102 mg, 1.5 mmol) in dry N,N-dimethylformamide (2 mL) was stirred at room temperature under a nitrogen atmosphere for 1 h. The mixture was then diluted with ethyl acetate (15 mL), and the solution was washed with water (4×15 mL). The separated organic phase was dried over anhydrous Na$_2$SO$_4$, and then the solvent was removed under reduced pressure to afford a residue that was chromatographed on a silica gel column using ethyl acetate as mobile phase to give 4-(4-bromophenyl)-1-(1H-imidazol-1-yl)-2-butanone as a white solid (111 mg, 76%): mp 79-80° C., $R_f$=0.50 (ethyl acetate-methanol 4:1 v/v); $^1$H NMR (400 MHz, CDCl$_3$): δ 2.70 (t, J=7.2 Hz, 2H), 2.83 (t, J=7.2 Hz, 2H), 4.65 (s, 2H), 6.81 (bs, 1H), 7.02 (d, J=7.6 Hz, 2H), 7.09 (s, 1H), 7.37-7.40 (m, 3H); $^{13}$C NMR (100 MHz, CDCl$_3$): δ 28.6, 40.9, 55.7, 120.1, 120.4, 130.0, 131.8, 138.0, 139.1, 202.3; HRMS (EI) Calcd. for C$_{13}$H$_{13}$BrN$_2$O: 292.0211 (M$^+$). Found: 292.0219.

Steps (d, e). Synthesis of 1-((2-(2-(4-Bromophenyl) ethyl)-1,3-dioxolan-2-yl)methyl)-1H-imidazole Hydrochloride (QC-56):

A mixture of 4-(4-bromophenyl)-1-(1H-imidazol-1-yl)-2-butanone (0.5 mmol), ethylene glycol (62 mg, 58 µL, 1 mmol), p-toluenesulfonic acid monohydrate (190 mg, 1 mmol) in toluene (20 mL) was charged in a flask with a Dean-Stark trap and was heated at reflux temperature under nitrogen until the Dean-Stark trap had filled (1 h). The trap was then emptied, fresh toluene (10 mL) was added to the reaction mixture, and heating at reflux temperature continued for 7 h. The reaction mixture was then cooled to room temperature, diluted with ethyl acetate (15 mL), and washed sequentially with saturated NaHCO$_3$ solution (15 mL), water (15 mL), and brine (15 mL). The organic layer was dried over anhydrous Na$_2$SO$_4$, and then concentrated under reduced pressure. The resulting residue was separated by chromatography by silica gel using EtOAc as eluent to afford a free base dioxolane. A hydrochloride salt dioxolane was prepared by mixing the free base and 37% aqueous HCl (molar ratio 1:1.3) in 2-propanol (1-2 mL). The mixture was concentrated and dried under high vacuum to afford a residue that was recrystallized from 2-propanol. The resulting solid was collected and washed with diethyl ether to give 1-((2-(2-(4-bromophenyl)ethyl)-1,3-dioxolan-2-yl)methyl)-1H-imidazole hydrochloride (QC-56) as a white solid (110 mg, 59%): mp 205-207° C., $R_f$=0.0 (ethyl acetate); $^1$H NMR (400 MHz, D$_2$O): δ 1.97-2.03 (m, 2H), 2.66-2.72 (m, 2H), 3.60-3.65 (m, 2H), 3.96-4.01 (m, 2H), 4.42 (s, 2H), 7.16 (d, J=8 Hz, 2H), 7.45-7.49 (m, 4H), 8.72 (s, 1H); $^{13}$C NMR (100 MHz, D$_2$O): δ 28.0, 36.7, 53.3, 65.8, 107.9, 119.2, 119.3, 123.4, 130.2, 131.4, 135.7, 140.5; HRMS (ESI) Calcd. for C$_{15}$H$_{18}$$^{81}$BrN$_2$O$_2$: 339.0525 [M+H$^+$]. Found: 339.0510. Anal. Calcd. for C$_{15}$H$_{18}$BrClN$_2$O$_2$: C, 48.21; H, 4.86; N, 7.50. Found: C, 48.40; H, 4.73; N, 7.43.

I.III Synthesis of QC-82

To a solution of 1-(adamantan-1-yl)-2-bromoethanone (735 mg, 2.86 mmol) in DMF (9 mL) at 0° C. was added imidazole (1.56 g, 22.91 mmol, 8 equiv) and the mixture was stirred at 0° C. for 0.5 h, then stirred at room temperature for 7 days. The mixture was diluted with aqueous Na$_2$CO$_3$ solution, extracted with EtOAc (4×), and the combined organic extracts were washed with brine (2×), and then dried (MgSO$_4$). The solution was concentrated and dried under high-vacuum to give a pink solid. The solid was ground under H120 (15 mL) and the mixture stirred at room temperature for 0.5 h. The solid was removed by filtration and washed with H$_2$O (10×10 mL). The pinkish-white solid was dried under high-vacuum to afford the clean free base (545 mg, 2.23 mmol, 78%). To a solution of the free base in warm EtOH (5 mL) was added a solution of 37% aqueous HCl (250 mg, 2.54 mmol, 1.1 equiv) in EtOH (2 mL). The mixture was concentrated and dried under high vacuum. The beige solid was dissolved in a minimum amount of hot EtOH (~4 mL), the solution cooled in the freezer, and the product allowed to crystallize overnight. The solid was removed by filtration and washed twice with EtOH (1 mL). High-vacuum drying afforded 478 mg (1.70 mmol, 59%) of 1-(adamantan-1-yl)-2-imidazol-1-yl-ethanone hydrochloride (QC-82) as a beige solid: mp 261-262° C.; $^1$H NMR (400 MHz, CD$_3$OD): δ 1.76-1.88 (m, 6H), 1.96-2.00 (m, 6H), 2.06-2.12 (m, 3H), 5.52 (s, 2H), 7.51 (~t, J=1.6 Hz, 1H), 7.58 (~t, J=1.6 Hz, 1H), 8.87 (s, 1H); $^{13}$C NMR (100 MHz, CD$_3$OD): δ 29.3, 37.4, 38.9, 46.9, 54.7, 120.4, 124.8, 137.9, 207.3; HRMS (ES) [M−Cl]$^+$ Calcd. for C$_{15}$H$_{21}$N$_2$O: 245.1654. Found: 245.1646. Anal. Calcd for C$_{15}$H$_{21}$ClN$_2$O: C, 64.16; H, 7.54; N, 9.98. Found: C, 64.30; H, 7.52; N, 9.90.

I.IV Synthesis of QC-105

To a mixture of 4-(4-chlorophenyl)-1-(1H-imidazol-1-yl)-2-butanone (187 mg, 0.75 mmol) (Vlahakis et al 2005), potassium hydroxide (0.50 g, 8.91 mmol, 11.9 equiv), and ethylene glycol (1.5 mL) was added anhydrous 98% hydrazine (375 µL, 383 mg, 11.71 mmol, 15.6 equiv) and the mixture was heated at 100° C. for 2 h, then at 195° C. for 6 h. The mixture was cooled, diluted with water, extracted with EtOAc (3×), and the combined organic extracts were washed with water (2×), and then dried (MgSO$_4$). The solution was concentrated, and the brown oily residue (R$_f$~0.26 in EtOAc) purified by flash chromatography on silica gel (EtOAc) to give 60 mg (0.26 mmol, 35%) of the free base as an oil. To a solution of the oil in EtOH (2 mL) was added a solution of 37% aqueous HCl (48 mg, 0.49 mmol, 1.9 equiv) in EtOH (2 mL). The mixture was concentrated and dried under high vacuum. The residue was dissolved in a minimum amount of hot 2-propanol, the solution cooled in the freezer, a small amount of Et$_2$O added, and the product allowed to crystallize overnight. The solid was removed by filtration and washed twice with Et$_2$O. High-vacuum drying afforded 46 mg (0.17 mmol, 23%) of 1-[4-(4-chlorophenyl)butyl]-1H-imidazole hydrochloride (QC-105) as a brown solid: mp 121-122° C.; $^3$H NMR (400 MHz, CD$_3$OD): δ 1.63-1.68 (m, 2H), 1.88-1.94 (m, 2H), 2.67 (t, J=7.6 Hz, 2H), 4.28 (t, J=7.2 Hz, 2H), 7.18 (d, J=8.8 Hz, 2H), 7.26 (d, J=8.4 Hz, 2H), 7.57 (~t, J=1.6 Hz, 1H), 7.65 (~t, J=1.6 Hz, 1H), 8.97 (s, 1H); $^{13}$C NMR (100 MHz, CD$_3$OD): δ 29.0, 30.7, 35.3, 50.4, 121.2, 123.3, 129.5, 131.0, 132.8, 136.3, 141.7; HRMS (ES) [M−Cl]$^+$ Calcd. for C$_{13}$H$_{16}$ClN$_2$: 235.1002. Found: 235.0997.

I.V Synthesis of QC-16, QC-21, QC-17 and QC-4

The diastereomeric tosylates QC-16, QC-21, QC-17, and QC-4 were prepared as previously reported (Vlahakis, J.; Kinobe, R. T.; Bowers, R. J.; Brien, J. F.; Nakatsu, K.; Szarek, W. A. Bioorg. Med. Chem. Lett. 2005, 15, 1457-1461). As shown in Scheme 1, the methyl-terminated compounds QC-13, QC-25, QC-26, and QC-27 were obtained by the reduction of tosylates QC-16, QC-21, QC-17, and QC-4, respectively, using lithium aluminum hydride in THF. Since the reduction was performed on only one diastereomeric tosylate, only one methyl-terminated diastereomer was produced, thus avoiding the production of a mixture of all four diastereomers which would have resulted by acid-catalyzed acetalation of 4-(4-chlorophenyl)-1-(1H-imidazol-1-yl)-2-butanone (Se) using racemic 1,2-propanediol.

Scheme 1.

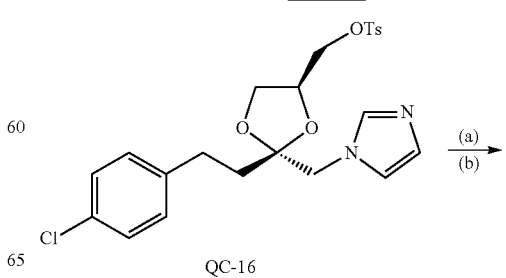

QC-16

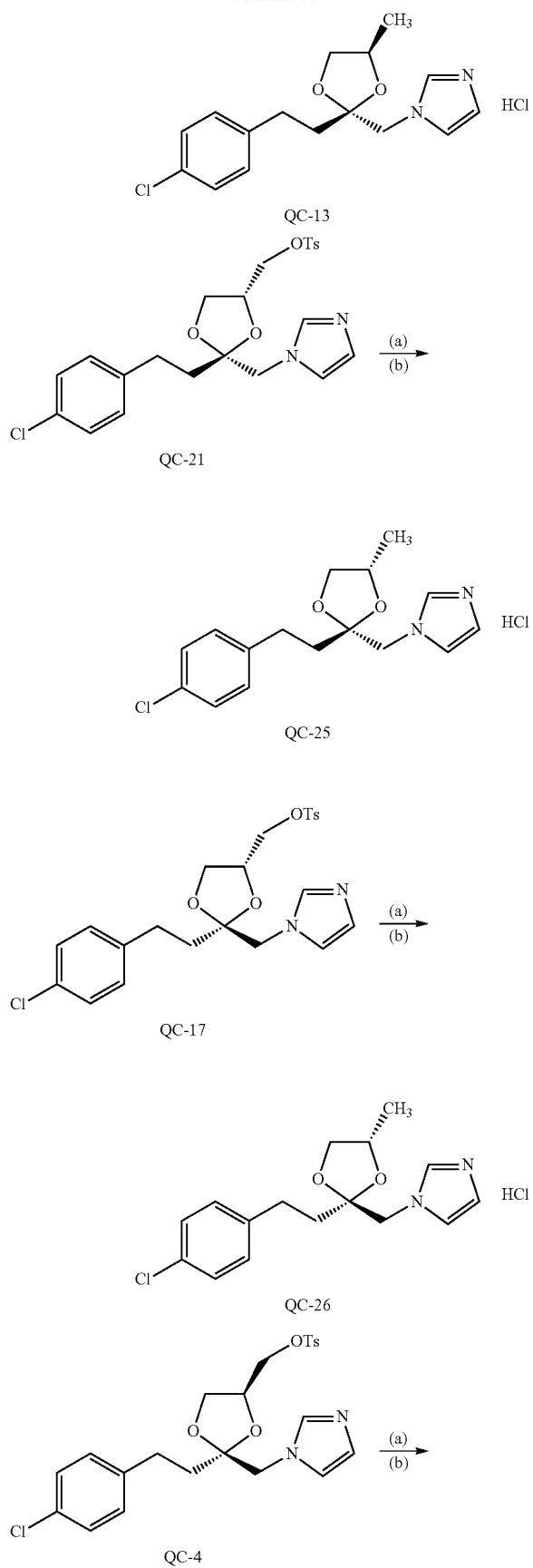

Reagents and conditions:
(a) LiAlH₄, THF, reflux;
(b) 37% aq HCl, 2-propanol, rt.

Representative Procedure for the Reduction of Tosylates Using Lithium Aluminum Hydride to Afford QC-13, QC-25, QC-26, and QC-27 as Outlined in Scheme 1:

(2R,4R)-2-[2-(4-Chlorophenyl)ethyl]-2-[(1H-imidazol-1-yl)methyl]-4-methyl-1,3-dioxolane hydrochloride (QC-13). Under a $N_2$ atmosphere, a solution of the tosylate QC-16 (Vlahakis, J. Z.; Kinobe, R. T.; Bowers, R. J.; Brien, J. F.; Nakatsu, K.; Szarek, W. A. *Bioorg. Med. Chem. Lett.* 2005, 15, 1457-1461) (200 mg, 0.42 mmol) in THF (2 mL) was cooled to 0° C., and a suspension of LiAlH₄ (31 mg, 0.83 mmol) in THF (2 mL) was added; the mixture was heated at reflux temperature for 4 hr. The mixture was cooled to 0° C., diluted with Et₂O, and then carefully quenched with wet Et₂O. After dilution with H₂O, the mixture was extracted twice with Et₂O. The combined extracts were washed sequentially with a saturated aqueous solution of Na₂CO₃ and water, dried (MgSO₄), and concentrated to a yellow oil. Purification by preparative scale (1-cm thick) thin-layer chromatography (EtOAc) gave 73 mg (0.24 mmol, 57%) of the free base which was dissolved in hot 2-propanol (2 mL), and the solution was treated with a solution of 37% aqueous HCl (40 mg, 0.41 mmol) in 2-propanol (1 mL). The mixture was concentrated and dried under high vacuum. The residue was recrystallized (2-propanol-Et₂O), and the solid was removed by filtration and washed with Et₂O. High-vacuum drying afforded 85 mg (0.25 mmol, 59%) of QC-13 as a white solid: mp 172-173° C.; $R_f$=0.24 (EtOAc); $[\alpha]_D^{22}$=−10.2° (c=2.17, D₂O); ¹H NMR (400 MHz, D₂O): δ 1.24 (d, J=6.0 Hz, 3H), 1.93-2.08 (m, 2H), 2.73 (t, J=8.2 Hz, 2H), 3.51 (t, J=8.6 Hz, 1H), 3.69-3.78 (m, 1H), 4.10 (dd, J=8.0, 6.0 Hz, 1H), 4.43 (d, J=2.4 Hz, 2H), 7.23 (d, J=8.4 Hz, 2H), 7.34 (d, J=8.4 Hz, 2H), 7.49-7.52 (m, 2H, 8.76 (s, 1H); ¹³C NMR (100 MHz, D₂O): δ 17.0, 28.3, 37.5, 54.0, 71.9, 74.7, 108.4, 119.7, 123.7, 128.8, 130.2, 131.5, 136.0, 140.2; HRMS (ES) [M−Cl]⁺ Calcd. for C₁₆H₂₀ClN₂O₂: 307.1207. Found: 307.1193.

Characterization of Compounds QC-25, QC-26, QC-27 Synthesized Following the Representative Procedure for the Reduction of Tosylates (Shown Above for QC-13) as Outlined in Scheme 1:

(2R,4S)-2-[2-(4-Chlorophenyl)ethyl]-2-[(1H-imidazol-1-yl)methyl]-4-methyl-1,3-dioxolane hydrochloride (QC-25). Beige solid in 64% yield from QC-21 (Vlahakis, J. Z.; Kinobe, R. T.; Bowers, R. J.; Brien, J. F.; Nakatsu, K.; Szarek, W. A. *Bioorg. Med. Chem. Lett.* 2005, 15, 1457-1461): mp 148-149° C.; $R_f$=0.21 (EtOAc); $[\alpha]_D^{22}$=+15.1° (c=1.19, CD₃OD); 1H NMR (400 MHz, CD₃OD): δ 1.04 (d, J=6.0 Hz, 3H), 1.95-2.05 (m, 2H), 2.70-2.85 (m, 3H), 4.08 (dd, J=8.0, 6.0 Hz, 1H), 4.26-4.35 (m, 1H), 449 (s, 2H), 7.22 (d, J=8.4 Hz, 2H), 7.28 (d, J=8.4 Hz, 2H), 7.58 (s, 1H), 7.62 (s, 1H), 8.96 (s, 1H); ¹³C NMR (100 MHz, CD₃OD): δ 18.0, 30.1, 39.2, 54.7, 73.0, 74.7, 109.2, 120.2, 125.4, 129.6, 130.9, 132.8, 137.9, 141.5; HRMS (ES) [M−Cl]⁺ Calcd. for C₁₆H₂₀ClN₂O₂: 307.1207. Found: 307.1203.

(2S,4S)-2-[2-(4-Chlorophenyl)ethyl]-2-[(1H-imidazol-1-yl)methyl]-4-methyl-1,3-dioxolane hydrochloride (QC-26). White solid in 38% yield from QC-17 (Vlahakis, J. Z.; Kinobe, R. T.; Bowers, R. J.; Brien, J. F.; Nakatsu, K.; Szarek, W. A. *Bioorg. Med. Chem. Lett.* 2005, 15, 1457-1461): mp 172-173° C.; $R_f$=0.18 (EtOAc); $[\alpha]_D^{22}$=+15.7° (c=1.65, $D_2O$); $^1H$ NMR (400 MHz, $D_2O$): δ 1.22 (d, J=6.0 Hz, 3H), 1.92-2.08 (m, 2H), 2.72 (t, J=8.4 Hz, 2H), 3.50 (t, J=8.6 Hz, 1H), 3.67-3.75 (m, 1H), 4.08 (dd, J=8.0, 6.0 Hz, 1H), 4.41 (d, J=2.0 Hz, 2H), 7.22 (d, J=8.4 Hz, 2H), 7.33 (d, J=8.4 Hz, 2H), 7.48 (s, 1H), 7.50 (s, 1H), 8.74 (s, 1H); $^{13}C$ NMR (100 MHz, $D_2O$): δ 16.9, 28.2, 37.5, 54.0, 71.9, 74.6, 108.4, 119.7, 123.7, 128.8, 130.2, 131.5, 136.0, 140.2; HRMS (ES) $[M-Cl]^+$ Calcd. for $C_{16}H_{20}ClN_2O_2$: 307.1207. Found: 307.1204.

(2S,4R)-2-[2-(4-Chlorophenyl)ethyl]-2-[(1H-imidazol-1-yl)methyl]-4-methyl-1,3-dioxolane hydrochloride (QC-27). White solid in 51% yield from QC-4 (Vlahakis, J. Z.; Kinobe, R. T.; Bowers, R. J.; Brien, J. F.; Nakatsu, K.; Szarek, W. A. *Bioorg. Med. Chem. Lett.* 2005, 15, 1457-1461): mp 152-153° C.; $R_f$=0.21 (EtOAc); $[\alpha]_D^{22}$=−21.0° (c=1.33, $D_2O$); $^1H$ NMR (400 MHz, $D_2O$): δ 0.97 (d, J=6.0 Hz, 3H), 1.88-1.98 (m, 2H), 2.64 (t, J=8.2 Hz, 2H), 2.73 (t, J=8.4 Hz, 1H), 4.02 (t, J=7.2 Hz, 1H), 4.19-4.27 (m, 1H), 4.37 (s, 2H, 7.15 (d, J=8.4 Hz, 2H), 7.25 (d, J=8.0 Hz, 2H), 7.43 (s, 1H), 7.44 (s, 1H), 8.70 (s, 1H); $^{13}C$ NMR (100 MHz, $D_2O$): δ 16.8, 28.5, 37.6, 53.7, 71.8, 74.1, 108.3, 119.5, 123.9, 128.7, 130.1, 131.4, 136.1, 140.2; HRMS (ES) $[M-Cl]^+$ Calcd. for $C_{16}H_{20}ClN_2O_2$: 307.1207. Found: 307.1207.

I.VI Synthesis of QC-53, QC-54, QC-55, QC-56, QC-57, QC-65, QC-73, QC-74, QC-76, QC-78, QC-79

One synthetic approach that leads to a large number of the test compounds is illustrated in Scheme 2, and was devised as a general strategy granting access to imidazole-ketones, imidazole-alcohols, and imidazole-dioxolanes variously substituted in the benzene ring. This synthesis debuts with the preparation of 4-aryl-2-butanones (such as 3a-d) by way of a base-catalyzed condensation of the appropriate benzyl halides with 2,4-pentanedione (Boatman, S.; Harris, T. M.; Hauser, C. R. *J. Org. Chem.* 1965, 60, 3321.), followed by the bromination of these materials to afford the intermediate 1-bromo-4-aryl-2-butanones (such as 4a-d). The formation of the undesired isomeric 3-bromo-4-arylketones has been abated by the use of methanol as a solvent instead of the usual halogenated solvents (Gaudry, M.; Marquet, A. *Tetrahedron* 1970, 26, 5611). Alkylation of imidazole with the 1-bromo-4-aryl-2-butanones provided easy access to the key intermediate imidazole-ketones (such as 5a-d), which were subsequently converted into either the corresponding imidazole-dioxolanes (such as QC-57, QC-55, QC-56, QC-78) upon heating at refluxing temperature in ethylene glycol-toluene in the presence of p-toluenesulfonic acid and with continuous azeotropic removal of water, or into the corresponding imidazole-alcohols (such as QC-76, QC-79, QC-74) by reduction with sodium borohydride in methanol.

Scheme 2. General approach for the synthesis of imidazole-ketones, imidazole-dioxolanes, and imidazole-alcohols.

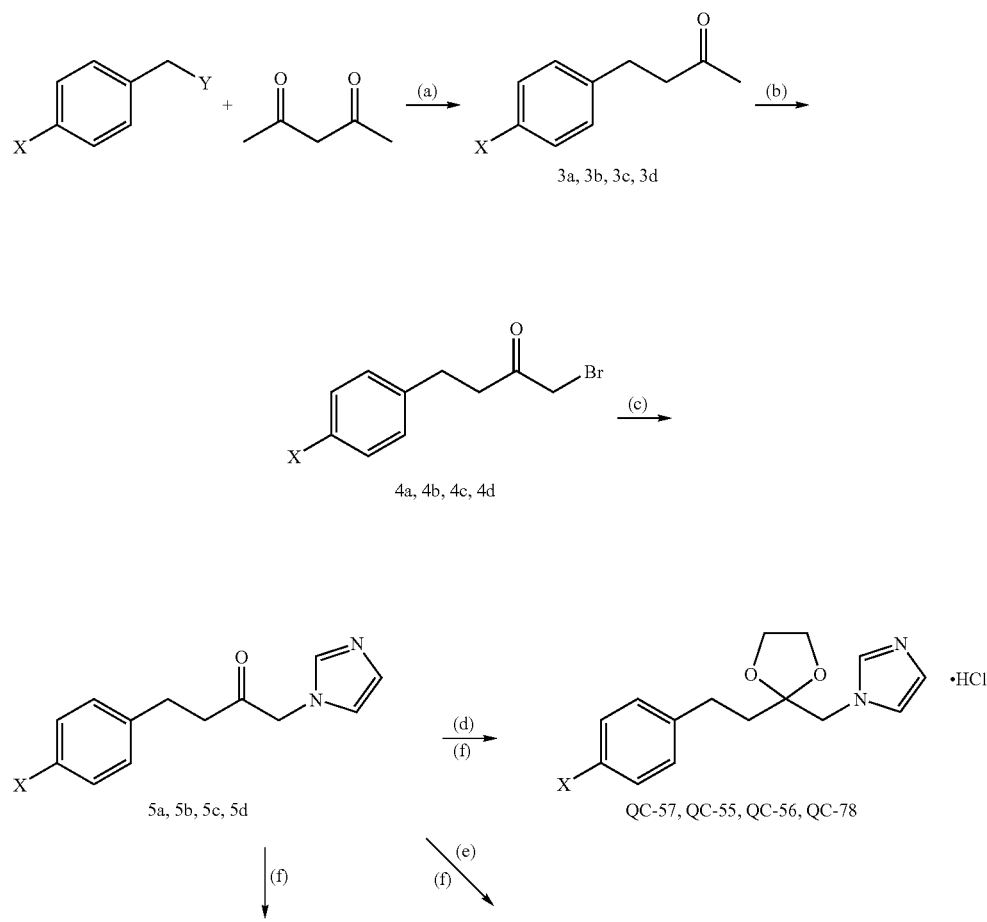

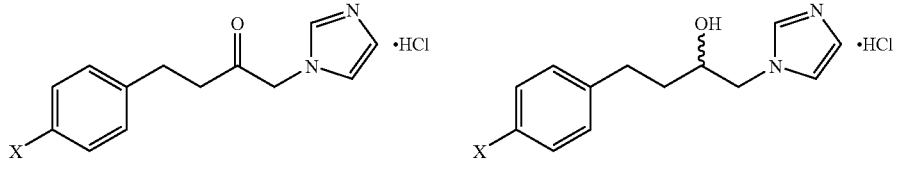

QC-65, QC-54, QC-53, QC-73    QC-76, QC-79, QC-74

Reagents and conditions:
(a) anh $K_2CO_3$, MeOH, reflux, 16 h;
(b) $Br_2$, MeOH, rt. 2 h;
(c) imidazole, DMF, rt, 1 h;
(d) ethylene glycol, p-TsOH $H_2O$, toluene, reflux, 2 h;
(e) $NaBH_4$, MeOH, rt. 3 h;
(f) 37% aq HCl, 2- propanol, rt.
a, X = H; b, X = F; c, X = Br; d, X = I.
Y = Cl, Br General Procedure for the Synthesis of 4-Aryl-2-Butanones (3a-d as Outlined in Scheme 2:

A mixture of 2,4-pentanedione (200 mg, 206 μL, 2 mmol), the 4-substituted benzyl halide (2 mmol), and anhydrous potassium carbonate (276 mg, 2 mmol) in methanol (10 mL) was heated at reflux temperature for 16 h. The mixture was then cooled to room temperature, methanol was removed under reduced pressure, and the resulting residue was partitioned between ethyl acetate (10 mL) and water (10 mL). The organic layer was separated, and the aqueous layer was extracted further with ethyl acetate (3×10 mL). The combined organic phase was washed with water (10 mL), dried over anhydrous $Na_2SO_4$, and then the solvent was removed under pressure. The resulting oil was chromatographed on a silica gel column using hexanes-ethyl acetate as the mobile phase to give the title compounds.

Characterization of Compounds (3a-d) Synthesized Following the General Procedure Above for the Synthesis of 4-Aryl-2-Butanones as Outlined in Scheme 2:

4-Phenyl-2-butanone (3a) (Fleming, I.; Newton, T. W.; Sabin, V.; Zammatio, F. *Tetrahedron* 1992, 48, 7793; and Murphy, J. A.; Commeureuc, A. G. J.; Snaddon, T. N.; McGuire, T. M.; Khan, T. A.; Hisler, K.; Dewis, M. L.; Carling, R. *Org. Lett.* 2005, 7, 1427). Clear liquid (169 mg, 57% from benzyl bromide), $R_f$=0.63 (hexanes-ethyl acetate 3:1 v/v); $^1$H NMR (300 MHz, $CDCl_3$): δ 2.14 (s, 3H), 2.76 (t, J=7.2 Hz, 2H), 2.90 (t, J=7.2 Hz, 2H), 7.15-7.23 (m, 3H), 7.26-7.32 (m, 2H); $^{13}$C NMR (75 MHz, $CDCl_3$): δ 29.8, 30.1, 45.2, 126.2, 128.4, 128.6, 141.1, 208.0; HRMS (EI) Calcd. for $C_{10}H_{12}O$: 148.0888 (M$^+$). Found: 148.0885.

4-(4-Fluorophenyl)-2-butanone (3b) (Berthiol, F.; Doucet, H.; Santelli, M. *Tetrahedron* 2006, 62, 4372). Clear liquid (177 mg, 54% from 4-fluorobenzyl chloride), $R_f$=0.62 (hexanes-ethyl acetate 3:1 v/v); $^1$H NMR (400 MHz, $CDCl_3$): δ 2.14 (s, 3H), 2.74 (t, J=7.2 Hz, 2H), 2.87 (t, J=7.2 Hz, 2H), 6.92-7.00 (m, 2H), 7.10-7.17 (m, 2H); $^{13}$C NMR (100 MHz, $CDCl_3$): δ 29.0, 30.2, 45.3, 115.2 (d, $J^2_{C,F}$=21 Hz), 129.8 (d, $J^3_{C,F}$=8 Hz), 136.6 (d, $J^4_{C,F}$=3 Hz), 161.5 (d, $J^1_{C,F}$=242 Hz), 208; $^{19}$F NMR (376 MHz, $CDCl_3$): δ −118.3.

4-(4-Bromophenyl)-2-butanone (3c) (Harris, M. C.; Huang, X.; Buchwald, S. L. *Org. Lett.* 2002, 4, 2885). Clear liquid (302 mg, 67% from 4-bromobenzyl bromide), $R_f$=0.38 (hexanes-ethyl acetate 3:1 v/v); $^1$H NMR (400 MHz, $CDCl_3$): δ 2.15 (s, 3H), 2.75 (t, J=7.2 Hz, 2H), 2.86 (t, J=7.2 Hz, 2H), 7.07 (d, J=8 Hz, 2H), 7.40 (d, J=8.4 Hz, 2H); $^1$H NMR (100 MHz, $CDCl_3$): δ 29.2, 30.2, 44.9, 120.0, 130.2, 131.7, 140.2, 207.4; HRMS (ESI) Calcd. for $C_{10}H_{11}BrONa$: 248.9891 [M+Na$^+$]. Found: 248.9880.

4-(4-Iodophenyl)-2-butanone (3d). White solid (318 mg, 58% from 4-iodobenzyl bromide), mp 75-76° C., $R_f$=0.60 (hexanes-ethyl acetate 3:1 v/v); $^1$H NMR (300 MHz, $CDCl_3$): δ 2.13 (s, 3H), 2.73 (t, J=7.2 Hz, 2H), 2.83 (t, J=7.2 Hz, 2H), 6.94 (d, J=7.8 Hz, 2H), 7.59 (d, J=7.8 Hz, 2H); $^{13}$C NMR (75 MHz, $CDCl_3$): δ 29.2, 30.2, 44.9, 91.3, 130.6, 137.6, 140.8, 207.6; HRMS (EI) Calcd. for $C_{10}H_{11}IO$: 273.9855 (M. Found: 273.9853.

General Procedure for the Synthesis of 1-Bromo-4-Aryl-2-Butanones (4a-d) by the Bromination of 4-Aryl-2-Butanones (3a-d) as Outlined in Scheme 2:

To a solution of the 4-aryl-2-butanone (1 mmol) in methanol (8 mL) stirred at room temperature, a solution of bromine (160 mg, 51.6 μL, 1 mmol) in methanol (1 mL) was added in one portion. The orange reaction mixture was then stirred at room temperature for 2 h, and, after the ketone had been consumed (TLC monitoring, hexanes-ethyl acetate 4:1 v/v), the reaction was quenched by adding a 0.3 M sodium thiosulfate solution (618 μL), and diluted with ethyl acetate (15 mL). The resulting mixture was washed with water (15 mL), the organic layer was separated, and the aqueous layer was extracted further with ethyl acetate (3×15 mL). The combined organic phase was dried over anhydrous $Na_2SO_4$, and concentrated under reduced pressure to give a residue that was chromatographed on a silica gel column using hexanes-ethyl acetate (15:1 v/v) as the mobile phase to give the desired 1-bromo-4-aryl-2-butanone.

Characterization of Compounds (4a-d) Synthesized Following the General Procedure Above for the Synthesis of 1-Bromo-4-Aryl-2-Butanones as Outlined in Scheme 2:

1-Bromo-4-phenyl-2-butanone (4a) (Barlin, G. B.; Davies, L. P.; Ireland, S. J.; Zhang, J. *Aust. J. Chem.* 1992, 45, 1281; and Ackrell, J.; Franco, F.; Greenhouse, R.; Guzman, A.; Muchowski, S. M. *J. Heterocycl. Chem.* 1980, 17, 1081). White solid (131 mg, 58% from 3a), mp 37-38° C., $R_f$=0.53 (hexanes-ethyl acetate 4:1 v/v); $^1$H NMR (400 MHz, $CDCl_3$): δ 2.98 (t, J=6.8 Hz, 2H), 3.02 (t, J=6.8 Hz, 2H), 3.88 (s, 2H), 7.19-7.24 (m, 3H), 7.28-7.33 (m, 2H); $^{13}$C NMR (100 MHz, $CDCl_3$): δ 30.0, 34.4, 41.6, 126.6, 128.6, 128.7, 140.5, 201.4; HRMS (EI) Calcd. for $C_{10}H_{11}BrO$: 225.9993 (Mt). Found: 225.9997.

1-Bromo-4-(4-fluorophenyl)-2-butanone (4b). White solid (159 mg, 65% from 3b), $R_f$=0.45 (hexanes-ethyl acetate 4:1 v/v); $^1$H NMR (400 MHz, $CDCl_3$): δ 2.95 (t, J=6.8 Hz, 2H), 2.99 (m, J=6.8 Hz, 2H), 3.88 (s, 2H), 6.93-7.01 (m, 2H), 7.11-7.18 (m, 2H); $^{13}$C NMR (100 MHz, $CDCl_3$): δ 29.1, 34.4, 41.5, 115.4 (d, $J^2_{C,F}$=21 Hz), 129.9 (d, $J^3_{C,F}$=8 Hz), 136.1 (d, $J^4_{C,F}$=3 Hz), 161.6 (d, $J^1_{C,F}$=243 Hz), 201.1; $^{19}$F NMR (376 MHz, CDCl$_3$): δ −117.8; HRMS (EI) Calcd. for C$_{10}$H$_{10}$BrFO: 243.9902 (M$^+$). Found: 243.9899.

1-Bromo-4-(4-bromophenyl)-2-butanone (4c). White solid (193 mg, 63% from 3c), mp 63-64° C., R$_f$=0.42 (hexanes-ethyl acetate 4:1 v/v); $^1$H NMR (400 MHz, CDCl$_3$): δ 2.89 (t, J=6.8 Hz, 2H), 2.96 (t, J=6.8 Hz, 2H), 3.84 (s, 2H), 7.07 (d, J=8 Hz, 2H), 7.41 (d, J=8 Hz, 2H); $^{13}$C NMR (100 MHz, CDCl$_3$): δ 29.3, 34.3, 41.2, 120.2, 130.2, 131.7, 139.4, 201.0; HRMS (EI) Calcd. for C$_{10}$H$_{10}$Br$_2$O: 303.9098 (M$^+$). Found: 303.9090.

1-Bromo-4-(4-iodophenyl)-2-butanone (4d). White solid (208 mg, 59% from 3d), mp 76-77° C., R$_f$=0.50 (hexanes-ethyl acetate 4:1 v/v); $^1$H NMR (400 MHz, CDCl$_3$): δ 2.88 (t, J=7.2 Hz, 2H), 2.96 (t, J=7.2 Hz, 2H), 3.84 (s, 2H), 6.94 (d, J=8 Hz, 2H), 7.60 (d, J=8 Hz, 2H); $^{13}$C NMR (100 MHz, CDCl$_3$): δ 29.4, 34.2, 41.1, 91.6, 130.6, 137.8, 140.1, 201.0; HRMS (EI) Calcd. for C$_{10}$H$_{10}$BrIO: 351.8960 (M$^+$). Found: 351.8963.

General Procedure for the Preparation of Imidazole-Ketones (5a-d) and their Hydrochlorides (QC-65, QC-54, QC-53, and QC-73) from 1-Bromo-4-Aryl-2-Butanones (4a-d as Outlined in SCHEME 2:

A mixture of the 1-bromo-4-aryl-2-butanone (0.5 mmol) and imidazole (102 mg, 1.5 mmol) in dry N,N-dimethylformamide (2 mL) was stirred at room temperature under a nitrogen atmosphere for 1 h. The mixture was then diluted with ethyl acetate (15 mL), and the solution was washed with water (4×15 mL). The separated organic phase was dried over anhydrous Na$_2$SO$_4$, and then the solvent was removed under reduced pressure to afford a residue that was chromatographed on a silica gel column using ethyl acetate-methanol as the mobile phase to give the imidazole-ketones (5a-d) as free bases. The free bases (5a, 5b, 5c, and 5d) (0.2 mmol) were turned into the corresponding hydrochlorides (QC-65, QC-54, QC-53, and QC-73, respectively) upon treatment with 37% aqueous HCl (26 mg, 22 µL, 0.26 mmol) in 2-propanol (1 mL). The mixture was then concentrated and dried under high vacuum to afford a residue that was dissolved in the least amount of hot 2-propanol. The solution was cooled at room temperature, and then to −25° C. in a freezer prior to gradual addition of diethyl ether to complete the precipitation of the hydrochlorides, which were collected by filtration and washed with diethyl ether.

Characterization of Compounds (5a-d and QC-65, QC-54, QC-53, and QC-73) Synthesized Following the General Procedure Above for the Synthesis of Imidazole-Ketones and their Hydrochlorides as Outlined in Scheme 2:

1-(1H-Imidazol-1-yl)-4-phenyl-2-butanone (5a) (Cuevas-Yañez, E.; Serrano, J. M.; Huerta, G.; Muchowski, J. M.; Cruz-Almanza, R. Tetrahedron 2004, 60, 9391). White solid (64 mg, 60% from 4a), mp 71-72° C., R$_f$=0.44 (ethyl acetate-methanol 8:1 v/v); $^1$H NMR (400 MHz, CDCl$_3$): δ 2.74 (t, J=7.2 Hz, 2H), 2.93 (t, J=7.2 Hz, 2H), 4.61 (s, 2H), 6.78 (s, 1H), 7.06 (s, 1H), 7.15 (d, J=7.6 Hz, 2H), 7.23 (d, J=7.2 Hz, 1H), 7.28-7.33 (m, 3H); $^{13}$C NMR (100 MHz, CDCl$_3$): δ 29.6, 41.1, 55.6, 120.0, 126.5, 128.4, 128.7, 129.6, 137.9, 140.1, 202.7; HRMS (ESI) Calcd. for C$_{13}$H$_{15}$N$_2$O: 215.1184 [M+H]$^+$. Found: 215.1195.

1-(1H-Imidazol-1-yl)-4-phenyl-2-butanone hydrochloride (QC-65). White solid (43 mg, 86% from 5a), mp 170-171° C. (Walker, K. A. M., 1982, U.S. Pat. No. 4,359,475). mp 171-173° C.), R$_f$=0.0 (ethyl acetate); $^1$H NMR (400 MHz, D$_2$O): δ 2.96 (t, J=6.8 Hz, 2H), 3.04 (t, J=6.8 Hz, 2H), 5.27 (s, 2H), 7.27-7.33 (m, 4H), 7.34-7.41 (m, 2H), 7.48 (s, 1H), 8.59 (s, 1H); $^{13}$C NMR (100 MHz, D$_2$O): δ 28.7, 40.6, 57.0, 119.5, 122.9, 126.6, 128.4, 128.8, 135.7, 140.5, 204.7; HRMS (ESI) Calcd. for C$_{13}$H$_{15}$N$_2$O: 215.1184 [M+H]$^+$. Found: 215.1195.

Anal. Calcd. for C$_{13}$H$_{15}$ClN$_2$O: C, 62.28; H, 6.03; N, 11.17. Found: C, 62.33; H, 5.85; N, 10.99.

4-(4-Fluorophenyl)-1-(1H-imidazol-1-yl)-2-butanone (5b). White solid (76 mg, 66% from 4b), mp 69-70° C., R$_f$=0.52 (ethyl acetate-methanol 8:1 v/v); $^1$H NMR (400 MHz, CDCl$_3$): δ 2.71 (t, J=7.2 Hz, 2H), 2.90 (t, J=7.2 Hz, 2H), 4.66 (s, 2H), 6.83 (bs, 1H), 6.93-6.99 (m, 2H), 7.08-7.14 (m, 3H), 7.44 (bs, 1H); $^{13}$C NMR (100 MHz, CDCl$_3$): δ 28.7, 41.3, 55.8, 115.6 (d, J$^2_{C,F}$=21 Hz), 120.0, 129.7, 129.9 (d, J$^3_{C,F}$=8 Hz), 135.8 (d, J$^4_{C,F}$=3 Hz), 137.9, 161.7 (d, J$^1_{C,F}$=243 Hz), 202.5; $^{19}$F NMR (376 MHz, CDCl$_3$): δ −117.5; HRMS (EI) Calcd. for C$_{33}$H$_{13}$FN$_2$O: 232.1012 (M$^+$). Found: 232.1006.

4-(4-Fluorophenyl)-1-(1H-imidazol-1-yl)-2-butanone hydrochloride (QC-54). White solid (43 mg, 80% from 5b), mp 160-162° C., R$_f$=0.0 (ethyl acetate); $^1$H NMR (400 MHz, D$_2$O): δ 2.90 (t, J=7.2 Hz, 2H), 3.00 (t, J=7.2 Hz, 2H), 5.26 (s, 2H), 7.01-7.08 (m, 2H), 7.20-7.27 (m, 2H), 7.29 (s, 1H), 7.46 (s, 1H), 8.60 (s, 1H); $^{13}$C NMR (100 MHz, D$_2$O): δ 27.8, 40.6, 57.0, 115.2 (d, J$^2_{C,F}$=21 Hz), 19.4, 122.9, 129.9 (d, J$^3_{C,F}$=8 Hz), 135.7, 136.2 (d, J$^4_{C,F}$=3 Hz), 161.2 (d, J$^1_{C,F}$=240 Hz), 204.5; $^{19}$F NMR (376 MHz, D$_2$O): δ −118.5; MS (ESI) Calcd. for C$_{13}$H$_{14}$FN$_2$O: 233.1090 [M+H]$^+$. Found: 233.1089. Anal. Calcd. for C$_{13}$H$_{14}$ClFN$_2$O: C, 58.11; H, 5.25; N, 10.43. Found: C, 58.25; H, 5.17; N, 10.61.

4-(4-Bromophenyl)-1-(1H-imidazol-1-yl)-2-butanone (5c). White solid (111 mg, 76% from 4c), mp 79-80° C., R$_f$=0.50 (ethyl acetate-methanol 4:1 v/v); $^1$H NMR (400 MHz, CDCl$_3$): δ 2.70 (t, J=7.2 Hz, 2H), 2.83 (t, J=7.2 Hz, 2H), 4.65 (s, 2H), 6.81 (bs, 1H), 7.02 (d, J=7.6 Hz, 2H), 7.09 (s, 1H), 7.37-7.40 (m, 3H); $^{13}$C NMR (100 MHz, CDCl$_3$): δ 28.6, 40.9, 55.7, 120.1, 120.4, 130.0, 131.8, 138.0, 139.1, 202.3; HRMS (EI) Calcd. for C$_{13}$H$_{13}$BrN$_2$O: 292.0211 (CM). Found: 292.0219.

4-(4-Bromophenyl)-1-(1H-imidazol-1-yl)-2-butanone hydrochloride (QC-53). White solid (51 mg, 77% from 5c), mp 174-175° C., R$_f$=0.0 (ethyl acetate); $^1$H NMR (400 MHz, D$_2$O): δ 2.91 (t, J=7.2 Hz, 2H), 3.01 (t, J=7.2 Hz, 2H), 5.27 (s, 2H), 7.18 (d, J=8 Hz, 2H), 7.30 (s, 1H), 7.46-7.50 (m, 3H), 8.61 (s, 1H); $^{13}$C NMR (100 MHz, CD$_3$OD): δ 29.4, 41.8, 57.9, 120.8, 121.0, 124.6, 131.5, 132.6, 137.7, 141.2, 201.7; HRMS (ESI) Calcd. for C$_{13}$H$_{14}$BrN$_2$O: 293.0290 [M+H$^+$]. Found: 293.0279. Anal. Calcd. for C$_{13}$H$_{14}$BrClN$_2$O: C, 47.37; H, 4.28; N, 8.50. Found: C, 47.60; H, 4.13; N, 8.34.

1-(1H-Imidazol-1-yl)-4-(4-iodophenyl)-2-butanone (5d). Off-white solid (121 mg, 71% from 4d), mp 124-125° C., R$_f$=0.19 (ethyl acetate); $^1$H NMR (400 MHz, CDCl$_3$): δ 2.71 (t, J=7.6 Hz, 2H), 2.86 (t, J=7.6 Hz, 2H), 4.65 (s, 2H), 6.81 (s, 1H), 6.90 (d, J=8 Hz, 2H), 7.09 (s, 1H), 7.39 (s, 1H), 7.60 (d, J=8 Hz, 2H); $^{13}$C NMR (100 MHz, CDCl$_3$): δ 29.0, 40.9, 55.7, 91.8, 120.0, 130.1, 130.6, 137.9, 138.0, 139.8, 202.3; HRMS (EI) Calcd. for C$_{13}$H$_{13}$IN$_2$O: 340.0073 (M$^+$). Found: 340.0074.

1-(1H-Imidazol-1-yl)-4-(4-iodophenyl)-2-butanone hydrochloride (QC-73). Off-white solid (46 mg, 61% from 5d), mp 202-203° C., R$_f$=0.0 (ethyl acetate); $^1$H NMR (400 MHz, CD$_3$OD): δ 2.90 (t, J=6.8 Hz, 2M, 2.96 (t, J=6.8 Hz, 2H), 5.31 (s, 2H), 7.04 (d, J=8 Hz, 2H), 7.49 (s, 2H), 7.56-7.64 (m, 3H), 8.84 (s, 1H); $^{13}$C NMR (100 MHz, CD$_3$OD): δ 29.4, 41.7, 57.9, 91.6, 120.5, 124.7, 131.7, 137.7, 138.7, 141.8, 201.7; HRMS (ESI) Calcd. for C$_{13}$H$_{14}$IN$_2$O: 341.0151 [M+H]$^+$. Found 341.0147. Anal. Calcd. for C$_{13}$H$_{14}$ClIN$_2$O: C, 41.46; H, 3.75; N, 7.44. Found: C, 41.59; H, 4.00; N, 7.37.

4-(4-Chlorophenyl)-1-(1H-imidazol-t-yl)-2-butanone (5e) (Walker, K. A. M.; Braemer, A. C.; Hitt, S.; Jones, R. E.; Matthews, T. R. J. Med. Chem. 1978, 21, 840) and its hydrochloride form 4-(4-chlorophenyl)-1-(1H-imidazol-1-yl)-2- butanone hydrochloride (QC-9) (Walker, K. A. M.; Braemer, A. C.; Hitt, S.; Jones, R. E.; Matthews, T. R. *J. Med. Chem.* 1978, 21, 840) were prepared according to the reported procedures.

General Procedure for the Preparation of Imidazole-Dioxolane Hydrochlorides (QC-57, QC-55, QC-56, and QC-78) from Imidazole-Ketones (5a, 5b, 5c, and 5d, Respectively) as Outlined in Scheme 2:

A mixture of an imidazole-ketone (0.5 mmol), ethylene glycol (62 mg, 58 µL, 1 mmol), p-toluenesulfonic acid monohydrate (190 mg, 1 mmol) in toluene (20 mL) was heated at reflux temperature under nitrogen until the Dean-Stark trap had filled (1 h). The trap was then emptied, fresh toluene (10 mL) was added to the reaction mixture, and heating at reflux temperature continued for another hour until the trap had refilled. The reaction mixture was then cooled to room temperature, diluted with ethyl acetate (15 mL), and washed sequentially with saturated $NaHCO_3$ solution (15 mL), water (15 mL), and brine (15 mL). The organic layer was dried over anhydrous $Na_2SO_4$, and then concentrated under reduced pressure to give a residue that was chromatographed on silica gel to afford the imidazole-dioxolanes as free bases. The imidazole-dioxolane hydrochlorides (QC-57, QC-55, QC-56, and QC-78) were prepared starting from the corresponding free bases and 37% aqueous HCl (molar ratio 1:1.3) in 2-propanol (1-2 mL) in a manner identical to the one described for the hydrochlorides of the imidazole-ketones.

Characterization of Compounds (QC-57, QC-55, QC-56, and QC-78) Synthesized Following the General Procedure Above for the Synthesis of Imidazole-Dioxolane Hydrochlorides as Outlined in Scheme 2:

1-((2-(2-Phenylethyl)-1,3-dioxolan-2-yl)methyl)-1H-imidazole hydrochloride (QC-57). White solid (90 mg, 61% from 5a), mp 164-165° C., $R_f$=0.0 (ethyl acetate); $^1$H NMR (400 Hz, $D_2O$): δ 2.00-2.06 (m, 2H), 2.72-2.78 (m, 2H), 3.66 (t, J=8 Hz, 2H), 4.02 (t, J=7.2 Hz, 2H), 4.43 (s, 2H), 7.26-7.31 (m, 3H), 7.34-7.40 (m, 2H), 7.48 (s, 1H), 7.49 (s, 1H), 8.72 (s, 1H); $^{13}$C NMR (100 MHz, $D_2O$): δ 28.6, 37.0, 53.4, 65.8, 108.0, 119.3, 123.4, 126.3, 128.4, 128.8, 135.7, 141.4; HRMS (ESI) Calcd. for $C_{15}H_{19}N_2O_2$: 259.1446 [M+H]$^+$. Found: 259.1441. Anal. Calcd. for $C_{15}H_{19}ClN_2O_2 \cdot H_2O$: C, 57.60; H, 6.77; N, 8.96. Found: C, 57.79; H, 6.53; N, 8.99.

1-((2-(2-(4-Fluorophenyl)ethyl)-1,3-dioxolan-2-yl)methyl)-1H-imidazole hydrochloride (QC-55). White solid (91 mg, 58% from 5b), mp 153-154° C., $R_f$=0.0 (ethyl acetate); $^1$H NMR (400 MHz, $D_2O$): δ 1.99-2.04 (m, 2H), 2.69-2.75 (m, 2H), 3.64 (t, J=6.4 Hz, 2H), 4.00 (t, J=7.2 Hz, 2H), 4.43 (s, 2H), 7.02-7.09 (m, 2H), 7.22-7.27 (m, 2H), 7.46 (s, 1H), 7.48 (s, 1H), 8.71 (s, 1H); $^{13}$C NMR (100 MHz, $D_2O$): δ 27.8, 37.1, 53.4, 65.8, 108.0, 115.2 (d, $J^2_{C,F}$=21 Hz), 119.3, 123.4, 129.8 (d, $J^3_{C,F}$=8 Hz), 135.8, 137.1 (d, $J^4_{C,F}$=3 Hz), 161.1 (d, $J^1_{C,F}$=240 Hz); $^{19}$F NMR (376 MHz, $D_2O$): δ −118.9; HRMS (ESI) Calcd. for $C_{15}H_{18}FN_2O_2$: 277.1352 [M+H]$^+$. Found: 277.1340. Anal. Calcd. for $C_{15}H_{18}ClFN_2O_2$: C, 57.60; H, 5.80; N, 8.96. Found: C, 57.86; H, 5.82; N, 8.98.

1-((2-(2-(4-Bromophenyl)ethyl)-1,3-dioxolan-2-yl)methyl)-1H-imidazole hydrochloride (QC-56). White solid (110 mg, 59% from 5c), mp 205-207° C., $R_f$=0.0 (ethyl acetate); $^1$H NMR (400 MHz, $D_2O$): δ 1.97-2.03 (m, 2H), 2.66-2.72 (m, 2H), 3.60-3.65 (m, 2H), 3.96-4.01 (m, 2H), 4.42 (s, 2H), 7.16 (d, J=8 Hz, 2H), 7.45-7.49 (m, 4l, 8.72 (s, 1H); $^{13}$C NMR (100 MHz, $D_2O$): δ 28.0, 36.7, 53.3, 65.8, 107.9, 119.2, 119.3, 123.4, 130.2, 131.4, 135.7, 140.5; HRMS (ESI) Calcd. for $C_{15}H_{18}^{81}BrN_2O_2$: 339.0525 [+H]$^+$. Found: 339.0510. Anal. Calcd. for $C_{15}H_{18}BrClN_2O_2$: C, 48.21; H, 4.86; N, 7.50. Found: C, 48.40; H, 4.73; N, 7.43.

1-((2-(2-(4-Iodophenyl)ethyl)-1,3-dioxolan-2-yl)methyl)-1H-imidazole hydrochloride (QC-78). White solid (105 mg, 50% from 5d), mp 241-243° C. (dec.), $R_f$=0.0 (ethyl acetate); $^1$H NMR (400 MHz, $CD_3OD$): δ 1.94-2.01 (m, 2H), 2.68- 2.77 (m, 2H), 3.58-3.67 (m, 2H), 3.93-4.03 (m, 2H), 4.47 (s, 2H), 7.02 (d, J=8.4 Hz, 2H), 7.56 (s, 1H), 7.59-7.64 (m, 3H), 8.93 (s, 1H); $^{13}$C NMR (100 MHz, $CD_3OD$): δ 30.0, 38.7, 54.6, 66.9, 91.6, 109.0, 120.4, 125.2, 131.6, 137.8, 138.7, 142.5; HRMS (ESI) Calcd. for $C_{15}H_{18}IN_2O_2$: 385.0413 [M+H]$^+$. Found: 385.0406. Anal. Calcd. for $C_{15}H_{18}ClIN_2O_2$: C, 42.83; H, 4.31; N, 6.66. Found: C, 42.87; H, 4.38; N, 6.54.

General Procedure for the Preparation of Imidazole-Alcohol Hydrochlorides (QC-76, QC-79, and QC-74) Through the Reduction of Imidazole-Ketones (5a, 5c, and 5d, Respectively) as Outlined in Scheme 2:

A solution of an imidazole-ketone (0.5 mmol) in methanol (10 mL) was gradually treated with sodium borohydride (57 mg, 1.5 mmol). After the reducing agent had been added, the reaction mixture was further stirred for 3 h, and then the solvent was removed in vacuo to give a solid residue that was partitioned between ethyl acetate (10 mL) and water (10 mL). The aqueous phase was extracted further with ethyl acetate (2×10 mL), the combined organic phase was dried over anhydrous $Na_2SO_4$, and then the solvent was removed to give the desired alcohols as free bases. These compounds were turned into the corresponding imidazole-alcohol hydrochlorides upon treatment with 37% aqueous HCl (molar ratio 1:1.3) in 2-propanol (1-2 mL) in a manner similar to the one described for the preparation of the hydrochlorides of the imidazole-ketones.

Characterization of Compounds (QC-76, QC-79, and QC-74) Synthesized Following the General Procedure Above for the Synthesis of Imidazole-Alcohol Hydrochlorides as Outlined in Scheme 2:

(±)-1-(1H-imidazol-1-yl)-4-phenyl-2-butanol hydrochloride (QC-76). White solid (102 mg, 81% from 5a), mp 56-57° C., $R_f$=0.16 (ethyl acetate); $^1$H NMR (400 MHz, $CD_3OD$): δ 1.66-1.80 (m, 1H), 1.82-1.93 (m, 1H), 2.71-2.81 (m, 1H), 2.84-2.94 (m, 1H), 3.86-3.95 (m, 1H), 4.19 (dd, J=8.0 and 14.0 Hz, 1H), 4.41 (dd, J=3.0 and 13.8 Hz, 1H), 7.21-7.38 (m, 5H), 7.64 (s, 1H), 7.70 (s, 1H), 8.99 (s, 1H); $^{13}$C NMR (100 MHz, $CD_3OD$): δ 32.5, 37.4, 56.0, 69.9, 120.8, 124.0, 127.1, 129.6, 129.7, 137.0, 143.1; HRMS (ESI) Calcd. for $C_{13}H_{17}N_2O$: 217.1341 [M+H]$^+$. Found: 217.1344. Anal. Calcd. for $C_{13}H_{17}ClN_2O$: C, 61.78; H, 6.78; N, 11.08. Found: C, 61.68; H, 6.87; N, 10.95.

(±)-4-(4-Bromophenyl)-1-(1H-imidazol-1-yl)-2-butanol hydrochloride (QC-79). White solid (111 mg, 67% from 5c), mp 174-175° C., $R_f$=0.0 (ethyl acetate); $^1$H NMR (400 MHz, $CD_3OD$): δ 1.65-1.76 (m, 1H), 1.78-189 (m, 1H), 2.64-2.74 (m, 1H), 2.77-2.88 (m, 1H), 3.81-3.89 (m, 1H), 4.17 (dd, J=8.4 and 13.6 Hz, 1H), 4.36 (dd, J=3.0 and 13.8 Hz, 1H), 7.16 (d, J=8.0 Hz, 1H), 7.42 (d, J=8.4 Hz, 1H), 7.56 (s, 1H), 7.63 (s, 1H), 8.90 (s, 1H); $^{13}$C NMR (100 MHz, $CD_3OD$): δ 31.9, 37.07, 56.2, 70.0, 120.6, 124.1, 131.5, 132.5, 136.9, 142.1; HRMS (ESI) Calcd. for $C_{13}H_{16}BrN_2O$: 295.0446 [M+H]$^+$. Found: 295.0432. Anal. Calcd. for $C_{13}H_{16}BrClN_2O$: C, 47.08; H, 4.86; N, 8.45. Found: C, 47.19; H, 5.00; N, 8.56.

(±)-1-(1H-Imidazol-1-yl)-4-(4-iodophenyl)-2-butanol hydrochloride (QC-74). White solid (136 mg, 72% from 5d), mp 196-197° C., $R_f$=0.0 (ethyl acetate); $^1$H NMR (400 MHz, $D_2O$): δ 1.64-1.75 (m, 1H), 1.78-1.88 (m, 1H), 2.63-2.73 (m, 1H), 2.75-2.85 (m, 1H), 3.81-3.89 (m, 1H), 4.13 (dd, J=8.4 and 14.6 Hz, 1H), 4.36 (d, J=14 Hz, 1H), 7.03 (d, J=8 Hz, 2H), 7.56 (s, 1H), 7.58-7.65 (m, 3H), 8.92 (s, 1H); C NMR (100 MHz, $D_2O$): δ2.0, 37.0, 56.3, 70.0, 91.6, 120.7, 124.1, 131.8, 136.9, 138.7, 142.7; HRMS (ESI) Calcd. for $C_{13}H_{16}IN_2O$: 343.0307 [M+H]$^+$. Found: 343.0319. Anal. Calcd. for $C_{13}H_{16}ClIN_2O$: C, 41.24; H, 4.26; N, 7.40. Found: C, 41.20; H, 4.44; N, 7.32.

I.VII Synthesis of QC-9, QC-10, QC-15, QC-42, and QC-50

An alternate synthetic pathway (Scheme 3) to form imidazole-alcohols, imidazole-ketones, and imidazole-dioxolanes is based on the methodology of Walker et al. (Walker, K. A. M.; Braemer, A. C.; Hitt, S.; Jones, R. E.; Matthews, T. R. *J. Med. Chem.* 1978, 21, 840) and was used for the synthesis of imidazole-alcohols (10b, 10e) only in the case of the commercially available halogen-substituted benzyl halides whose benzylic halogen atoT is more reactive than the halogen substituent in the aromatic ring. Treatment of the Grignard reagents derived from either p-fluorobenzyl chloride or p-chlorobenzyl chloride with racemic epichlorohydrin led to the intermediate optically inactive 1-chloro-2-butanols (9b, 9e), which yielded the imidazole-alcohols (10b, 10e) as free bases through the N-alkylation of imidazole. The free bases led to the corresponding hydrochlorides (QC-50, QC-10) upon treatment with hydrochloric acid. The imidazole-alcohols (10b, 10e) are also oxidized to ketones such as 4-(4-chlorophenyl)-1-(1H-imidazol-1-yl)-2-butanone hydrochloride (5e), which form very useful intermediates in the syntheses.

General Procedure for the Preparation of Chloro Alcohols (9b and 9e) from 4-Halobenzyl Chlorides and (±)-Epichlorohydrin as Outlined in Scheme 3:

To a suspension of magnesium turnings (168 mg, 6.92 mmol) in diethyl ether (3 mL), stirred under a nitrogen atmosphere, was added a small portion (0.15 mL) of a solution of 4-halobenzyl chloride (6.92 mmol) in diethyl ether (2 mL), followed by a crystal of iodine. The remaining solution of 4-halobenzyl chloride was then added over a period of 15 minutes, and then the mixture was heated at reflux temperature for 15 minutes. The resulting Grignard reagent was then cooled to room temperature, and added dropwise, using a syringe, to a solution of (±)-epichlorohydrin (640 mg, 541 μL, 6.92 mmol) in diethyl ether (3 mL) over a period of 10 minutes. The reaction mixture was then stirred at room temperature for 30 min, then heated at reflux temperature for 2 h, and diluted with water (10 mL) and ethyl acetate (10 mL). Hydrochloric acid (10 mL, 1.0 M) was then added dropwise

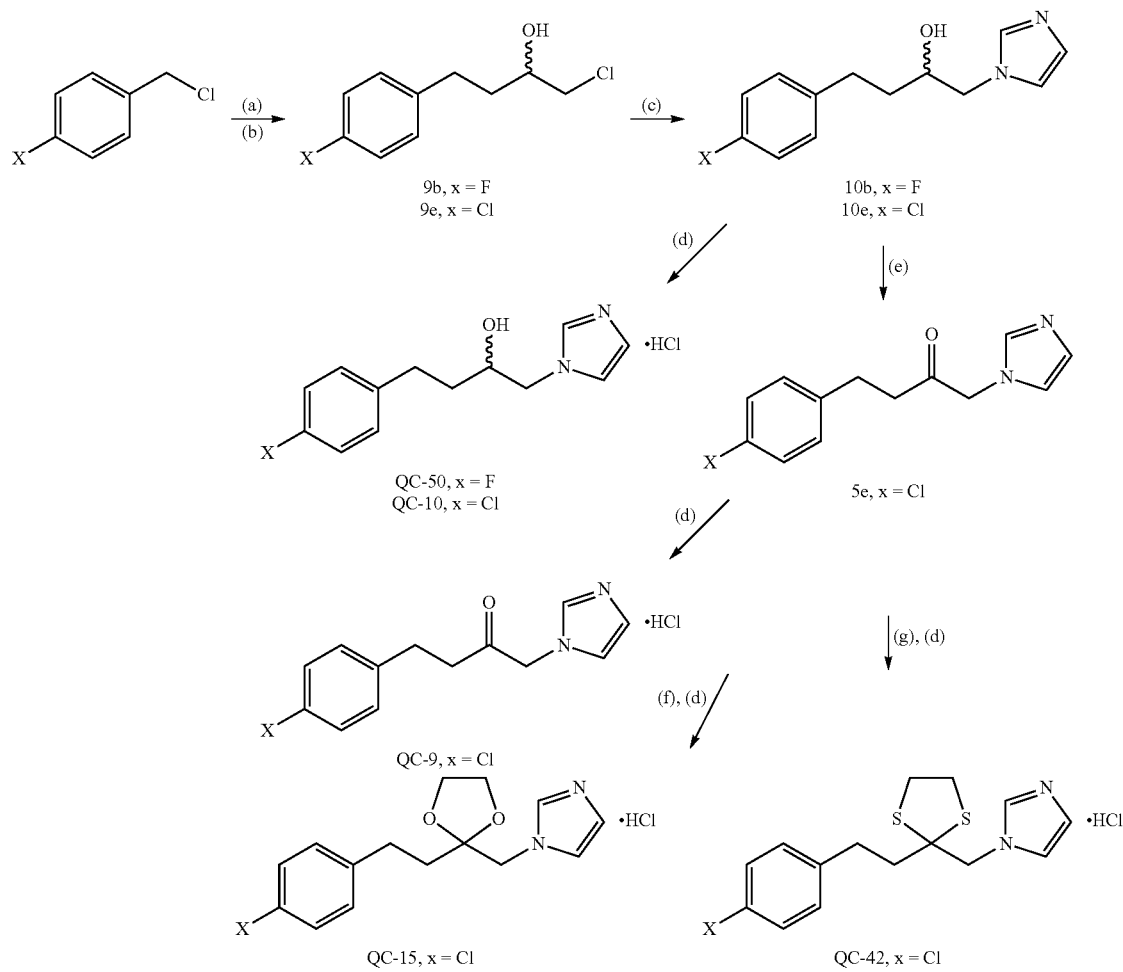

Scheme 3. Alternative synthesis.

Reagents and conditions:
(a) Mg, anhydrous diethyl ether, reflux, 15 min;
(b) (+)-epichlorohydrin, anhydrous diethyl ether, reflux, 2 h;
(c) imidazole, NaH, anhydrous DMF, 70-80° C., 4.5;
(d) 37% aq HCl, 2-propanol, rt;
(e) oxalyl chloride, DMSO, Et₃N;
(f) ethylene glycol, p-TsOH·H₂O,
    toluene, reflux, 2 h;
(g) p-TsOH·H₂O, 1,2-ethanedithiol, toluene, reflux until all of the solids dissolved. The organic layer was then separated, and the aqueous layer extracted with ethyl acetate (3×10 mL). The combined organic phase was then washed with water (10 mL), dried over anhydrous $Na_2SO_4$, and concentrated. The resulting oil was chromatographed on a column of silica gel using hexanes-ethyl acetate as the mobile phase to give the chloro-alcohol.

Characterization of the New Compounds (9b, 9e) Synthesized Following the General Procedure Above for the Synthesis of Chloro Alcohols as Outlined in Scheme 3:

(±)-1-Chloro-4-(4-fluorophenyl)-2-butanol (9b). Clear oil (964 mg, 69% from 4-fluorobenzyl chloride), $R_f$=0.68 (hexanes-ethyl acetate 1:1 v/v); $^1$H NMR (400 MHz, $CDCl_3$): δ 1.83 (m, 2H), 2.70-2.75 (m, 1H), 2.80-2.83 (m, 1H), 3.51 (dd, J=7.1 and 11.1 Hz, 1H), 3.65 (dd, J=3.2 and 7.8 Hz, 1H), 3.81 (m, 2H), 7.00 (t, J=8.6 Hz, 2H), 7.18 (t, J=5.6 Hz, 2H); $^{13}$C NMR (100 MHz, $CDCl_3$): δ 30.9, 35.9, 50.5, 70.4, 115.2 (d, $J^2_{C,F}$=21.2 Hz), 129.8 (d, $J^3_{C,F}$=7.8 Hz), 161.4 (d, $J^1_{C,F}$=243.8); HRMS (EI) Calcd. for $C_{10}H_{12}ClFO$: 202.0561 ($M^+$). Found: 202.0566.

(±)-1-Chloro-4-(4-chlorophenyl)-2-butanol (9e) (Walker, K. A. M.; Braemer, A. C.; Hitt, S.; Jones, R. E.; Matthews, T. R. J. Med. Chem. 1978, 21, 840). Golden oil (860 mg, 57% from 4-chlorobenzyl chloride), $R_f$=0.18 (hexanes-ethyl acetate 9:1 v/v); $^1$H NMR (400 MHz, $CDCl_3$): δ 1.73-1.90 (m, 2H), 2.20 (br s, 1H), 2.63-2.73 (m, 1H), 2.76-2.87 (m, 1H), 3.49 (dd, J=7.0 and 11.0 Hz, 1H), 3.62 (dd, J=3.2 and 11.2 Hz, 1H), 3.74-3.83 (m, 1H), 7.13 (d, J=8.0 Hz, 2H), 7.26 (d, J=8.4 Hz, 2H); $^{13}$C NMR (100 MHz, $CDCl_3$): δ 31.2, 35.8, 50.6, 70.6, 128.8, 129.9, 132.0, 139.9; HRMS (EI) Calcd. for $C_{10}H_{12}Cl_2O$: 218.0265 (MS). Found 218.0260.

General Procedure for the Preparation of Imidazole-Alcohol Hydrochlorides (QC-50 and QC-10) Through the N-Alkylation of Imidazole with Chloro Alcohols (9b and 9e) as Outlined in Scheme 3:

A dispersion of 60% sodium hydride in mineral oil (960 mg, 24 mmol) was washed twice with hexanes under a nitrogen atmosphere, the solid suspended in dry DMF (5 mL), and added portionwise to a cooled stirred solution of imidazole (1.7 g, 25 mmol) in dry DMF (5 mL). The mixture was brought to room temperature and stirred until the evolution of hydrogen ceased, then warmed at 70-80° C. A solution of the chloro alcohol (5 mmol) in DMF (5 mL) was then added dropwise, using a syringe, and the reaction mixture was further stirred at 70-80° C. for 4.5 h, then cooled to room temperature. (±)-4-(4-Fluorophenyl)-1-(1H-imidazol-1-yl)-2-butanol (10b) was isolated by pouring the mixture onto ice (50 g), followed by extraction with ethyl acetate (50 mL). The organic phase was washed with brine (3×50 mL), dried over anhydrous $Na_2SO_4$, then the solvent was removed to give a residue from which the desired compound was separated by chromatography on silica gel using ethyl acetate-methanol (4:1 v/v) as the mobile phase. Alternatively, (±)-4-(4-chlorophenyl)-1-(1H-imidazol-1-yl)-2-butanol (10e) was isolated from the reaction mixture by addition of hexanes (10 mL), followed by addition of ice-cold water until a precipitate started to form. This mixture was then poured in small portions onto ice-water, the separated solid was removed by filtration, washed thoroughly, sequentially with cold water, cold hexanes, and finally with cold water again to give the desired imidazole-alcohol as a free base (10b or 10c). In order to prepare the corresponding imidazole-alcohol hydrochlorides (QC-50 or QC-10), the free bases of imidazole-alcohols were treated with 37% aqueous HCl (molar ratio 1:1.3) in 2-propanol (5-7 mL) in a manner similar to the one described for the preparation of the hydrochlorides of the imidazole-ketones.

Characterization of Compounds (QC-50, QC-10) Synthesized Following the General Procedure Above for the Synthesis of Imidazole-Alcohol Hydrochlorides as Outlined in Scheme 3:

(±)-4-(4-Fluorophenyl)-1-(1H-imidazol-1-yl)-2-butanol hydrochloride (QC-50). Colorless solid (839 mg, 62% from 9b), mp 86-87° C., $R_f$=0.0 (ethyl acetate); $^1$H NMR (400 MHz, $D_2O$): δ 1.65-1.78 (m, 1H), 1.82-1.92 (m, 1H), 2.64-2.75 (m, 1H), 2.77-2.87 (m, 1H), 3.86-3.96 (m, 1H), 4.13 (dd, J=8.1 and 14.2 Hz, 1H), 4.32 (dd, J=2.9 and 14.2 Hz, 1H), 7.06 (t, J=8.9 Hz, 2H), 7.24-7.32 (m, 2H), 7.43 (s, 2H), 8.66 (s, 1H); $^{13}$C NMR (100 MHz, $D_2O$): δ 30.0, 34.9, 54.6, 68.6, 115.1 (d, $J^2_{C,F}$=21.2 Hz), 119.6, 122.3, 130.0 (d, $J^3_{C,F}$=8.0 Hz), 137.2 (d, $J^4_{C,F}$=3.0 Hz), 161.1 (d, $J^1_{C,F}$=241.2); $^{19}$F NMR (376 MHz, $D_2O$): δ −119.0; HRMS (ESI) Calcd. for $C_{13}H_{16}FN_2O$: 235.1247 $[M+H]^+$. Found: 235.1247. Anal. Calcd. for $C_{13}H_{16}ClFN_2O$: C, 57.67; H, 5.96; N, 10.35. Found: C, 57.75; H, 5.94; N, 10.49.

(±)-4-(4-Chlorophenyl)-1-(1H-imidazol-1-yl)-2-butanol hydrochloride (QC-10). Colorless solid (775 mg, 54% from 9e), mp 138-140° C., $R_f$=0.0 (ethyl acetate); $^1$H NMR (400 MHz, $D_2O$): δ 1.70-1.78 (m, 1H), 1.82-1.91 (m, 1H), 2.67-2.74 (m, 1H), 2.78-2.86 (m, 1H), 3.88-3.94 (m, 1H), 4.15 (dd, J=8.0 and 14.0 Hz, 1H), 4.34 (dd, J=3.0 and 14.2 Hz, 1H), 7.25 (d, J=8.4 Hz, 2H), 7.35 (d, J=8.4 Hz, 2H), 7.45 (s, 1H), 7.46 (s, 1H), 8.68 (s, 1H); $^{13}$C NMR (100 MHz, $D_2O$): δ 30.5, 35.0, 54.9, 69.0, 120.0, 122.6, 128.8, 130.4, 131.4, 135.3, 140.5; HRMS (ESI) Calcd. for $C_{13}H_{16}ClN_2O$: 251.0945 $[M+H]^+$. Found: 251.0949. Anal. Calcd. for $C_{13}H_{16}Cl_2N_2O$: C, 54.37; H, 5.62; N, 9.75. Found: C, 54.56; H, 5.72; N, 9.18.

As previously stated, the intermediate 4-(4-chlorophenyl)-1-(1H-imidazol-1-yl)-2-butanone hydrochloride (Se) (which is the free base form of QC-9) was prepared by the Swern oxidation (oxalyl chloride, DMSO, $Et_3N$) of 10e. (Walker, K. A. M.; Braemer, A. C.; Hitt, S.; Jones, R. E.; Matthews, T. R. J. Med. Chem. 1978, 21, 840; and Walker, K. A. M., 1982, U.S. Pat. No. 4,359,475).

As shown in Scheme 3, the 1,3-dioxolane compound QC-15 was prepared (Vlahakis, J. Z.; Kinobe, R. T.; Bowers, R. J.; Brien, J. F.; Nakatsu, K.; Szarek, W. A. J. Med. Chem. 2006, 49, 4437-4441) from 5e by an acid-catalyzed acetalation reaction in toluene using ethylene glycol, according to a procedure similar to that reported by Walker et al. (EP 0 492 474 B1). The corresponding 1,3-dithiolane derivative QC-42 was also prepared (Vlahakis, J. Z.; Kinobe, R. T.; Bowers, R. J.; Brien, J. F.; Nakatsu, K.; Szarek, W. A. J. Med. Chem. 2006, 49, 4437-4441) in this manner from 5e using 1,2-ethanedithiol.

Characterization of the New Compounds (QC-15, QC-42) Synthesized Following the General Procedure Above for the Synthesis of Imidazole-Dioxolane Hydrochlorides (QC-57, QC-55, QC-56, QC-78) as Outlined in Scheme 3:

2-[2-(4-Chlorophenyl)ethyl]-2-[(1H-imidazol-1-yl)methyl]-1,3-dioxolane hydrochloride (QC-15) (Vlahakis, J. Z.; Kinobe, R. T.; Bowers, R. J.; Brien, J. F.; Nakatsu, K.; Szarek, W. A. J. Med, Chem. 2006, 49, 4437-4441). White solid (125 mg, 24% from 5e; Vlahakis, J. Z.; Kinobe, R. T.; Bowers, R. J.; Brien, S. F.; Nakatsu, K.; Szarek, W. A. Bioorg. Med. Chem. Lett. 2005, 15, 1457-1461), mp 168-169° C.; $R_f$=0.17 (EtOAc); $^1$H NMR (400 Liz, $D_2O$): δ 1.94-2.02 (m, 2H), 2.64-2.72 (m, 2H), 3.58-3.68 (m, 2H), 3.92-4.02 (m, 2H), 4.41 (s, 2H), 7.18 (d, J=8.0 Hz, 2H), 7.29 (d, J=8.0 Hz, 2H), 7.47 (s, 2H), 8.72 (s, 1H); $^{13}$C NMR (100 MHz, $D_2O$): δ 28.3, 37.1, 53.7, 66.1, 108.2, 119.7, 123.7, 128.8, 130.1, 131.4, 136.1, 140.3; HRMS (ES) $[M−Cl]^+$ Calcd. for $C_{15}H_{18}ClN_2O_2$: 293.1051. Found: 293.1040.

2-[2-(4-Chlorophenyl)ethyl]-2-[(1H-imidazol-1-yl)methyl]-1,3-dithiolane hydrochloride (QC-42). The title compound was synthesized from ketone 5e (Vlahakis, J. Z.; Kinobe, R. T.; Bowers, R. J.; Brien, J. F.; Nakatsu, K.; Szarek, W. A. *Bioorg. Med. Chem. Lett.* 2005, 15, 1457-1461) by the procedure employed for the synthesis of QC-15, except using 1,2-ethanedithiol instead of ethylene glycol, to afford a beige solid in 32% yield after recrystallization (2-propanol): mp 204-205° C.; $R_f$=0.21 (EtOAc); $^1$H NMR (400 MHz, CD$_3$OD): δ 2.17-2.25 (m, 2H), 2.94-3.06 (m, 4H), 3.28-3.38 (m, 2H), 4.65 (s, 2H), 7.21 (d, J=8.4 Hz, 2H), 7.28 (d, J=8.4 Hz, 2H), 7.56 (s, 1H), 7.81 (s, 1H), 9.11 (s, 1H); $^{13}$C NMR (100 MHz, D$_2$O): δ 32.6, 41.6, 43.4, 59.8, 71.2, 119.9, 125.5, 129.6, 131.1, 133.0, 138.2, 141.3; HRMS (ES) [M−Cl]$^+$ Calcd. for C$_{15}$H$_{18}$ClN$_2$S$_2$: 325.0600. Found: 325.0587.

I.VIII Synthesis of QC-30, QC-32, QC-41, QC-48, QC-49, QC-52, QC-60, QC-80, QC-115, QC-121, QC-164, QC-171, and QC-171

As shown in Scheme 4, the substituted arylsulfanyl-terminated compounds QC-30, QC-32, QC-41, QC-48, QC-49, QC-52, QC-60, QC-80, QC-115, QC-121, QC-164, QC-171, and QC-171 were obtained by a nucleophilic displacement reaction of tosylate QC-16 with various substituted arylthiols, along with cesium carbonate in acetone at reflux temperature.

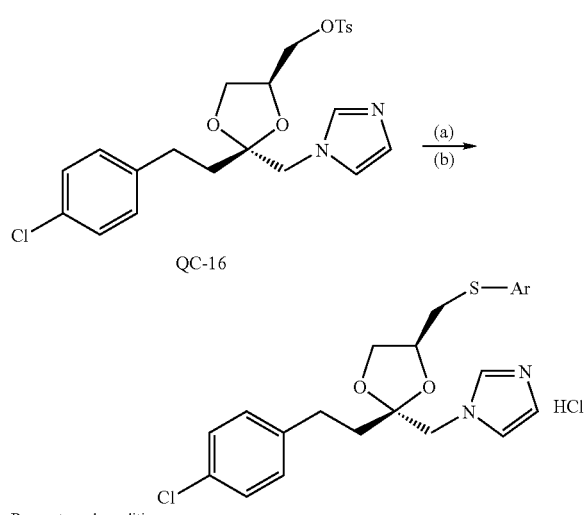

Scheme 4.

QC-16

Reagents and conditions:
(a) ArSH, Cs$_2$CO$_3$, acetone, reflux;
(b) 37% aq HCl, 2-propanol, rt.

Representative Procedure for the Displacement of Tosyloxy Groups Using Thiophenol-Containing Nucleophiles:

(2R,4S)-1-{2-[2-(4-Chlorophenyl)ethyl]-4-phenylsulfanylmethyl-[1,3]dioxolan-2-ylmethyl}-1H-imidazole hydrochloride (QC-30). Under a N$_2$ atmosphere, a mixture of (2R,4S)-2-[2-(4-chlorophenyl)ethyl]-2-[(1H-imidazol-1-yl)methyl]-4-[(p-toluenesulfonyloxy)methyl]-1,3-dioxolane (QC-16) (178 mg, 0.37 mmol), benzenethiol (82 mg, 0.74 mmol, 2 equiv), and cesium carbonate (241 mg, 0.74 mmol, 4 equiv) in acetone (7 mL) was heated at reflux temperature with stirring for 6 h. The solids were removed by filtration, and washed with hot acetone and then with hot ethyl acetate. The filtrate was concentrated, and the residue (R$_f$=0.2 in EtOAc) purified by flash chromatography on silica gel (EtOAc) to give 150 mg (0.36 mmol, 98%) of the free base as an oil. To a solution of the oil in warm 2-propanol (2 mL) was added a solution of 37% aqueous HCl (50 mg, 0.51 mmol, 1.4 equiv) in 2-propanol (2 mL). The mixture was concentrated and dried under high vacuum. The residue was dissolved in 2-propanol (0.5 mL), the solution cooled in the freezer, and then a few drops of Et$_2$O were added and the product allowed to crystallize overnight. The solid was removed by filtration and washed with Et$_2$O. High-vacuum drying left 150 mg (0.33 mmol, 89%) of QC-30 as a white solid: mp 134-135° C.; $R_f$=0.24 (EtOAc); [α]$_D^{23}$=−8.2° (c=1.7, CD$_3$OD); $^1$H NMR (400 MHz, CD$_3$OD): δ 1.97 (t J=8.4 Hz, 2H), 2.66-2.84 (m, 2H), 3.09 (dd, J=13.8, 5.8 Hz, 1H), 3.19 (dd, J=14.0, 4.8 Hz, 1H), 3.66-3.75 (m, 2H), 4.00-4.90 (m, 1H), 4.45 (s, 2H), 7.16 (d, J=8.4 Hz, 2H), 7.20-7.42 (m, 7H), 7.50 (br s, 1H), 7.58 (br s, 1H), 8.92 (br s, 1H); $^{13}$C NMR (100 MHz, CD$_3$OD): δ 29.8, 36.7, 39.2, 54.7, 70.9, 78.0, 109.9, 120.5, 125.0, 127.7, 129.5, 130.2, 130.9, 131.0, 132.8, 136.8, 137.7, 141.4; HRMS (ES) [M−Cl]$^+$ Calcd. for C$_{22}$H$_{24}$ClN$_2$O$_2$S: 415.1247. Found: 415.1233. Anal. Calcd for C$_{22}$H$_{24}$Cl$_2$N$_2$O$_2$S: C, 58.54; H, 5.36; N, 6.21. Found: C, 58.44; H, 5.28; N, 6.06.

Characterization of Compounds Synthesized Following the Representative Procedure for the Displacement of Tosyloxy Groups Using Thiophenol-Containing Nucleophiles (Shown Above for QC-30) as Outlined in Scheme 4:

(2R,4S)-4-{2-[2-(4-Chlorophenyl)ethyl]-2-imidazol-1-ylmethyl-[1,3]dioxolan-4-ylmethylsulfanyl}-pyridine dihydrochloride (QC-32). Hygroscopic white solid in 76% yield from QC-16: [α]$_D^{24}$=+22.3° (c=2.0, CD$_3$OD); $^1$H NMR (400 MHz, CD$_3$OD): δ 1.93-2.05 (m, 2H), 2.65-2.82 (m, 2H), 3.45 (dd, J=14.2, 58 Hz, 1H), 3.64 (dd, J=14.8, 4.8 Hz, 1H), 3.87 (t, J=8.2 Hz, 1H), 4.00-4.10 (m, 1H), 4.19 (dd J=8.6, 6.2 Hz, 1H), 4.47 (s, 2H), 7.14 (d, J=8.4 Hz, 2H), 7.26 (d, J=8.4 Hz, 2H), 7.59 (t, J=1.6 Hz, 1H), 7.65 (t, J=1.6 Hz, 1H), 7.90 (d, J=7.2 Hz, 2H), 8.50 (d, J=6.4 Hz, 2H), 8.99 (s, 1H); $^{13}$C NMR (100 MHz, CD$_3$OD): δ 29.8, 33.8, 38.7, 54.3, 70.2, 76.7, 110.3, 120.7, 123.9, 125.1, 129.6, 130.9, 132.9, 137.8, 140.7, 141.1, 165.9; HRMS (ES) [M−Cl]$^+$ Calcd. for C$_{21}$H$_{23}$ClN$_3$O$_2$S: 416.1199. Found: 416.1183. Anal. Calcd for C$_{21}$H$_{24}$Cl$_3$N$_3$O$_2$S: C, 51.59; H, 4.95; N, 8.60. Found: C, 49.19; H, 5.22; N, 7.88.

(2R,4S)-1-{4-[(4-Bromophenylsulfanyl)methyl]-2-[2-(4-chlorophenyl)-ethyl]-[1,3]dioxolan-2-ylmethyl}-1H-imidazole hydrochloride (QC-41). White solid in 96% yield from QC-16: mp 141-142° C.; $R_f$=0.23 (EtOAc); [α]$_D^{22}$=−4.5° (c=0.9, CD$_3$OD); $^1$H NMR (400 MHz, CD$_3$OD): δ 1.95 (t, J=8.4 Hz, 2H), 2.64-2.80 (m, 2H), 3.13 (dd, J=14.0, 5.6 Hz, 1H), 3.19 (dd, J=14.0, 5.2 Hz, 1H), 3.69-3.79 (m, 2H), 4.01-4.09 (m, 1H), 4.45 (s, 2H), 7.14 (d, J=8.4 Hz, 2H), 7.26 (d, J=8.4 Hz, 2H), 7.30 (d, J=8.8 Hz, 2H), 7.45 (d, J=8.8 Hz, 2H), 7.52 (br s, 1H), 7.59 (br s, 1H), 8.92 (br s, 1H); $^{13}$C NMR (100 MHz, CD$_3$OD): δ 29.8, 36.6, 39.1, 54.6, 70.8, 78.0, 110.0, 120.6, 121.2, 125.1, 129.6, 131.0, 132.3, 132.9, 133.2, 136.6, 137.8, 141.3; HRMS (ES) [M−Cl]$^+$ Calcd. for C$_{22}$H$_{23}$BrClN$_2$O$_2$S: 493.0352. Found: 493.0336. Anal. Calcd for C$_{22}$H$_{23}$BrCl$_2$N$_2$O$_2$S: C, 49.83; 1, 4.37; N, 5.28. Found: C, 50.52; H, 4.50; N, 4.66.

(2R,4S)-1-[2-[2-(4-Chlorophenyl)ethyl]-4-(4-methoxyphenylsulfanylmethyl)-[1,3]dioxolan-2-ylmethyl]-1H-imidazole hydrochloride (QC-48). Beige solid in 73% yield from QC-16: mp 139-140° C.; $R_f$=0.16 EtOAc); [α]$_D^{22}$=−9.2° (c=0.9, CD$_3$OD); $^1$H NMR (400 MHz, CD$_3$OD): δ 1.95 (t, J=8.4 Hz, 2H), 2.64-2.78 (m, 2H), 2.93 (dd, J=13.8, 5.8 Hz, 1H), 3.07 (dd, J=13.8, 5.0 Hz, 1H), 3.59-3.68 (m, 2H), 3.79 (s, 3H), 3.98-4.05 (m, 1H), 4.43 (s, 2H), 6.89 (d, J=8.8 Hz, 2H), 7.17 (d, J=8.4 Hz, 2H), 7.26 (d, J=8.4 Hz, 2H), 7.36 (d, J=8.4 Hz, 2H), 7.51 (br s, 1H), 7.58 (br s, 1H), 8.89 (br s, 1H); $^{13}$C NMR (100 MHz, CD$_3$OD): δ 29.8, 38.9, 39.2, 54.7, 55.8, 71.0, 78.4, 109.8, 115.8, 120.7, 125.0, 126.6, 129.5, 131.0, 132.8, 134.8, 137.8, 141.4, 161.0; HRMS (ES) [M−Cl]$^+$ Calcd. For C$_{23}$H$_{26}$ClN$_2$O$_3$S: 445.1353. Found: 445.1362. Anal. Calcd for C$_{23}$H$_{26}$Cl$_2$N$_2$O$_3$S: C, 57.38; H, 5.44; N, 5.82. Found: C, 57.68; H, 5.73; N, 6.06.

(2R,4S)-1-[2-[2-(4-Chlorophenyl)ethyl]-4-(4-chlorophenylsulfanylmethyl)-[1,3]dioxolan-2-ylmethyl]-1H-imidazole hydrochloride (QC-49). White solid in 80% yield from QC-16: mp 128-129° C.; R$_f$=0.20 (EtOAc); [α]$_D^{22}$=−5.2° (c=0.8, CD$_3$OD); $^1$H NMR (400 MHz, CD$_3$OD): δ 1.96 (t, J=8.4 Hz, 2H), 2.64-2.81 (m, 2H), 3.12 (dd, J=14.2, 5.4 Hz, 1H), 3.19 (dd, J=14.0, 5.2 Hz, 1H), 3.69-3.78 (m, 2H), 4.01-4.09 (m, 1H), 4.45 (s, 2H), 7.15 (d, J=8.4 Hz, 2H), 7.26 (d, J=8.4 Hz, 2H), 7.31 (d, J=8.8 Hz, 2H), 7.37 (d, J=8.4 Hz, 2H), 7.52 (br s, 1H), 7.59 (br s, 1H), 8.92 (br s, 1H); $^{13}$C NMR (100 MHz, CD$_3$OD): δ 29.8, 36.8, 39.1, 54.6, 70.8, 78.0, 109.9, 120.6, 125.1, 129.6, 130.2, 131.0, 132.2, 132.9, 133.5, 135.9, 137.8, 141.3; HRMS (ES) [M−Cl]$^+$ Calcd. for C$_{22}$H$_{23}$Cl$_2$N$_2$O$_2$S: 449.0857. Found: 449.0851. Anal. Calcd for C$_{22}$H$_{23}$Cl$_3$N$_2$O$_2$S: C, 54.39; H, 4.77; N, 5.77. Found: C, 54.53; H, 4.71; N, 5.64.

(2R,4S)-1-[2-[2-(4-Chlorophenyl)ethyl]-4-(4-fluorophenylsulfanylmethyl)-[1,3]dioxolan-2-ylmethyl]-1H-imidazole hydrochloride (QC-52). Hygroscopic beige solid in 70% yield from QC-16: mp 112-113° C.; R$_f$=0.25 (EtOAc); [α]$_D^{24}$=−9.4° (c=1.9, CD$_3$OD); $^1$H NMR (400 MHz, CD$_3$OD): δ 1.96 (t, J=8.4 Hz, 2H), 2.65-2.80 (m, 2H), 3.05 (dd, J=14.0, 5.6 Hz, 1H), 3.15 (dd, J=13.8, 5.0 Hz, 1H), 3.64-3.74 (m, 2H), 4.01-4.09 (m, 1H), 4.46 (s, 2H), 7.07 (t, J=8.8 Hz, 2H), 7.17 (d, J=8.4 Hz, 2H), 7.26 (d, J=8.4 Hz, 2H), 7.44 (~dd, J=8.8, 5.2 Hz, 2H), 7.53 (br s, 1H), 7.60 (br s, 1H), 8.93 (br s, 1H); $^{13}$C NMR (100 MHz, CD$_3$OD): δ 29.8, 38.0, 39.1, 54.6, 70.9, 78.1, 109.9, 117.1 (d, $^2J_{C-F}$=22.2 Hz), 120.6, 125.1, 129.5, 131.0, 132.0 (d, $^4J_{C-F}$=3.6 Hz), 132.8, 134.0 (d, $^3J_{C-F}$=8.0 Hz), 137.8, 141.3, 163.5 (d, $^1J_{C-F}$=44.5 Hz); $^{19}$F NMR (376 MHz, CD$_3$OD): δ −118.1 (t, $^1J_{F-C}$=6.6 Hz); HRMS (ES) [M−Cl]$^+$ Calcd. for C$_{22}$H$_{23}$ClFN$_2$O$_2$S: 433.1153. Found: 433.1154. Anal. Calcd for C$_{22}$H$_{23}$Cl$_2$FN$_2$O$_2$S: C, 56.29; H, 4.94; N, 5.97. Found: C, 56.12; H, 5.04; N, 6.02.

(2R,4S)-1-[2-[2-(4-Chlorophenyl)ethyl]-4-(4-nitrophenylsulfanylmethyl)-[1,3]dioxolan-2-ylmethyl]-1H-imidazole hydrochloride (QC-60). Hygroscopic yellow solid in 55% yield from QC-16: mp moistens at 70° C.; R$_f$=0.14 (EtOAc); [α]$_D^{23}$=+8.9° (c=0.7, CD$_3$OD); $^1$H NMR (400 MHz, CD$_3$OD): δ 1.97 (t, J=8.4 Hz, 2H), 2.64-2.81 (m, 2H), 3.30-3.41 (m, 2H), 3.80 (t, J=8.2 Hz, 1H), 3.84-3.92 (m, 1H), 4.12 (dd, J=8.0, 5.6 Hz, 1H), 4.45 (s, 2H), 7.12 (d, J=8.4 Hz, 2H), 7.24 (d, J=8.4 Hz, 2H), 7.52 (d, J=9.2 Hz, 2H), 7.54 (br s, 1H), 7.62 (br s, 1H), 8.14 (d, J=8.8 Hz, 2H), 8.94 (br s, 1H); $^{13}$C NMR (100 MHz, CD$_3$OD): δ 29.8, 34.6, 39.0, 54.5, 70.6, 77.5, 110.1, 120.7, 124.9, 125.1, 128.1, 129.5, 130.9, 132.9, 137.8, 141.2, 146.8, 147.9; HRMS (ES) [M−Cl]$^+$ Calcd. for C$_{22}$H$_{23}$ClN$_3$O$_4$S: 460.1098. Found: 460.1075. Anal. Calcd for C$_{22}$H$_{23}$Cl$_{1-2}$N$_3$O$_4$S: C, 53.23; H, 4.67; N, 8.46. Found: C, 53.09; H, 4.70; N, 8.23.

(2R,4S)-2-{2-[2-(4-Chlorophenyl)ethyl]-2-imidazol-1-ylmethyl-[1,3]dioxolan-4-ylmethylsulfanyl}-5-trifluoromethylpyridine hydrochloride (QC-80). White solid in 90% yield from QC-16: mp 156-157° C.; [α]$_D^{20}$=−24.2° (c=0.8, CD$_3$OD); $^1$H NMR (400 MHz, CD$_3$OD): δ 2.00 (t, J=8.4 Hz, 2H), 2.69-2.88 (m, 2H), 3.48 (dd, J=14.0, 6.0 Hz, 1H), 3.57 (dd, J=14.0, 5.2 Hz, 1H), 3.77 (t, J=8.4 Hz, 1H), 3.88-3.97 (m, 1H), 4.08 (dd, J=8.4, 6.0 Hz, 1H), 4.47 (~s, 2H), 7.19 (d, J=8.4 Hz, 2H), 7.27 (d, J=8.4 Hz, 2H), 7.45 (d, J=8.4 Hz, 1H), 7.54 (br s, 1H), 7.62 (br s, 1H), 7.85 (dd, J=8.6, 2.2 Hz, 1H), 8.68 (br s, 1H), 8.94 (br s, 1H); $^{13}$C NMR (100 MHz, CD$_3$OD): δ 29.8, 32.3, 39.1, 54.6, 70.6, 77.7, 109.9, 120.6, 123.2, 123.9 (d, $^2J_{C-F}$=33.2 Hz), 125.1, 125.3 (q, $^1J_{C-F}$=271.0 Hz), 129.6, 130.9, 132.9, 134.4 (d, $^3J_{C-F}$=3.5 Hz), 137.8, 141.3, 147.2 (d, $^3J_{C-F}$=3.9 Hz), 164.6; $^{19}$F NMR (376 MHz, CD$_3$OD): δ −64.6; HRMS (ES) [M−Cl]$^+$ Calcd. for C$_{22}$H$_{22}$ClF$_3$N$_3$O$_2$S: 484.1073. Found: 484.1056. Anal. Calcd for C$_{22}$H$_{22}$Cl$_2$F$_3$N$_3$O$_2$S: C, 50.78; H, 4.26; N, 8.07. Found: C, 50.59; H, 4.26; N, 7.97.

(2R,4S)-1-{2-[2-(4-Chlorophenyl)ethyl]-4-cyclohexylsulfanylmethyl-[1,3]dioxolan-2-ylmethyl}-1H-imidazole hydrochloride (QC-115). White solid in 81% yield from QC-16: mp 172-173° C.; R$_f$=0.36 (free base, EtOAc); [α]$_D^{23}$=−18.1° (c=0.4, CD$_3$OD); $^1$H NMR (400 MHz, CD$_3$OD): δ 1.20-1.40 (m, 5H), 1.58-1.68 (m, 1H), 1.71-1.82 (m, 2H), 1.90-2.00 (m, 2H), 2.00 (dd, J=9.2, 7.6 Hz, 2H), 2.62-2.73 (m, 2H), 2.73-2.86 (m, 3H), 3.68-3.76 (m, 2H), 4.04-4.12 (m, 1H), 4.47 (s, 2H), 7.21 (d, J=8.4 Hz, 2H), 7.28 (d, J=8.4 Hz, 2H), 7.59 (~t, J=1.6 Hz, 1H), 7.64 (~t, J=1.6 Hz, 1H), 8.96 (br s, 1H); $^{13}$C NMR (100 MHz, CD$_3$OD): δ 26.9, 27.0, 29.8, 33.0, 34.8, 34.9, 39.2, 45.3, one peak under solvent, 54.7, 71.1, 79.1, 109.8, 120.6, 125.1, 129.6, 131.0, 132.9, 137.8, 141.4; HRMS (ES) [M−Cl]$^+$ Calcd. for C$_{22}$H$_{30}$ClN$_2$O$_2$S: 421.1716. Found: 421.1698. Anal. Calcd for C$_{22}$H$_{30}$Cl$_2$N$_2$O$_2$S: C, 57.76; H, 6.61; N, 6.12; S, 7.01. Found: C, 58.11; H, 6.70; N, 6.13; S, 6.79.

(2R,4S)-1-[2-[2-(4-Chlorophenyl)ethyl]-4-(naphthalen-2-ylsulfanylmethyl)-[1,3]dioxolan-2-ylmethyl]-1H-imidazole hydrochloride (QC-121). White solid in 90% yield from QC-16: mp 156-157° C.; R$_f$=0.26 (free base, EtOAc); [α]$_D^{24}$=−7.4° (c=0.5, CD$_3$OD); $^1$H NMR (400 MHz, CD$_3$OD): δ 1.94 (t, J=8.4 Hz, 2H), 2.62-2.78 (m, 2H), 3.19-3.34 (m, 2H), 3.73-3.83 (m, 2H), 4.07 (dd, J=7.2, 4.8 Hz, 1H), 4.43 (s, 2H), 7.08 (d, J=8.4 Hz, 2H), 7.22 (d, J=8.4 Hz, 2H), 7.38 (~t, J=1.6 Hz, 1H), 7.43-7.53 (m, 3H), 7.56 (~t, J=1.6 Hz, 1H), 7.75-7.88 (m, 4H), 8.90 (br s, 1H); $^{13}$C NMR (100 MHz, CD$_3$OD): δ 29.8, 36.5, 39.2, 54.6, 70.9, 78.2, 109.9, 120.4, 125.0, 127.1, 127.9, 128.2, 128.6, 128.7, 128.8, 129.5, 129.7, 130.9, 132.8, 133.5, 134.4, 135.2, 137.7, 141.3; HRMS (EI) (M$^+$)$^+$ Calcd. for C$_{26}$H$_{25}$ClN$_2$O$_2$S: 464.1325. Found: 464.1347.

(2R,4S)-1-{4-(3-Bromophenylsulfanylmethyl)-2-[2-(4-chlorophenyl)ethyl]-[1,3]dioxolan-2-ylmethyl}-1H-imidazole hydrochloride (QC-164). White solid in 90% yield from QC-16: mp 128-129° C.; R$_f$=0.32 (free base, EtOAc); [α]$_D^{23}$=−6.7° (c=0.7, CD$_3$OD); $^1$H NMR (400 MHz, CD$_3$OD): δ 1.96 (t, J=8.6 Hz, 2H), 2.65-2.79 (m, 2H), 3.14-3.25 (m, 2H), 3.70-3.82 (m, 2H), 4.07 (dd, J=7.2, 4.8 Hz, 1H), 4.46 (s, 2H), 7.14 (d, J=8.0 Hz, 2H), 7.19-7.25 (m, 1H), 7.26 (d, J=8.4 Hz, 2H), 7.33-7.39 (m, 2H), 7.54 (br s, 1H), 7.56 (t, J=1.8 Hz, 1H), 7.60 (br s, 1H), 8.93 (br s, 1H); $^{13}$C NMR (100 MHz, CD$_3$OD): δ 29.8, 36.2, 39.1, 54.6, 70.7, 78.0, 110.0, 120.6, 123.8, 125.1, 129.0, 129.5, 130.4, 131.0, 131.7, 132.6, 132.9, 137.8, 139.9, 141.3; HRMS (ES) [M−Cl]$^+$ Calcd. for C$_{22}$H$_{23}$BrClN$_2$O$_2$S: 493.0352. Found: 493.0333. Anal. Calcd for C$_{22}$H$_{23}$BrCl$_2$N$_2$O$_2$S: C, 49.83; H, 4.37; N, 5.28. Found: C, 49.95; H, 4.58; N, 5.19.

(2R,4S)-1-{4-(2-Bromophenylsulfanylmethyl)-2-[2-(4-chlorophenyl)ethyl]-[1,3]dioxolan-2-ylmethyl}-1H-imidazole hydrochloride (QC-171). Hygroscopic white solid in 100% yield from QC-16: R$_f$=0.28 (free base, EtOAc); [α]$_D^{22}$=−14.4° (c=0.6, CD$_3$OD); $^1$H NMR (400 MHz, CD$_3$OD): δ 1.97 (t, J=8.6 Hz, 2H), 2.67-2.80 (m, 2H), 3.14-3.25 (m, 2H), 3.73-3.80 (m, 2H), 4.04-4.11 (m, 1H), 4.46 (s, 2H), 7.11 (~td, J=7.8, 1.6 Hz, 1H), 7.16 (d, J=8.4 Hz, 2H), 7.25 (d, J=8.4 Hz, 2H), 7.34 (~td, J=7.6, 1.2 Hz, 1H), 7.44 (dd, J=8.0, 1.6 Hz, 1H), 7.52 (br s, 1H), 7.57 (dd, J=8.0, 1.2 Hz, 1H), 7.60 (br s, 1H), 8.92 (br s, 1H); $^{13}$C NMR (100 MHz, CD$_3$OD): δ 29.8, 35.8, 39.2, 54.6, 70.8, 77.7, 110.0, 120.7, 124.9, 125.1, 128.5, 129.2, 129.5, 130.4, 131.0, 132.8, 134.2, 137.8, 138.3, 141.3; HRMS (ES) [M–Cl]⁺ Calcd. for C$_{22}$H$_{23}$BrClN$_2$O$_2$S: 493.0352. Found: 493.0343. Anal. Calcd for C$_{22}$H$_{23}$BrCl$_2$N$_2$O$_2$S: C, 49.83; 1, 4.37; N, 5.28. Found: C, 49.66; H, 4.47; N, 5.08.

I.IX Synthesis of QC-116, QC-39, QC-46, QC-81, QC-119, QC-120, QC-129, QC-132, QC-140, and QC-173

As shown in Scheme 5, the substituted aryloxo-terminated compounds QC-116, QC-39, QC-46, QC-81, QC-119, QC-120, QC-129, QC-132, QC-140, and QC-173 were obtained by a nucleophilic displacement of the tosyloxy group in QC-16 with various substituted aryl alcohols (substituted phenols). These displacement reactions required higher temperature conditions than those with thiol-based nucleophiles. Thus, cesium carbonate in DMF at 90° C. was used for phenol-based nucleophiles.

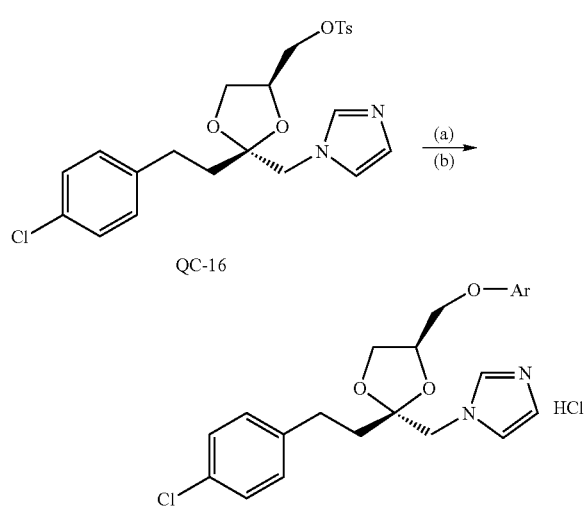

Scheme 5.

Reagents and conditions:
(a) ArOH, Cs$_2$CO$_3$, DMF, 90° C.;
(b) 37% aq HCl, 2-propanol, rt.

Representative Procedure for the Displacement of Tosyloxy Groups Using Phenol-Containing Nucleophiles:

(2R,4S)-1-{2-[2-(4-Chlorophenyl)ethyl]-4-phenoxymethyl-[1,3]dioxolan-2-ylmethyl}-1H-imidazole hydrochloride (QC-116). Under a N$_2$ atmosphere, a mixture of (2R,4S)-2-[2-(4-chlorophenyl)ethyl]-2-[(1H-imidazol-1-yl)methyl]-4-[(p-toluenesulfonyloxy)methyl]-1,3-dioxolane (QC-16) (100 mg, 0.21 mmol), phenol (79 mg, 0.84 mmol, 4 equiv), and cesium carbonate (205 mg, 0.63 mmol, 6 equiv) in N,N-dimethylformamide (3 mL) was heated at 90° C. with stirring for 8 h. The mixture was diluted with H$_2$O, extracted with EtOAc (3×), and the combined organic extracts were washed sequentially with a saturated aqueous solution of Na$_2$CO$_3$, and brine, and then dried (MgSO$_4$). The solution was concentrated, and the residue was purified by flash chromatography on silica gel (EtOAc) to give the free base (60 mg, 0.15 mmol) as an oil (R$_f$=0.38, EtOAc). To a solution of this oil in warm 2-propanol (2 mL) was added a solution of 37% aqueous HCl (34 mg, 0.35 mmol, 2.3 equiv) in 2-propanol (2 mL). The mixture was concentrated and dried under high vacuum. The residue was dissolved in 2-propanol (0.5 mL), the solution cooled in the freezer, and then a few drops of Et$_2$O were added and the product allowed to crystallize overnight. The solid was removed by filtration and washed with Et$_2$O. High-vacuum drying left 79 mg (0.18 mmol, 86%) of QC-116 as a white solid: mp 139-140° C.; [α]$_D^{23}$=–18.3° (c=0.5, CD$_3$OD); $^1$H NMR (400 MHz, CD$_3$OD): δ 2.04 (t, J=8.4 Hz, 2H), 2.70-2.88 (m, 2H), 3.96 (t, J=7.6 Hz, 1H), 4.00-4.08 (m, 2H), 4.09-4.17 (m, 2H), 4.52 (s, 2H), 6.88-6.91 (m, 2H), 6.94 (t, J=7.4 Hz, 1H), 7.15 (d, J=8.4 Hz, 2H), 7.20-7.31 (m, 4H), 7.59 (br s, 1H), 7.67 (br s, 1H), 9.00 (br s, 1H); $^{13}$C NMR (100 MHz, CD$_3$OD): δ 29.8, 39.0, 54.6, 68.2, 68.3, 77.5, 110.0, 115.6, 120.6, 122.3, 125.1, 129.5, 130.6, 131.0, 132.8, 137.8, 141.5, 160.0; HRMS (ES) [M–Cl]⁺ Calcd. for C$_{22}$H$_{24}$ClN$_2$O$_3$: 399.1475. Found: 399.1466. Anal. Calcd for C$_{22}$H$_{24}$Cl$_2$N$_2$O$_3$: C, 60.70; H, 5.56; N, 6.43. Found: C, 60.90; H, 5.51; N, 6.39.

Characterization of Compounds Synthesized Following the Representative Procedure for the Displacement of Tosyloxy Groups Using Phenol-Containing Nucleophiles (Shown Above for QC-116) as Outlined in Scheme 5:

(2R,4S)-4-{2-[2-(4-Chlorophenyl)ethyl]-2-imidazol-1-ylmethyl-[1,3]dioxolan-4-ylmethoxy}phenylamine dihydrochloride (QC-39). Hygroscopic white solid in 54% yield from QC-16: R$_f$=0.17 (free base, EtOAc); [α]$_D^{22}$=–12.9° (c=0.9, CD$_3$OD); $^1$H NMR (400 MHz, CD$_3$OD): δ 2.04 (t, J=8.4 Hz, 2H), 2.70-2.88 (m, 2H), 3.97 (t, J=6.8 Hz, 1H), 4.03-4.20 (m, 4H), 4.53 (s, 2H), 7.06 (d, J=8.8 Hz, 2H), 7.16 (d, J=8.0 Hz, 2H), 7.24 (d, J=8.4 Hz, 2H, 7.33 (d, J=8.8 Hz, 2H), 7.60 (br s, 1H), 7.67 (br s, 1H), 9.00 (br s, 1H); $^{13}$C NMR (100 MHz, CD$_3$OD): δ 29.8, 38.9, 54.5, 68.1, 68.9, 77.3, 110.1, 117.0, 120.6, 125.1, 125.2, 125.3, 129.5, 131.0, 132.8, 137.9, 141.5, 160.2; HRMS (ES) [M–Cl]⁺ Calcd. for C$_{22}$H$_{25}$ClN$_3$O$_3$: 414.1584. Found: 414.1565. Anal. Calcd for C$_{22}$H$_{26}$Cl$_3$N$_3$O$_3$: C, 54.28; H, 5.38; N, 8.63. Found: C, 54.48; H, 5.60; N, 8.59.

(2R,4S)-4-{2-[2-(4-Chlorophenyl)ethyl]-2-imidazol-1-ylmethyl-[1,3]dioxolan-4-ylmethoxy}phenol hydrochloride (QC-46). White solid in 33% yield from QC-16: mp 128-130° C.; R$_f$=0.17 (EtOAc); [α]$_D^{22}$=–14.4° (c=0.8, CD$_3$OD); $^1$H NMR (400 MHz, CD$_3$OD): δ 2.03 (t, J=8.6 Hz, 2H), 2.70-2.87 (m, 2H), 3.88-4.12 (m, 5H), 4.51 (s, 2H), 6.70 (d, J=8.8 Hz, 2H), 6.75 (d, J=9.2 Hz, 2H), 7.15 (d, J=8.4 Hz, 2H), 7.24 (d, J=8.4 Hz, 2H), 7.58 (~t, J=1.6 Hz, 1H), 7.65 (~t, J=1.6 Hz, 1H), 8.97 (br s, 1H); $^{13}$C NMR (100 MHz, CD$_3$OD): δ 29.8, 39.1, 54.7, 68.3, 69.4, 77.7, 110.0, 116.8, 116.9, 120.6, 125.2, 129.5, 131.0, 132.8, 137.8, 141.5, 152.9, 153.3; HRMS (ES) [M–Cl]⁺ Calcd. for C$_{22}$H$_{24}$ClN$_2$O$_4$: 415.1425. Found: 415.1407. Anal. Calcd for C$_{22}$H$_{24}$Cl$_2$N$_2$O$_4$: C, 58.54; H, 5.36; N, 6.21. Found: C, 58.50; H, 5.47; N, 6.13.

(2R,4S)-1-{4-(4-Adamantan-1-yl-phenoxymethyl)-2-[2-(4-chlorophenyl)ethyl]-[1,3]dioxolan-2-ylmethyl}-1H-imidazole hydrochloride (QC-81). White solid in 72% yield from QC-16: mp 132-134° C.; R$_f$=0.22 (free base, EtOAc); [α]$_D^{22}$=–11.8° (c=0.6, CD$_3$OD); $^1$H NMR (400 MHz, CD$_3$OD): δ 1.74-1.91 (m, 13H), 2.02 (t, J=8.6 Hz, 2H), 2.04-2.10 (m, 2H), 2.70-2.84 (m, 2H), 3.94-4.05 (m, 3H), 4.06-4.15 (m, 2H), 4.51 (s, 2H), 6.84 (d, J=9.2 Hz, 2H), 7.13 (d, J=8.4 Hz, 2H), 7.23 (d, J=8.4 Hz, 2H), 7.26 (d, J=8.8 Hz, 2H), 7.59 (br s, 1H), 7.66 (br s, 1H), 8.98 (br s, 1H); $^{13}$C NMR (100 MHz, CD$_3$OD): δ 29.8, 30.5, 36.7, 37.9, 39.0, 44.6, 54.6, 68.2, 68.5, 77.7, 110.0, 115.2, 120.6, 125.1, 126.9, 129.5, 131.0, 132.8, 137.8, 141.5, 145.6, 157.8; HRMS (ES) [M–Cl]⁺ Calcd. for C$_{32}$H$_{38}$ClN$_2$O$_3$: 533.2571. Found: 533.2581. Anal. Calcd for C$_{32}$H$_{38}$Cl$_2$N$_2$O$_3$: C, 67.48; H, 6.72; N, 4.92. Found: C, 66.85; H, 7.33; N, 4.37.

(2R,4S)-1-{4-(4-Bromophenoxymethyl)-2-[2-(4-chlorophenyl)ethyl]-[1,3]dioxolan-2-ylmethyl}-1H-imidazole hydrochloride (QC-119). Hygroscopic white solid in 76% yield from QC-16: mp 55-57° C. in air; R$_f$=0.22 (free base, EtOAc); [α]$_D^{25}$=–16.3° (c=0.6, CD$_3$OD); $^1$H NMR (400 MHz, CD$_3$OD): δ 2.02 (t, J=8.4 Hz, 2H), 2.69-2.84 (m, 2H), 3.88-4.06 (m, 3H), 4.11 (t, J=6.8 Hz, 2H), 4.51 (s, 2H), 6.85

(d, J=9.2 Hz, 2H), 7.14 (d, J=8.8 Hz, 2H), 7.24 (d, J=8.8 Hz, 2H), 7.39 (d, J=8.8 Hz, 2H), 7.59 (br s, 1H), 7.66 (br s, 1H), 8.98 (br s, 1H); $^{13}$C NMR (100 MHz, CD$_3$OD): δ 29.8, 38.9, 54.6, 68.1, 68.7, 77.4, 110.1, 114.3, 117.6, 120.7, 125.1, 129.6, 131.0, 132.9, 133.5, 137.9, 141.4, 159.2; HRMS (ES) [M−Cl]$^+$ Calcd. for C$_{22}$H$_{23}$BrClN$_2$O$_3$: 477.0581. Found: 477.0557. Anal. Calcd for C$_{22}$H$_{23}$BrCl$_2$N$_2$O$_3$: C, 51.38; H, 4.51; N, 5.45. Found: C, 51.44; H, 4.37; N, 5.25.

(2R,4S)-1-[2-[2-(4-Chlorophenyl)ethyl]-4-(4-fluorophenoxymethyl)-[1,3]dioxolan-2-ylmethyl]-1H-imidazole hydrochloride (QC-120). Hygroscopic white solid in 86% yield from QC-16: mp 50-52° C. in air; R$_f$=0.23 (free base, EtOAc); [α]$_D^{24}$=−20.8° (c=0.5, CD$_3$OD); $^1$H NMR (400 MHz, CD$_3$OD): δ 2.04 (t, J=8.4 Hz, 2H), 2.71-2.87 (m, 2H), 3.88-4.15 (m, 5H), 4.52 (s, 2H), 6.86-6.93 (m, 2H), 7.00 (~t, J=8.8 Hz, 2H), 7.16 (d, J=8.4 Hz, 2H), 7.25 (d, J=8.4 Hz, 2H), 7.59 (br s, 1H), 7.66 (br s, 1H), 8.98 (br s, 1H); $^{13}$C NMR (100 MHz, CD$_3$OD): δ 29.8, 39.0, 54.6, 68.2, 69.2, 77.5, 110.1, 116.8 (d, $^2J_{C-F}$=11.9 Hz), 116.9 (d, $^3J_{C-F}$=3.5 Hz), 120.6, 125.1, 129.5, 131.0, 132.8, 137.8, 141.5, 156.2 (d, $^4J_{C-F}$=1.8 Hz), 158.9 (d, $^1J_{C-F}$=237.5 Hz); $^{19}$F NMR (376 MHz, CD$_3$OD): δ −126.6; HRMS (ES) [M−Cl]$^+$ Calcd. for C$_{22}$H$_{23}$ClFN$_2$O$_3$: 417.1381. Found: 417.1366. Anal. Calcd for C$_{22}$H$_{23}$Cl$_2$FN$_2$O$_3$: C, 58.29; H, 5.11; N, 6.18. Found: C, 58.27; H, 5.16; N, 6.00.

(2R,4S)-1-{4-Biphenyl-4-yloxymethyl)-2-[2-(4-chlorophenyl)ethyl]-[1,3]dioxolan-2-ylmethyl}-1H-imidazole hydrochloride (QC-129). White solid in 43% yield from QC-16: mp 162-163° C.; R$_f$=0.12 (EtOAc); [α]$_D^{13}$=−23.5° (c=0.6, CD$_3$OD); $^1$H NMR (400 MHz, CD$_3$OD): δ 2.04 (t, J=8.4 Hz, 2H), 2.70-2.90 (m, 2H), 3.98 (t, J=7.4 Hz, 1H), 4.02-4.10 (m, 2H), 4.10-4.15 (m, 1H), 4.16-4.22 (m, 1H), 4.52 (s, 2H), 6.99 (d, J=8.8 Hz, 2H), 7.14 (d, J=8.4 Hz, 2H), 7.23 (d, J=8.4 Hz, 2H), 7.28 (t, J=7.4 Hz, 1H), 7.39 (t, J=7.8 Hz, 2H), 7.50-7.56 (m, 4H), 7.60 (br s, 1H), 7.67 (br s, 1H), 9.00 (br s, 1H); $^{13}$C NMR (100 MHz, CD$_3$OD): δ 29.8, 39.0, 54.6, 68.2, 68.5, 77.6, 110.1, 116.0, 120.6, 125.1, 127.6, 127.8, 129.1, 129.5, 129.8, 131.0, 132.8, 135.6, 137.8, 141.5, 141.9, 159.6; FMS (ES) [M−Cl]$^+$ Calcd. for C$_{28}$H$_2$ClN$_2$O$_3$: 475.1788. Found: 475.1779. Anal. Calcd for C$_{28}$H$_{28}$Cl$_2$N$_2$O$_3$: C, 65.76; H, 5.52; N, 5.48. Found: C, 65.58; H, 5.42; N, 5.37.

(2R,4S)-1-[2-[2-(4-Chlorophenyl)ethyl]-4-(4-methoxyphenoxymethyl)-[1,3]dioxolan-2-ylmethyl]-1H-imidazole hydrochloride (QC-132). White solid in 81% yield from QC-16: mp 128-129° C.; R$_f$=0.29 (free base, EtOAc); [α]$_D^{23}$=−16.8° (c=0.5, CD$_3$OD); $^1$H NMR (400 MHz, CD$_3$OD): δ 2.03 (t, J=8.4 Hz, 2H), 2.71-2.86 (m, 2H), 3.73 (s, 3H), 3.90-4.04 (m, 3H), 4.04-4.13 (m, 2H), 4.51 (s, 2H), 6.83 (br s, 4H), 7.15 (d, J=8.4 Hz, 2H), 7.24 (d, J=8.4 Hz, 2H), 7.59 (br s, 1H), 7.66 (br s, 1H), 8.98 (br s, 1H); $^{13}$C NMR (100 MHz, CD$_3$OD): δ 29.8, 39.0, 54.6, 56.1, 68.3, 69.2, 77.6, 110.0, 115.7, 116.6, 120.6, 125.1, 129.5, 131.0, 132.8, 137.8, 141.5, 154.1, 155.8; HRMS (ES) [M−Cl]$^+$ Calcd. for C$_{23}$H$_{26}$ClN$_2$O$_4$: 429.1581. Found: 429.1567. Anal. Calcd for C$_{23}$H$_{26}$Cl$_2$N$_2$O$_4$: C, 59.36; H, 5.63; N, 6.02. Found: C, 59.50; H, 5.56; N, 6.03.

(2R,4S)-1-[2-[2-(4-Chlorophenyl)ethyl]-4-(4-iodophenoxymethyl)-[1,3]dioxolan-2-ylmethyl]-1H-imidazole hydrochloride (QC-140). White solid in 67% yield from QC-16: mp 113-114° C.; R$_f$=0.29 (free base, EtOAc); [α]$_D^{24}$=−12.7° (c=0.7, CD$_3$OD); $^1$H NMR (400 MHz, CD$_3$OD): 2.01 (t, J=8.4 Hz, 2H), 2.69-2.84 (m, 2H), 3.90-3.97 (m, 1H), 3.98-4.07 (m, 2H), 4.08-4.16 (m, 2H), 4.51 (s, 2H), 6.73 (d, J=8.8 Hz, 2H), 7.13 (d, J=8.4 Hz, 2H), 7.24 (d, J=8.4 Hz, 2H), 7.56 (d, J=8.8 Hz, 2H), 7.58 (br s, 1H), 7.65 (br s, 1H), 8.97 (br s, 1H); $^{13}$C NMR (100 MHz, CD$_3$OD): δ 29.8, 38.9, 54.6, 68.1, 68.5, 77.4, 110.1, 118.1, 120.7, 125.1, 129.5, 131.0, 132.8, 137.9, 139.5 (2C), 141.4, 160.0; MS (ES) [M−Cl]$^+$ Calcd. for C$_{22}$H$_{23}$Cl$_1$N$_2$O$_3$: 525.0442. Found: 525.0440. Anal. Calcd for C$_{22}$H$_{23}$Cl$_2$IN$_2$O$_3$: C, 47.08; H, 4.13; N, 4.99. Found: C, 47.21; H, 4.33; N, 4.95.

(2R,4S)-1-[2-[2-(4-Chlorophenylethyl]-4-(4-cyanophenoxymethyl)-[1,3]dioxolan-2-ylmethyl]-1H-imidazole hydrochloride (QC-173). Hygroscopic white solid in 100% yield from QC-16: R$_f$=0.26 (free base, EtOAc); [α]$_D^{21}$=−15.3° (c=0.5, CD$_3$OD); $^1$H NMR (400 MHz, CD$_3$OD): δ 2.03 (dd, J=9.2, 7.6 Hz, 2H), 2.70-2.85 (m, 2H), 3.96 (t, J=7.8 Hz, 1H), 4.04-4.17 (m, 3H), 4.23 (dd, J=10.2, 3.0 Hz, 1H), 4.52 (s, 2H), 7.06 (d, J=8.8 Hz, 2H), 7.15 (d, J=8.4 Hz, 2H), 7.24 (d, J=8.4 Hz, 2H), 7.60 (br s, 1H), 7.63-7.68 (m, 3H), 8.99 (br s, 1H); $^{13}$C NMR (100 MHz, CD$_3$OD): δ 29.7, 38.8, 54.5, 68.0, 68.7, 77.2, 105.4, 110.2, 116.6, 119.9, 120.7, 125.1, 129.6, 131.0, 132.9, 135.3, 137.9, 141.4, 163.4; HRMS (ES) [M−Cl]$^+$ Calcd. for C$_{23}$H$_{23}$ClN$_3$O$_3$: 424.1428. Found: 424.1409. Anal. Calcd for C$_{23}$H$_{23}$Cl$_2$N$_3$O$_3$: C, 60.01; H, 5.04; N, 9.13. Found: C, 59.84; H, 5.09; N, 8.96.

I.X Synthesis of QC-38, QC-40, QC-47, QC-112, QC-190, QC-197 and QC-200

As shown in Scheme 6, many QC compounds were obtained by nucleophilic displacement reactions of tosylate QC-16 with various nucleophiles such as: hydroxide to obtain QC-38, thiomethoxide to obtain QC-40, fluoride to obtain QC-47, azide to obtain QC-112 (which was then reduced to the amine QC-190), thiocyanide to obtain QC-197, and methoxide to obtain QC-200.

Scheme 6.

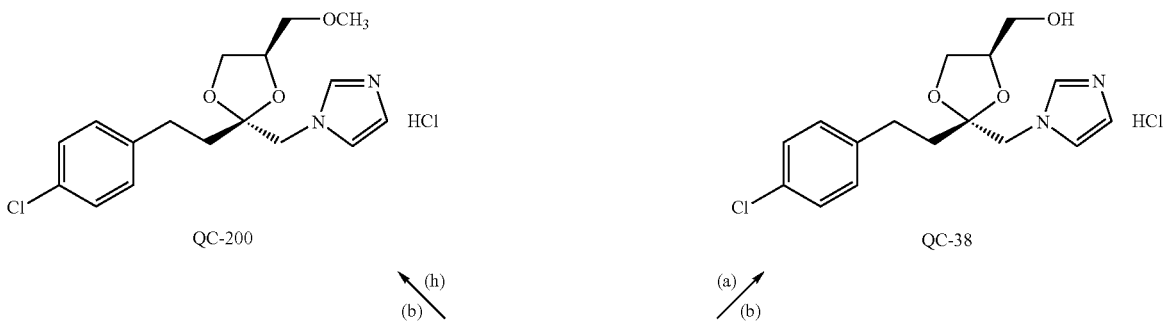

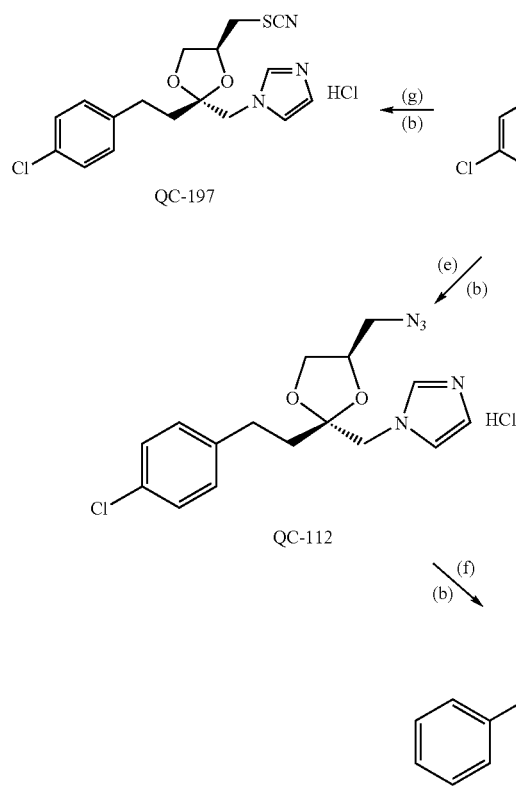
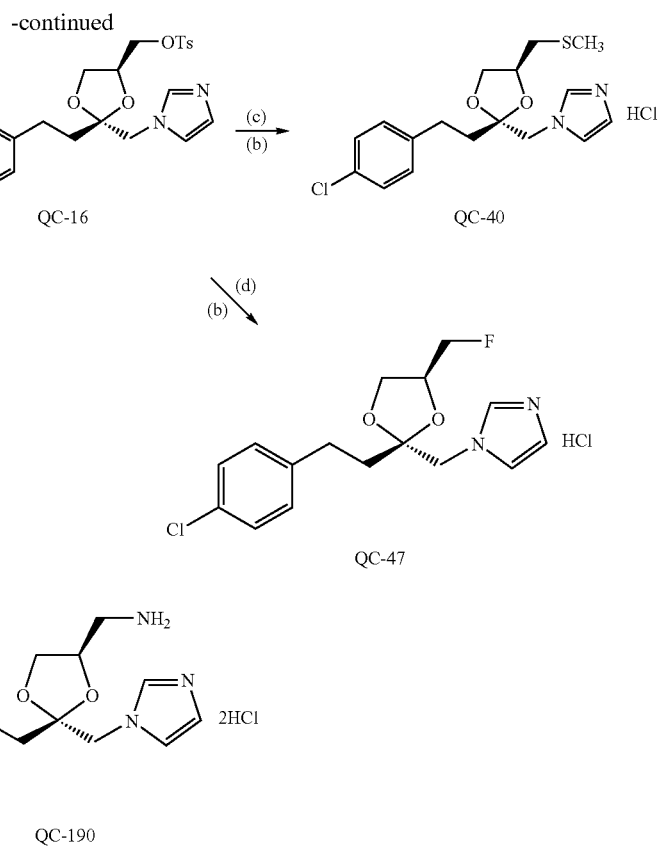

Reagents and conditions:
(a) KOH, LiOH, DMF, 120° C., 9 h;
(b) 37% aq HCl, 2-propanol, rt;
(c) NaSCH$_3$, Cs$_2$CO$_3$, acetone, reflux, 6 h;
(d) Bu$_4$NF, THF, reflux, 18.5 h;
(e) NaN$_3$, DMF, 110° C., 2 h;
(f) Nh$_4$OCOH, 10% Pd/C, CH$_3$OH, reflux, 3 h;
(g) KSCN, DMF, 100° C., 26 h;
(h) NaOCH$_3$—CH$_3$OH, DMF, 120° C., 7 h.

Representative Procedures for the Displacement Reactions of the Tosyloxy Group in QC-16 Using Various Nucleophilic Reagents:

(2R,4R)-2-[2-(4-Chlorophenyl)ethyl]-2-[(1H-imidazol-1-yl)methyl]-4-(hydroxymethyl)-1,3-dioxolane hydrochloride (QC-38). To a mixture of QC-16 (91 mg, 0.19 mmol) in N,N-dimethylformamide (6 mL) was added potassium hydroxide (210 mg, 3.74 mmol, 20 equiv) and a small amount of LiOH. The mixture was heated at 120° C. with stirring for 9 h. The reaction mixture was cooled to room temperature, diluted with H$_2$O, extracted with EtOAc (2×), and the combined organic extracts were washed sequentially with a saturated aqueous solution of Na$_2$CO$_3$, and water, and then dried (MgSO$_4$). The solution was concentrated, and the residue was purified by preparative scale thin-layer chromatography on silica gel (load with MeOH, elute with EtOAc) to give the free base (40 mg, 0.12 mmol) as an oil (R$_f$~0.2-0.3, EtOAc). To a solution of the free base in warm 2-propanol (2 mL) was added a solution of 37% aqueous HCl (20 mg, 0.20 mmol, 1.7 equiv) in 2-propanol (2 mL). The mixture was concentrated, dried under high vacuum, and washed with Et$_2$O. High-vacuum drying left 30 mg (0.08 mmol, 42%) of QC-38 as a white solid: mp 159-160° C.; R$_f$=0.07 (EtOAc); $[\alpha]_D^{22}$=−6.3° (c=0.6, CD$_3$OD); $^1$H NMR (400 MHz, CD$_3$OD): δ 1.98 (t, J=8.6 Hz, 2H), 2.70-2.88 (m, 2H), 3.53-3.67 (m, 2H), 3.68-3.79 (m, 2H), 4.01 (t, J=6.6 Hz, 1H), 4.47 (s, 2H), 7.20 (d, J=8.0 Hz, 2H), 7.27 (d, J=8.4 Hz, 2H), 7.57 (br s, 1H), 7.63 (br s, 1H), 8.94 (br s, 1H); $^{13}$C NMR (100 MHz, CD$_3$OD): δ 29.7, 39.2, 54.7, 62.8, 68.4, 79.6, 109.7, 120.7, 125.1, 129.5, 131.0, 132.8, 137.9, 141.5; HRMS (ES) [M−Cl]$^+$ Calcd. for C$_{16}$H$_{20}$ClN$_2$O$_3$: 323.1162. Found: 323.1170.

(2R,4S)-2-[2-(4-Chlorophenyl)ethyl]-2-[(1H-imidazol-1-yl)methyl]-4-[(methylthio)methyl]-1,3-dioxolane hydrochloride (QC-40). A mixture of QC-16 (135 mg, 0.28 mmol), sodium thiomethoxide (51 mg, 0.73 mmol, 2.6 equiv), and cesium carbonate (91 mg, 0.28 mmol, 2 equiv) in acetone (6 mL) was heated at reflux temperature with stirring for 6 h. The reaction mixture was concentrated, and hot EtOAc was added. The solids were filtered off and washed with hot EtOAc and then with acetone. The organic filtrate was concentrated, and the residue was purified by flash chromatography on silica gel (EtOAc) to give the free base (~110 mg) as a golden oil (R$_f$=0.28, EtOAc). To a solution of the free base in warm 2-propanol (2 mL) was added a solution of 37% aqueous HCl (35 mg, 0.36 mmol, 1.3 equiv) in 2-propanol (2 mL). The mixture was concentrated and dried under high vacuum. The residue was dissolved in 2-propanol (1 mL), the solution cooled in the freezer, and then a few drops of Et$_2$O were added and the product allowed to crystallize overnight. The solid was removed by filtration and washed with Et$_2$O. High-vacuum drying left 98 mg (0.25 mmol, 89%) of QC-40 as a white solid: mp 142-143° C.; R$_f$=0.20 (EtOAc); $[\alpha]_D^{22}$=−

11.9 (C=1.0, CD$_3$OD); $^1$H NMR (400 MHz, CD$_3$OD): δ 2.00 (dd, J=9.4, 7.8 Hz, 2H), 2.65 (dd, J=13.6, 6.0 Hz, 1H), 2.70-2.85 (m, 31, 3.71 (t, J=8.0 Hz, 1H), 3.75-3.82 (m, 1H), 4.09 (dd, J=8.0, 5.6 Hz, 1H), 4.48 (s, 2H), 4.86 (s, 31), 7.21 (d, J=8.8 Hz, 2H), 7.27 (d, J=8.4 Hz, 2H), 7.59 (br s, 1H), 7.64 (br s, 1H), 8.96 (br s, 1H); $^{13}$C NMR (100 MHz, CD$_3$OD): δ 16.4, 29.9, 37.0, 39.2, 54.7, 71.1, 78.8, 109.8, 120.6, 125.1, 129.6, 131.0, 132.9, 137.8, 141.4; HRMS (ES) [M−Cl]$^+$ Calcd. for C$_{17}$H$_{22}$ClN$_2$O$_2$S: 353.1090. Found: 353.1086. Anal. Calcd for C$_{17}$H$_{22}$Cl$_2$N$_2$O$_2$S: C, 52.44; H, 5.70; N, 7.20. Found: C, 52.51; H, 5.51; N, 7.12.

(2R,4S)-2-[2-(4-Chlorophenyl)ethyl]-2-[(1H-imidazol-1-yl)methyl]-4-(fluoromethyl)-1,3-dioxolane hydrochloride (QC-47). To a sample of QC-16 (120 mg, 0.25 mmol) was added a 1M solution of tetrabutylammonium fluoride in THF (5 mL, 5.0 mmol, 20 equiv) and the mixture was heated at reflux temperature with stirring for 18.5 h. The reaction mixture was cooled to room temperature, diluted with H$_2$O, extracted with EtOAc (3×), and the combined organic extracts were washed sequentially with a saturated aqueous solution of Na$_2$CO$_3$, and water, and then dried (MgSO$_4$). The solution was concentrated and the residue purified by flash column chromatography on silica gel (EtOAc) to give the free base (70 mg, 0.22 mmol) as a golden oil (R$_f$=0.21, EtOAc). To a solution of the free base in warm 2-propanol (2 mL) was added a solution of 37% aqueous HCl (25 mg, 0.25 mmol, 1.1 equiv) in 2-propanol (2 mL). The mixture was concentrated and dried under high vacuum. The residue was dissolved in 2-propanol (1 mL), the solution cooled in the freezer, and then a few drops of Et$_2$O were added and the product allowed to crystallize overnight. The solid was removed by filtration and washed with Et$_2$O. High-vacuum drying left 72 mg (0.20 mmol, 80%) of QC-47 as a white solid: mp 128-129° C.; [α]$_D^{22}$=−6.0° (c=1.0, CD$_3$OD); $^1$H NMR (400 MHz, CD$_3$OD): δ 1.99 (t, J=8.6 Hz, 2H), 2.69-2.84 (m, 2H), 3.86 (t, J=7.8 Hz, 1H), 3.90-4.00 (m, 1H), 4.06 (t, J=6.6 Hz, 1H), 4.35 (~dd, J=10.8, 4.0 Hz, 0.5H), 4.44-4.49 (m, 1H), 4.51 (s, 2H), 4.61 (~dd, J=10.6, 2.6 Hz, 0.5H), 7.20 (d, J=8.4 Hz, 2H), 7.27 (d, J=8.4 Hz, 2H), 7.59 (br s, 1H), 7.64 (br s, 1H), 8.98 (br s, 1H); $^{13}$C NMR (100 Hz, CD$_3$OD): δ 29.7, 38.9, 54.4, 66.7 (d, $^3J_{C-F}$=7.6 Hz), 77.7 (d, $^2J_{C-F}$=19.5 Hz), 82.8 (d, $^1J_{C-F}$=172.7 Hz), 110.1, 120.6, 125.1, 129.6, 131.0, 132.8, 137.8, 141.4; $^{19}$F-$^1$H$^{dec}$ NMR (376 MHz, CD$_3$OD): δ −234.1; HRMS (ES) [M−Cl]$^+$ Calcd. for C$_{16}$H$_{19}$ClFN$_2$O$_2$: 325.1119. Found: 325.1124. Anal. Calcd for C$_{16}$H$_{19}$Cl$_2$FN$_2$O$_2$: C, 53.20; H, 5.30; N, 7.75. Found: C, 53.21; H, 5.23; N, 7.59.

1-{4-Azidomethyl-2-[2-(4-chlorophenyl)ethyl]-[1,3]dioxolan-2-ylmethyl}-1H-imidazole (QC-112). To a mixture of QC-16 (201 mg, 0.42 mmol) in N,N-dimethylformamide (3 mL) was added sodium azide (546 mg, 8.40 mmol, 20 equiv). The mixture was heated at 110° C. with stirring for 2 h. The reaction mixture was cooled to room temperature, diluted with H$_2$O, extracted with EtOAc (3×), and the combined organic extracts were washed sequentially with a saturated aqueous solution of Na$_2$CO$_3$, and 1120, and then dried (Na$_2$SO$_4$). The solution was concentrated and the golden oily residue purified by flash column chromatography on silica gel (EtOAc) to give the free base as an oil (R$_f$=0.29, EtOAc). High-vacuum drying left 121 mg (0.35 mmol, 83%) of QC-112 as a colorless oil: [α]$_D^{24}$=+6.6° (c=0.7, CDCl$_3$); $^1$H NMR (400 MHz, CDCl$_3$): δ 1.90-2.05 (m, 2H), 2.66-2.81 (m, 2), 3.20 (dd, J=13.2, 5.2 Hz, 1H), 3.39 (dd, J=13.2, 4.0 Hz, 1H), 3.44-3.51 (m, 1H), 3.64 (t, J=8.0 Hz, 1H), 3.78 (dd, J=8.0, 6.4 Hz, 1H), 4.02 (s, 2H), 6.98 (br s, 1H), 7.05 (br s, 1H), 7.12 (d, J=8.4 Hz, 2H), 7.25 (d, J=8.4 Hz, 2H), 7.49 (br s, 1H); $^{13}$C NMR (100 MHz, CDCl$_3$): δ 29.0, 38.7, 51.8, 53.0, 67.9, 76.1, 109.9, 120.9, 128.8, 129.3, 129.8, 132.1, 138.7, 139.6; HRMS (EI) [M+H]$^+$ Calcd. for C$_{16}$H$_{19}$ClN$_5$O$_2$: 348.1227. Found: 348.1234.

(2-[2-(Phenyl)ethyl]-2-imidazol-1-ylmethyl-[1,3]dioxolan-4-yl)-methylamine dihydrochloride (QC-190). To a sample of 10% Pd/C catalyst (25 mg) under an atmosphere of N$_2$, was carefully added MeOH (5 mL). To this suspension was then added the azide QC-112 (87 mg, 0.25 mmol) along with ammonium formate (100 mg, 1.59 mmol, 6.4 equiv). The mixture was heated to reflux temperature for 3 h, and then filtered through Celite. The filter cake was washed with MeOH, and the filtrate and washings were combined and concentrated. The residue was diluted with a saturated aqueous solution of Na$_2$CO$_3$, extracted with EtOAc (2×), and the combined organic extracts were washed sequentially with a saturated aqueous solution of Na$_2$CO$_3$, and brine, and then dried (MgSO$_4$). The solution was concentrated and dried under high vacuum. To a solution of the free base (~30 mg, 0.10 mmol) in warm EtOH (2 mL) was added a solution of 37% aqueous HCl (40 mg, 0.41 mmol, 4.6 equiv) in EtOH (2 mL); the mixture was concentrated. High-vacuum drying left 40 mg (0.10 mmol, 40%) of QC-190 as a white hygroscopic solid: [α]$_D^{19}$=+3.7° (c=1.7, CD$_3$OD); $^1$H NMR (400 MHz, CD$_3$OD): δ 2.00-2.10 (m, 2H), 2.76-2.86 (m, 2H), 3.14 (dd, J=13.4, 9.8 Hz, 1H), 3.26 (dd, J=13.2, 2.0 Hz, 1H), 3.78 (t, J=8.0 Hz, 1H), 4.14-1.24 (m, 1H), 4.25 (dd, J=8.4, 6.4 Hz, 1H), 4.56 (s, 2H), 7.15-7.34 (m, 5H), 7.61 (s, 1H), 7.69 (s, 1H), 9.06 (s, 1H); $^{13}$C NMR (100 MHz, CD$_3$OD): δ 30.3, 38.8, 48.0, 54.3, 69.5, 74.7, 111.3, 120.8, 125.0, 127.2, 129.4, 129.6, 137.8, 142.3; HRMS (ES) [M−Cl]$^+$ Calcd. for C$_{16}$H$_{22}$N$_3$O$_2$: 288.1712. Found: 288.1705.

1-{2-[2-(4-Chlorophenyl)ethyl]-4-thiocyanatomethyl-[1,3]dioxolan-2-ylmethyl}-1H-imidazole hydrochloride (QC-197). To a mixture of QC-16 (100 mg, 0.21 mmol) in N,N-dimethylformamide (4 mL) was added potassium thiocyanate (789 mg, 8.12 mmol, 39 equiv). The mixture was heated at 100° C. with stirring for 26 h. The reaction mixture was cooled to room temperature, diluted with saturated aqueous Na$_2$CO$_3$ solution, extracted with EtOAc (2×), and the combined organic extracts were washed sequentially with a saturated aqueous solution of Na$_2$CO$_3$, and brine, and then dried (MgSO$_4$). The solution was concentrated, and the residue was purified by preparative scale thin-layer chromatography on silica gel (EtOAc) to give the free base (63 mg, 0.17 mmol, 81%) as a beige solid (R$_f$~0.2, EtOAc). To a solution of the free base in warm EtOH (2 mL) was added a solution of 37% aqueous HCl (30 mg, 0.30 mmol, 1.8 equiv) in EtOH (2 mL). The mixture was concentrated, dried under high vacuum, and washed with Et$_2$O. High-vacuum drying left 70 mg (0.17 mmol, 81%) of QC-197 as a white hygroscopic solid: mp ~45-50° C.; [α]$_D^{20}$=+22.0° (c=0.5, CD$_3$OD); $^1$H NMR (400 Liz, CD$_3$OD): δ 1.95-2.12 (m, 2H), 2.76-2.90 (m, 2H), 3.18 (dd, J=13.8, 7.0 Hz, 1H), 3.26-3.34 (m, 1H), 3.79 (t, J=8.2 Hz, 1H), 3.78-3.83 (m, 1H), 4.16 (dd, J=8.2, 6.2 Hz, 1H), 4.48-4.60 (m, 2H), 7.23 (d, J=8.0 Hz, 2H), 7.27 (d, J=8.4 Hz, 2H), 7.60 (s, 1H), 7.67 (s, 1H), 9.00 (s, 1H); $^{13}$C NMR (100 MHz, CD$_3$OD): δ 29.8, 36.3, 39.1, 54.4, 70.1, 77.7, 110.4, 113.5, 120.7, 125.1, 129.6, 131.0, 132.9, 137.8, 141.2; HRMS (ES) [M−Cl]$^+$ Calcd. for C$_{17}$H$_{19}$ClN$_3$O$_2$S: 364.0886. Found: 364.0889.

1-{2-[2-(4-Chlorophenyl)ethyl]-4-methoxymethyl-[1,3]dioxolan-2-ylmethyl}-1H-imidazole hydrochloride (QC-200). A solution of sodium methoxide in methanol was prepared by carefully adding sodium (195 mg, 8.48 mmol) to dry methanol (3 mL) under a nitrogen atmosphere, and allowing this solution to cool back to room temperature. This solution was then added to a mixture of QC-16 (133 mg, 0.28 mmol)

in N,N-dimethylformamide (2 mL). The mixture was heated at 120° C. with stirring for 7 h. The solution was then concentrated to remove methanol, diluted with a saturated aqueous solution of Na$_2$CO$_3$, and extracted with EtOAc (3×). The combined organic extracts were washed sequentially with a saturated aqueous solution of Na$_2$CO$_3$, and brine, and then dried (Mg$_2$SO$_4$). The solution was concentrated and the golden oily residue purified by flash column chromatography on silica gel (EtOAc) to give the free base as an oil (R$_f$=0.13, EtOAc). To a solution of the free base (61 mg, 0.18 mmol, 64%) in warm 2-propanol (2 mL) was added a solution of 37% aqueous HCl (31 mg, 0.31 mmol, 1.7 equiv) in 2-propanol (2 mL); the mixture was concentrated. High-vacuum drying left 63 mg (0.17 mmol, 61%) of QC-200 as a white hygroscopic solid: mp 92-93° C.; [α]$_D^{24}$=−11.6° (c=0.8, CD$_3$OD); $^1$H NMR (400 MHz, CD$_3$OD): δ 1.98 (t, J=8.4 Hz, 2H), 2.69-2.84 (m, 2H), 3.36 (s, 3H), 3.42-3.50 (m, 2H), 3.75 (dd, J=16.0, 8.4 Hz, 1H), 3.76-3.84 (m, 1H), 4.02 (dd, J=7.4, 5.8 Hz, 1H), 4.48 (s, 2H), 7.20 (d, J=8.4 Hz, 2H), 7.27 (d, J=8.4 Hz, 2H), 7.58 (br s, 1H), 7.63 (br s, 1H), 8.96 (br s, 1H); $^{13}$C NMR (100 MHz, CD$_3$OD): δ 29.8, 39.0, 54.7, 59.6, 68.5, 73.5, 77.9, 109.9, 120.5, 125.1, 129.6, 131.0, 132.8, 137.8, 141.5; HRMS (EI) [M+H]$^+$ Calcd. for C$_{17}$H$_{22}$ClN$_2$O$_3$: 337.1319. Found: 337.1306.

I.XI Synthesis of QC-37, QC-51, QC-108, QC-172, QC-202, and QC-207

4-(4-Chlorophenyl)-2-(4-fluorobenzyloxy)-1-(1H-imidazol-1-yl)butane hydrochloride (QC-37). To a solution of 4-(4-chlorophenyl)-1-(1H-imidazol-1-yl)butan-2-ol (70 mg, 0.28 mmol) in THF (2 mL) was added a suspension of NaH (12 mg, 0.50 mmol) in THF (1 mL). The mixture was stirred at rt for 1 h and then a solution of 4-fluorobenzyl chloride (44 mg, 0.30 mmol) in THF (1 mL) was added. The mixture was stirred at rt for 24 h, heated at reflux temperature for 1.5 h, and then concentrated. After dilution with H$_2$O, the mixture was extracted with EtOAc (3×) and the combined organic extracts were washed with H$_2$O, dried (MgSO$_4$), and concentrated. The resulting residue was purified by flash column chromatography on silica gel (EtOAc) to give the free base (50 mg, 0.14 mmol) as an oil (R$_f$=0.2, EtOAc). To a solution of this oil in hot 2-propanol (1 mL) was added a solution of 37% aqueous HCl (16 mg, 0.16 mmol) in 2-propanol (1 mL). The mixture was concentrated and dried under high vacuum. The residue was recrystallized from 2-propanol-Et$_2$O to give QC-37 (40 mg, 0.10 mmol, 36%) as a white solid: R$_f$=0.18 (EtOAc); mp 125-127° C.; $^1$H NMR (400 MHz, CD$_3$OD): δ 1.80-1.94 (m, 2H), 2.74 (t, J=7.8 Hz, 2H), 3.76-3.82 (m, 1H), 4.29 (dd, J=14.4, 7.6 Hz, 1H), 4.38 (d, J=11.6 Hz, 1H), 4.48-4.53 (m, 1H), 4.54 (d, J=11.6 Hz, 1H), 7.00-7.06 (m, 2H), 7.17-7.23 (m, 4H), 7.28 (d, J=8.4 Hz, 2H), 7.51 (s, 1H), 7.56 (s, 1H), 8.85 (s, 1H); $^{13}$C NMR (100 MHz, CD$_3$OD): δ 31.3, 34.2, 53.2, 71.8, 77.4, 116.2 (d, J$_{CF}$=21.6 Hz), 120.9, 124.1, 129.6, 131.0, 131.2 (d, J$_{CF}$=8.2 Hz), 132.9, 135.1 (d, J$_{CF}$=3.0 Hz), 137.1, 141.5, 163.9 (d, J$_{CF}$=245.2 Hz); HRMS (ESI) [M−Cl]$^+$ Calcd. for C$_{20}$H$_{21}$ClFN$_2$O: 359.1326. Found: 359.1330; Anal. Calcd. for C$_{20}$H$_{21}$Cl$_2$FN$_2$O: N, 7.09. Found: N, 6.93.

(2R,4R)-2-[2-(4-Chlorophenyl)ethyl]-2-[(1H-imidazol-1-yl)methyl]-4-[(1H-imidazol-1-yl)methyl]-1,3-dioxolane dihydrochloride dihydrate (QC-51). To a mixture of (2R,4S)-2-[2-(4-chlorophenyl)ethyl]-2-[(1H-imidazol-1-yl)methyl]-4-[(p-toluenesulfonyloxy)methyl]-1,3-dioxolane (105 mg, 0.22 mmol) in N,N-dimethylformamide (2.5 mL) was added imidazole (120 mg, 1.76 mmol, 8 equiv). The reaction mixture heated at 110° C. with stirring for 30 h. The reaction mixture was cooled to room temperature, diluted with H$_2$O, and extracted with CHCl$_3$ (3×), and the combined organic extracts were washed with water, and then dried (Na$_2$SO$_4$). The solution was concentrated, and the residue was purified by flash column chromatography on silica gel (load with hot EtOAc, elute with acetone) to give the free base (80 mg, 0.21 mmol) as an oil (R$_f$=0.16, EtOAc). To a solution of the free base in warm 2-propanol (1 mL) was added a solution of 37% aqueous HCl (56 mg, 0.57 mmol, 2.7 equiv) in 2-propanol (1 mL). The mixture was concentrated, CH$_2$Cl$_2$ (5 mL) added, and the mixture concentrated again. High-vacuum drying gave QC-51 (90 mg, 0.19 mmol, 86%) as a hygroscopic white solid in the dihydrochloride dihydrate form: mp ~60-145° C.; [α]$_D^{22}$=+6.8° (c=0.9, CD$_3$OD); $^1$H NMR (400 MHz, CD$_3$OD): δ 1.90-2.06 (m, 2H), 2.63-2.82 (m, 2H), 3.79 (t, J=8.6 Hz, 1H), 4.07-4.15 (m, 1H), 4.25 (dd, J=8.6, 6.6 Hz, 1H), 4.39 (dd, J=14.4, 7.2 Hz, 1H), 4.54 (s, 2H), 4.60 (dd, J=14.4, 2.8 Hz, 1H), 7.22 (d, J=8.4 Hz, 2H), 7.28 (d, J=8.4 Hz, 2H), 7.56-7.72 (m, 4H), 8.98 (s, 1H), 9.02 (s, 1H); $^{13}$C NMR (100 MHz, CD$_3$OD): δ 29.6, 38.6, 51.6, 54.2, 68.5, 76.9, 110.8, 120.8, 121.2, 124.2, 125.0, 129.6, 131.0, 133.0, 137.3, 137.8, 141.1; HRMS (ESI) [M−Cl—HCl-2H$_2$O]$^+$ Calcd. for C$_{19}$H$_{22}$ClN$_4$O$_2$: 373.1431. Found: 373.1429. Anal. Calcd for C$_{19}$H$_{27}$Cl$_3$N$_4$O$_4$: C, 47.36; H, 5.65; N, 11.63. Found: C, 47.83; H, 5.51; N, 11.41.

(2R,4S)-1-{4-Chloromethyl-2-[2-(4-chlorophenyl)ethyl]-[1,3]dioxolan-2-ylmethyl}-1H-imidazole hydrochloride hydrate (QC-108). To a mixture of (2R,4S)-2-[2-(4-chlorophenyl)ethyl]-2-[(1H-imidazol-1-yl)methyl]-4-[(p-toluenesulfonyloxy)methyl]-1,3-dioxolane (108 mg, 0.23 mmol) in N,N-dimethylformamide (3 mL) was added lithium chloride (192 mg, 4.53 mmol, 19.7 equiv). The mixture was heated at 110° C. with stirring for 1 h. The reaction mixture was cooled to room temperature, diluted with H$_2$O, and extracted with EtOAc (3×), and the combined organic extracts were washed sequentially with a saturated aqueous solution of Na$_2$CO$_3$, and H$_2$O, and then dried (Na$_2$SO$_4$). The solution was concentrated and dried under high-vacuum to give the clean free base (90 mg) as an oil (R$_f$=0.24, EtOAc). To a solution of the free base in warm 2-propanol (2 mL) was added a solution of 37% aqueous HCl (40 mg, 0.41 mmol, 2.7 equiv) in 2-propanol (2 mL). The mixture was concentrated and dried under high-vacuum. The residue was dissolved in the minimal amount of hot 2-propanol, the solution cooled at room temperature, and then at −25° C. in a freezer prior to the gradual addition of diethyl ether to complete the precipitation of the hydrochloride. The product was collected by filtration and washed with diethyl ether. High-vacuum drying gave QC-108 (74 mg, 0.19 mmol, 83%) as a white solid in the hydrochloride hydrate form: mp 118-119° C.; [α]$_D^{24}$=−16.2° (c=0.4, CD$_3$OD); $^1$H NMR (400 MHz, CD$_3$OD): δ 1.96-2.05 (m, 2H), 2.72-2.86 (m, 2H), 3.63-3.73 (m, 2H), 3.86 (t, J=8.0 Hz, 1H), 3.91-3.98 (m, 1H), 4.09 (dd, J=8.4, 6.0 Hz, 1H), 4.44 14.55 (m, 2H), 7.21 (d, J=8.8 Hz, 2H), 7.27 (d, J=8.4 Hz, 2H), 7.59 (s, 1H), 7.65 (s, 1H), 8.97 (s, 1H); $^{13}$C NMR (100 MHz, CD$_3$OD): δ 29.8, 39.0, 44.7, 54.4, 69.3, 78.2, 110.2, 120.7, 125.1, 129.6, 131.0, 132.9, 137.8, 141.3; HRMS (ESI) [M−Cl—H$_2$O]$^+$ Calcd. for C$_{16}$H$_{19}$Cl$_2$N$_2$O$_2$: 341.0824. Found: 341.0817. Anal. Calcd for C$_{16}$H$_{21}$Cl$_3$N$_2$O$_3$: C, 48.56; H, 5.35; N, 7.08. Found: C, 49.88; H, 5.16; N, 6.30.

1-(3-Phenylpropyl)-1H-imidazole hydrochloride (QC-172). Under an atmosphere of N$_2$, a mixture of imidazole (376 mg, 5.52 mmol, 1.1 equiv) and sodium hydroxide (221 mg, 5.52 mmol, 1.1 equiv) in DMSO (2 mL) was heated at 70-80° C. with stirring for 1.5 h. To this mixture was added a solution of 1-bromo-3-phenylpropane (1.00 g, 5.02 mmol, 1 equiv) in DMSO (2 mL), and the mixture heated at 70-80° C. with stirring for 13 h. Heating was slightly elevated and the DMSO was removed by blowing a stream of air over the reaction mixture. High-vacuum drying left a yellow residue. After dilution with H$_2$O, the mixture was extracted with benzene (3×50 mL) and the combined organic extracts were washed with brine (2×), dried (MgSO$_4$), and concentrated to give the free base (914 mg, 4.91 mmol, 98%). To a solution of this free base in hot EtOH (3 mL) was added a solution of 37% aqueous HCl (500 mg, 5.08 mmol, 1.03 equiv) in EtOH (2 mL). The warm mixture was filtered through a syringe filter (0.45 μm) and the filtrate was concentrated and dried under high vacuum. The residue was recrystallized from 2-propanol-Et$_2$O to give QC-172 (1.05 g, 4.71 mmol, 94%) as a white solid: mp 95-96° C.; $^1$H NMR (400 MHz, CD$_3$OD): δ 2.25 (5-tet, 2H), 2.70 (t, J=7.6 Hz, 2H), 4.29 (t, J=7.4 Hz, 2H), 7.16-7.22 (m, 3H), 7.22-7.30 (m, 2H), 7.55 (s, 1H), 7.67 (s, 1H), 8.95 (s, 1H); $^{13}$C NMR (100 MHz, CD$_3$OD): δ 32.6, 33.4, 50.2, 121.1, 123.3, 127.4, 129.4, 129.6, 136.4, 141.5; HRMS (ESI) [M−Cl]$^+$ Calcd. for C$_{12}$H$_{15}$N$_2$: 187.1235. Found: 187.1242; Anal. Calcd. for C$_{12}$H$_{15}$ClN$_2$: C, 64.71, H, 6.79; N, 12.58. Found: C, 64.95, H, 6.65; N, 12.40.

1-[(1,3-Dioxolan-2-yl)methyl]-1H-imidazole hydrochloride (QC-202). Under an atmosphere of N$_2$, a mixture of imidazole (1.22 g, 18.00 mmol, 1.5 equiv) and sodium hydroxide (0.72 g, 18.00 mmol, 1.5 equiv) in DMSO (3 mL) was heated at 70-80° C. with stirring for 1 h. To this was slowly added a solution of 2-bromomethyl-1,3-dioxolane (2.00 g, 12.00 mmol, 1 equiv) in DMSO (2 mL), and the mixture heated at 70-80° C. with stirring for 26 h. Heating was slightly elevated and the DMSO was removed by blowing a stream of air over the reaction mixture. High-vacuum drying left a residue that was diluted with H$_2$O; the mixture was extracted with benzene (3×25 mL) and also with EtOAc (2×25 mL). The combined organic extracts were dried (MgSO$_4$) and concentrated to give the free base (814 mg, 5.28 mmol, 44%) as a golden oil. To a solution of this free base in hot 2-propanol (3 mL) was added a solution of 37% aqueous HCl (546 mg, 5.54 mmol, 1.05 equiv) in 2-propanol (3 mL). The solution was concentrated and dried under high vacuum. The residue was recrystallized from EtOH-2-propanol to give QC-202 (613 mg, 3.22 mmol, 27%) as a white solid: mp 173-174° C.; $^1$H NMR (400 MHz, CD$_3$OD): δ 3.73-3.82 (m, 2H), 3.85-3.93 (m, 2H), 4.51 (d, J=2.4 Hz, 2H), 5.23 (t, J=2.6 Hz, 1H), 7.56 (s, 1H), 7.61 (s, 1H, 8.94 (s, 1H); $^{13}$C NMR (100 MHz, CD$_3$OD): δ 51.7, 66.6, 101.2, 120.4, 125.1, 137.7; HRMS (EI) [M−HCl]$^+$ Calcd. for C$_7$H$_{10}$N$_2$O$_2$: 154.0742. Found: 154.0742; Anal. Calcd. for C$_7$H$_{11}$ClN$_2$O$_2$: C, 44.10, H, 5.82; N, 14.70. Found: C, 44.22, H, 5.60; N, 14.75.

1-Phenethyl-1H-imidazole (QC-207). Under an atmosphere of N$_2$, a mixture of imidazole (788 mg, 11.57 mmol, 2.1 equiv) and potassium carbonate (370 mg, 2.68 mmol, 1 equiv) in dry THF (18 mL) was stirred at rt for 10 min. To this was added a solution of (2-bromoethyl)benzene (1.00 g, 5.40 mmol, 1 equiv) in THF (1 mL) and the mixture was heated at reflux temperature for 14 h. The mixture was filtered and the filtrate was concentrated to a clear oil. The oil was dissolved in CH$_2$Cl$_2$ and the organic phase was washed with water (2×). The CH$_2$Cl$_2$ layer was then extracted with dilute aqueous HCl (3×). The aqueous extract was then neutralized with solid NaHCO$_3$, and the free base extracted using CH$_{12}$Cl$_2$ (3×). The combined organic extracts were dried Na$_2$SO$_4$) and concentrated. High-vacuum drying gave QC-207 (420 mg, 2.44 mmol, 45%) as a clear oil: $^1$H NMR (400 MHz, CDCl$_3$): δ 3.05 (t, J=7.0 Hz, 2H), 4.17 (t, J=7.0 Hz, 2H), 6.83 (s, 1H), 7.01-7.09 (m, 3H), 7.22-7.34 (m, 4H); $^{13}$C NMR (100 Adz, CDCl$_3$): δ 38.0, 48.6, 118.9, 127.1, 128.7, 128.9, 129.6, 137.2, 137.6.

I.XII Large-Scale Synthesis of QC-56

Figure 2:
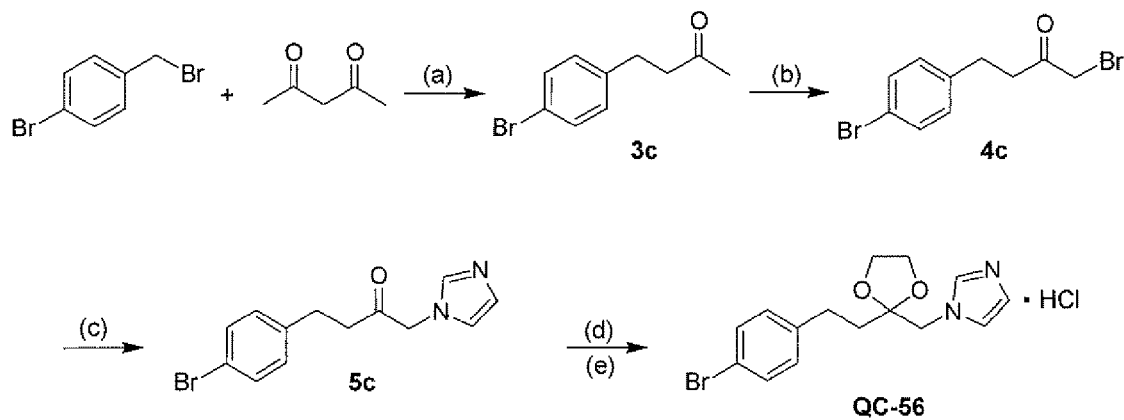
FIG. 2 is a synthetic scheme for the preparation of 2-(2-(4-bromophenyl)ethyl)-2-((1H-imidazol-1-yl)methyl)-1,3-dioxolane hydrochloride (QC-56).

Since the procedure shown in FIG. 2 (see also in Scheme 2) for the production of QC-56 strictly relies on column chromatography as the main method of purification for the intermediates 4-(4-bromophenyl)-2-butanone (3c) and 1-bromo-4-(4-bromophenyl)-2-butanone (4c), we have also developed a more convenient synthesis that does not involve any chromatographic separations and is ideally suited for large-scale applications. The approach is applicable for the synthesis of 2-[2-(substituted-phenyl)ethyl]-2-[(1H-imidazol-1-yl)methyl]-1,3-dioxolane derivatives in general and is shown in Scheme 7.

Scheme 7. General approach for the large-scale production of 2-[2-(substituted-phenyl)ethyl]-2-[(1H-imidazol-1-yl)methyl]-1,3-dioxolane derivatives.

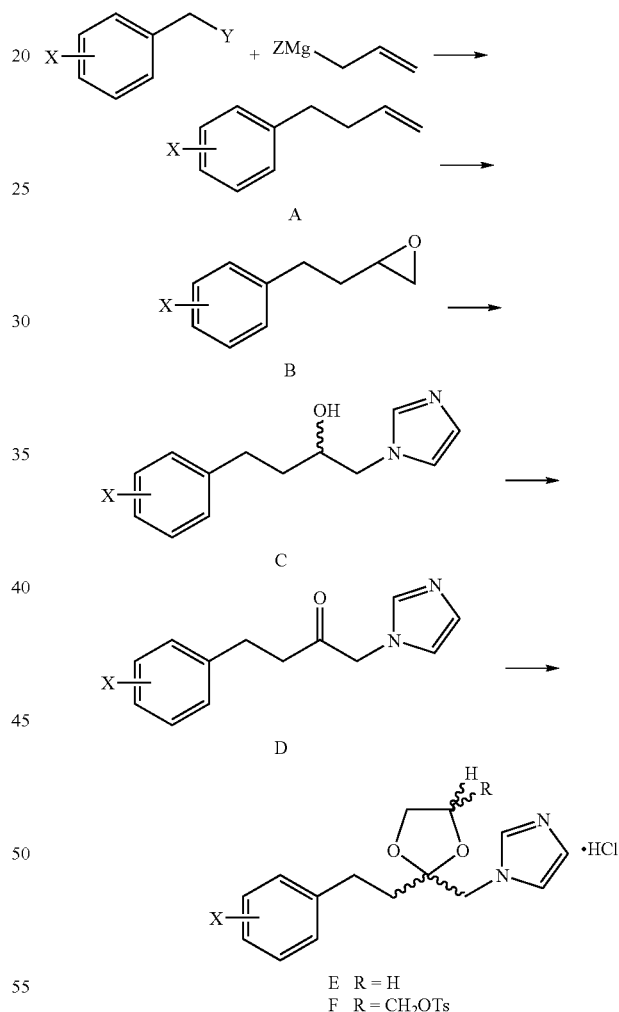

X = a variety of substituents excluding nitro, carbonyl, carboxylic acid derivative groups, and protic groups
Y = Br or Cl
Z = Br or Cl The method involves the reaction of a substituted benzyl halide with an allyl Grignard reagent to give the intermediate A, which is then converted into the corresponding epoxide B using, for example, a peroxy acid solution such as 32% peracetic acid (in dilute aqueous acetic acid). The epoxide B is then converted into the imidazole C by reaction with imidazole in the presence of sodium hydride. Oxidation of the hydroxyl group in C afforded the ketone D, which is then converted into the 1,3-dioxolane E by treatment with ethylene glycol in the presence of an acid catalyst such as p-toluenesulfonic acid in an appropriate solvent, such as toluene. Alternatively, treatment of the ketone D with either (+) or (−) 4-p-toluenesulfonyloxymethyl-2,2-dimethyl-1,3-dioxolane afforded the dioxolane F, which can be converted by way of nucleophilic displacement of the p-tosyloxy group into a variety of derivatives as described herein.

The specific application of the approach to the large-scale synthesis of QC-56 is shown in Scheme 7A.

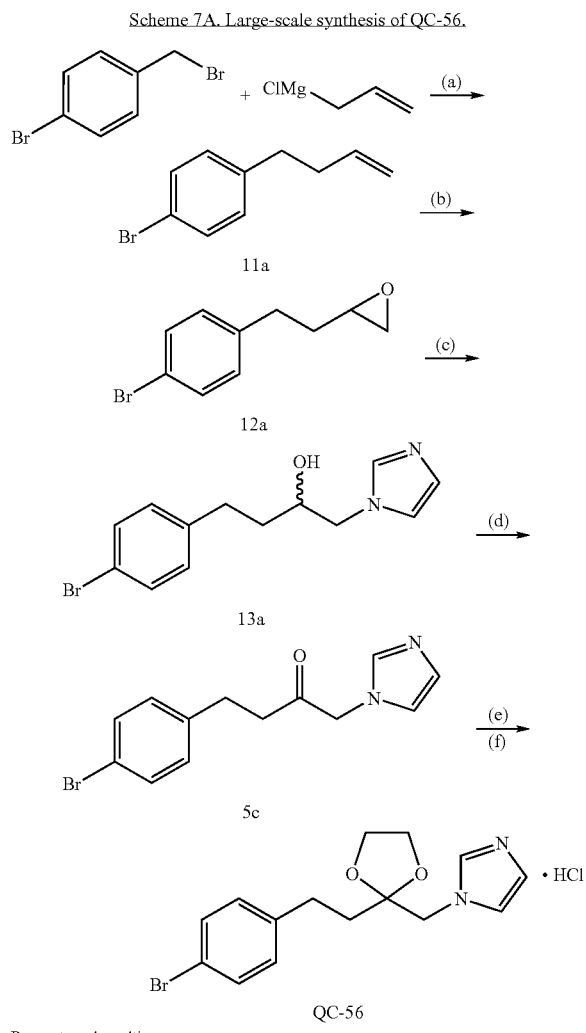

Reagents and condtions:
(a) THF, 0° C., 1 h, rt, 28 h;
(b) 32% peracetic acid (in dil aq AcOH), NaOAc, CH$_2$Cl$_2$, reflux, 3 h;
(c) imidazole, NaH, DMF, rt, 24 h;
(d) DMSO, P$_2$O$_5$, rt, 3 days, then aq K$_2$CO$_3$;
(e) ethylene glycol, p-TsOH•H$_2$O, toluene, Dean-Stark tube, reflux, 11 h;
(f) 38% aq HCl, EtOH.

The synthesis starts from the inexpensive, commercially available starting materials 4-bromobenzyl bromide and allylmagnesium chloride (solution in THF). Alkylation of allylmagnesium chloride by 4-bromobenzyl bromide in THF gave 4-(4-bromophenyl)-1-butene (11a) in 96% yield (8-gram scale); the product was easily isolated by extraction with ethyl acetate. Following the general procedure of Walker (Walker, K. A. M.; Burton, P. M.; Swinney, D. C., Eur. Patent 0 492 474 B1, Mar. 5, 1997), the alkene 11a was converted into (±)-4-(4-bromophenyl)-1,2-epoxybutane (12a) using peracetic acid-sodium acetate in methylene chloride; the clean product was easily isolated (in 98% yield at 10-gram scale) by extraction with methylene chloride. Following the general procedure of Walker (Walker, K. A. M.; Burton, P. M.; Swinney, D. C., Eur. Patent 0 492 474 B1, Mar. 5, 1997), the nucleophilic ring-opening of the epoxide 12a led to the desired product (+)-4-(4-bromophenyl)-1-(1H-imidazol-1-yl)-2-butanol (13a); in our modification, the solid product was easily precipitated from the reaction mixture with water and collected by filtration (the excess of imidazole is simply washed away with water leaving the pure product in 84% yield). In our original synthetic route, we oxidized such imidazole-alcohol derivatives using Swern-oxidation conditions. An improvement to the Swern-oxidation procedure for the oxidation of secondary alcohols (such as 13a) was also accomplished. In particular, we wanted to circumvent the use of large quantities of anhydrous halogenated solvent and also the cumbersome external cooling conditions. After much experimentation, we managed to successfully replace the typical Swern conditions (DMSO oxalyl chloride in CH$_2$Cl$_2$ at −78° C.) with those of another DMSO-based oxidation procedure utilizing DMSO-P$_2$O$_5$ at room temperature. Thus, the imidazole-alcohol 13a (equivalent to the free base form of QC-79) was oxidized using this procedure to give 4-(4-bromophenyl)-1-(1H-imidazol-1-yl)-2-butanone (5c) in 88% yield; the solid product was easily precipitated from the reaction mixture using an aqueous solution of potassium carbonate, and collected by filtration (the excess of DMSO and potassium phosphate salts are simply washed away with water leaving the pure product). The imidazole-ketone 5c obtained from this method can be used to form the imidazole-dioxolane QC-56 by the acid-catalyzed ketal formation reaction (ethylene glycol, p-TsOH.H$_2$O, toluene) already described in section I.II step (d,e). The advantage of this large-scale synthetic route is the high-yielding reactions in combination with the simple isolation of products in relatively pure form, avoiding the numerous distillations [helpful in the purification of 3c] and chromatographic separations of our original synthetic route.

Synthetic Procedures and Characterization of the Compounds Synthesized as Outlined in Scheme 7 for the Large-Scale Production of QC-56:

4-(4-Bromophenyl)-1-butene (11a). To a 2M solution of allylmagnesium chloride in THF (24 mL, 48.00 mmol, 1.5 equiv) at 0° C. was added, under an atmosphere of N$_2$, 4-bromobenzyl bromide (8.00 g, 32.01 mmol, 1.0 equiv) neat in 10 portions over a period of 5 min. The mixture was stirred for 1 h at 0° C. and then at rt for 28 h. The mixture was carefully quenched with water (100 mL) and then extracted with ethyl acetate (3×150 mL). The combined extracts were washed with brine (2×50 mL), dried over anhydrous Na$_2$SO$_4$, and concentrated. High-vacuum drying gave 11a (6.51 g, 30.84 mmol, 96%) as a clear oil: R$_f$=0.94 (ethyl acetate); $^1$H NMR (400 MHz, CDCl$_3$): δ 2.32-2.38 (m, 2H), 2.67 (t, J=7.8 Hz, 2H), 4.98-5.06 (m, 2H), 5.78-5.86 (m, 1H), 7.06 (d, J=8.4 Hz, 2H), 7.40 (d, J=8.4 Hz, 2H); $^{13}$C NMR (100 MHz, CDCl$_3$): δ 34.9, 35.4, 115.4, 119.7, 130.4, 131.5, 137.7, 140.9; HRMS (EI) Calcd. for C$_{10}$H$_{11}$Br: 210.0044 (M$^+$). Found: 210.0053.

(±)-4-(4-Bromophenyl)-1,2-epoxybutane (12a). To a sample of sodium acetate (2.50 g, 30.48 mmol, 0.63 equiv) under a N$_2$ atmosphere was added a 32% solution (in dilute aqueous acetic acid) of peracetic acid (50 mL, 18.08 g, 237.74 mmol, 4.92 equiv). The mixture was stirred at rt for 10 min to completely dissolve the NaOAc. This peroxide solution was then added dropwise over a period of 5 min to a solution of alkene ha (10.20 g, 48.32 mmol, 1 equiv) in dichloromethane (100 mL) at rt. The mixture was heated at reflux temperature with stirring for 3 h. Monitoring by TLC (silica gel, hexanes) confirmed the completion of the reaction. Water (100 mL) was added and the organic phase separated. The aqueous phase was extracted with $CH_2Cl_2$ (3×100 mL), and the combined organic extracts were washed sequentially with a saturated solution of sodium hydrogencarbonate (2×), and brine, dried over anhydrous $Na_2SO_4$, and then concentrated. High-vacuum drying afforded the epoxide 12a (10.80 g, 47.56 mmol, 98%) as a clear oil: $R_f$~0.2 (hexanes); $^1$H NMR (400 MHz, $CDCl_3$): δ 1.73-1.92 (m, 2H), 2.45-2.49 (4-tet, 1H), 2.66-2.82 (m, 3H), 2.90-2.96 (m, 1H), 7.08 (d, J=8.4 Hz, 2H), 7.41 (d, J=8.4 Hz, 2H); $^{13}$C NMR (100 MHz, $CDCl_3$): δ 31.8, 34.2, 47.3, 51.7, 119.9, 130.3, 131.6, 140.3; HRMS (EI) Calcd. for $C_{10}H_{11}BrO$: 225.9993 ($M^+$). Found: 225.9996.

(±)-4-(4-Bromophenyl)-1-(1H-imidazol-1-yl)-2-butanol (13a). To a sample of pure sodium hydride (1.60 g, 66.58 mmol, 1.4 equiv) under a $N_2$ atmosphere was added DMF (40 mL). The mixture was cooled to 0° C. and imidazole (4.86 g, 71.34 mmol, 1.5 equiv) was added in many small portions over 1 h. Stirring was continued for an additional 0.5 h at 0° C. To the mixture was added dropwise the neat epoxide 12a (10.80 g, 47.56 mmol, 1 equiv); the epoxide container was rinsed with DMF (10 mL) and the rinse solution was added to the reaction mixture. The mixture was stirred at 0° C. for 0.5 h and then at rt for 24 h. Monitoring by TLC (silica gel, EtOAc) confirmed the completion of the reaction. Water (20 mL) was added, the mixture cooled to 0° C., and more water (200 mL) was added without stirring. After 1 h at 0° C. an additional 100 mL of water were added. The white solid was removed by filtration and washed with water (3×250 mL), and then with hexanes (200 mL). High-vacuum drying gave the imidazole-alcohol 13a (11.80 g, 39.98 mmol, 84%) as a white solid: mp 121-122° C., $R_f$=0.08 (ethyl acetate); $^1$H NMR (400 MHz, $CDCl_3$): δ 1.68-1.82 (m, 2H), 2.68-2.76 (m, 1H), 2.82-2.89 (m, 1H), 3.75-3.94 (m, 3H), 6.80 (s, 1H), 6.84 (s, 1H), 7.08 (d, J=8.4 Hz, 2H), 7.31 (s, 1H), 7.40 (d, J=8.4 Hz, 2H); $^{13}$C NMR (100 Adz, $CDCl_3$): δ 31.3, 36.0, 54.1, 69.5, 119.9, 128.5, 130.4, 131.6, 140.6; HAS (EI) Calcd. for $C_{13}H_{15}BrN_2O$: 294.0368 ($M^+$). Found: 294.0375.

4-(4-Bromophenyl)-1-(1H-imidazol-1-yl)-2-butanone (5c). To a sample of phosphorus pentoxide (11.35 g, 39.98 mmol, 1 equiv) at 0° C. was added VERY CAREFULLY WITH CAUTION (in 0.5 mL portions at first), under an atmosphere of $N_2$, DMSO (57 mL). The mixture was stirred at 0° C. for 5 min, then at rt for 10 min. External cooling to 0° C. was again initiated and 13a (11.80 g, 39.98 mmol, 1 equiv) was added portionwise (3×4 g). The mixture was stirred at 0° C. for 0.5 h (solidification occurred), then at rt for 3 days. The mixture was cooled to 0° C., and a solution of potassium carbonate (20 g) in water (200 mL) was added (in 1-mL portions), a procedure which caused the mixture to evolve dimethyl sulfide. The mixture was stirred at 0° C. for 10 min and then poured into ice-water (200 mL). The beige solid was removed by filtration and washed with a solution of potassium carbonate (5 g) in water (100 mL), and then with water (10×100 mL). High-vacuum drying left the imidazole-ketone 5c (10.30 g, 35.13 mmol, 88%) as a beige solid: mp 71-73° C., $R_f$=0.09 (ethyl acetate); $^1$H NMR (400 MHz, $CDCl_3$): δ 2.73 (t, J=7.2 Hz, 2H), 2.89 (t, J=7.2 Hz, 2H), 4.70 (s, 2H), 6.84 (s, 1H), 7.03 (d, J=−8.0 Hz, 2H), 7.12 (s, 1H), 7.41 (d, J=8.0 Hz, 2H), 7.52 (s, 1H); $^{13}$C NMR (100 MHz, $CDCl_3$): δ 28.9, 40.9, 55.7, 120.0, 120.5, 130.2, 130.3, 131.9, 138.0, 139.1; HRMS (EI) Calcd. for $C_{13}H_{13}BrN_2O$: 292.0211 ($M^+$). Found: 292.0213.

I.XIII Reduction of Imidazole-Ketones: Synthesis of QC-199, QC-105, and QC-234

As shown in Scheme 8, we have developed a general procedure to reduce the keto functionality of imidazole-ketone derivatives (such as 5c, 5e, and QC-221) using Wolff-Kisner conditions to afford the fully reduced straight-chain derivatives QC-199, QC-105, and QC-234, respectively.

Scheme 8.
General approach for the Wolff-Kishner reduction of imidazole-ketones.

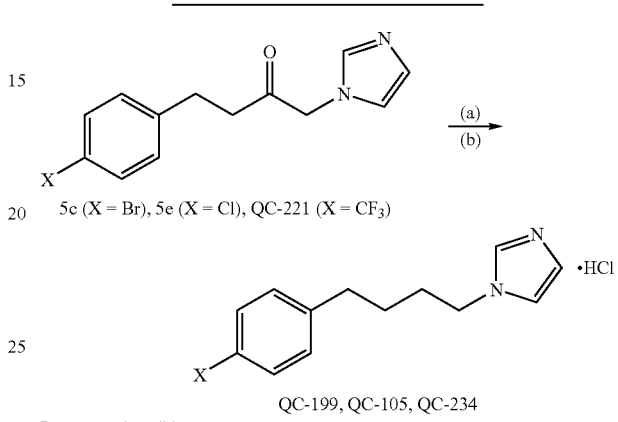

Reagents and conditions:
(a) KOH, ethylene glycol, 98% hydrazine, 100° C. 4 h, 195° C. 8.5 h;
(b) 37% aq HCl, EtOH, rt.

Representative Procedure for the Wolff-Kishner Reduction of Imidazole-Ketones to Afford QC-199, QC-105, and QC-234 as Outlined in Scheme 8:

1-[4-(4-Bromophenyl)butyl]-1H-imidazole hydrochloride (QC-199). Under a $N_2$ atmosphere, a mixture of ketone 5c (628 mg, 2.14 mmol, 1 equiv), potassium hydroxide (1.43 g, 25.49 mmol, 11.9 equiv), ethylene glycol (4.3 mL), and 98% hydrazine (1.1 mL, 1.12 g, 34.25 mmol, 16 equiv) was heated at 100° C. for 4 h, then at 195° C. for 8.5 h. The mixture was cooled to rt, diluted with water, and extracted with warm EtOAc (2×). The combined organic extracts were washed sequentially with a saturated aqueous solution of $Na_2CO_3$, and brine, dried ($Na_2SO_4$), and concentrated to a golden oil. Purification by flash chromatography on silica gel (EtOAc) gave the free base (278 mg, 0.99 mmol, 46%) which was dissolved in hot ethanol (2 mL); the solution was treated with a solution of 37% aqueous HCl (128 mg, 1.30 mmol, 1.3 equiv) in ethanol (2 mL) and concentrated. High-vacuum drying afforded QC-199 (302 mg, 0.96 mmol, 45%) as a beige solid: mp 147-148° C.; $R_f$ (free base form)=0.2 (EtOAc); $^1$H NMR (400 MHz, $CD_3OD$): δ 1.60-1.69 (m, 2H), 1.87-1.97 (m, 2H), 2.66 (t, J=7.6 Hz, 2H), 4.28 (t, J=7.2 Hz, 2H), 7.12 (d, J=8.4 Hz, 2H), 7.41 (d, J=8.4 Hz, 2H), 7.57 (~t, J=1.6 Hz, 2H), 7.65 (~t, J=1.8 Hz, 1H), 8.97 (s, 1H); $^{13}$C NMR (100 MHz, $CD_3OD$): δ 28.9, 30.6, 35.4, 50.4, 120.6, 121.2, 123.3, 131.4, 132.5, 136.3, 142.2; HRMS (ESI) [M−Cl]$^+$ Calcd. for $C_{13}H_{15}N_2Br$: 278.0419. Found: 278.0411.

Characterization of the Compounds (QC-105 and QC-234) Synthesized Following the Representative Procedure for the Wolif-Kishner Reduction of Imidazole-Ketones (Described Above for QC-199) as Outlined in Scheme 8:

1-[4-(4-Chlorophenyl)butyl]-1H-imidazole hydrochloride (QC-105). Beige solid in 23% yield from 5e: mp 121-122° C.; $^1$H NMR (400 MHz, $CD_3OD$): δ 1.63-1.68 (m, 2H), 1.88-1.94 (m, 2H), 2.67 (t, J=7.6 Hz, 2H), 4.28 (t, J=7.2 Hz, 2H), 7.18 (d, J=8.8 Hz, 2H), 7.26 (d, J=8.4 Hz, 2H), 7.57 (~t, J=1.6

Hz, 1H), 7.65 (~t, J=1.6 Hz, 1H), 8.97 (s, 1H); $^{13}$C NMR (100 MHz, CD$_3$OD): δ 29.0, 30.7, 35.3, 50.4, 121.2, 123.3, 129.5, 131.0, 132.8, 136.3, 141.7; HRMS (ESI) [M−Cl]$^+$ Calcd. for C$_{13}$H$_{16}$ClN$_2$: 235.1002. Found: 235.0997.

1-[4-(4-(Trifluoromethyl)phenyl)butyl]-1H-imidazole hydrochloride (QC-234). White solid in 51% yield from QC-221 (synthesis described above): mp 110-111° C.; $^1$H NMR (400 MHz, CD$_3$OD): δ 1.64-1.76 (m, 2H), 1.89-1.99 (m, 2H), 2.78 (t, J=7.6 Hz, 2H), 4.30 (t, J=7.2 Hz, 2H), 7.40 (d, J=8.0 Hz, 2H), 7.51-7.60 (m, 3H), 7.67 (s, 1H), 8.99 (s, 1H); $^{13}$C NMR (100 MHz, CD$_3$OD): δ 28.8, 30.7, 35.8, 50.4, 121.2, 123.3, 126.3 (apparent d, $J_{C,F}$=3.7 Hz), 130.1, 136.3, 147.6, missing two other $^{13}$C signals due to excessive $^{19}$F splitting; $^{19}$F NMR (376 MHz, CD$_3$OD): δ −64.8; HRMS (ESI) [M−Cl]$^+$ Calcd. for C$_{14}$H$_{16}$F$_3$N$_2$: 269.1260. Found: 269.1263.

Synthesis of Compound QC-221:

4-(4-(Trifluoromethyl)phenyl)-1-(1H-imidazol-1-yl)-2-butanone hydrochloride (QC-221). A mixture of 1-bromo-4-(4-(trifluoromethyl)phenyl)-2-butanone (892 mg, 3.02 mmol, 1 equiv, synthesized by the general procedure used to produce 4a-d) and imidazole (616 mg, 9.06 mmol, 3 equiv) in dry N,N-dimethylformamide (7 mL) was stirred at room temperature under a N$_2$ atmosphere for 3 h. The mixture was then diluted with ethyl acetate, and the solution was washed with brine (3×). The separated organic phase was dried over anhydrous Na$_2$SO$_4$, and then concentrated to a golden brown oil. Purification by flash column chromatography on silica gel (EtOAc) gave the free base (359 mg, 1.27 mmol, 42%). A portion of the free base (200 mg, 0.71 mmol) was dissolved in hot ethanol (2 mL); the solution was treated with a solution of 37% aqueous HCl (100 mg, 1.02 mmol, 1.4 equiv) in ethanol (2 mL) and concentrated. High-vacuum drying afforded QC-221 (160 mg, 0.50 mmol, 30%) as a beige solid: mp 170-171° C.; $^1$H NMR (400 MHz, CD$_3$OD): δ 3.05 (br s, 4H), 5.36 (s, 2H), 7.46 (d, J=8.0 Hz, 2H), 7.53 (s, 1H), 7.55-7.65 (m, 3H), 8.88 (s, 1H); $^{13}$C NMR (100 MHz, CD$_3$OD): δ 29.7, 41.5, 57.9, 120.5, 124.7, 126.4 (apparent d, $J_{C,F}$=3.7 Hz), 130.2, 137.7, 146.7, 201.5, missing two other $^{13}$C signals due to excessive $^{19}$F splitting; $^{19}$F NMR (376 MHz, CD30): δ −64.9; HRMS (ESI) [M−Cl]$^+$ Calcd. for C$_{14}$H$_{14}$N$_2$OF$_3$: 283.1058. Found: 283.1055.

II. Materials & Methods

II.I Human HO-1 cDNA Plasmid Construction

An hHO-1 construct was prepared consisting of pcDNA3.1/Zeo.CMV.Flag.hHO-1 containing the entire protein-coding region (866 bp) of the human HO-1 gene. Plasmid assembly was enabled using a forward primer (5'-TTC ATA CAA GCT TAT GGA GCG TCC GCA ACC-3') containing a HindIII site and a reverse primer (5'-TCA ATG GAT CCT CAC ATG GCA TAA AGC CCT-3') containing a BamRI site designed to match the multiple cloning sites in pcDNA3.1/Zeo.CMV.Flag. The hHO-1 fragment was amplified by pfu DNA polymerase-catalyzed PCR and adenine overhangs were added to the PCR product with Taq DNA polymerase. After purification of the PCR products, the HindIII/BamHI fragment of hHO-1 was subcloned into pGEM-T easy vector (Promega) for color screening of recombinant clones. hHO-1 fragment (HindIII/BamHI) was excised from recombinant pGEM-T by digestion with HindIII and BamHI and inserted into the HindIII and BamHI sites of pcDNA3.1/Zeo.CMV.Flag. Identical plasmids minus the hHO-1 cDNA were used for sham (control) transfections. Correct orientation and sequence of the hHO-1-Flag and Flag-only constructs were confirmed on sequencing gels.

II.II Primary Astrocyte Cultures

Primary neuroglial cell cultures were prepared by mechanoenzymatic dissociation of cerebral tissue as previously described (Chopra 1995). Cells were grown in Ham's F12 and high glucose DMEM (50:50 v/v) supplemented with 10 mM HEPES, 5% heat-inactivated horse serum, 5% heat-inactivated fetal bovine serum, and penicillin-streptomycin (50 U/mL and 50 Atg/mL, respectively). Cells were seeded in T25 or T75 cm$^2$ tissue culture flasks at a density of 1×10$^6$ cells/mL. The cultures were incubated at 37° C. in humidified 95% air-5% CO$_2$ for 6 h at which time they were vigorously shaken 20-30 times with replacement of fresh media to remove adherent oligodendroglia and microglia from the astrocytic monolayers. The cultures were incubated under the above-mentioned conditions for 6 days at which time more than 98% of the cells comprising the monolayer were astroglia as determined by immunohistochemical labeling for the astrocyte-specific marker, glial fibrillary acidic protein (GFAP) (Chopra 1995).

II.III Transfection of Human HO-1 cDNA and HO-1 Inhibitor Treatment

Upon reaching >90% confluence, 1×10$^6$ cells were transiently transfected with 4.0 μg of plasmid DNA-Lipofectamine 2000 complex using Lipofectamine 2000 method according to manufacturer instructions (Invitrogen'). This level of transfection was previously shown to elicit robust oxidative modifications of lipids, proteins and nucleic acids in rat astroglia cultured under similar conditions (Song 2006). 12 μg of plasmid DNA and 16 μl of Lipofectamine 2000 reagent were diluted in 1.5 mL opti-MEM I reduced serum medium and incubated for 5 minutes at room temperature with gentle mixing. The two solutions were combined, incubated at room temperature for 20 minutes to promote formation of DNA-lipid complexes and administered to the cells. 2 mL opti-MEM I reduced serum medium was added to the flasks to ensure coverage of the monolayer by the transfection mixture. Following incubation for 6 hours at 37° C., the transfection mixture was replaced with 10 mL of complete media without antibiotics. Transfection efficiency was determined by assessment of enhanced green fluorescence protein (EGFP) expression in astrocytes co-transfected with hHO-1 cDNA plasmid and pEGFP.C1 vector as previously reported (Song 2006). The transfection efficiency was ~40% consistent with our previous studies. HO activity in these transfected cells is increased ~3-fold relative to sham-transfected controls (Song 2006). At 54 hours post-transfection, some cultures were treated with QC-47 or QC-56, for 18 h. In the presence of QC-47 (6.5 μM, concentration of IC$_{50}$) or QC-56 (same concentration as QC-47 treatment), HO activity in the HO-1-transfected astroglia is suppressed to levels akin to those of non-transfected and sham-transfected controls. Cells were harvested at 72 h post-transfection for the measurements of HO enzyme activity and oxidative substrate damage as described below.

II.IV Purification of Rat Liver Biliverdin Reductase

A young adult male rat was gas-anesthetized, laid on ice and systemically perfused with ice-cold 0.9% NaCl to get rid of all blood from liver. The liver was then excised on ice and transferred to a cold room (4° C.) and cut into small pieces in cold 0.9% NaCl (3 mL per gram of tissue) with surgical scissors in and placed in a 50 mL tube. The tissue chunks were homogenized with an electric tissue homogenizer and centrifuged at 150×g for 5 min at 4° C. Similarly, all of the following steps, including centrifugations, were performed at 4° C. The supernatant was centrifuged at 18,000×g for 10 min and further at 30,000×g for 30 min. A saturated solution of ammonium sulfate was added to the 30,000×g supernatant to attain 40% saturation and placed on ice for 10 min. The mixture was centrifuged at 10,000×g for 10 min and supernatant was recovered and transferred to a fresh tube. Sixty percent of saturation was achieved by adding saturation solution of ammonium sulfate to the supernatant. The mixed solution was centrifuged again at 10,000×g for 10 min and supernatant was discarded. The pellet was suspended in 1 mL of 0.01 M $KPO_4$, pH7.4 and dialyzed in distilled water for 24 h. The dialysate was centrifuged at 10,000 g for 10 min and pellet was discarded. The protein concentration of the supernatant was measured with Bradford reagent (BioRad laboratories, Hercules, Calif.) and adjusted to 10 mg/mL with 0.01 M $KPO_4$, pH7.4. The supernatant was aliquoted and stored at −20° C. ready for use.

II.V HO Enzyme Activity

HO activity in rat spleen and brain microsomal fractions was determined by the quantification of CO formed from the degradation of methemalbumin (heme complexed with albumin) (Vreman et al 1988, Cook et al 1995). Spleen and brain (Sprague-Dawley rats) microsomal fractions were prepared according to the procedure outlined by Appleton et al (1999). Protein concentration of microsomal fractions was determined by a modification of the biuret method (Cook et al 1995). Incubations for HO activity analysis were done under conditions for which the rate of CO formation (pmol $CO \times min^{-1} \times mg\ protein^{-1}$) was linear with respect to time and microsomal protein concentration. Briefly, reaction mixtures (150 µL) consisting of 100 mM phosphate buffer (pH 7.4), 50 µM methemalbumin, and 1 mg/mL protein were pre-incubated with the inhibitors at final concentrations ranging from 0.1-100 µM for 10 minutes at 37° C. Reactions were initiated by adding NADPH at a final concentration of 1 mM and incubations were performed for an additional 15 minutes at 37° C. Reactions were stopped by instantly freezing the reaction mixture on dry ice, and CO formation was monitored by gas chromatography according to the method described by Vreman et al (1988).

II.VI Subcellular Fractionation

Subcellular fractionation was performed as previously described (Schipper 1999). Briefly, cells were scraped, centrifuged and resuspended in 10 volumes of lysis buffer (Ponka 1982) containing 4 mM $MgCl_2$, 2 mM Tris-HCl pH 7.4, and 1 mM AEBSF. The cells were sonicated (Sonics & Materials, Danbury, Conn.) at a power level of 50 for 3×20 s in a cooled water bath. Cell sonicates were suspended in 12.2% (v/v) Ficoll in 250 mM sucrose, 100 mM Tris-HCl pH 7.4 and 1 mM EDTA, and centrifuged at 55,000 g for 40 min. The fractionation procedure results in ~65-fold enrichment for mitochondria as determined by cytochrome-c oxidase assay (Schipper 1999). Whole-cell and mitochondrial preparations were assayed for protein carbonyls as described below.

II.VII Protein Carbonyl Assay

Protein carbonyl content, a widely-used measure of oxidative protein modification (Buss 1997, Winterbourn 1999) was determined by ELISA. Protein carbonyls were reacted with 2,4-dinitrophenylhydrazine (DNP) and the hydrazone adducts were detected with anti-DNP antisera. Quantification was achieved by comparison with oxidized BSA standards. Oxidized (carbonylated) BSA was prepared by reacting natural BSA (at 50 mg/mL in PBS) with hypochlorous acid (5 mM) for 1 h at 37° C., followed by overnight dialysis against PBS at 4° C. Fully reduced BSA was prepared by reacting natural BSA (at 0.5 g/100 mL in PBS) with sodium borohydride (0.1 g) for 30 min at room temperature, followed by slow neutralization with 2 M HCl and overnight dialysis against PBS. DNP was combined with the BSA standards and carbonyl content determined calorimetrically by absorbance at 375 nm ($\epsilon=22,000/M/cm$) (Winterbourn 1999). Astroglial monolayers from each T75 flask was washed twice with 6 mL of ice-cold PBS and then scraped in 12 mL of lysis buffer (10 mM Tris, pH7.4, 50 mM NaCl, 1 mM EDTA, 2.5 µg/mL of butylated hydroxytoluene—BHT) and collected by centrifugation at 150×g at 4° C. The pellet was resuspended in 2 mL of same buffer, sonicated on ice 2×15 s at 20 W and centrifuged for 20 min at 4° C. at 1,303×g. Protein concentration of supernatant was measured with the RC DC protein assay based on the Lowry protocol (Bio-Rad Laboratories, Hercules, Calif.). All samples were adjusted to 4.0 mg protein/mL. The standards and samples were incubated with 3 volumes of 10 mM DNP in 6 M guanidine-HCl and 0.5 M potassium phosphate (pH 2.5) for 45 min at room temperature with mixing every 10-15 min. Five microliters aliquots of each reaction mixture were mixed with 1 mL PBS and 200 µL replicates were added per well to 96-well immunoplates and incubated overnight at 4° C. After washing with PBS, non-specific binding sites were blocked with 0.1% Tween 20 in PBS. Wells were incubated with biotinylated anti-DNP antibody (1:1,000 dilutions in 0.1% Tween 20/PBS) for 1 h at 37° C. followed by incubation with streptavidin-biotinylated horseradish peroxidase (1:3,000 dilution in 0.1% Tween 20/PBS). An o-phenylenediamine/peroxide solution (200 µL) was added to the reaction mixture for 4-7 min (terminated with 100 µL of 2.5 M sulfuric acid) and read at 490 nm. A 6-point standard curve of reduced and oxidized BSA was generated for each plate analyzed. Specific absorbance for each sample was calculated by subtracting basal absorbance of the DNP reagent from the total absorbance.

II.VIII In Vitro HO Enzyme Activity Measurement

Cytosol extracts were prepared for HO activity measurement by the method of Ryter (Ryter, Kvam, Tyrrell 2000). Astroglial monolayers were washed with ice-cold PBS and scraped in ice-cold PBS-EDTA (1 mM, pH 8.0) containing 50 µg/mL protease inhibitor (AEBSF), centrifuged at 150×g at 4° C. and resuspended in 20 mM Tris-HCl (pH 7.4) and 0.25 M sucrose containing protease inhibitors. Cell suspensions were sonicated on ice 2×15 s at 20 W and centrifuged for 20 min at 4° C. at 15,000×g. Protein concentration of supernatant was measured with Bradford method. Final reaction concentrations were 25 µM heme, 2 mM glucose 6-phosphate, 2 unit glucose 6-phosphate dehydrogenase, 1 mM β-NADPH, 0.5 mg/mL cytosol extract, and 2 mg/mL partially purified rat liver biliverdin reductase. Reaction mixtures were incubated at 37° C. in the dark for 60 min with hard vortex every 10 min. The reactions were terminated by addition of 1 volume chloroform. Bilirubin concentrations in the chloroform extracts were determined spectrophotometrically by absorbance at 464-530 nm. HO activity was calculated as nanomoles bilirubin per miligram protein per min, assuming an extinction coefficient of 40/mM/cm in chloroform (see FIG. 8).

II.IX Tumor Cell Line Cultures

Rat C6 glioma cells were cultivated in high glucose DMEM supplemented with 10% heat-inactivated fetal bovine serum, 200 mM glutamine, and penicillin-streptomycin (50 U/mL and 50 µg/mL, respectively). Pancreatic tumor cells were grown in RPMI 1640 medium supplemented with 10% heat-inactivated fetal bovine serum, 2 mM L-glutamine adjusted to contain 1.5 g/L sodium bicarbonate, 4.5 g/L glucose, 10 mM HEPES, and 1.0 mM sodium pyruvate, and same antibiotics as described above. All cultures were incubated at 37° C. in humidified 95% air-5% $CO_2$.

II.X Transfection of Human HO-1 cDNA and HO-1 Inhibitor Treatment

Cells were seeded in 24-well plates at $1\times10^6$ cells/mL/well. Upon reaching >90% confluence, cells in each well were transiently transfected with 1.6 µg of plasmid DNA-Lipofectamine 2000 complex using Lipofectamine 2000 method according to manufacturer instructions (Invitrogen). 1.6 µg of plasmid DNA and 4 µL of Lipofectamine 2000 reagent were diluted individually in 100 µL opti-MEM I and incubated for 5 minutes at room temperature with gentle mixing. The two solutions were combined, incubated at room temperature for 20 minutes to promote formation of DNA-lipid complexes and administered to the cells plus 1 mL of complete medium without antibiotics. At 36 or 50 hours post-transfection, some cultures were treated with 6.5 µM QC-56, a specific HO-1 inhibitor and [3H] thymidine for 18 h. Cells were harvested after the treatments for proliferation assay, as described below. According to manufacturer instructions (Invitrogen) and our experience, transfection efficiency for tumor cell lines was equal or more than 80%.

II.XI Cell Proliferation Assay

Cell proliferation was determined by [$^3$H] thymidine incorporation: Cells were plated in 24-well plates at $10^6$ cells/mL/well in complete medium. [3H] thymidine (0.73 µCi/mL) was added to the culture media for 18 h prior to cell harvesting. The cells were trypsinized and collected, air-dried on 21 mm glass microfibre filters (Whatman International Ltd., Maidstone, England) and analyzed by scintillation counting in a Wallac-Liquid Scintillator Counter (Perkin Elmer Life Sciences, Boston, Mass., USA). [$^3$H] thymidine incorporation was expressed as counts per min (cpm) per mL.

II.XII Western Blot Analysis

Cells were rinsed twice with cold PBS (pH 7.4) and scraped in iced lysis buffer consisting of 1% Nonidet P-40, 50 mM Tris.HCl (pH 7.4), 30 mM NaCl, 25 mM β-glycerophosphate, 10 mM EDTA, 10 mM EGTA, 1 mM $MgCl_2$, and protease inhibitors (10 mM sodium fluoride, 50 µg/mL AEBBSF, 5 µg/mL leupeptin, 5 µg/mL pepstatin, 5 µg/mL aprotinin). Supernatants were obtained by centrifugation at 15,000 rpm for 15 min at 4° C. Protein contents were determined using the Bradford method. Twenty µg aliquots plus 6×SDS-PAGE loading buffer (300 mM Tris.HCl pH 6.8, 600 mM DTT, 12% SDS, 0.6% bromophenol blue, 60% glycerol) were subjected to 10% sodium dodecyl sulfate-polyacrylamide gel electrophoresis and transferred to the polyvinylidene fluoride membranes. Nonspecific binding was blocked by incubation in Tris buffer saline (pH 7.4) containing 3% nonfat milk and 0.1% Tween 20 for 1 h at room temperature. Blots were probed with mouse anti-FLAG monoclonal antibody (1:200 diluted) and anti-β-actin monoclonal antibody (1:500 diluted). The secondary antibody consisted of horseradish peroxidase-conjugated goat anti-mouse antibody (1:4000 dilution). Protein bands were visualized by enhanced chemiluminescence using ECL western blotting reagents.

III. In Vitro Analysis

III.I Inhibition of HO-1 Activity

III.I (i) Animals

Brain, liver; lung and spleen tissue were obtained from adult male Sprague-Dawley rats (250-300 g) purchased from Charles River Inc. (Montreal, Canada). Rats were maintained on 12 hr light cycles and ad libitum access to water and standard Ralston Purina laboratory chow 5001 (Ren's Feed Supplies, Ltd., Oakville, Ontario, Canada). All animals were cared for in accordance with principles and guidelines of the Canadian Council on Animal Care and experimental protocols were approved by the Queen's University Animal Care Committee.

III.I (ii) Preparation of Brain, Spleen and Liver Microsomal Fractions

Brain, liver and spleen microsomal fractions were prepared for HO and CRP activity assays according to previously described procedures (Appleton et al. 1999). Briefly, tissue homogenate (15% w/v) was prepared in ice-cold buffer (20 mM $KH_2PO_4$, 135 M KCl and 0.1 mM ETA, pH 7.4) using a 60S Sonic Dismembrator (Fisher Scientific Ltd., Ottawa, ON, Canada). Microsomal fractions were obtained by differential centrifugation of the homogenate at 10,000×g for 20 min at 4° C., followed by centrifugation of the supernatant at 100, 000×g for 60 min at 4° C. Microsomes (100,000×g pellet) were resuspended in buffer (100 mM $KH_2PO_4$, 20% vv glycerol and 1 mM EDTA adjusted to pH 7.4) and then stored at −0° C. until used. Spleen microsomes were used as a source of HO-1 Maines, 1988; Braggins et al., 1986) while brain microsomes were used as a source of HO-2 (Trakshel et al., 1988).

III.I (iii) Measurement of HO-1 and HO-2 Protein Expression

Forty micrograms of rat spleen and brain tissue homogenate protein (10,000×g supernatant fraction) were subjected to sodium dodecylsulfate-polyacrylamide gel electrophoresis (SDS-PAGE) under reducing conditions, and then the protein was transferred onto nitrocellulose Immobilon-P membranes (Millipore, Bedford, Mass., USA) according to the method of Laemmli (1970). To block non-specific binding sites, membranes were incubated in phosphate-buffered saline (137 mM NaCl 2.7 mM KCl, 8.1 mM $Na_2HPO_4$, 1.5 mM $KH_2PO_4$, pH 7.4) containing 10% (w/v) skimmed milk powder at 4° C. for 1618 hours. The blots were then incubated with a 1:2,000 dilution of the polyclonal anti-human HO-1 (SPA-896, StressGen, Victoria, BC, Canada) or anti-human HO-2 (SPA-897, StressGen) antibodies. The specificity of anti-HO antibodies under these conditions was confirmed previously (Lash et at., 2003). Membranes were subsequently incubated with a peroxidase-labeled goat anti-rabbit IgG secondary antibody (Vector Laboratories, Burlingame, Calif., USA). Peroxidase activity was detected by enhanced chemiluminescence detection kit according to the manufacturer's instructions (Amersham, Toronto, ON, Canada). All gels were calibrated with prestained, broad-range molecular weight markers (Bio-Rad, Hercules, Calif., USA). Rat recombinant human HO-1 (SPP 730) or HO-2 NSP-550, StressGen) were also used as standard markers. Relative HO-1 and HO-2 expression was quantified by optical densitometry using an NIH-imager. To ensure uniform protein loading on all the gels, membranes that were used for HO quantification were stripped in buffer (200 mM glycine, pH 2.6, blocked as described above and then probed with a mouse antibody again β-actin. Densitometric units for HO-1 and HO-2 expression were normalised to β-actin protein expression in all the samples.

III.I (iv) Measurement of HO Enzymatic Activity

HO activity in rat spleen and brain microsomal fractions was determined by the quantitation of CO formed from the degradation of methemalbumin, i.e., haem complexed with albumin according to Vreman and Stevenson (1999) and Cook et al. (1995). Incubations for HO activity analysis were done under conditions for which the rate of CO formation (pmol CO/mg protein/minute) was linear with respect to time and mircrosomal protein concentration. Briefly, reaction mixtures (150 µL) consisting of 100 mM phosphate buffer (pH 7.4), 50 µM methemalbumin and 1 mg/mL protein were pre-incubated with the vehicle (ethanol or water in which the inhibitors were dissolved), or inhibitors at final concentrations ranging from 0.1-1000 µM for 10 minutes at 37° C. Reactions were initiated by adding β-NADPH at a final concentration of 1 mM and incubations were carried out for an additional 15 minutes at 37° C. Reactions were stopped by instantly fling the reaction mixture on pulverized dry ice and CO formation was measured by gas chromatography using a TA 3000R Process Gas Analyzer (Trace Analytical/Ametek, Newark, Del., USA).

III.I (v) Results

The data resulting from the above-described experiments of III.I (and see Kinobe et al. 2006) was plotted as non-linear regression (sigmoidal dose-response) curves using version 3 of GraphPad Prism™ computer program. The values on the abscissa represent the decimal logarithm of the inhibitor's concentration (in μM), whereas the values of the activity on the ordinate are expressed as a percentage of the control experiments without inhibitor. From these curves, the value of the concentration ($EC_{50}$) of the inhibitor at which the enzyme's activity is halfway between the bottom and top plateau of the curve, as well as the top and the bottom plateau values of the curves have been retrieved using the same program, and input in the following equation (I) to give the calculated values of the concentration ($IC_{50}$) of the compound under evaluation for which the activity of the enzyme was inhibited by 50% compared to the control.

$$IC_{50} = \frac{EC_{50}}{\frac{bottom - top}{50 - top} - 1} \quad (I)$$

The $IC_{50}$ value reported for each compound in Table 1 is the average of the values recorded in replicate experiments, and for each of these replicate experiments (consisting in their turn of two separate assays) an individual $IC_{50}$ value was calculated in the manner described. The $IC_{50}$ values for the replicate experiments were employed to generate the reported standard deviation value.

TABLE 1

| | | | |
|---|---|---|---|
| | | $IC_{50}$ HO-1 (rat spleen)/ μM | $IC_{50}$ HO-2 (rat brain)/ μM |
| Strucure | Name | | |
| CrMP | Chromium mesoporphyrin | 1.45 + 0.01 | 1.1 + 0.7 |
| 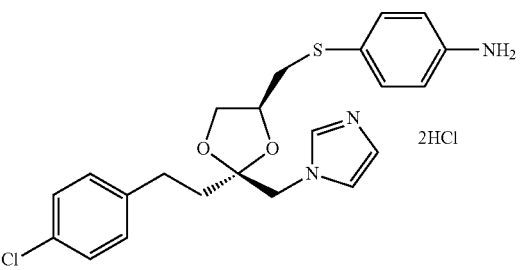 QC-1 | (2S,4S)-2-[2-(4-chlorophenyl)ethyl]-2-[(1H-imidazol-1-yl)methyl]-4-[{(4-aminophenyl)thio}methyl]-1,3-dioxolane dihydrochloride | 5 + 2 | 24 + 2 |
| 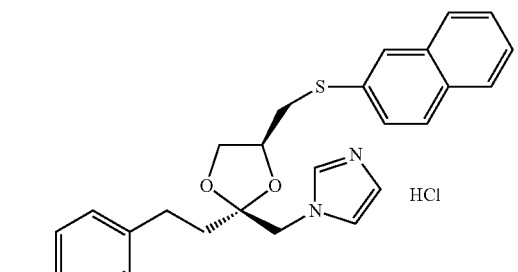 QC-2 | (2S,4S)-2-[2-(4-chlorophenyl)ethyl]-2-[(1H-imidazol-1-yl)methyl]-4-[{(2-naphthyl)thio}methyl]-1,3-dioxolane hydrochloride | 14 + 2 | 62 + 7 |

TABLE 1-continued

Structure, name and median inhibitory concentration (IC50) of select compounds

| Strucure | Name | IC$_{50}$ HO-1 (rat spleen)/ µM | IC$_{50}$ HO-2 (rat brain)/ µM |
|---|---|---|---|
| QC-3 | (2S,4S)-2-[2-(4-chlorophenyl)ethyl]-2-[(1H-imidazol-1-yl)methyl]-4-[{(2-aminophenyl)thio}methyl]-1,3-dioxolane dihydrochloride | 5.0 + 0.3 | 55 + 26 |
| QC-4 | (2S,4S)-2-[2-(4-chlorophenyl)ethyl]-2-[(1H-imidazol-1-yl)methyl]-4-[(p-toluenesulfonyloxy)methyl]-1,3-dioxolane hydrochloride | 19 + 9 | 48 + 6 |
| QC-5 | (2R,4S)-2-[2-(4-chlorophenyl)ethyl]-2-[(1H-imidazol-1-yl)methyl]-4-[{(4-aminophenyl)ethio}methyl]-1,3-dioxolane hydrochloride | 0.33 + 0.07 | 8 + 1 |
| QC-6 | (2S,4S)-2-[2-(4-chlorophenyl)ethyl]-2-[(1H-imidazol-1-yl)methyl]-4-[(p-toluenesulfonyloxy)methyl]-1,3-dioxolane | 21 + 2 | 23 + 6 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-7 | (2S,4S)-2-[2-(4-chlorophenyl)ethyl]-2-[(1H-imidazol-1-yl)methyl]-4-[{(3-aminophenyl)thio}methyl]-1,3-dioxolane dihydrochloride | 1.5 + 0.1 | 21 + 1 |
| QC-8 | (2S,4S)-2-[2-(4-chlorophenyl)ethyl]-2-[(1H-imidazol-1-yl)methyl]-4-[(4-methoxyphenyloxy)methyl]-1,3-dioxolane hydrochloride | 28 + 15 | 29 + 6 |
| QC-9 | 4-(4-chlorophenyl)-1-(1H-imidazol-1-yl)butan-2-one hydrochloride | 4.7 + 0.5 | 43 + 5 |
| QC-10 | 4-(4-chlorophenyl)-1-(1H-imidazol-1-yl)butan-2-ol hydrochloride | 0.5 + 0.1 | 4.0 + 0.6 |
| QC-11 | Benzimidazole | >>100 | >>100 |
| QC-12 | (2R,4S)-2-[2-(4-chlorophenyl)ethyl]-2-[(1H-imidazol-1-yl)methyl]-4-[{(2-aminophenyl)thio}methyl]-1,3-dioxolane dihydrochloride | 4 + 2 | 42 + 28 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-13 | (2R,4R)-2-[2-(4-chlorophenyl)ethyl]-2-[(1H-imidazol-1-yl)methyl]-4-methyl-1,3-dioxolane hydrochloride | 0.8 ± 0.2 | 305 ± 25 |
| QC-14 | (2R,4S)-2-[2-(4-chlorophenyl)ethyl]-2-[(1H-imidazol-1-yl)methyl]-4-[{(3-aminophenyl)thio}methyl]-1,3-dioxolane hydrochloride | 4 ± 2 | 6 ± 1 |
| QC-15 | 2-[2-(4-chlorophenyl)ethyl]-2-[(1H-imidazol-1-yl)methyl]-1,3-dioxolane hydrochloride | 4 ± 2 | >100 |
| QC-16 | (2R,4S)-2-[2-(4-chlorophenyl)ethyl]-2-[(1H-imidazol-1-yl)methyl]-4-[(p-toluenesulfonyloxy)methyl]-1,3-dioxolane | 6 ± 2 | 3 ± 1 |
| QC-17 | (2S,4R)-2-[2-(4-chlorophenyl)ethyl]-2-[(1H-imidazol-1-yl)methyl]-4-[(p-toluenesulfonyloxy)methyl]-1,3-dioxolane | 17 ± 1 | 120 ± 34 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 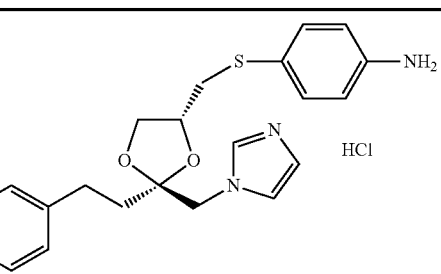<br>QC-18 | (2S,4R)-2-[2-(4-chlorophenyl)ethyl]-2-[(1H-imidazol-1-yl)methyl]-4-[{(4-aminophenyl)thio}methyl]-1,3-dioxolane hydrochloride | 14.8 + 0.5 | 18 + 4 |
| 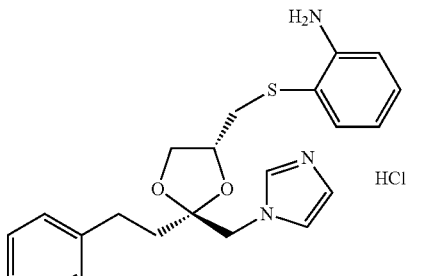<br>QC-19 | (2S,4R)-2-[2-(4-chlorophenyl)ethyl]-2-[(1H-imidazol-1-yl)methyl]-4-[{2-aminophenyl)thio}methyl]-1,3-dioxolane hydrochloride | >100 | >100 |
| 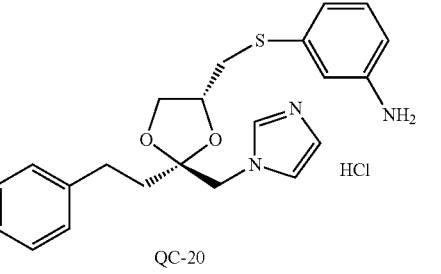<br>QC-20 | (2S,4R)-2-[2-(4-chlorophenyl)ethyl]-2-[(1H-imidazol-1-yl)methyl]-4-[{(3-aminophenyl)thio}methyl]-1,3-dioxolane hydrochloride | 5.2 + 0.4 | 24 + 4 |
| 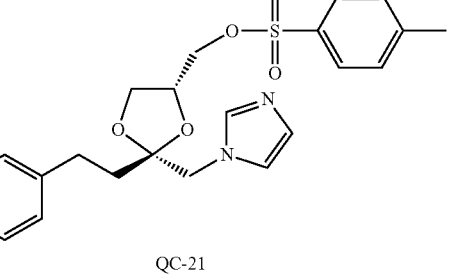<br>QC-21 | (2R,4R)-2-[2-(4-chlorophenyl)ethyl]-2-[(1H-imidazol-1-yl)methyl]-4-[(p-toluenesulfonyloxy)methyl]-1,3-dioxolane | 0.8 + 0.3 | 23 + 10 |
| 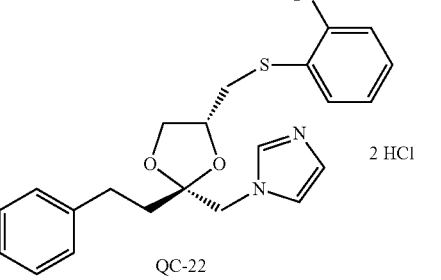<br>QC-22 | (2R,4R)-2-[2-(4-chlorophenyl)ethyl]-2-[(1H-imidazol-1-yl)methyl]-4-[{(2-aminophenyl)thio}methyl]-1,3-dioxolane dihydrochloride | 87 + 24 | >100 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-23 | (2R,4R)-2-[2-(4-chlorophenyl)ethyl]-2-[(1H-imidazol-1-yl)methyl]-4-[{(3-aminophenyl)thio}methyl]-1,3-dioxolane dihydrochloride | 38 + 2 | >100 |
| QC-24 | (2R,4R)-2-[2-(4-chlorophenyl)ethyl]-2-[(1H-imidazol-1-yl)methyl]-4-[{(4-aminophenyl)thio}methyl]-1,3-dioxolane dihydrochloride | 47 + 21 | >100 |
| QC-25 | (2R,4S)-2-[2-(4-chlorophenyl)ethyl]-2-[(1H-imidazol-1-yl)methyl]-4-methyl-1,3-dioxolane hydrochloride | 2.6 + 0.4 | >100 |
| QC-26 | (2S,4S)-2-[2-(4-chlorophenyl)ethyl]-2-[(1H-imidazol-1-yl)methyl]-4-methyl-1,3-dioxolane hydrochloride | 12 + 4 | >100 |
| QC-27 | (2S,4R)-2-[2-(4-chlorophenyl)ethyl]-2-[(1H-imidazol-1-yl)methyl]-4-methyl-1,3-dioxolane hydrochloride | 20 + 4 | >100 |
| QC-28 | 5-(3-methoxyphenyl)-1H-tetrazole | >>100 | >>100 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-29 | 5-(2-amino-4-chlorophenyl)-1H-tetrazole | >>100 | >>100 |
| QC-30 | (2R,4S)-2-[2-(4-chlorophenyl)ethyl]-2-[(1H-imidazol-1-yl)methyl]-4-[(phenylthio)methyl]-1,3-dioxolane hydrochloride | 1.03 + 0.07 | 34 + 12 |
| QC-31 | 1-(1H-imidaozl-1-yl)butan-2-ol hydrochloride | 131 + 38 | >>100 |
| QC-32 | (2R,4S)-2-[2-(4-chlorophenyl)ethyl]-2-[(1H-imidazol-1-yl)methyl]-4-[{(4-pyridinyl)thio}methyl]-1,3-dioxolane dihydrochloride | 25 + 5 | 69 + 8 |
| QC-33 | 4-(4-methoxyphenyl)-1-(1H-imidazol-1-yl)butan-2-ol hydrochloride | 0.7 + 0.1 | 6 + 4 |
| QC-34 | (2R,4S)-2-[2-(4-chlorophenyl)ethyl]-2-[(1H-imidazol-1-yl)methyl]-4-[{(4-hydroxyphenyl)thio}methyl]-1,3-dioxolane | 1.59 + 0.03 | 7 + 2 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-35 | (2R,4R)-2-[2-(4-phenyl)ethyl]-2-[(1H-imidazol-1-yl)methyl]-4-methyl-1,3-dioxolane hydrochloride | 2 + 1 | >43 |
| QC-36 | 1-acetoxy-2-(1H-imidazol-1-yl)-butane | >100 | >100 |
| QC-37 | 4-(4-chlorophenyl)-2-(4-fluorobenzyloxy)-1-(1H-imidazol-1-yl)butane hydrochloride | 0.9 + 0.3 | 1.00 + 0.01 |
| QC-38 | (2R,4R)-2-[2-(4-chlorophenyl)ethyl]-2-[(1H-imidazol-1-yl)methyl]-4-(hydroxymethyl)-1,3-dioxolane hydrochloride | 12 + 2 | >100 |
| QC-39 | (2R,4S)-2-[2-(4-chlorophenyl)ethyl]-2-[(1H-imidazol-1-yl)methyl]-4-[(4-aminophenyloxy)methyl]-1,3-dioxolane dihydrochloride | 1.4 + 0.3 | 13 + 4 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 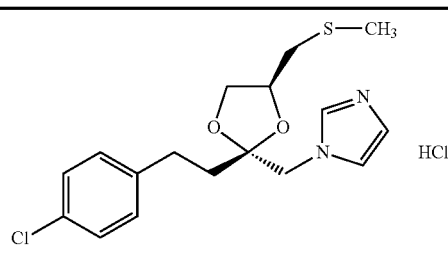 QC-40 | (2R,4S)-2-[2-(4-chlorophenyl)ethyl]-2-[(1H-imidazol-1-yl)methyl]-4-[(methylthio)methyl]-1,3-dioxolane hydrochloride | 9 + 2 | 19 + 7 |
| 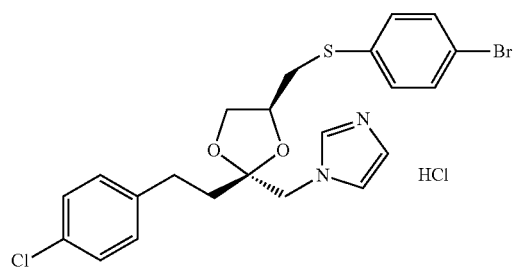 QC-41 | (2R,4S)-2-[2-(4-chlorophenyl)ethyl]-2-[(1H-imidazol-1-yl)methyl]-4-[{(4-bromophenyl)thio}methyl]-1,3-dioxolane hydrochloride | 2.1 + 0.9 | 2.4 + 0.1 |
| 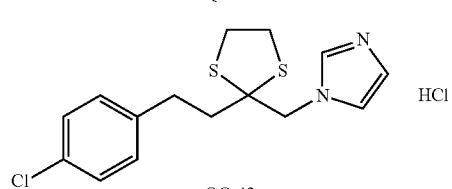 QC-42 | 2-[2-(4-chlorophenyl)ethyl]-2-[(1H-imidazol-1-yl)methyl]-1,3-dithiolane hydrochloride | 4.7 + 0.6 | 16 + 4 |
| 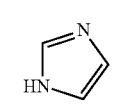 QC-43 | Imidazole | >>100 | >>100 |
| 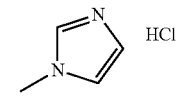 QC-44 | 1-methylimidazole hydrochloride | >>100 | >>100 |
| 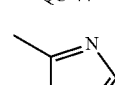 QC-45 | 2-methylimidazole | >>100 | >>100 |
| 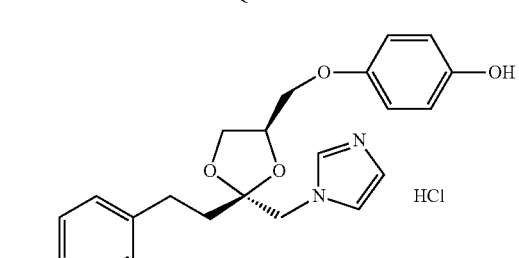 QC-46 | (2R,4S)-2-[2-(4-chlorophenyl)ethyl]-2-[(1H-imidazol-1-yl)methyl]-4-[(4-hydroxyphenyloxy)methyl]-1,3-dioxolane hydrochloride | 1.8 + 0.5 | 7.1 + 0.7 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 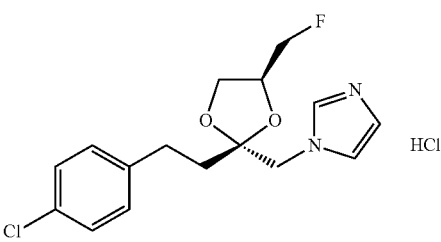<br>QC-47 | (2R,4S)-2-[2-(4-chlorophenyl)ethyl]-2-[(1H-imidazol-1-yl)methyl]-4-(fluoromethyl)-1,3-dioxolane hydrochloride | 6 + 3 | >100 |
| 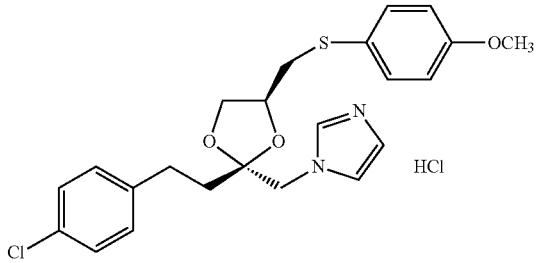<br>QC-48 | (2R,4S)-2-[2-(4-chlorophenyl)ethyl]-2-[(1H-imidazol-1-yl)methyl]-4-[{(4-methoxyphenyl)thio}methyl]-1,3-dioxolane hydrochloride | 0.7 + 0.3 | 2.5 + 0.4 |
| 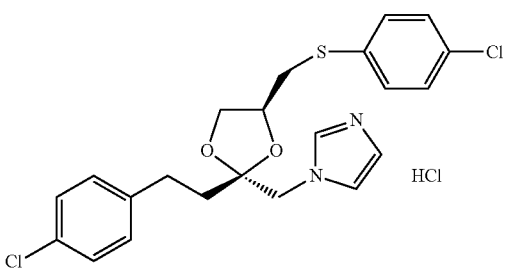<br>QC-49 | (2R,4S)-2-[2-(4-chlorophenyl)ethyl]-2-[(1H-imidazol-1-yl)methyl]-4-[{(4-chlorophenyl)thio}methyl]-1,3-dioxolane hydrochloride | 2.8 + 0.4 | 12 + 5 |
| 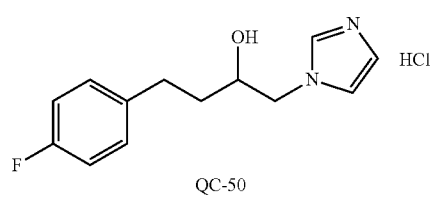<br>QC-50 | 4-(4-fluorophenyl)-1-(1H-imidazol-1-yl)butan-2-ol hydrochloride | 1.4 + 1.1 | 18 + 12 |
| 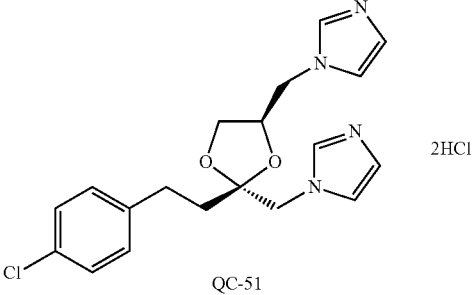<br>QC-51 | (2R,4R)-2-[2-(4-chlorophenyl)ethyl]-2-[(1H-imidazol-1-yl)methyl]-4-[(1H-imidazol-1-yl)methyl]-1,3-dioxolane dihydrochloride | 10 + 6 | 26 + 3 |

TABLE 1-continued

Structure, name and median inhibitory concentration (IC50) of select compounds

| Strucure | Name | IC$_{50}$ HO-1 (rat spleen)/ µM | IC$_{50}$ HO-2 (rat brain)/ µM |
|---|---|---|---|
| QC-52 | (2R,4S)-2-[2-(4-chlorophenyl)ethyl]-2-[(1H-imidazol-1-yl)methyl]-4-[{(4-fluorophenyl)thio}methyl]-1,3-dioxolane hydrochloride | 2.2 + 0.2 | 5 + 4 |
| QC-53 | 4-(4-bromophenyl)-1-(1H-imidazol-1-yl)butan-2-one hydrochloride | 1.7 + 0.7 | 10 + 5 |
| QC-54 | 4-(4-fluorophenyl)-1-(1H-imidazol-1-yl)butan-2-one hydrochloride | 2.7 + 0.9 | 2.0 + 0.2 |
| QC-55 | 2-[2-(4-fluorophenyl)ethyl]-2-[(1H-imidazol-1-yl)methyl]-1,3-dioxolane hydrochloride | 4 + 1 | >100 |
| QC-56 | 2-[2-(4-bromophenyl)ethyl]-2-[(1H-imidazol-1-yl)methyl]-1,3-dioxolane hydrochloride | 1.9 + 0.2 | >100 |
| QC-57 | 2-[2-phenylethyl]-2-[(1H-imidazol-1-yl)methyl]-1,3-dioxolane hydrochloride | 0.7 + 0.4 | >100 |
| QC-58 | 4-(4-bromophenyl)butan-2-one | >>100 | >>100 |

TABLE 1-continued

Structure, name and median inhibitory concentration (IC50) of select compounds

| Strucure | Name | IC$_{50}$ HO-1 (rat spleen)/ µM | IC$_{50}$ HO-2 (rat brain)/ µM |
|---|---|---|---|
| QC-59 | 1-bromo-4-(4-bromophenyl)butan-2-one | 42 + 5 | 125 + 22 |
| QC-60 | (2R,4S)-2-[2-(4-chlorophenyl)ethyl]-2-[(1H-imidazol-1-yl)methyl]-4-[{(4-nitrophenyl)thio}methyl]-1,3-dioxolane hydrochloride | 6 + 2 | 19 + 2 |
| QC-61 | 4-(4-bromophenyl)-1-[(2-methyl)-1H-imidazol-1-yl]butan-2-one hydrochloride | >>100 | >>100 |
| QC-62 | 4-(4-bromophenyl)-1-(1H-benzimidazol-1-yl)butan-2-one hydrochloride | >>100 | >>100 |
| QC-63 | N-benzyl-2-(1H-imidazol-1-yl)-acetamide hydrochloride | 12 + 5 | >>100 |
| QC-64 | 4-(4-bromophenyl)-1-[1,2,4]triazol-1-yl-butan-2-one hydrochloride | 0.39 + 0.02 | 3 + 2 |
| QC-65 | 4-phenyl-1-(1H-imidazol-1-yl)butan-2-one hydrochloride | 4 + 2 | 11 + 5 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-66 | Imidazol-1-yl-acetic acid | >>100 | >>100 |
| QC-67 | Histamine dihydrochloride | >>100 | >>100 |
| QC-68 | L-histidine hydrochloride monohydrate | >>100 | >>100 |
| QC-69 | D-methionine | >>100 | >>100 |
| QC-70 | 2-[2-(4-chlorophenyl)ethyl]-2-[(1H-imidazol-1-yl)methyl]-1,3-dioxane hydrochloride | 20 + 4 | >100 |
| QC-71 | 1-{2-[2-(4-Chloro-phenyl)-ethyl]-hexahydro-benzo[1,3]dioxol-2-ylmethyl}-1H-imidazole | 69 + 7 | >100 |
| QC-72 | 1-(1H-imidazol-1-yl)-4-(4-methoxyphenyl)-2-butanone hydroxchloride | 2.2 + 0.9 | 29 + 19 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-73 | 4-(4-iodophenyl)-1-(1H-imidazol-1-yl)butan-2-one hydrochloride | 0.11 + 0.06 | 1.8 + 0.7 |
| QC-74 | 4-(4-iodophenyl)-1-(1H-imidazol-1-yl)butan-2-ol hydrochloride | 0.06 + 0.03 | 2 + 1 |
| QC-75 | 1-(2-hydroxy-phenyl)-3-imidazol-1-yl-propan-1-one | 25 + 12 | >100 |
| QC-76 | 4-phenyl-1-(1H-imidazol-1-yl)butan-2-ol hydrochloride | 6 + 1 | 16 + 8 |
| QC-77 | N-trifluoroacetylimidazole | >>100 | >>100 |
| QC-78 | 2-[2-(4-iodophenyl)ethyl]-2-[(1H-imidazol-1-yl)methyl]-1,3-dioxolane hydrochloride | 4 + 1 | >100 |
| QC-79 | 4-(4-bromophenyl)-1-(1H-imidazol-1-yl)butan-2-ol hydrochloride | 0.1 + 0.1 | 2.6 + 0.5 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-80 | (2R,4S)-2-[2-(4-chlorophenyl)ethyl]-2-[(1H-imidazol-1-yl)methyl]-4[{(5-trifluoromethyl-pyridin-2-yl)thio}methyl]-1,3-dioxolane hydrochloride | 2.1 + 0.6 | 16 + 8 |
| QC-81 | (2R,4S)-2-[2-(4-chlorophenyl)ethyl]-2-[(1H-imidazol-1-yl)methyl]-4[(4-adamantan-1-yl-phenoxy)methyl]-1,3-dioxolane hydrochloride | >100 | >>100 |
| QC-82 | 1-(adamantan-1-yl)-2-imidazol-1-yl-ethanone hydrochloride | 3 + 1 | >100 |
| QC-83 | 4-(4-chlorophenyl)-3-imidazol-1-yl-butan-2-one hydrochloride | >>100 | >>100 |
| QC-84 | 1-(4-chlorophenyl)-3-dimethylamino-propan-1-one | >>100 | >>100 |
| QC-85 | 1-(4-chlorophenyl)-3-imidazol-1-yl-propan-1-one hydrochloride | 32 + 3 | >100 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-86 | 4-phenyl-1-[1,2,4]triazol-1-yl-butan-2-one hydrochloride | 2.6 + 0.9 | 34 + 3 |
| QC-87 | 4-phenyl-1-pyrazol-1-yl-butan-2-one hydrochloride | >>100 | >>100 |
| QC-88 | 1,4-bis-(1H-imidazol-1-yl)butane dihydrochloride | >100 | >>100 |
| QC-89 | 1,6-bis-(1H-imidazol-1-yl)hexane dihydrochloride | >>100 | >>100 |
| QC-90 | Fluconazole | 80 + 6 | >100 |
| QC-91 | 4-phenyl-1-(1H-[1,2,3]triazol-1-yl)butan-2-one | 89 + 1 | >100 |
| QC-92 | Mebendazole | >100 | >>100 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
| --- | --- | --- | --- |
| QC-93 | Alendazole | >>100 | >>100 |
| QC-94 | Oxibendazole | >>100 | >100 |
| QC-95 | 2-phenylethyl-2-[(1H-pyrazole-1-yl)methyl]-1,3-dioxolane hydrochloride | >>100 | >>100 |
| QC-96 | 4-(4-chlorophenyl)-3-imidazol-1-yl-butan-2-ol hydrochloride | 40 + 2 | >>100 |
| QC-97 | 1-(4-phenyl-2-oxo-butyl)-pyrazin-1-ium bromide | 163 + 10 | >100 |
| QC-98 | Cyclopropyl-(4-imidazol-1-yl-phenyl)methanone hydrochloride | >>100 | >>100 |
| QC-99 | 1-(2-methyl-imidazol-1-yl)-4-phenyl-butan-2-one hydrochloride | >>100 | >>100 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 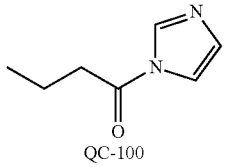 QC-100 | N-butyrylimidazole | >>100 | >>100 |
| 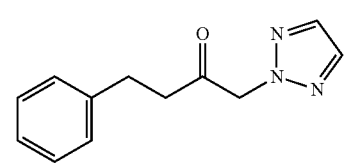 QC-101 | 4-phenyl-1-[1,2,3]triazol-2-yl-butan-2-one | >>100 | >>100 |
| 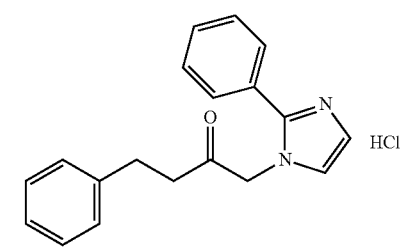 QC-102 | 4-phenyl-1-(2-phenyl-imidazol-1-yl)butan-2-one hydrochloride | >>100 | >>100 |
| 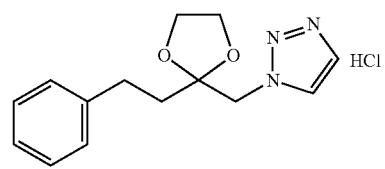 QC-103 | 2-(2-phenethyl)-2-{(1H-[1,2,3]triazol-1-yl)methyl}-1,3-dioxolane hydrochloride | >100 | >>100 |
| 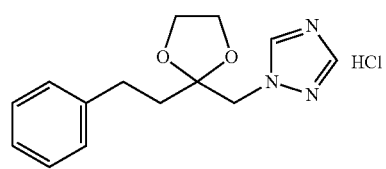 QC-104 | 2-(2-phenethyl)-2-{(1H-[1,2,4]triazol-1-yl)methyl}-1,3-dioxolane hydrochloride | 14 ± 3 | >>100 |
| 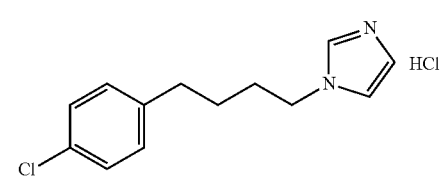 QC-105 | 4-(4-chlorophenyl)-1-(1H-imidazol-1-yl)butane hydrochloride | 0.5 ± 0.3 | >100 |
| 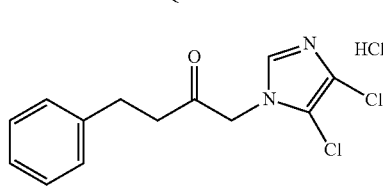 QC-106 | 1-(4,5-Dichloro-imidazol-1-yl)-4-phenyl-butan-2-one hydrochloride | >>100 | >>100 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 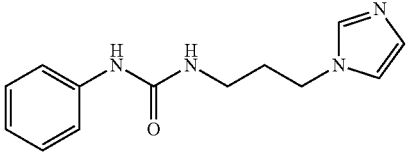 QC-107 | 1-(3-Imidazol-1-yl-propyl)-3-phenyl-urea | >>100 | >100 |
| 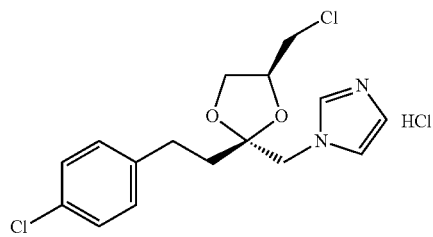 QC-108 | 1-{4-Chloromethyl-2-[2-(4-chloro-phenyl)-ethyl]-[1,3]dioxolan-2-ylmethyl}-1H-imidazole hydrochloride | 3.5 + 0.1 | 122 + 30 |
| 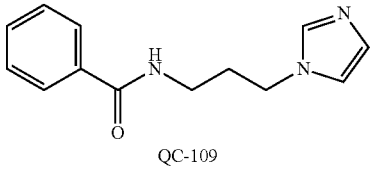 QC-109 | N-(3-Imidazol-1-yl-propyl)-benzamide | >100 | >100 |
| 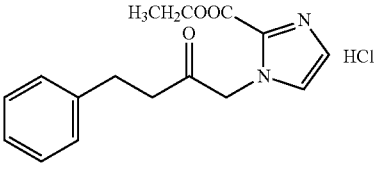 QC-110 | 1-(2-Oxo-4-phenyl-butyl)-1H-imidazole-2-carboxylic acid ethyl ester hydrochloride | >>100 | >>100 |
| 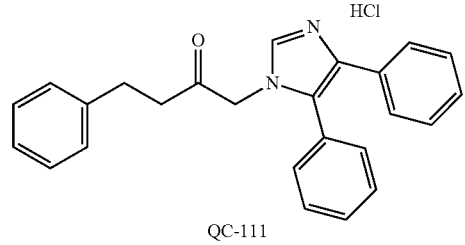 QC-111 | 1-(4,5-Diphenyl-imidazol-1-yl)-4-phenyl-butan-2-one hydrochloride | 40 + 2 | >100 |
| 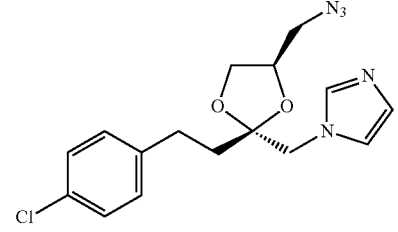 QC-112 | 1-{4-Azidomethyl-2-[2-(4-chloro-phenyl)-ethyl]-[1,3]dioxolan-2-ylmethyl}-1H-imidazole hydrochloride | 3.6 + 0.2 | 38 + 5 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-113 | 1-(2-Methylsulfanyl-imidazol-1-yl)-4-phenyl-butan-2-one | >>100 | >>100 |
| QC-114 | 2-(2-Phenethyl-[1,3]dioxolan-2-ylmethyl)-2H-[1,2,3]triazole | >>100 | >>100 |
| QC-115 | 1-{2-[2-(4-Chloro-phenyl)-ethyl]-4-cyclohexylsulfanylmeth-yl-[1,3]dioxolan-2-ylmethyl}-1H-imidazole hydrochloride | 0.94 + 0.09 | 13 + 2 |
| QC-116 | 1-{2-[2-(4-Chloro-phenyl)-ethyl]-4-phenoxymethyl-[1,3]dioxolan-2-ylmethyl}-1H-imidazole hydrochloride | 0.59 + 0.04 | 1.6 + 0.3 |
| QC-117 | 4-Phenyl-1-tetrazol-2-yl-butan-2-one hydrochloride | 9.6 + 0.2 | 37 + 25 |
| QC-118 | 4-Phenyl-1-tetrazol-1-yl-butan-2-one hydrochloride | 2.6 + 0.9 | 20 + 10 |

TABLE 1-continued

Structure, name and median inhibitory concentration (IC50) of select compounds

| Structure | Name | IC$_{50}$ HO-1 (rat spleen)/ µM | IC$_{50}$ HO-2 (rat brain)/ µM |
|---|---|---|---|
| 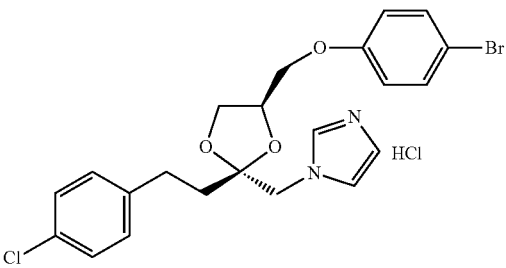<br>QC-119 | 1-{4-(4-Bromo-phenoxymethyl)-2-[2-(4-chloro-phenyl)-ethyl]-[1,3]dioxolan-2-ylmethyl}-1H-imidazole hydrochloride | 3.5 + 0.2 | 22 + 8 |
| 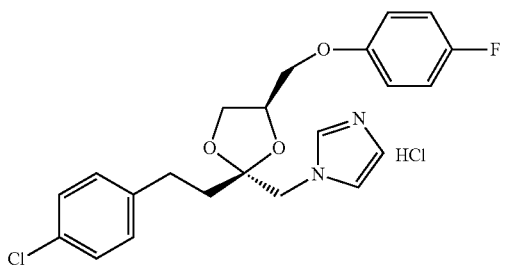<br>QC-120 | 1-[2-[2-(4-Chloro-phenyl)-ethyl]-2-(4-fluoro-phenylsulfanylmethyl)-[1,3]dioxolan-2-ylmethyl]-1H-imidazole hydrochloride | 0.28 + 0.01 | 0.5 + 0.2 |
| 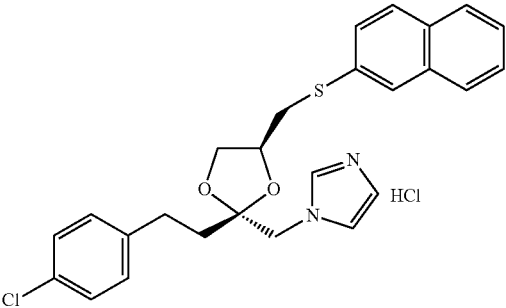<br>QC-121 | 1-[2-[2-(4-Chloro-phenyl)-ethyl]-4-(naphthalen-2-ylsulfanylmethyl)-[1,3]dioxolan-2-ylmethyl]-1H-imidazole hydrochloride | 0.9 + 0.1 | 30 + 4 |
| 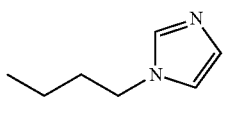<br>QC-122 | 1-Butyl-1H-imidazole | >100 | >>100 |
| 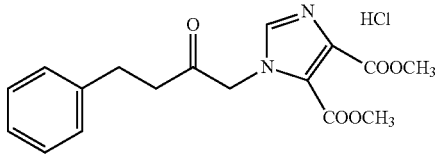<br>QC-123 | 1-(2-Oxo-4-phenyl-butyl)-1H-imidazole-4,5-dicarboxylic acid dimethyl ester hydrochloride | >>100 | >>100 |

TABLE 1-continued

Structure, name and median inhibitory concentration (IC50) of select compounds

| Strucure | Name | $IC_{50}$ HO-1 (rat spleen)/ μM | $IC_{50}$ HO-2 (rat brain)/ μM |
|---|---|---|---|
| QC-124 | 4-Phenyl-1-(4-phenyl-imidazol-1-yl)-butan-2-one hydrochloride | 9 + 2 | 145 + 54 |
| QC-125 | 1-(2-Methanesulfonyl-imidazol-1-yl)-4-phenyl-butan-2-one | >100 | >100 |
| QC-126 | 1-(4-Bromo-imidazol-1-yl)-4-phenyl-butan-2-one | >>100 | >>100 |
| QC-127 | 1-(4-Nitro-imidazol-1-yl)-4-phenyl-butan-2-one | >>100 | >>100 |
| QC-128 | 1-Benzoimidazol-1-yl-4-phenyl-butan-2-one | >>100 | >>100 |
| QC-129 | 1-{4-(Biphenyl-4-yloxymethyl)-2-[2-(4-chloro-phenyl)-ethyl]-[1,3]dioxolan-2-ylmethyl}-1H-imidazole hydrochloride | 2 + 1 | 43 + 3 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-130 | 1-Benzotriazol-2-yl-4-phenyl-butan-2-one | >>100 | >>100 |
| QC-131 | 1-Benzotriazol-1-yl-4-phenyl-butan-2-one | >>100 | >>100 |
| QC-132 | 1-[2-[2-(4-Chloro-phenyl)-ethyl]-4-(4-methoxy-phenoxymethyl)-[1,3]dioxolan-2-ylmethyl]-1H-imidazole hydrochloride | 1.33 + 0.03 | 19 + 7 |
| QC-133 | 1-(2-Oxo-4-phenyl-butyl)-1H-imidazole-4-carboxylic acid methyl ester | >>100 | >>100 |
| QC-134 | 3-(2-Oxo-4-phenyl-butyl)-3H-imidazole-4-carboxylic acid methyl ester | 55 + 2 | >>100 |
| QC-135 | 1-(2-Oxo-4-phenyl-butyl)-1H-[1,2,4]triazole-3-carboxylic acid methyl ester | >>100 | >>100 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
| --- | --- | --- | --- |
| QC-136 | 2-(2-Oxo-4-phenyl-butyl)-2H-[1,2,4]triazole-3-carboxylic acid methyl ester | >>100 | >>100 |
| QC-137 | 1-(3,5-Dibromo-[1,2,4]triazol-1-yl)-4-phenyl-butan-2-one | >>100 | >>100 |
| QC-138 | N-[2-(1H-Imidazol-4-yl)-ethyl]-acetamide | >>100 | >>100 |
| QC-139 | 1,8-bis-(1H-imidazol-1-yl)octane dihydrochloride | Activity not available | Activity not available |
| QC-140 | 1-[2-[2-(4-Chloro-phenyl)-ethyl]-4-(4-iodo-phenoxymethyl)-[1,3]dioxolan-2-ylmethyl]-1H-imidazole | 9 ± 3 | 15 ± 4 |
| QC-141 | 2-Imidazol-1-yl-1-phenyl-ethanone hydrochloride | 28 ± 4 | >>100 |

TABLE 1-continued

Structure, name and median inhibitory concentration (IC50) of select compounds

| Strucure | Name | IC$_{50}$ HO-1 (rat spleen)/ µM | IC$_{50}$ HO-2 (rat brain)/ µM |
|---|---|---|---|
| QC-142 | 1-(4-Chloro-phenyl)-2-imidazol-1-yl-ethanone hydrochloride | 4 + 2 | 20 + 8 |
| QC-143 | 1-(2-Phenethyl-[1,3]dioxolan-2-ylmethyl)-1H-tetrazole hydrochloride | 39 + 5 | >100 |
| QC-144 | (1H-Benzoimidazol-2-yl)-(5-piperidin-1-yl-pentyl)-amine | >>100 | >>100 |
| QC-145 | (1H-Benzoimidazol-2-yl)-[5-(4-chloro-phenoxy)-pentyl]-amine | ~100 | ~100 |
| QC-146 | 5-(4-Piperidin-1-yl-butoxy)-1H-benzoimidazol-2-ylamine dihydrochloride 3/2 hydrate | >>100 | >>100 |
| QC-147 | [2-(1H-Imidazol-4-yl)-ethyl]-(1-methyl-1H-benzoimidazol-2-yl)-amine dihydrochloride | >100 | >100 |
| QC-148 | 2-(4-Ethyl-piperazin-1-yl)-1H-benzoimidazole dihydrochloride hemihydrate | >>100 | >>100 |

TABLE 1-continued

Structure, name and median inhibitory concentration (IC50) of select compounds

| Strucure | Name | $IC_{50}$ HO-1 (rat spleen)/ μM | $IC_{50}$ HO-2 (rat brain)/ μM |
|---|---|---|---|
| QC-149 | (1H-Benzoimidazol-2-yl)-[4-(3H-imidazol-4-yl)-cyclohexyl]-amine dihydrochloride | >>200 | >200 |
| QC-150 | 1-(5-Methylsulfanyl-[1,2,4]triazol-1-yl)-4-phenyl-butan-2-one hydrochloride | >>100 | >>100 |
| QC-151 | 1-(3-Methylsulfanyl-[1,2,4]triazol-1-yl)-4-phenyl-butan-2-one | >>100 | >>100 |
| QC-152 | 1-(3-Nitro-[1,2,4]triaozl-1-yl)-4-phenyl-butan-2-one | >>100 | >>100 |
| QC-153 | 2-(2-Phenethyl-[1,3]dioxolan-2-ylmethyl)-2H-tetrazole hydroxhlodie | 72 + 1 | >100 |
| QC-154 | 1-(2-Oxo-4-phenyl-butyl)-1H-imidazole-4,5-dicarbonitrile hydrochloride | >>100 | >>100 |
| QC-155 | 1-(3-Methanesulfonyl-[1,2,4]triazol-1-yl)-4-phenyl-butan-2-one | >>100 | >>100 |

TABLE 1-continued

Structure, name and median inhibitory concentration (IC50) of select compounds

| Structure | Name | IC$_{50}$ HO-1 (rat spleen)/ µM | IC$_{50}$ HO-2 (rat brain)/ µM |
|---|---|---|---|
| QC-156 | 1-(5-Methanesulfonyl-[1,2,4]triazol-1-yl)-4-phenyl-butan-2-one | >>100 | >>100 |
| QC-157 | 1-Phenyl-2-[1,2,4]triazol-1-yl-ethanone hydrochloride | 12.0 + 0.9 | >100 |
| QC-158 | 1-(4-Chloro-phenyl)-2-[1,2,4]triazol-1-yl-ethanone hydrochloride | 2.2 + 0.5 | 122.0 + 0.1 |
| QC-159 | 2-Imidazol-1-yl-1-(4-nitro-phenyl)-ethanone hydrochloride | 2.5 + 0.2 | >100 |
| QC-160 | 1-(2-Nitro-imidazol-1-yl)-4-phenyl-butan-2-one hydrochloride | >>100 | >>100 |
| QC-161 | 1-(4-Bromo-phenyl)-2-imidazol-1-yl-ethanone hydrochloride | 3.2 + 0.8 | 14 + 2 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
| --- | --- | --- | --- |
| QC-162 | 2-Imidazol-1-yl-1-naphthalen-2-yl-ethanone hydrochloride | 1.9 + 0.1 | 12.00 + 0.05 |
| QC-163 | 2-Imidazol-1-yl-1-(4-methoxy-phenyl)-ethanone hydrochloride | 32 + 4 | 62 + 3 |
| QC-164 | 1-{4-(3-Bromo-phenylsulfanylmethyl)-2-[2-(4-chloro-phenyl)-ethyl]-[1,3]dioxolan-2-ylmethyl}-1H-imidazole hydrochloride | 5 + 2 | 22 + 9 |
| QC-165 | 2-Imidazol-1-yl-1-p-tolyl-ethanone hydrochloride | 17 + 4 | 69 + 16 |
| QC-166 | 1-Biphenyl-4-yl-2-imidazol-1-yl-ethanone hydrochloride | 2.1 + 0.7 | 3.0 + 0.7 |
| QC-167 | 1,10-bis-(1H-imidazol-1-yl)decane dihydrochloride | Activity not available | Activity not available |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-168 | 2-Imidazol-1-yl-1-phenyl-propan-1-one hydrochloride | 49 + 2 | >100 |
| QC-169 | 1,12-bis-(1H-imidazol-1-yl)dodecane dihydrochloride | Activity not available | Activity not available |
| QC-170 | 2-Imidazol-1-yl-1-pyren-1-yl-ethanone hydrochloride | Activity not available | Activity not available |
| QC-171 | 1-{4-(2-Bromo-phenylsulfanylmethyl)-2-[2-(4-chloro-phenyl)-ethyl]-[1,3]dioxolan-2-ylmethyl}-1H-imidazole hydrochloride | 6 + 1 | 12.3 + 0.5 |
| QC-172 | 1-(3-Phenyl-propyl)-1H-imidaozle hydrochloride | Activity not available | Activity not available |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
|---|---|---|---|
| QC-173 | 4-{2-[2-(4-Chloro-phenyl)-ethyl]-2-imidazol-1-ylmethyl-[1,3]dioxolan-4-ylmethoxy}-benzonitrile hydrochloride | 0.67 + 0.02 | 1.7 + 0.2 |
| QC-174 | 4-Phenyl-1-(5-phenyl-tetrazol-2-yl)-butan-2-one | Activity not available | Activity not available |
| QC-175 | 4-Phenyl-1-(5-phenyl-tetrazol-1-yl)-butan-2-one | >>100 | >>100 |
| QC-176 | 1-(5-Methylsulfanyl-tetrazol-2-yl)-4-phenyl-butan-2-one | >>100 | >>100 |
| QC-177 | 1-(5-Methylsulfanyl-tetrazol-1-yl)-4-phenyl-butan-2-one | >>100 | >>100 |
| QC-178 | [2-(2-Oxo-4-phenyl-butyl)-2H-tetrazol-5-yl]-acetic acid ethyl ester | >>100 | >>100 |

TABLE 1-continued

Structure, name and median inhibitory concentration (IC50) of select compounds

| Strucure | Name | IC$_{50}$ HO-1 (rat spleen)/ μM | IC$_{50}$ HO-2 (rat brain)/ μM |
| --- | --- | --- | --- |
| QC-179 | [1-(2-Oxo-4-phenyl-butyl)-1H-tetrazol-5-yl]-acetic acid ethyl ester | Activity not available | Activity not available |
| QC-180 | 1-(5-Methanesulfonyl-tetrazol-2-yl)-4-phenyl-butan-2-one | Activity not available | Activity not available |
| QC-181 | 1-(5-Methanesulfonyl-tetrazol-1-yl)-4-phenyl-butan-2-one | Activity not available | Activity not available |
| QC-182 | 4-Phenyl-1-tetrazol-2-yl-butan-2-ol Hydrochloride | >>100 | >>100 |
| QC-183 | 4-Phenyl-1-tetrazol-2-yl-butan-2-ol hydrochloride | Activity not available | Activity not available |
| QC-184 | 4-Phenyl-1-[1,2,4]triazol-1-yl-butan-2-ol hydrochloride | 10.0 + 0.2 | 54 + 12 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| 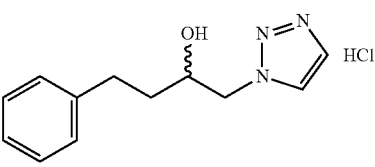<br>QC-185 | 4-Phenyl-1-[1,2,3]triazol-1-yl-butan-2-ol hydrochloride | Activity not available | Activity not available |
| 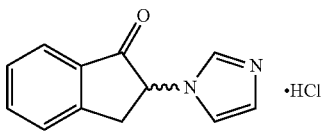<br>QC-186 | 2-Imidazol-1-yl-indan-1-one | >100 | >100 |
| 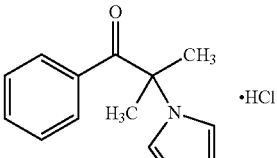<br>QC-187 | 2-Imidazol-1-yl-2-methyl-1-phenyl-propan-1-one | >100 | >100 |
| 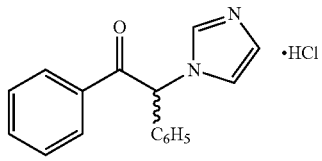<br>QC-188 | 2-Imidazol-1-yl-1,2-diphenyl-ethanone | 24 + 6 | >100 |
| 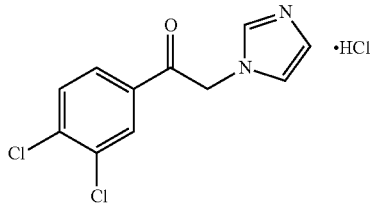<br>QC-189 | 1-(3,4-Dichloro-phenyl)-2-imidazol-1-yl-ethanone | 1.20 + 0.07 | 4.7 + 0.7 |
| 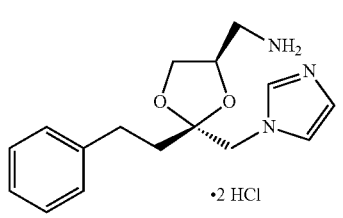<br>QC-190 | {2-[2-(phenyl)-ethyl]-2-imidazol-1-ylmethyl-[1,3]dioxolan-4-yl}-methylamine dihydrochloride | 21 + 3 | >100 |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-191 | 4-Phenyl-1-(3-phenyl-[1,2,4]triazol-1-yl)-butan-2-one | Activity not available | Activity not available |
| QC-192 | 1-(2-Phenethyl-[1,3]dioxolan-2-ylmethyl)-4-phenyl-1H-imidazole hydrochloride | Activity not available | Activity not available |
| QC-193 | 4-Phenyl-1-(4-phenyl-imidazol-1-yl)-butan-2-ol hydrochloride | Activity not available | Activity not available |
| QC-194 | 1-(4,5-Diphenyl-imidazol-1-yl)-4-phenyl-butan-2-ol | Activity not available | Activity not available |
| QC-195 | 1-(3,5-Diphenyl-[1,2,4]triazol-1-yl)-4-phenyl-butan-2-one | Activity not available | Activity not available |
| QC-196 | 1-Imidazol-1-yl-4-(4-methylphenyl)butan-2-one hydrochloride | Activity not available | Activity not available |

TABLE 1-continued

Structure, name and median inhibitory concentration (IC50) of select compounds

| Structure | Name | IC$_{50}$ HO-1 (rat spleen)/ μM | IC$_{50}$ HO-2 (rat brain)/ μM |
|---|---|---|---|
| QC-197 | 1-{2-[2-(4-Chloro-phenyl)-ethyl]-4-thiocyanatomethyl-[1,3]dioxolan-2-ylmethyl}-1H-imidazole hydrochloride | 3.0 + 0.9 | >100 |
| QC-198 | 1-Imidazol-1-yl-4-(4-isopropyl-phenyl)-butan-2-one hydrochloride | Activity not available | Activity not available |
| QC-199 | 1-[4-(4-Bromo-phenyl)-butyl]-1H-imidazole hydrochloride | 0.25 + 0.02 | 6.7 + 0.3 |
| QC-200 | 1-{2-[2-(4-Chloro-phenyl)-ethyl]-4-methoxymethyl-[1,3]dioxolan-2-ylmethyl}-1H-imidazole hydrochloride | 1.73 + 0.01 | 3.3 + 0.9 |
| QC-201 | 4-(4-tert-Butyl-phenyl)-1-(1H-imidazol-1-yl)-butan-2-one hydrochloride | Activity not available | Activity not available |
| QC-202 | 1-((1,3-Dioxolan-2-yl)methyl)-1H-imidazole hydrochloride | Activity not available | Activity not available |

TABLE 1-continued

Structure, name and median inhibitory concentration (IC50) of select compounds

| Structure | Name | $IC_{50}$ HO-1 (rat spleen)/ $\mu M$ | $IC_{50}$ HO-2 (rat brain)/ $\mu M$ |
|---|---|---|---|
| QC-203 | 1-(4-(1H-Imidazol-1-ylmethyl)benzyl)-1H-imidazole dihydrochloride | Activity not available | Activity not available |
| QC-204 | 4-(4-(1H-Imidazol-1-yl)-3-oxobutyl)phenyl benzoate hydrochloride | Activity not available | Activity not available |
| QC-205 | 1,3-Di-(1H-imidazol-1-yl)propan-2-ol dihydrochloride | Activity not available | Activity not available |
| QC-206 | 4-(4-Hydroxyphenyl)-1-(1H-imidazol-1-yl)butan-2-one hydrochloride | 382 | 251 |
| QC-207 | 1-Phenethyl-1H-imidazole | Activity not available | Activity not available |

III.II Oxidative Whole Cell & Mitochondrial Damage

Figure 3:
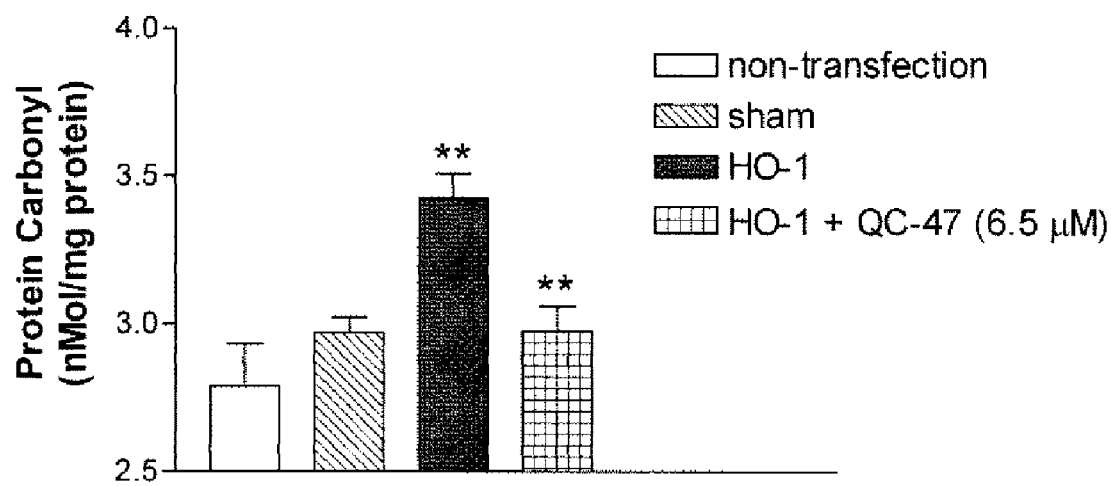
FIG. 3 is a bar graph depicting the effects of hHO-1 transfection on markers of oxidative stress in rat astroglial whole-cell compartments. Protein carbonyl contents in non-transfected astroglia, sham-transfected astroglia and cells transfected with hHO-1 plasmid DNA (4.0 μg per $10^6$ cells) in the presence and absence of QC-47 are depicted; n=46 per experimental group. Data shown represent means±SE.**$P<0.01$, relative to sham-transfected controls (HO-1 transfection) or relative to HO-1 transfected astroglia (HO-1 transfection+QC-47). All measurements were made on post-transfection day 3.
Figure 4:
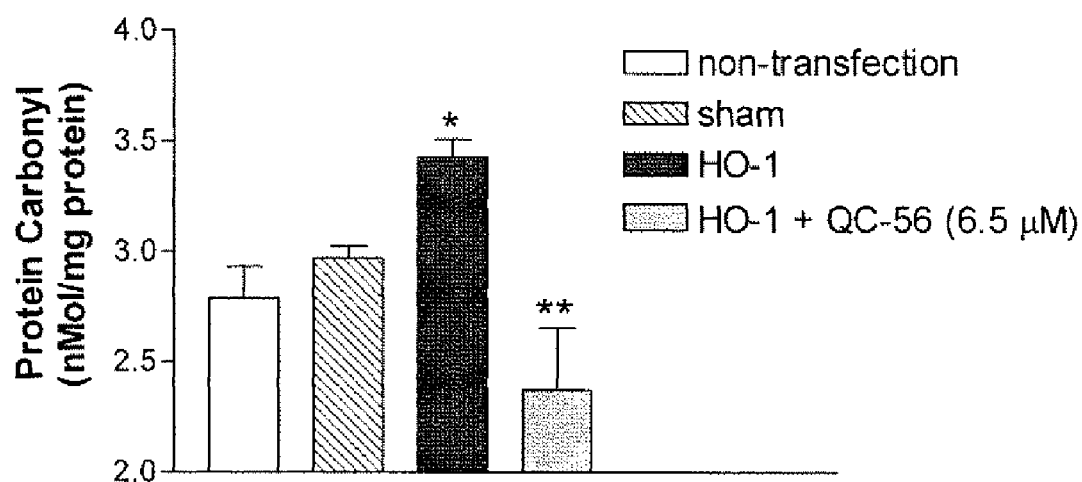
FIG. 4 is a bar graph depicting the effects of hHO-1 transfection on markers of oxidative stress in rat astroglial whole-cell compartments. Protein carbonyl contents in non-transfected astroglia, sham-transfected astroglia and cells transfected with hHO-1 plasmid DNA (4.0 μg per $10^6$ cells) in the presence and absence of QC-56 are depicted; n=4-6 per experimental group. Data shown represent means±SE. *$P<0.05$, relative to sham-transfected controls; **$P<0.01$, relative to HO-1 transfected astroglia. All measurements were made on post-transfection day 3.
Figure 5:
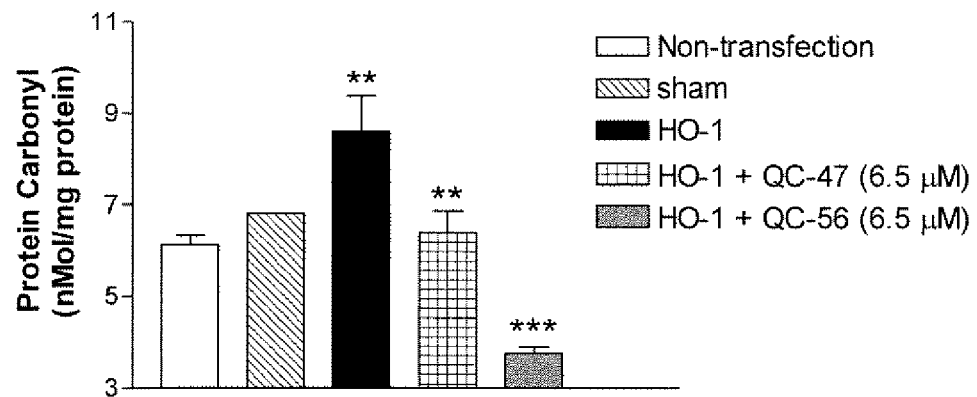
FIG. 5 is a bar graph depicting the effects of hHO-1 transfection on markers of oxidative stress in rat astroglial mitochondrial fractions. Protein carbonyl contents in non-transfected astroglia, sham-transfected astroglia and cells transfected with hHO-1 plasmid DNA (4.0 μg per $10^6$ cells) in the presence and absence of QC-47 or QC-56 are depicted; n=46 per experimental group (except for sham-transfection group). Data shown represent means±SE. $P<0.01$, relative to sham-transfected controls (HO-1 transfection) or relative to HO-1 transfected astroglia (HO-1 transfection+QC-47); *$P<0.001$, relative to HO-1 transfected astroglia. All measurements were made on post-transfection day 3.
Figure 6:
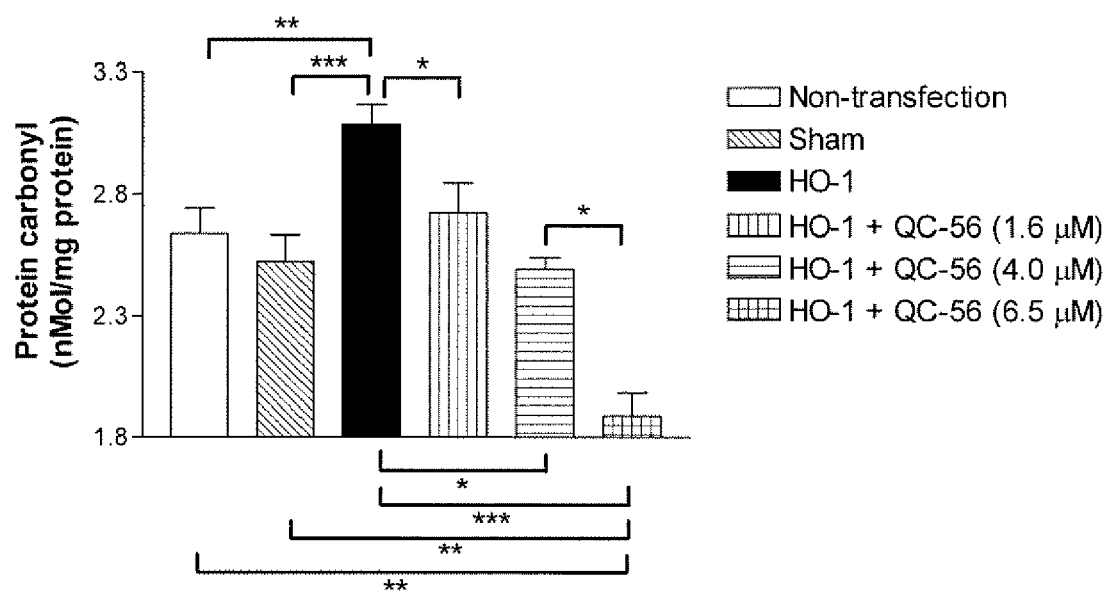
FIG. 6 is a bar graph depicting dose-dependant inhibition by QC-56 of protein carbonyls in whole-cell compartments of HO-1 transfected and control rat astroglia. Protein carbonyl contents in whole cell compartments in non-transfected astroglia, sham-transfected astroglia and cells transfected with hHO-1 plasmid DNA (4.0 μg per $10^6$ cells) in the presence and absence of QC-56 are depicted; n=46 per experimental group. Data shown represent means±SE. *$P<0.05$, $P<0.01$, *$P<0.001$. All measurements were made on post-transfection day 3.
Figure 7:
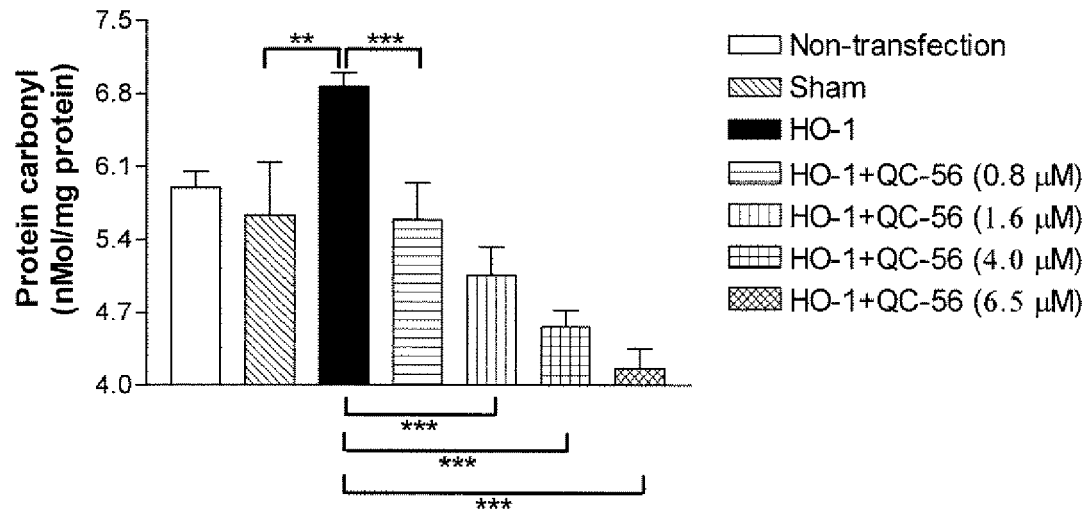
FIG. 7 is a bar graph depicting dose-dependant inhibition by QC-56 of protein carbonyls in mitochondrial fractions of HO-1 transfected and control rat astroglia. Protein carbonyl contents in mitochondrial fraction in non-transfected astroglia, sham-transfected astroglia and cells transfected with hHO-1 plasmid DNA (4.0 μg per $10^6$ cells) in the presence and absence of QC-56 are depicted; n=46 per experimental group. Data shown represent means±SE. *$P<0.05$, $P<0.01$, *$P<0.001$. All measurements were made on post-transfection day 3.

In primary rat astroglial cultures, transient transfection of hHO-1 significantly augmented the content of protein carbonyls in mitochondrial and whole cell compartments (FIGS. 3 and 5). Administration of 6.5 µM QC-47 & QC-56 significantly attenuated oxidative protein damage accruing from hHO-1 transfection in primary rat astroglial cultures (FIGS. 3-5). Both QC-47 & QC-56 produced significant dose dependant attenuations of oxidative protein damage in whole cell and mitochondrial compartments in the transiently transfected rat astroglial cultures (FIGS. 6 and 7).

III.III In Vitro HO-1 Expression and Ho Enzyme Activity

Figure 8:
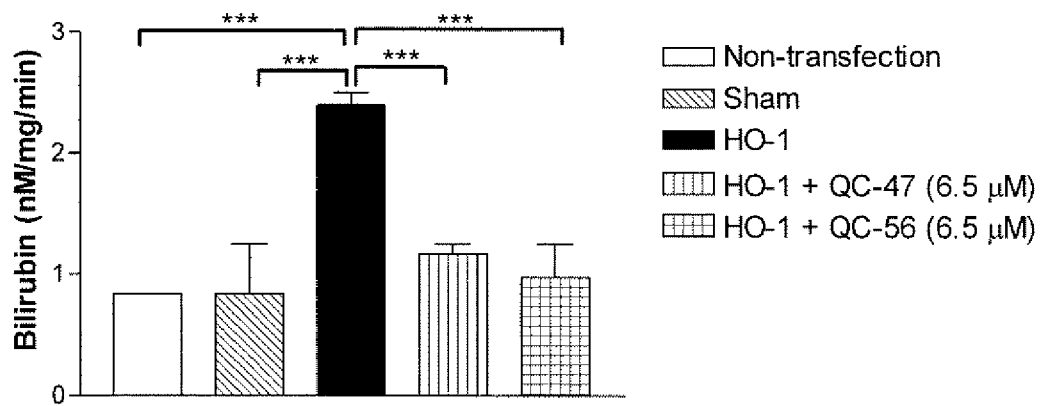
FIG. 8 is a bar graph depicting heme oxygenase activity in hHO-1-transfected and control astrocytes in the presence and absence of QC-47 and QC-56. n=4-6 sister cultures per experimental group. Data shown represent means±SE. ***$P<0.001$.

Flag-tagged HO-1 protein was expressed following transient transfection of primary rat astrocytes, transient transfection of rat C6 cells and transient transfection of human pancreatic tumor cells with peDNA3.1/Zeo.CMV.flag.hHO-1 (4.0 µg of plasmid DNA per $10^6$ cells). In these cells, heme oxygenase activity increased about 2.5 fold in parallel with hHO-1 protein expression. Administration of 6.5 µM QC-47 & QC-56 significantly attenuated heme oxygenase activity in the transiently transfected cells without affecting the expression level of flag-tagged HO-1 protein (FIG. 8).

III.IV Cell Proliferation

Figure 9:
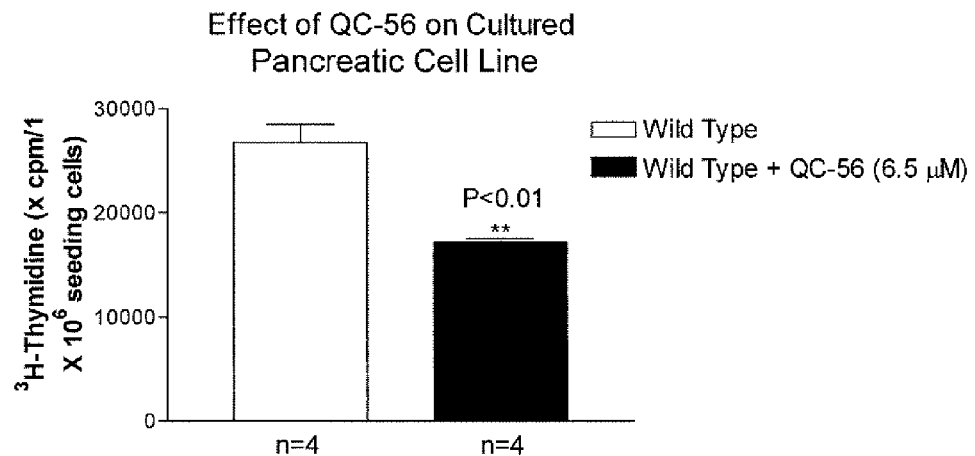
FIG. 9 is a bar graph depicting growth inhibitory effects of QC-56 on cultured pancreatic cell line. Cells were seeded on 24 well plates at $1 \times 10^6$ cells per mL per well. On day 3 post-seeding, cells were incubated with $^3$H-thymidine (0.73 μCi/mL) and QC-56 (6.5 μM) for 18 h. Cells were harvested onto glass fiber filters for scintillation counting.
Figure 10:
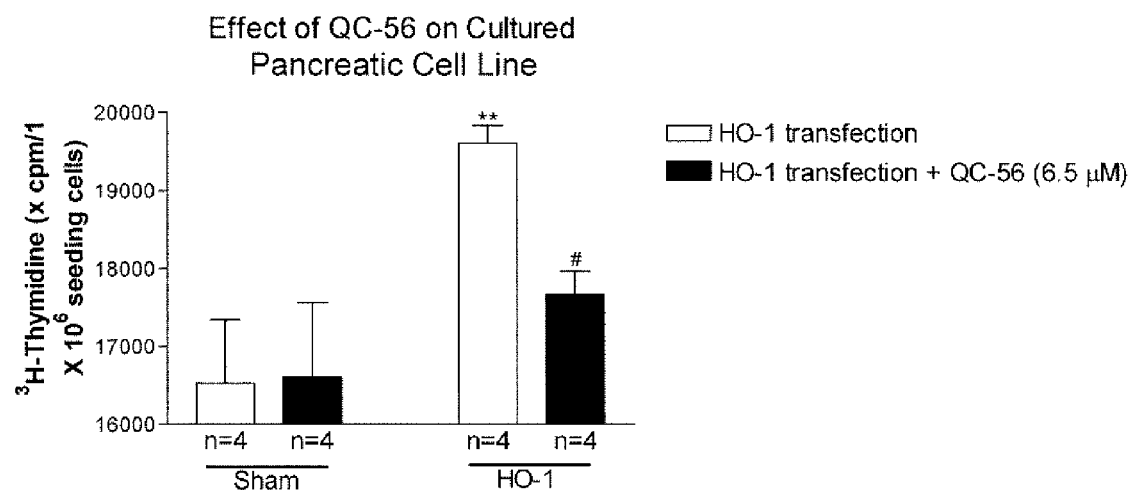
FIG. 10 is a bar graph depicting growth inhibitory effects of QC-56 on cultured pancreatic cell line transfected with hHO-1. At 24 h post-transfection, cells were incubated with $^3$H-thymidine (0.73 μCi/mL) and QC-56 (6.5 μM) for 18 h. Cells were harvested onto glass fiber filters for scintillation counting. ** $P<0.01$, compared with sham-transfection group; # $P<0.05$ compared with hHO-1 transfection group.
Figure 11:
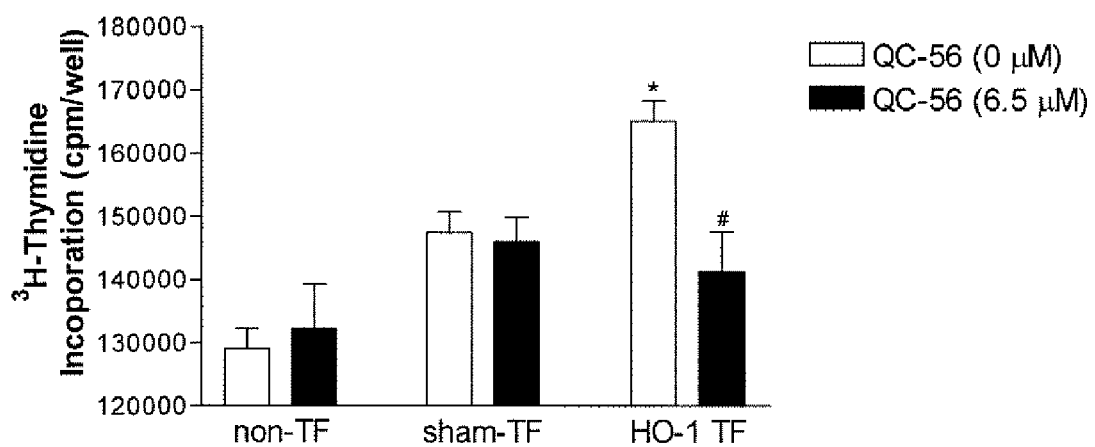
FIG. 11 is a bar graph depicting growth inhibitory effects of QC-56 on cultured rat glioma (C6) cells transfected with hHO-1. At 48 h post-transfection, cells were incubated with $^3$H-thymidine (0.73 μCi/mL) and QC-56 (6.5 μM) for 18 h. Cells were harvested onto glass fiber filters for scintillation counting. n=5 to 8 per experimental group. * $P<0.01$, compared with sham-transfection group; # $P<0.05$ compared with hHO-1 transfection group.
Figure 12:
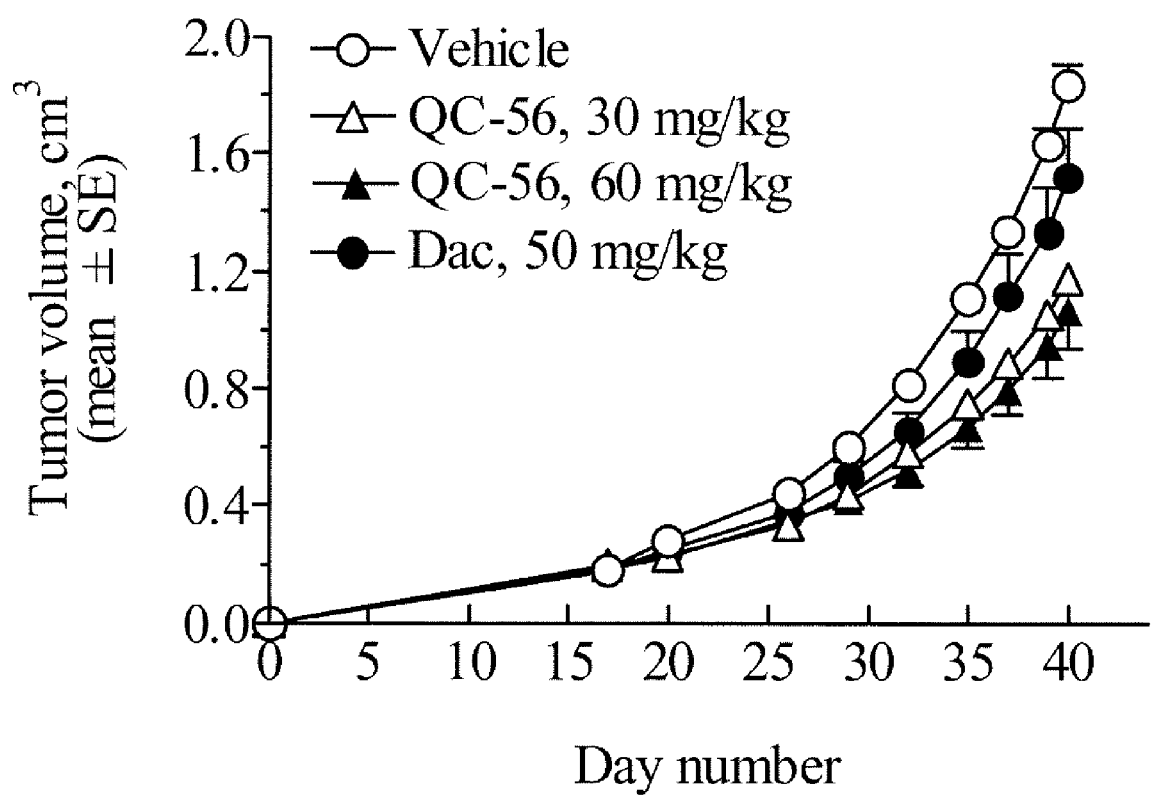
FIG. 12 is a line graph depicting the comparative impact of QC-56 on tumor growth for animals of the Human Melanoma Model (SKMEL-V).
Figure 13:
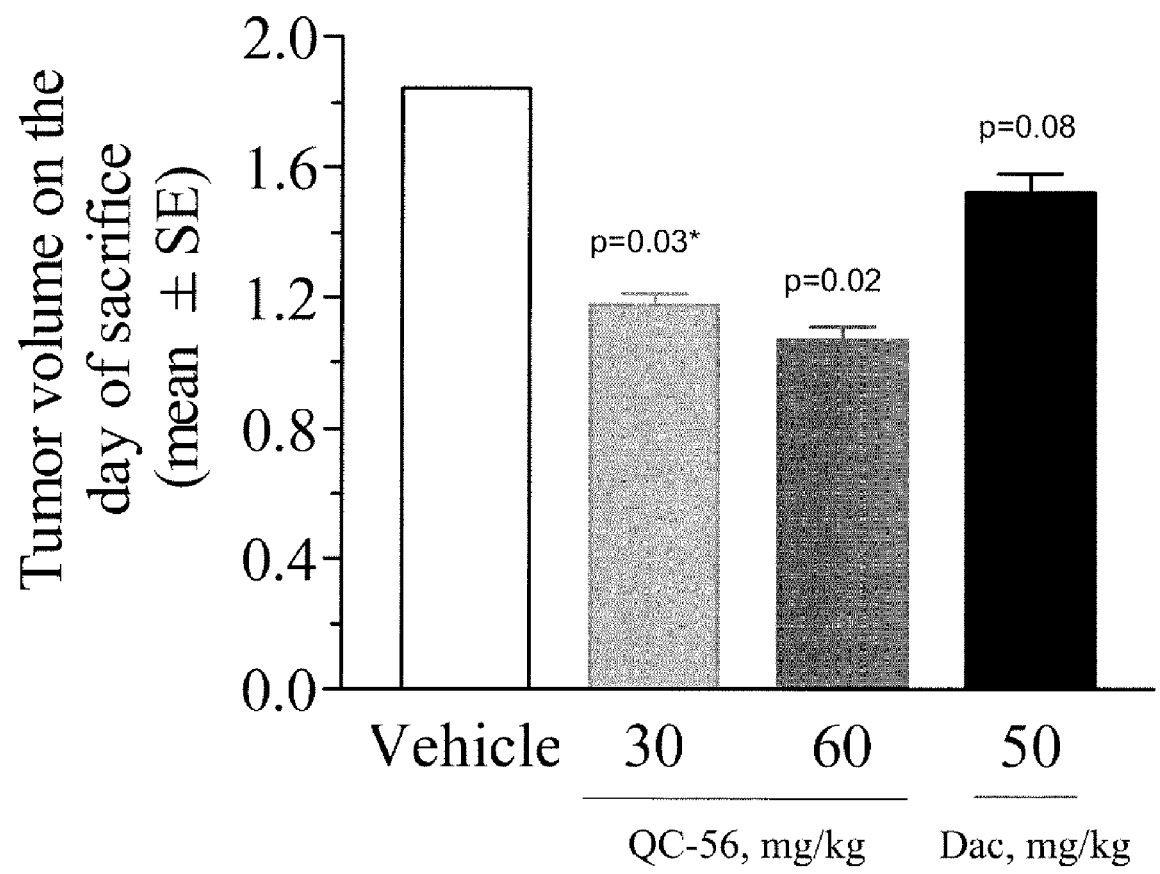
FIG. 13 is a bar graph depicting the comparative impact of QC-56 on tumor growth for animals of the Human Melanoma Model (SKMEL-V) (* t-test).
Figure 14:
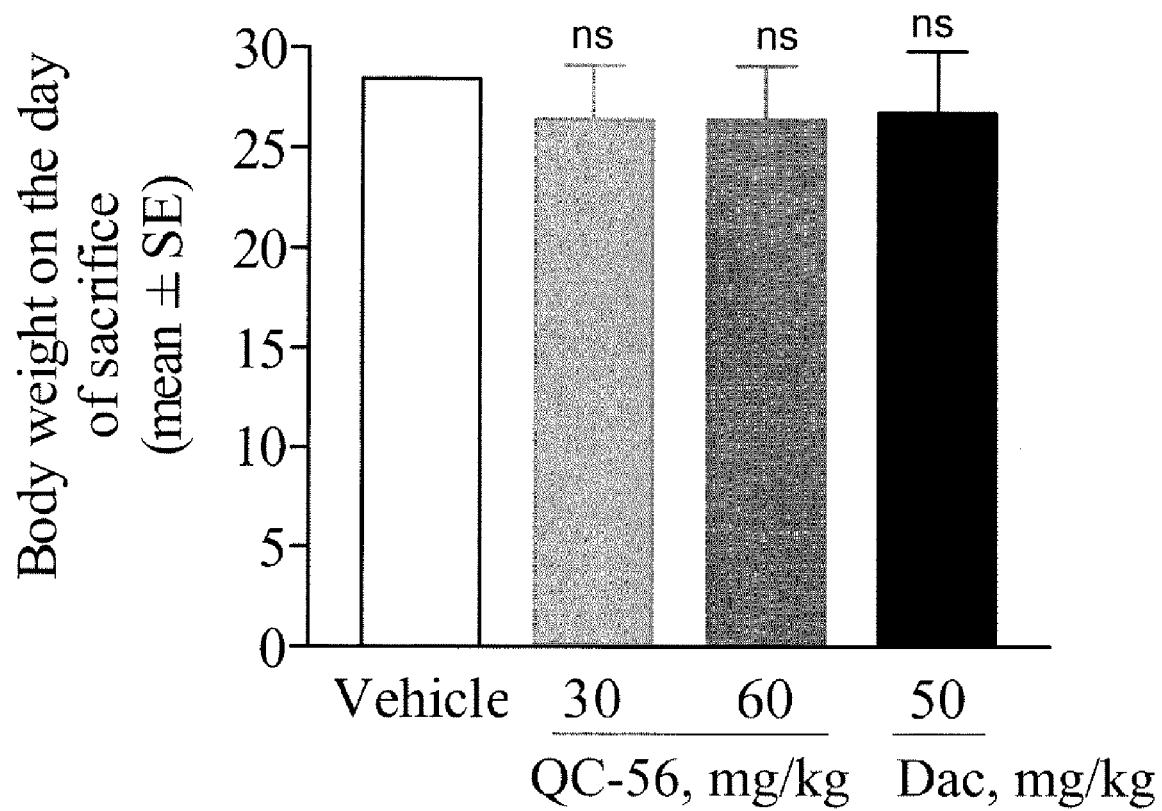
FIG. 14 is a bar graph depicting the body weights of animals treated with vehicle (control), QC-56, and Dacarbazine prior to sacrifice (ns, not significant, t-test).
Figure 15:
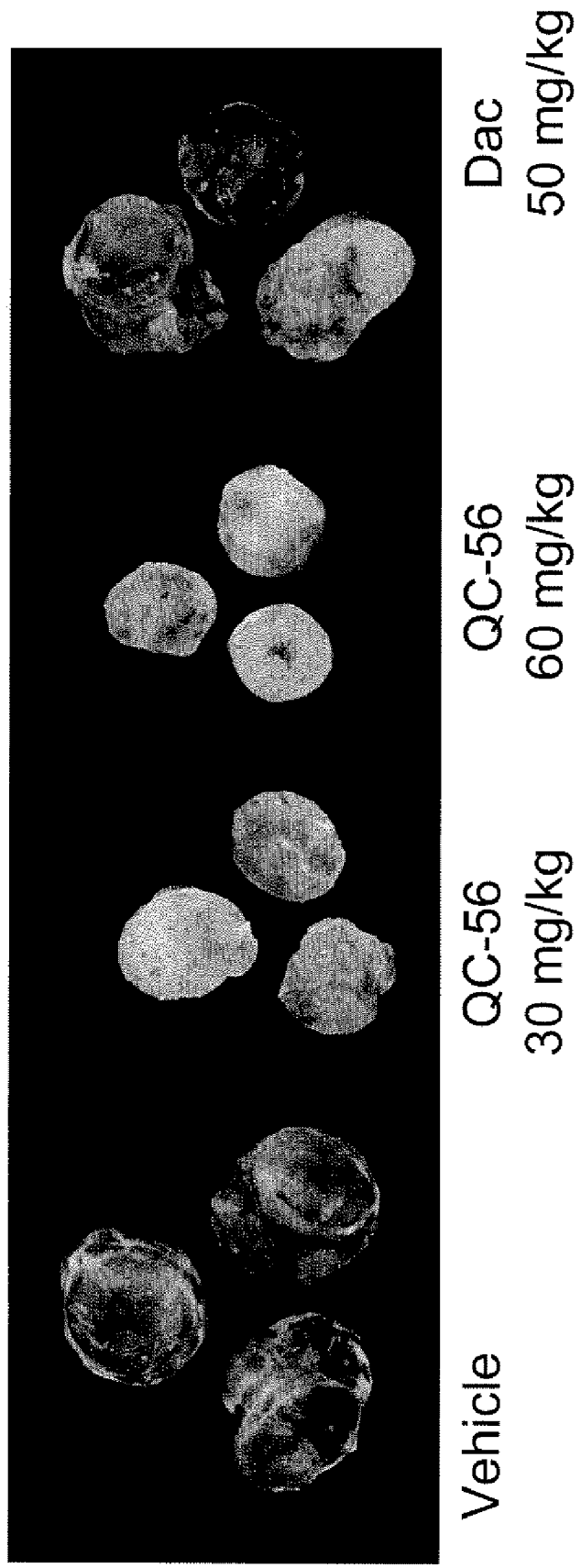
FIG. 15 is a photographic depiction of tumor appearance after surgery on the day of sacrifice for animals of the Human Melanoma Model (SKMEL-V) treated with vehicle (control), 30 mg/kg QC-56, 60 mg/kg QC-56, and 50 mg/kg Dacarbazine.
Figure 16:
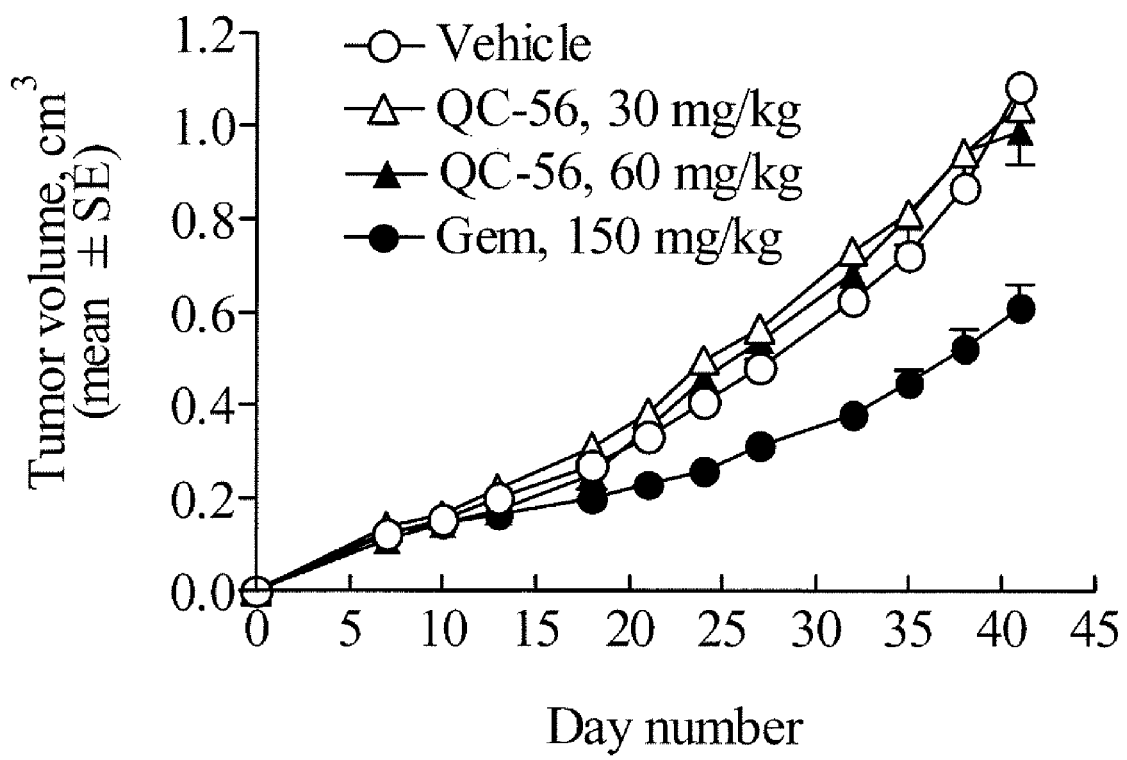
FIG. 16 is a line graph depicting the comparative impact of QC-56 on tumor growth for animals of the Human Pancreatic Cancer Model (Panc-1).
Figure 17:
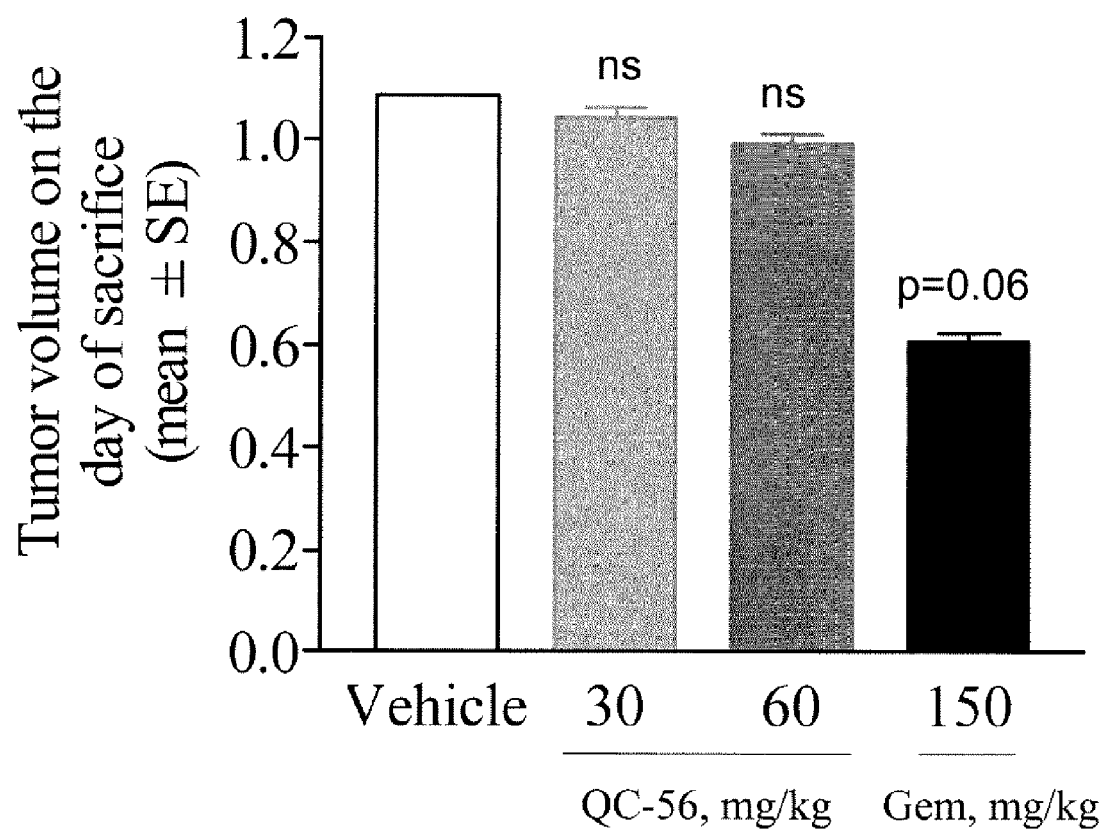
FIG. 17 is a bar graph depicting the comparative impact of QC-56 on tumor growth for animals of the Human Pancreatic Cancer Model (Panc-1) (ns, not significant, t-test).
Figure 18:
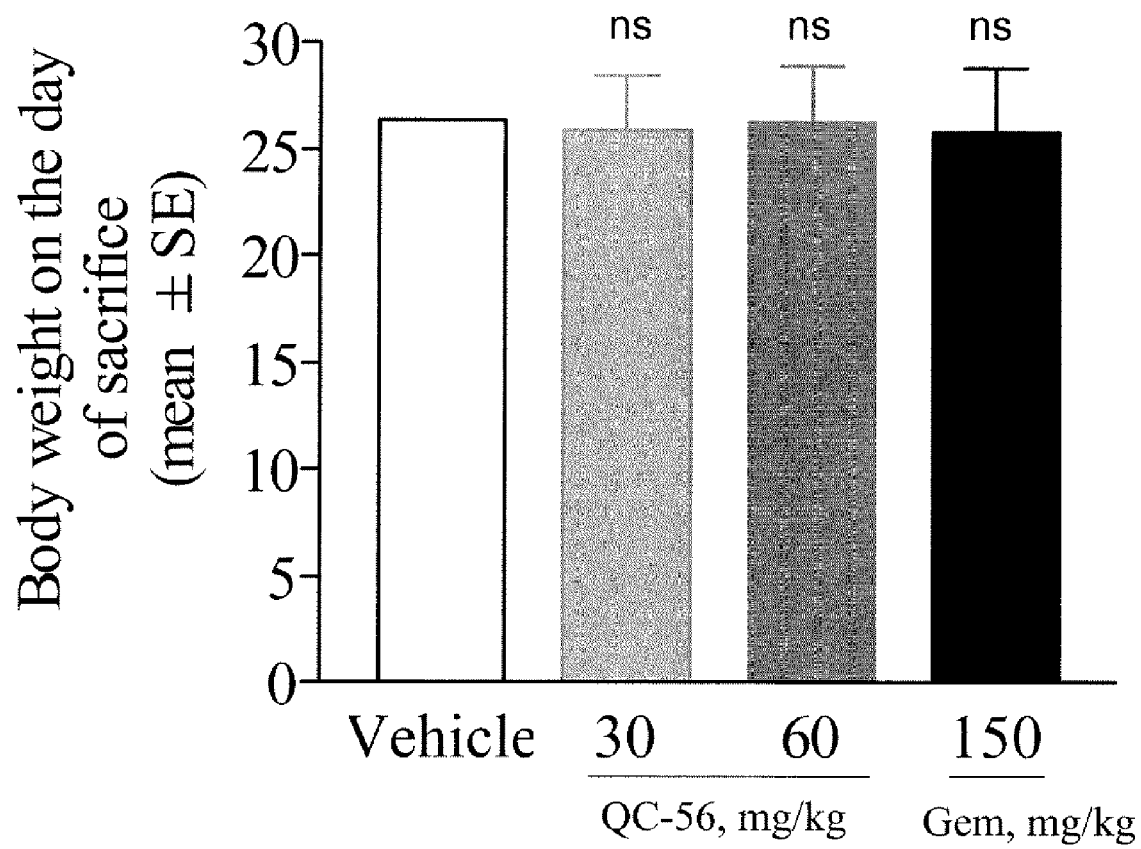
FIG. 18 is a bar graph depicting the body weights of animals treated with vehicle (control), 30 mg/kg QC-56, 60 mg/kg QC-56, and 150 mg/kg Gemcitabine prior to sacrifice (ns, not significant, t-test).
Figure 19:
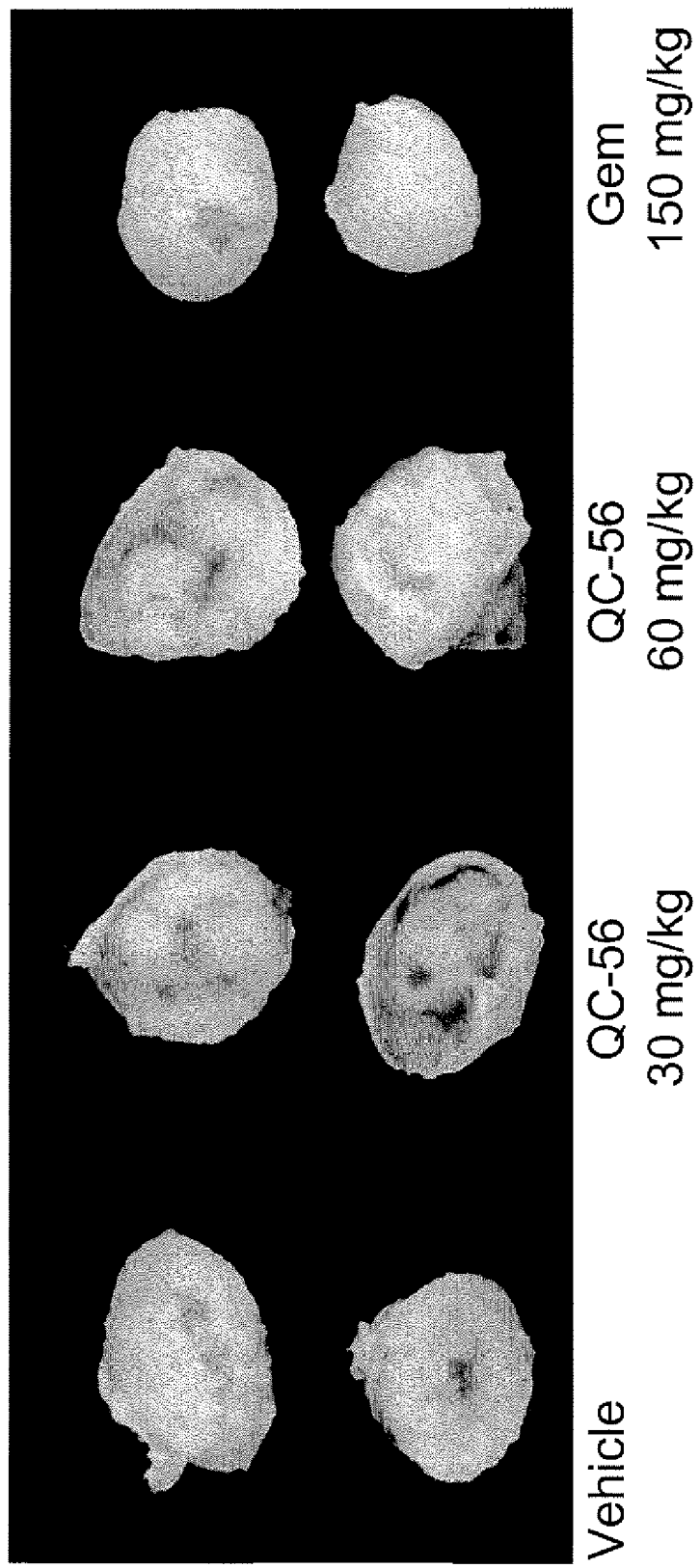
FIG. 19 is a photographic depiction of tumor appearance after surgery on the day of sacrifice for animals of the Human Pancreatic Cancer Model (Panc-1) treated with vehicle (control), 30 mg/kg QC-56, 60 mg/kg QC-56, and 150 mg/kg Gemcitabine.

Administration of 6.5 µM QC-56 significantly attenuated $^3$H-thymidine incorporation in human pancreatic tumor cells compared to the untreated cells (FIG. 9). $^3$H-thymidine incorporation in rat C6 glioma and human pancreatic tumor cells was augmented following transient transfection with hHO-1 cDNA (4.0 µg of plasmid DNA per $10^6$ cells) relative to sham- and non-transfected preparations (FIGS. 10 and 11). 6.5 µM QC-56 treatment significantly attenuated the effects of hHO-1 transfection on $^3$H-thymidine incorporation in human pancreatic tumor cells (FIG. 10) and in rat C6 glioma cells (FIG. 11).

IV. In Vivo Analysis

IV.I Antitumor Activity of QC-56 Using Immuno-Compromized Mice Bearing the Human Pancreatic Model Panc-1 and the Human Melanoma Model SKMEL-V+

IV.I (i) Test Agent

QC-56 was stored at −20° C. and protected against light. The administered solution was prepared by dissolving the powder in sterile water. The solution was mixed vigorously by a vortex machine for 1 minute prior to administration.

IV.I (ii) Gemcitabine and Dacarbazine

Clinical grade gemcitabine and dacarbazine were purchased from the Oncology Pharmacy at the Jewish General Hospital (Montreal, Quebec, Canada) and stored at 4° C.

IV.I (iii) Bioassay

Species and strain: Mouse (*Mus musculus*); SCID, male
Age at dosing initiation: 8 weeks old.
Body weight at dosing initiation: At the time of dosing, the mean body weight was 18.8±1.5 g.
Supplier: Charles River Laboratories, Inc., St-Constant, Quebec.
Acclimation: Mice were acclimated to laboratory conditions for 1 week prior to dosing.
Identification: Mice were identified by ear punch combination.
Housing: Mice were housed in groups of 4-5 per cage. They were fed Certified Diet™ #5001 (pellets; Purina Mills, Inc., St. Louis, Mich., U.S.A.) and autoclaved tap water were provided ad libitum.
Environment conditions: Temperature 22° C.; Relative humidity 40-50%; light/dark cycles: 12 h.

IV.I (iv) Cancer Models

Human pancreatic carcinoma cells ("Panc-1 cells") were originally received from the ATCC (American Type Culture Collection). Early passage Panc-1 cells (tested free of mycoplasma) were grown to 60% confluence in RPMI-1640 medium supplemented with amino acids, 10% fetal bovine serum, 4.5 g/L glucose, 10 mM Hepes, 1.5 g/L sodium bicarbonate, 10 mM sodium pyruvate, 2 mM glutamine, 0.01 mg/mL bovine insulin, and antibiotics. Cell harvesting was performed using trypsin-EDTA solution. Cells were centrifuged and washed twice with phosphate buffered saline solution and were re-suspended at a dilution of $1 \times 10^6$ cells/0.1 mL.

Human melanoma cells ("SKMEL-V cells") were derived from SKMEL-24 cells (ATCC) by over expression of mouse VEGF. Early passage cells (tested free of mycoplasma) were grown to 60% confluence in RPMI-1640 medium supplemented with 10% fetal calf serum, and antibiotics. Cell harvesting was performed using trypsin-EDTA solution. Cells were centrifuged and washed twice with phosphate buffered saline solution and were re-suspended at a dilution of $1 \times 10^6$ cells/0.1 mL.

IV.I (v) Cell Implantation

Exponentially growing cells were suspended at a dilution of $1\text{-}2 \times 10^6$ cells/0.1 mL. Cell viability was confirmed by trypan blue staining. Only those cells with >95% viability were used for in-vivo studies. Two million cells suspended in 0.1 mL phosphate buffer solution were implanted subcutaneously into the axillary region of the right flank of recipient SCID mice.

IV.I (vi) Tumor Measurement

Once tumors reached a size of approximately 0.7 cm³, they were removed under sterile condition, sliced into small pieces under a stereo-microscope. Each tissue piece was then re-inoculated subcutaneously. Only pieces of approximately the same size and with no signs of necrosis were used.

Primary tumor growth was monitored every second to fourth day using calipers. Relative tumor volume (cm³) was determined by the following equation (II):

$$\frac{[\text{Length(cm)} \times \text{Width(cm)}^2]}{2} \qquad (II)$$

IV.I (vii) Assignment to Experimental Groups

Once tumors became palpable, mice were randomized into experimental groups and the treatment was initiated. QC-56 was dissolved in sterile physiologic solution and was administered by intraperitoneal injection. Gemcitabine and dacarbazine (human clinical grade) were administered by intraperitoneal route using the clinical solution. When mice showed signs of toxicity or distress, treatment was delayed.

IV.I (viii) Terminal Procedures

At the end of the experiment, mice were sacrificed by cervical dislocation and full autopsies were conducted. A picture was taken of tumors from randomly selected mice. The tumors were then fixed in formalin for pathology examination.

IV.I (viii) Statistics

All data in this study are presented as mean±SE. Statistical analyses were performed by one-way ANOVA followed by Newman-Keuls post-hoc comparisons to assess significant main effects within groups. Statistical significance was set at $p<0.05$.

IV.II Evaluation of Toxicity and In-Vivo Activity of QC-56 in Immuno-Compromised Mice Bearing the Human Pancreatic Model Panc-1 and the Human Melanoma Model SKMEL-V+

QC-56 was found to be toxic when given intraperitoneally at a single dose of >100 mg/kg. QC-56 at 50 mg/kg was found to be well tolerated after multiple administrations. Doses between 60 and 100 mg/kg were not tested. As indicated in FIGS. 12-19, QC-56 was well tolerated at repeated doses of 30 and 60 mg/kg with minor changes in body weights with no apparent toxicity and was found to induce a clear anti-tumor activity in the melanoma model SKMEL-V+ but not in the pancreatic cancer model Panc-1. The dose-dependent effect was not apparent as only two dose levels were tested in this study. However, QC-56 was found to be quite active at both 30 and 60 mg/kg dose levels. A t-test comparison clearly shows statistically significant differences between the control groups vs the groups treated with QC-56 at both dose levels vs the group treated with dacarbazine at the time of sacrifice. QC-56 was found to be significantly more potent than dacarbazine, which is a widely used drug for metastatic melanoma.

V. Discussion

A role of human heme oxygenase-1 (hHO-1) in mediating oxidative damage to mitochondrial proteins, partial growth arrest and cell death in primary rat astrocytes is herein demonstrated. Moreover, overexpression of the hHO-1 gene in two transformed cell lines, namely rat C6 glioma cells and human pancreatic tumor cells, has been shown to stimulate cell proliferation.

Representative compounds of the general formula (I) described above have been shown to selectively inhibit heme oxygenase-1 activity (Table 1). A method of inhibiting heme oxygenase-1 with the described substituted imidazoles is also provided.

Transient transfection of rat primary astroglia with the hHO-1 gene was shown to increase the amount of protein carbonyls present in both mitochondrial fractions as well as whole cell extracts compared to non-transfected and sham transfected cells. Protein carbonyl content is a widely recognized measure of oxidative protein modification (Buss, 1997; Winterbourn, 1999). Administration of the compounds (2R,4S)-2-(2-(4-chlorophenyl)ethyl)-2-((1H-imidazol-1-yl)methyl)-4-(fluoromethyl)-1,3-dioxolane hydrochloride (QC-47) and 2-(2-(4-bromophenyl)ethyl)-2-((1H-imidazol-1-yl)methyl)-1,3-dioxolane hydrochloride (QC-56), in a dose dependent manner significantly decreased the amount of oxidative damage induced by hHO-1 overexpression (FIGS. 3-7).

Similarly, transient transfection of rat primary astrocytes with the hHO-1 gene was shown to increase the overall level of heme oxygenase activity in these cultures. Heme oxygenase acts as a catalyst in the breakdown of pro-oxidant heme and hemoproteins to the radical-scavenging bile pigments, biliverdin and bilirubin (Stocker et al. 1987; Nakagami et al. 1993; Llesuy and Tomaro 1994; IDore et al. 1999; Baranano and Snyder 2001). Therefore, heme oxygenase activity can be evaluated by measuring the total amount of bilirubin in the culture. Administration of the substituted imidazoles, (2R,4S)-2-(2-(4-chlorophenyl)ethyl)-2-((1H-imidazol-1-yl)methyl)-4-(fluoromethyl)-1,3-dioxolane hydrochloride (QC-47) and 2-(2-(4-bromophenyl)ethyl)-2-((1H-imidazol-1-yl) methyl)-1,3-dioxolane hydrochloride (QC-56), significantly decreased the activity of heme oxygenase-1 in these cultures FIG. 8).

In a human pancreatic cell culture, it was shown that the basal rate of cellular proliferation could be reduced by exposing the culture to a substituted imidazole of the present invention. In particular, human pancreatic cell cultures, exposed to 2-(2-(4-bromophenyl)ethyl)-2-((1H-imidazol-1-yl)methyl)-1,3-dioxolane hydrochloride (QC-56), showed a marked reduction in the rate of cellular proliferation when compared to the basal rates of proliferation for these particular cells (FIG. 9). Furthermore, when human pancreatic tumor cells and rat C6 glioma cells were transiently transfected with the hHO-1 gene, cellular proliferation in these cultures significantly increased compared to non-transfected and sham transfected cultures. This increase in proliferation can be attenuated by treatment of the culture with a substituted imidazole of the present invention, such as 2-(2-(4-bromophenyl)ethyl)-2-((1H-imidazol-1-yl)methyl)-1,3-dioxolane hydrochloride (QC-56). Similar results have been demonstrated in rat C6 glioma, wherein hHO-1 transfection caused the glioma cells to proliferate more rapidly than normal and this rate of proliferation was attenuated by treatment with a substituted imidazole of the present invention, in particular 2-(2-(4-bromophenyl)ethyl)-2-((1H-imidazol-1-yl)methyl)-1,3-dioxolane hydrochloride (QC-56) (FIG. 11).

These results indicate that the compounds described herein can modulate heme oxygenase-1 activity and oxidative damage, both of which can ultimately lead to cell death. Moreover, these compounds can attenuate cellular proliferation in transformed cells.

In a pilot study involving a total of 38 SCID male mice implanted with SKMEL-V human melanoma cells, the tumor volumes were found to be statistically significantly smaller in mice treated with QC-56 at 30 mg/kg (P<0.03) and 60 mg/kg (P<0.02) dose levels, compared with those treated with the vehicle alone or treated with dacarbazine (50 mg/kg, P<0.08). QC-56 was well tolerated in mice at both dose levels after multiple administrations, and was found to be significantly more potent than dacarbazine at both dose levels.

VI. Preclinical Studies of Drug Combinations Using HCT116, OVCAR3, PC-3, B16-BL6, and MDA231-M Preclinical Cancer Models Data from this large scale pre-clinical study confirm the above findings, showing a statistically significant reduction in tumor volumes in mice treated with QC-56 compared to untreated mice and mice treated with Dacarbazine. In addition, QC-56 was found to induce wide spectrum anti-tumor activity both in-vitro and in-vivo against a number of drug resistant and invasive tumors and synergized with a number of chemotherapy drugs.

QC-56 was well tolerated with no apparent signs of toxicity in mice at multiple doses up to 100 mg/kg dose compared to standard chemotherapy which exhibited significant toxicity and adverse effects. Robust anti-tumor activity was seen in the human prostate carcinoma model, human melanoma model, metastatic mouse melanoma model and human colorectal carcinoma model. The activity of QC-56 in these models was equal to or significantly greater than that of standard chemotherapeutic agents, namely, Taxol™ for prostate cancer, Dacarbazine for melanoma, and 5-Fluorouracil (5-FU) for colorectal cancer. In the PC-3 prostate cancer model, QC-56 showed significant activity (approximately 85% inhibition compared to vehicle alone and was about 3 times more effective in inhibiting tumor growth compared to Taxol™ alone) when combined with Taxol™. The combination of QC-56 and Taxol™ was well tolerated with mice exhibiting a significant gain in body weight. These studies clearly showed that the activity of QC-56 combined with Taxol™ significantly inhibited lung metastasis formation in mice. Furthermore, QC-56-treated tumors exhibited a significant reduction in the density of blood vessels that are critical for tumor growth.

These results establish that compounds of the present invention (as exemplified by QC-56), either alone or in combination with other chemotherapeutic agents, can be used for the treatment of metastatic and drug-resistant human cancers in a safe and effective fashion.

VI.I Material and Methods
VI.I (I) Test Agents

QC-56 was stored at −80° C., protected against light. Stock solutions were prepared freshly and stored at −80° C. Each solution was used for two-three consecutive administrations. In this case, tubes were thawed at room temperature before administration.

Taxol™, Cisplatin, Dacarbazine, 5-FU, and Herceptin (clinical grade) were purchased from the Oncology Pharmacy at the Jewish General Hospital and stored at 4° C. except for cisplatin, which was kept at RT (room temperature).

VI.I (ii) Bioassay
VI.I (ii)(a) Mouse Strain

Species and strain: Mouse (*Mus musculus*); female SCID (MDA231 and OVCAR3), male SCID (PC-3, HCT116); male CD57 B16 mice (BL16-BL6)

Age: 6-8 weeks old.

Supplier: Charles River Laboratories, Inc., St-Constant, Quebec, Canada.

Acclimation: Mice were acclimated to laboratory conditions for approximately 1 week prior to tumor cell inoculation.

Identification: Mice were identified by ear punch combination.

Housing: Mice were housed in groups of 3-5 in a designated animal facility with a temperature of 22° C., a relative humidity of 40-50%, and a 12 hr light/dark cycle. Mice were fed pellets (Purina Mills, Inc. Certified Diet™ #5001) and autoclaved tap water ad libitum.

Environment: Temperature 22° C.; Relative humidity 40 50%; light/dark cycles, 12 h.

VI.I (ii)(b) Tumor Cells

OVCAR-3 (human ovarian carcinoma). These cells were originally received from the ATCC. Early passage OVCAR-3 ovarian carcinoma cells (tested free of mycoplasma), were grown to 60% confluence in RPMI-1640 medium (Mediatech) supplemented with amino acids, 10% fetal bovine serum, 4.5 g/L glucose, 10 mM Hepes, 1.5 g/L sodium bicarbonate, 10 mM sodium pyruvate, 2 mM glutamine, 0.01 mg/mL bovine insulin, and antibiotics. Cell harvesting was performed using trypsin-EDTA solution. Cells were centrifuged and washed twice with phosphate buffered saline solution and were re-suspended at a dilution of $1 \times 10^6$ cells/0.1 mL.

PC-3 (human prostate carcinoma). These cells were originally received from the ATCC. Early passage cells (tested free of mycoplasma) were grown to 60% confluence in DMEM medium supplemented with 10% fetal bovine serum, and antibiotics. Cell harvesting was performed using trypsin-EDTA solution. Cells were centrifuged and washed twice with phosphate buffered saline solution and were re-suspended at a dilution of $1 \times 10^6$ cells/0.1 mL.

MDA231-M2. The metastatic cell variant MDA231-M2 was established from metastatic lung nodules induced in vivo by the corresponding parental cells engineered to overexpress the human ErbB2 cDNA and implanted into the mammary fat pad of SCID mice. Once primary tumor reached a size of 1 cm$^3$, tumor was removed and animals were maintained for an additional period of time (>6 months). After autopsy, lung nodules were isolated, expanded in culture, and reinoculated into the mammary fat pad for further selection. The metastatic cell variant MDA231-M2 was selected and established as highly invasive compared to parental cells. These cells were maintained in RPMI-1640 (Mediatech) medium supplemented with 10% fetal bovine serum and penicillin/streptomycin. The cells were tested to be free of mycoplasma.

SKMEL 28-V+ cells (human melanoma). These cells were originally from the ATCC and then engineered to overexpress VEGF. Cells were grown to 60% confluence in DMEM (Life Technologies) medium supplemented with 10% fetal bovine serum, 4.5 g/L glucose, 10 mM Hepes, 1.5 g/L sodium bicarbonate, 10 mM sodium pyruvate, 2 mM glutamine, and penicillin/streptomycin. The cells were tested to be free of mycoplasma.

B16-BL6 cells (mouse melanoma). B16-BL6 metastatic variant was derived from B16-F10. This cell variant was obtained from Dr. Linda D). Williams, Dept. of Cancer Biology, MD Anderson Cancer Center, Texas, USA. Cells were maintained in culture in a complete Eagle's minimum essential medium supplemented with 10% fetal bovine serum, L-glutamine, sodium pyruvate, nonessential amino acids, vitamin solution, and 1% penicillin-streptomycin antibiotics. Cells were maintained at 37° C. in a humidified atmosphere (5% $CO_2$, 95% air).

VI.I (ii)(c) Cell Implantation and Tumor Measurement.

Figure 20:
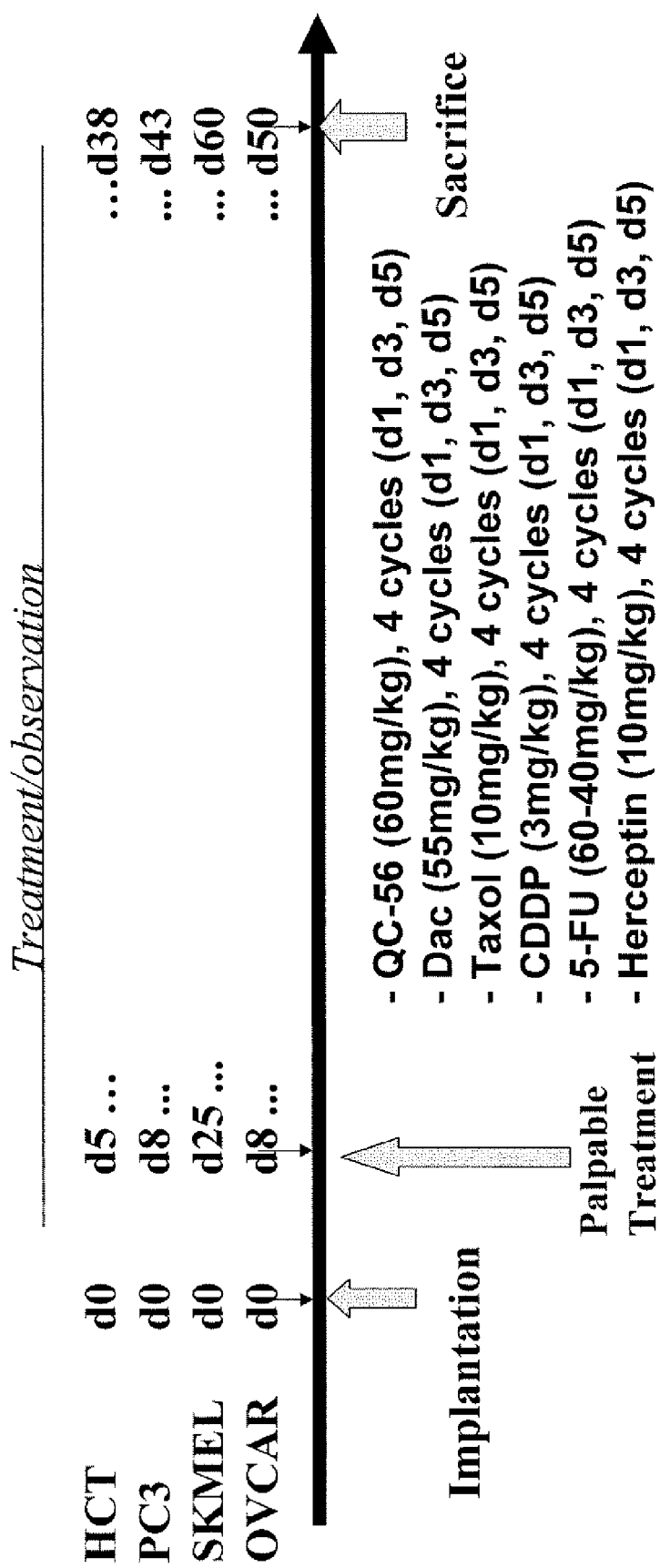
FIG. 20 illustrates the treatment schedule for preclinical testing of QC-56 in HCT, PC-3, SKMEL and OVCAR cancer models.
Figure 21:
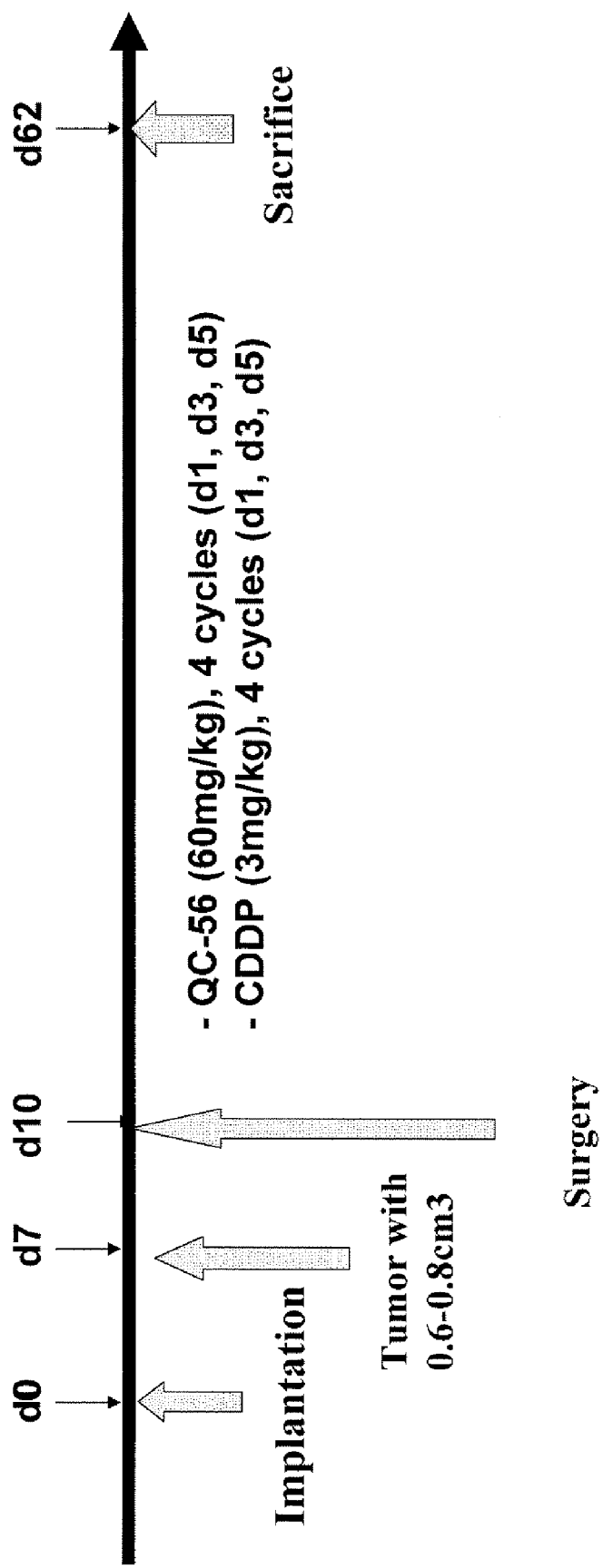
FIG. 21 illustrates the treatment schedule for preclinical testing of QC-56 in B16-BL6 model.

Exponentially growing cells were harvested using trypsin-EDTA solution. Cells were centrifuged and washed twice with phosphate buffered saline solution and were re-suspended at a dilution of $12 \times 10^6$ cells/0.1 mL. Cell viability was confirmed by trypan blue staining. Only those cells with >95% viability and "normal" morphology were used for in-vivo. One to 2 millions cells suspended in 0.1 mL phosphate buffer solution was implanted into the mammary fat pad (MCF7) or subcutaneously into the axillary region of the right flank of recipient SCID mice. All animals were inoculated at the same site. When tumors become palpable, mice were then blindly randomized to various experimental groups (based on the experimental plan outlined in Table 2) and treatment was initiated 24 h later (d1) as illustrated in FIGS. 20 and 21.

TABLE 2

Experimental design

| Group | OVCAR-3 | HCT116-ErbB | PC-3 | SKMEL | B16-BL6 |
|---|---|---|---|---|---|
| Vehicle | 8 | 8 | 8 | 8 | 8 |
| QC-56, 60 mg/kg | 8 | 8 | 8 | 8 | 8 |
| Dacarbazine, 60 mg/kg | — | — | — | 8 | 8 |
| QC-56 +Dacarbazine | — | — | — | 8 | 8 |
| Cisplatin, 3 mg/kg | 8 | — | — | — | — |
| QC-56 + Cisplatin | 8 | — | — | — | — |
| Taxol ™ | — | — | 8 | — | — |
| QC-56 + Taxol ™ | — | — | 8 | — | — |
| 5-FU | — | 8 | — | — | — |
| QC-56 + 5-FU | — | 8 | — | — | — |
| Spared | 3 | 3 | 3 | 3 | 3 |
| Total # mice | 36 | 36 | 36 | 36 | 36 |

End points: Body weight: every third or fourth day
Tumor volume: every second to fourth day
Tumor weight at sacrifice
Complete autopsy at sacrifice
Incidence of lung metastases when applicable
Fixation of tumor tissue for future pathology/immunohistochemistry studies In the case of B16-BL6, when the primary tumor reached a size of 0.6-0.5 cm$^3$, mice were subjected to surgery to remove the usually fast growing primary tumors to allow late lung metastases to form before sacrificing the mice. Mice were subjected to general examination on daily basis. QC-56 was given by intraperitoneal route for 4 cycles (d1, d3, and d5). Control groups received the vehicle alone. Chemotherapy drugs were also given by intraperitoneal route according to the schedule described below.

Primary tumor growth was monitored every second to fourth day using calipers. Relative tumor volume (cm$^3$) was determined by the formula:

$$\frac{[\text{Length(cm)} \times \text{Width(cm)}^2]}{2}$$

Body weights were monitored every third to fifth day. Animals experiencing signs of discomfort were sacrificed immediately (in some cases they were replaced by spared mice). In the case of BL6, the timing of sacrifice was decided based on the evidence of lung metastases after autopsy of spared untreated control mice. Mice were sacrificed by cervical dislocation and immediately subjected to full autopsy. Lungs were fixed in 10% Bouin's fixative, and lung surface metastases were counted using a stereomicroscope. In some cases, pathology was added to examine for lung metastases (e.g. PC-3 model).

VI.I (iii) Results

VI.I (iii)(a) Toxicity.

No apparent toxicity was seen with QC-56 in this study. In contrast, chemotherapy drugs, particularly Taxol™ and cisplatin induced some loss of body weights/mortality.

VI.I (iii)(b) Tumor Growth Delay.

Figure 22:
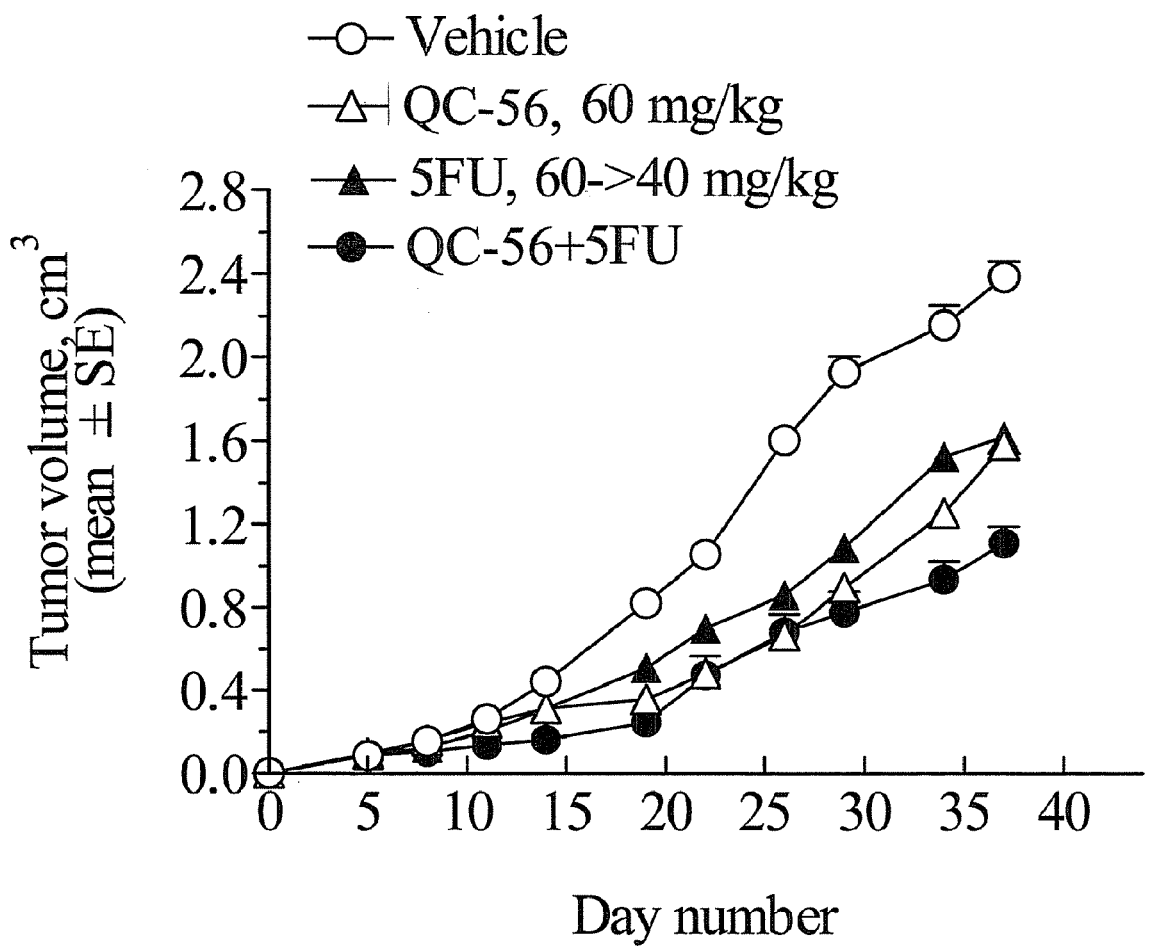
FIG. 22 is a graphical representation of measured tumor volumes throughout the duration of treatment with vehicle alone (○), QC-56 (△), 5FU (▲) and QC-56+5FU (●) in the colorectal carcinoma model HCT-116.
Figure 23:
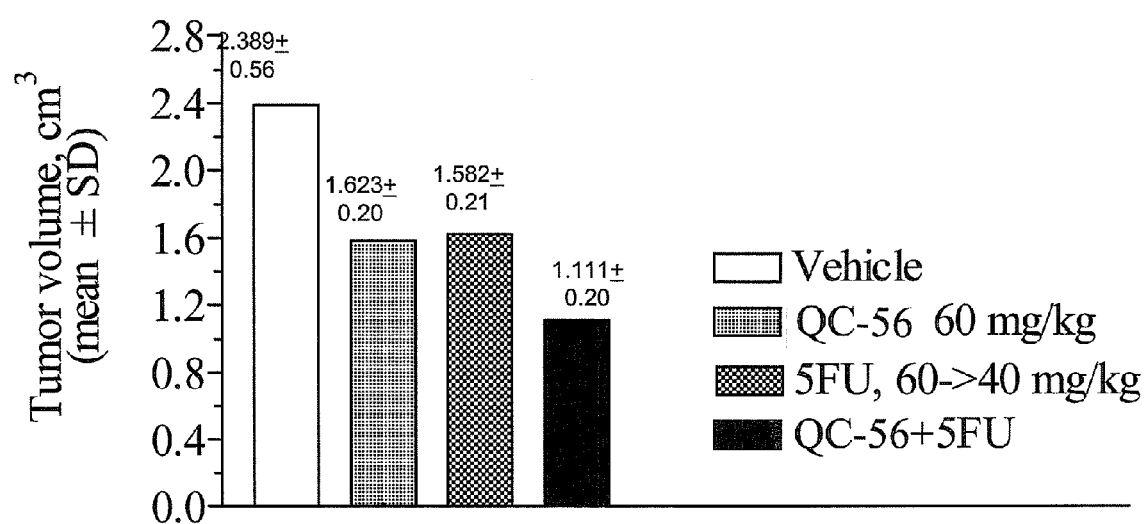
FIG. 23 is a graphical representation of tumor volumes on the day of sacrifice after treatment with vehicle alone, QC-56, 5FU and QC-56+5FU in the colorectal carcinoma model HCT-116.
Figure 24:
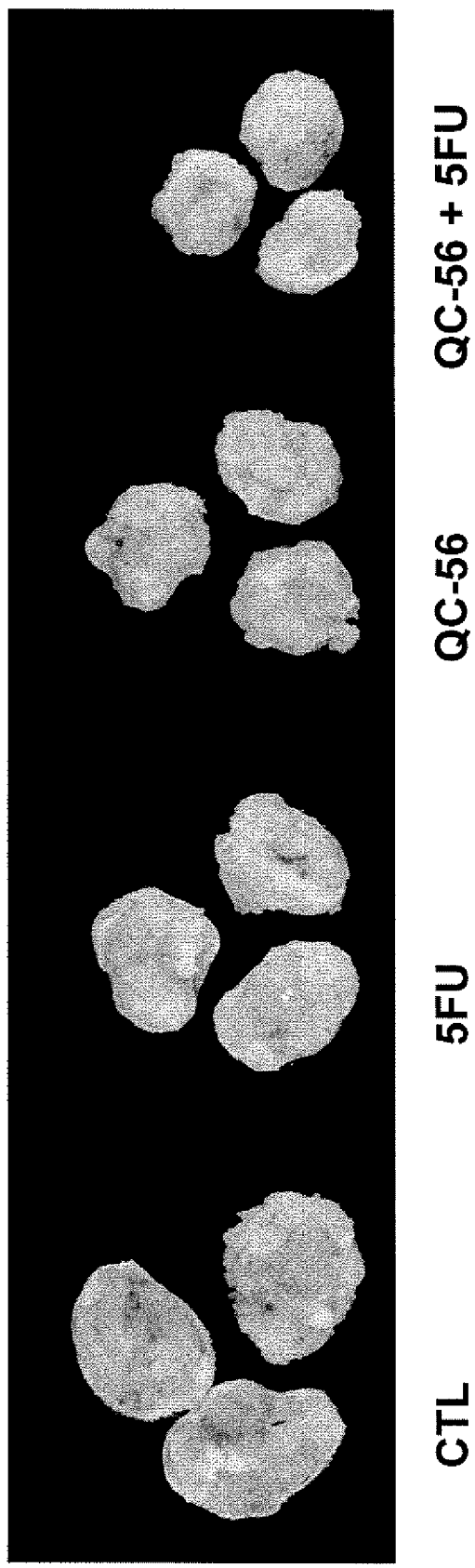
FIG. 24 shows photographs of HCT-116 tumors at sacrifice after treatment with vehicle alone, 5FU, QC-56, and QC-56+5FU.
Figure 25:
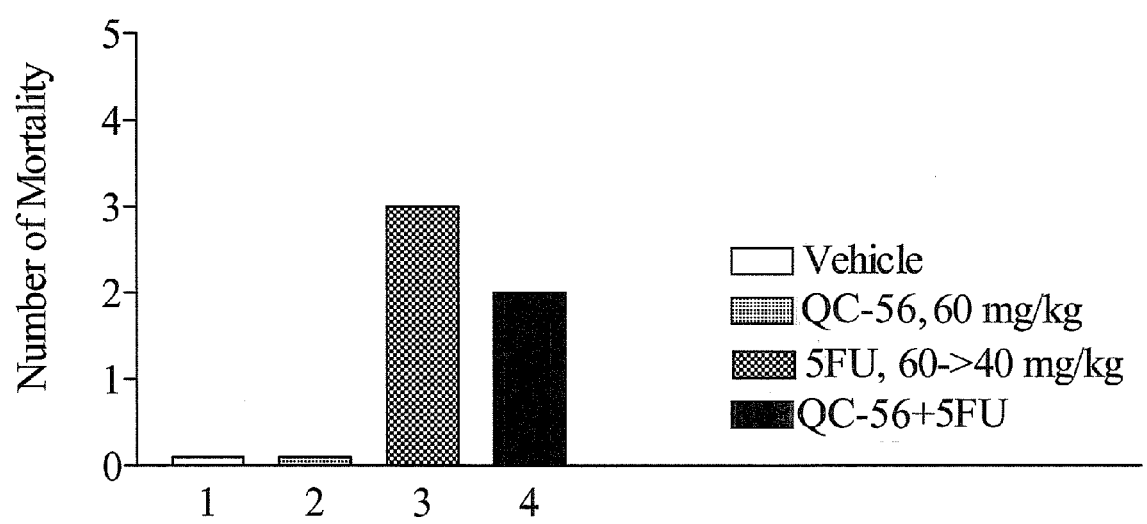
FIG. 25 is a graphical representation of the number of mouse mortalities after treatment with QC-56 and 5FU in the colorectal carcinoma model HCT-116 using a dosage of 60 mg/kg. As illustrated, 5-FU, but not QC-56, induced mortality at 60 mg/kg.

HCT-116: as seen in FIGS. 22, 23 and 24, treatment with QC-56 given at 60 mg/kg/ip was found to reduce tumor volume by approximately 23% at the time of sacrifice compared to control. This activity was similar to that observed with the maximally tolerated dose of 5-FU (60 mg/kg/ip which was reduced in the second cycle due to signs of toxicity and mortality as seen in FIG. 25. The dose of 5-FU was reduced to 40 mg/kg in both 5-FU and QC-56+5FU groups). Combination of QC-56 and 5-FU reduced tumor size by approximately 46%.

Figure 26:
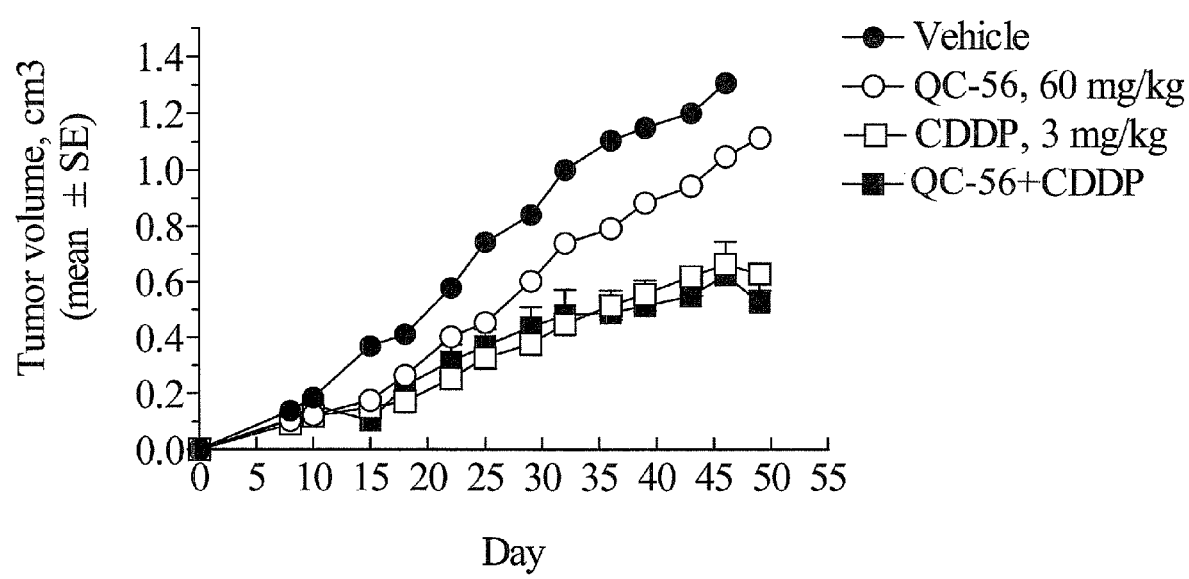
FIG. 26 is a graphical representation of measured tumor volumes throughout the duration of treatment with vehicle alone (●), QC-56 (○), CDDP (□) and QC-56+CDDP (■) in the ovarian carcinoma model OVCAR-3.
Figure 27:
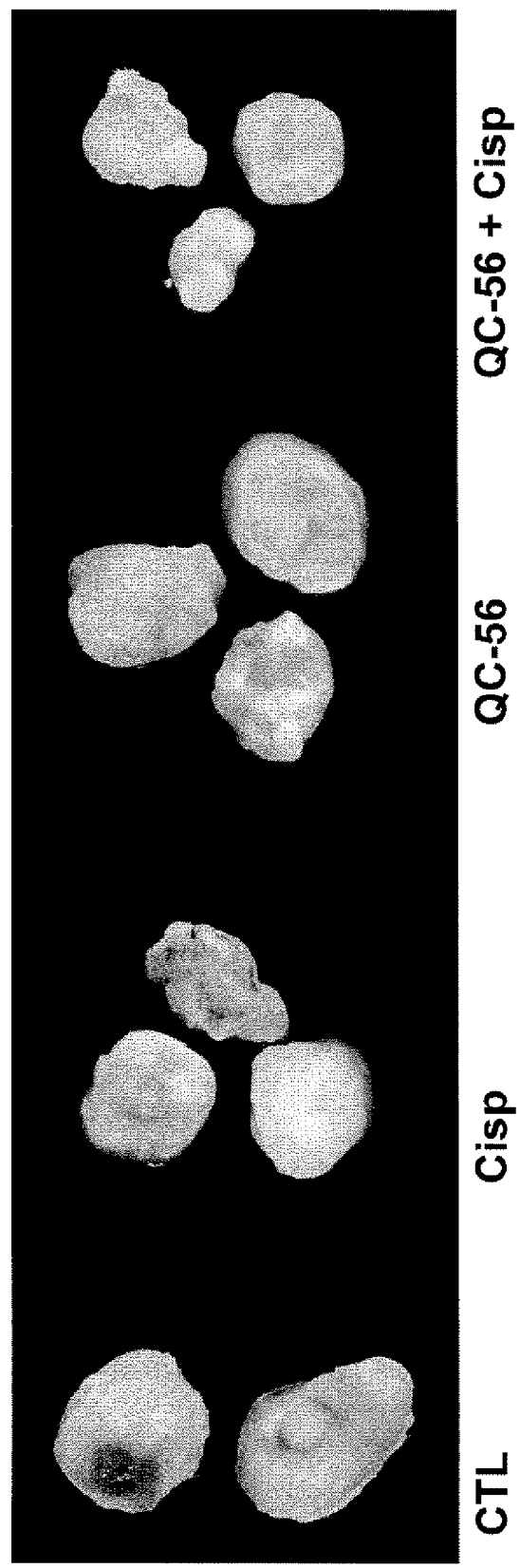
FIG. 27 shows photographs of OVCAR-3 tumors at sacrifice after treatment with vehicle alone, cisplatin (CDDP), QC-56, and QC-56+CDDP.
Figure 28:
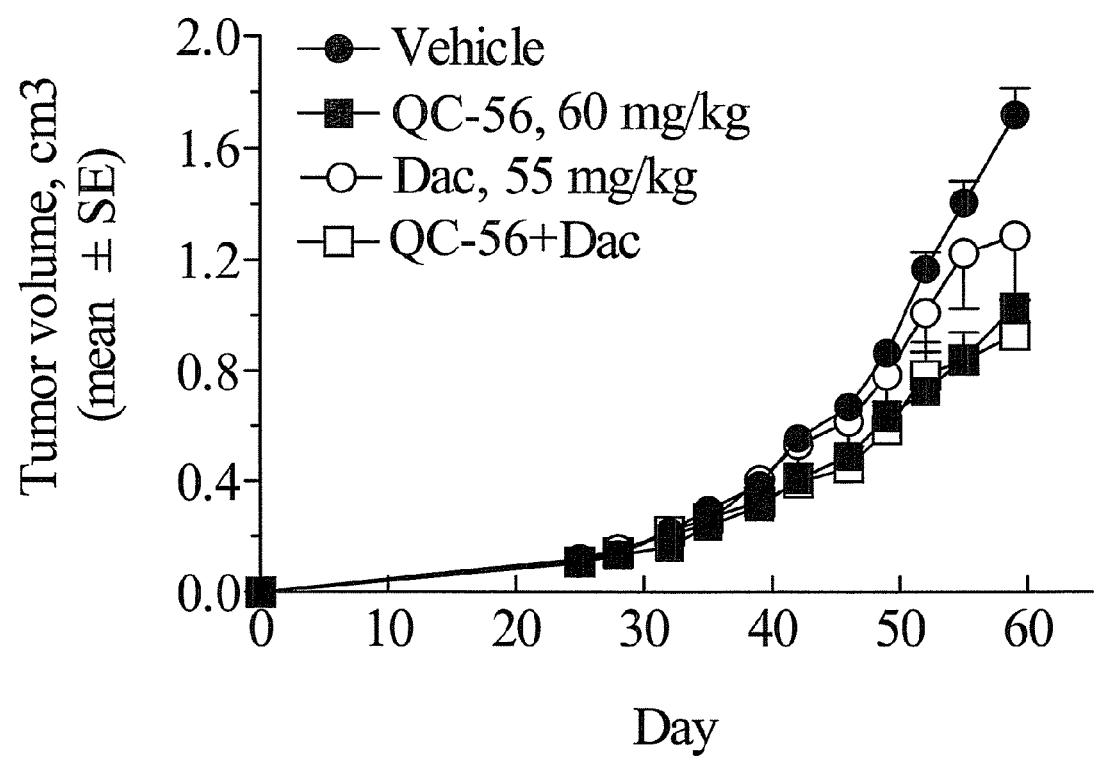
FIG. 28 is a graphical representation of measured tumor volumes throughout the duration of treatment with vehicle alone (●), QC-56 (■), dacarbazine (Dac) (○) and QC-56+Dac (□) in the ovarian melanoma model SKMEL-V+.
Figure 29:
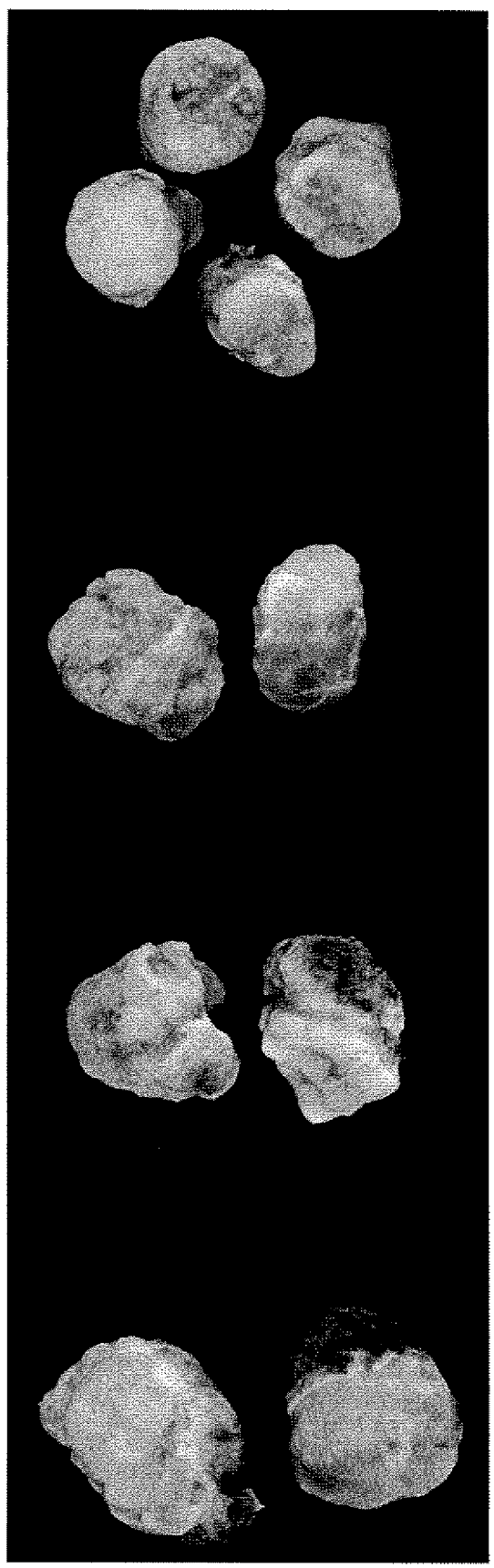
FIG. 29 shows photographs of SKMEL tumors at sacrifice after treatment with vehicle alone, Dac, QC-56, and QC-56+Dac.
Figure 30:
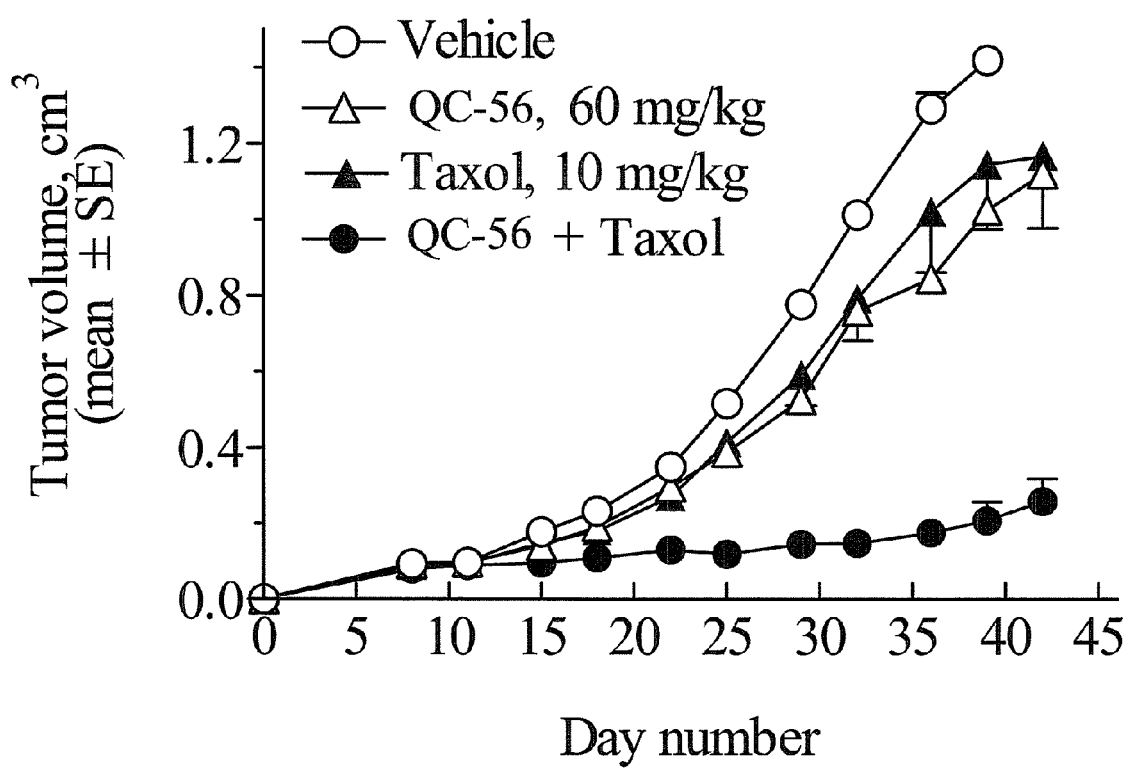
FIG. 30 is a graphical representation of measured tumor volumes throughout the duration of treatment with vehicle alone (○), QC-56 (△), Taxol™ (▲) and QC-56+Taxol™ (●) in the prostate carcinoma model PC-3.
Figure 31:
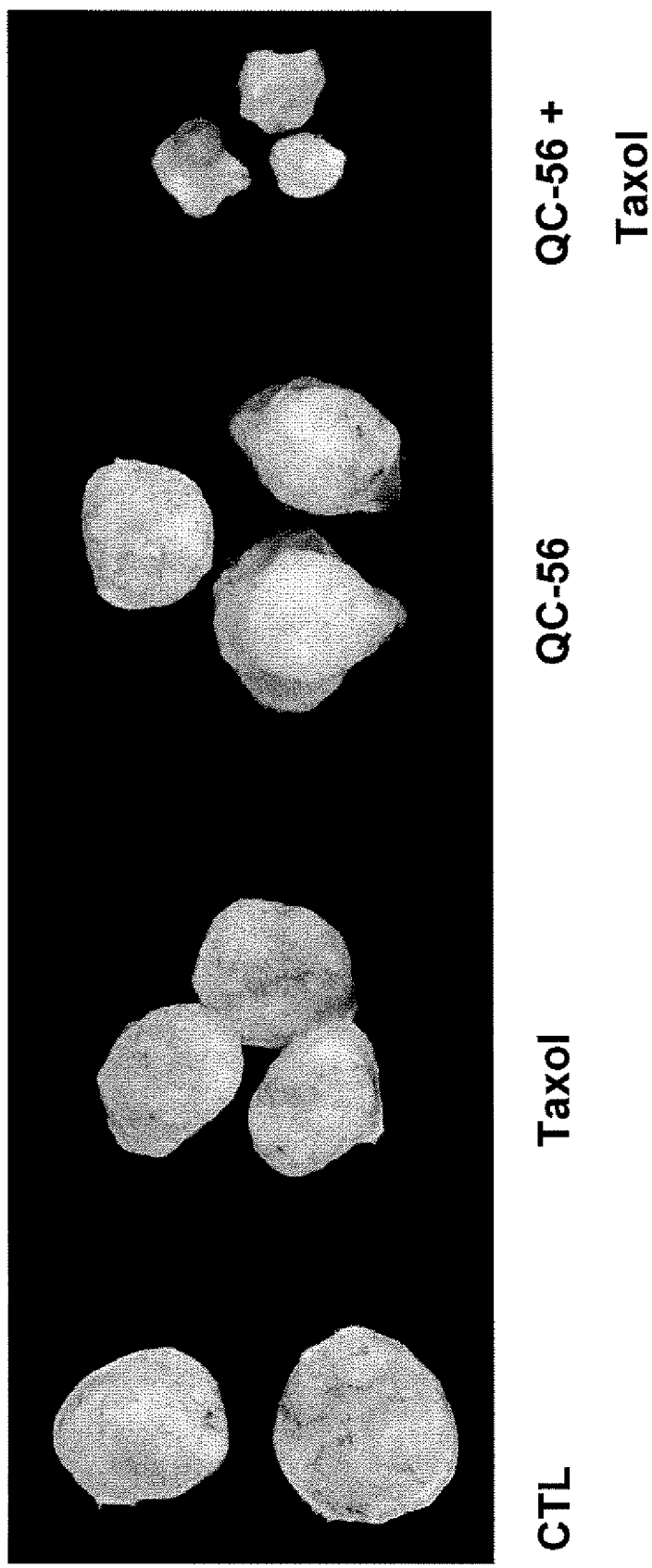
FIG. 31 shows photographs of PC-3 tumors at sacrifice after treatment with vehicle alone, Taxol™, QC-56, and QC-56+Taxol™.
Figure 32:
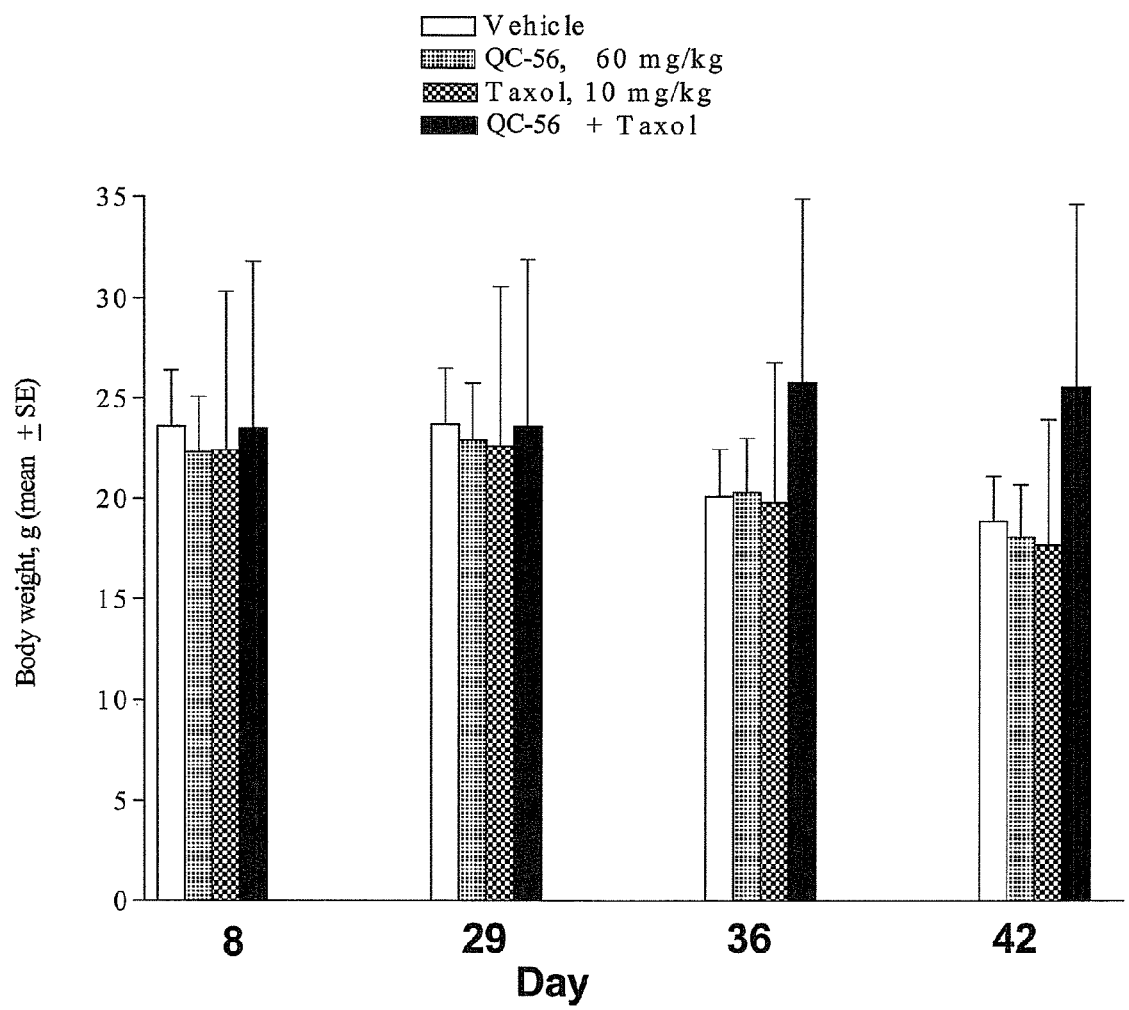
FIG. 32 is a graphical representation of the mean body weights of PC-3 mice treated with vehicle alone, QC-56, Taxol™ and QC-56+Taxol™, showing the impact of QC-56 on body weights at treatment day 8, 29, 36 and 42.

OVCAR-3: as seen in FIGS. 26 and 27, treatment with QC-56 given at 60 mg/kg/ip slightly reduced tumor growth (approximately 15%). Cisplatin given at 3 mg/kg was more active when cisplatin was combined with QC-56 in this model Tumor sizes on the day of sacrifice: Vehicle: $1.31\pm0.07$ cm$^3$
QC-56: $1.12\pm0.08$ cm$^3$
CDDP: $0.63\pm0.06$ cm$^3$
QC-56+CDDP: $0.53\pm0.11$ cm$^3$ SKMEL melanoma: as seen in FIGS. 28 and 29, treatment with QC-56 given at 60 mg/kg/ip induced approximately 42% inhibition of tumor growth compared to animals treated with the vehicle alone. Dacarbazine at 55 mg/kg was less active than QC-56 (approximately 24% inhibition compared to 42% for QC-56). Combination of QC-56 and Dacarbazine somewhat improved the therapeutic index, compared to QC-56 alone (46% for the combination compared to 42% for QC-56 alone).
Tumor sizes on the day of sacrifice: Vehicle: $1.72\pm0.27$ cm$^3$
QC-56: $1.03\pm0.16$ cm$^3$
Dac: $1.30\pm0.23$ cm$^3$
QC-56+Dac: $0.93\pm0.13$ cm$^3$ PC-3 model: as seen in FIGS. 30 and 31, treatment with QC-56 given at 60 mg/kg/ip or Taxol™ at 10 mg/kg induced approximately 25% and 28% inhibition of tumor growth compared to animals treated with the vehicle alone, respectively. However, treatment with a combination of QC-56 and Taxol™ resulted in approximately 83% inhibition, which is evidence of a significant synergistic effect. Tumors remained palpable with no further growth for almost 40 days. Interestingly, animals treated with a combination of QC-56 and Taxol™ gained weights in contrast to other groups where a body weight loss was noted (BW on d8 and d42 as shown in FIG. 32 and Table 3). Although it was noticed that lungs from untreated and Taxol™-treated animals present macroscopic lesions, a pathology examination of tissue sections by a prostate pathologist revealed only collapsed areas in the lungs with no or very few metastases. Lung sections from QC-56–Taxol™ treated mice were clear with no apparent lesions

TABLE 3

Impact of QC-56 on Body Weights (g) on d8 and d42 (mean + SE)

|  | d8 | d42 |
| --- | --- | --- |
| Vehicle | 23.60 ± 7.85 | 18.90 ± 6.30 |
| QC-56 | 22.30 ± 7.88 | 18.10 ± 7.38 |
| Taxol ™ | 22.40 ± 7.92 | 17.70 ± 6.25 |
| QC-56 + Taxol ™ | 23.50 ± 8.30 | 25.60 ± 9.06 |

VI.I (iii)(c) Antimetastatic Activity

Figure 33:
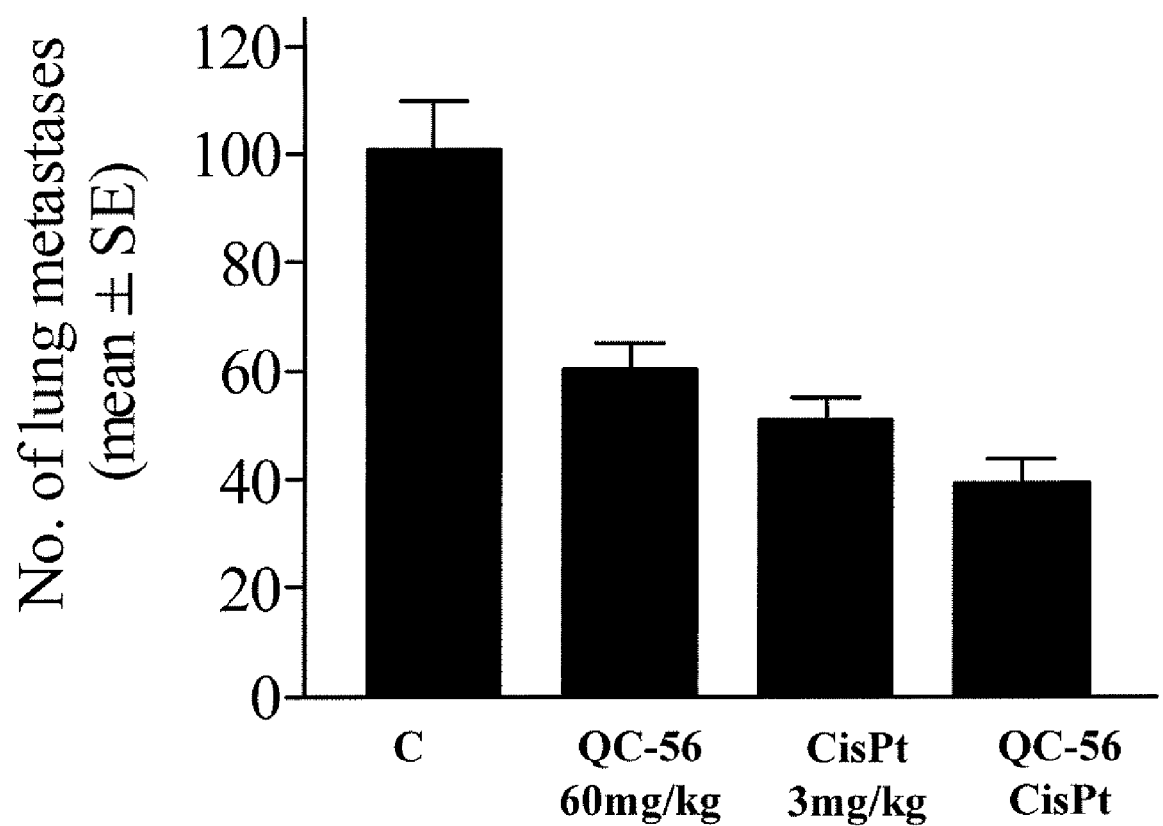
FIG. 33 is a graphical representation of the number of metastases (mean±SE) of extracted lungs from B16-BL6 melanoma mice treated with vehicle alone, QC-56, cisplatin and QC-56+cisplatin.
Figure 34:
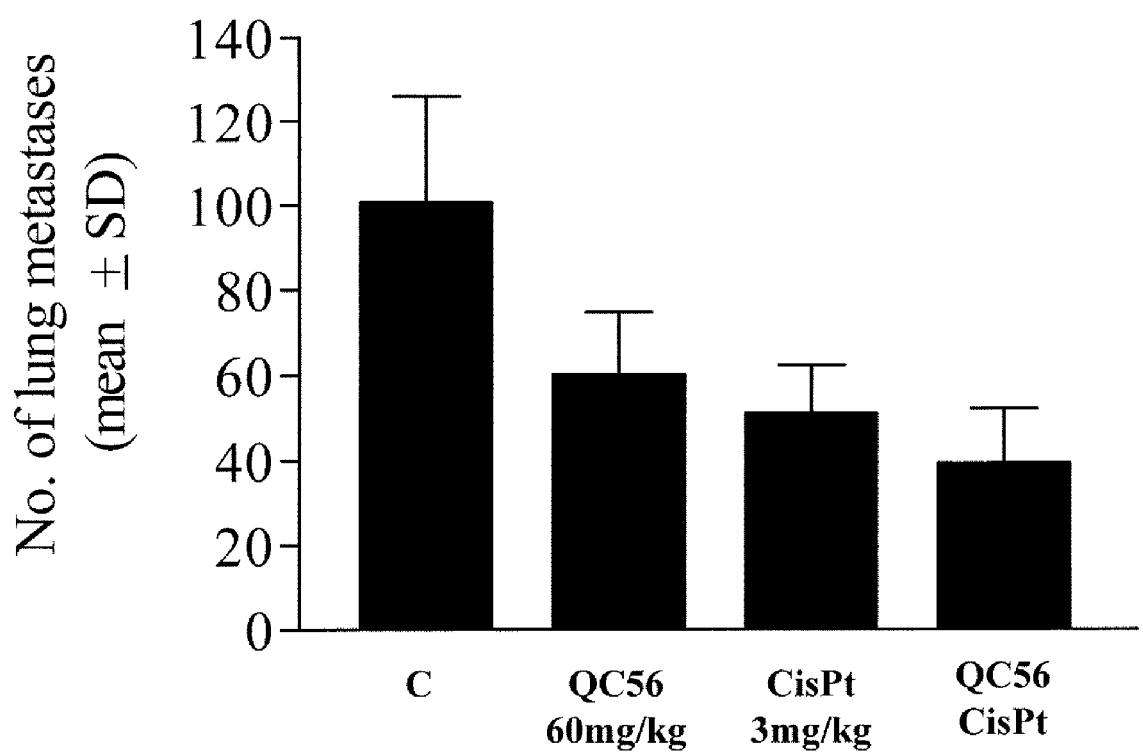
FIG. 34 is a graphical representation of the number of metastases (mean±SD) of extracted lungs from B16-BL6 melanoma mice treated with vehicle alone, QC-56, cisplatin and QC-56+cisplatin.
Figure 35:
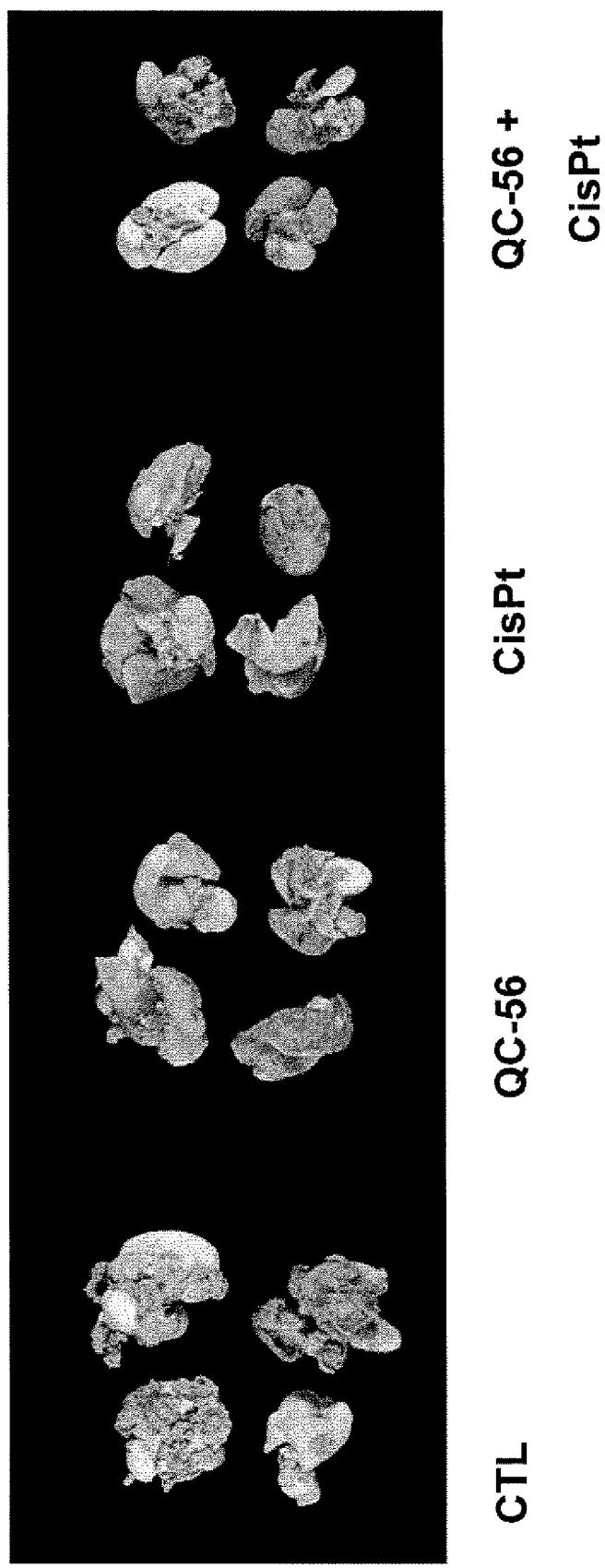
FIG. 35 shows photographs of extracted lungs from B16-BL6 melanoma mice treated with vehicle alone, QC-56, cisplatin and QC-56+cisplatin.

BL16-BL6: as illustrated in FIGS. 33, 34 and 35, in control group treated with the vehicle alone, an average of 101 macroscopic nodules were seen in the lungs, compared to 60 and 51 for cisplatin- and QC-56-treated groups, respectively. In the combination (QC-56+cisplatin) group, only 40 nodules were seen indicating a potentially additive antimetastatic effect of QC-56 with cisplatin.

VI.II Discussion and Summary

The antitumor activity of QC-56 is consistent between various models but the activity of QC-56 given alone at multiple cycles of 60 mg/kg range from moderate (OVCAR, HCT116) to potent (SKMEL) activity. QC-56 is found to be at least as active as the chemotherapy drugs 5-FU, Taxol™, and dacarbazine. In the combination experiments, a notable synergistic/additive effect was observed when QC-56 was combined with Taxol™ in the prostate model PC-3, whereas, lesser synergistic effects of QC-56 in combination with 5-FU and dacarbazine were seen in other cancer models.

In the metastatic B16-BL6 melanoma, QC-56 was active and inhibited lung metastasis to the same level as cisplatin. Statistical analysis is needed to interpret the result of the combination given the large variation in lung metastasis number seen between animals.

Here, we demonstrate the anti-tumor, anti-angiogenic and anti-metastatic activity of one example of the compounds of the present invention. QC-56, a substituted imidazole, was found to have highly selective inhibitory activity toward HO-1 but not HO-2 enzymatic activity, based on the IC50 inhibitory values for HO-1 (rat spleen) and HO-2 (rat brain), enzymes, respectively. QC-56 was well tolerated by mice at multiple doses up to 100 mg/kg dose when given by intraperitoneal as well as via intravenous routes. Antitumor activity was seen in the PC-3 prostate carcinoma model, SKMEL-24 melanoma model, HCT-116 colorectal carcinoma model and OVCAR-3 ovarian carcinoma model. The activity of QC-56 in these models was equal to or higher than that of the standard chemotherapy agents 5-FU, Taxol™, Dacarbazine, and Cisplatin. In the PC-3 model, QC-56 showed a significant activity (approximately 90% inhibition compared to vehicle alone) when combined with the chemotherapeutic drug Taxol™. Immunohistochemistry studies clearly indicate that the activity of QC-56 combined with Taxol™ significantly inhibited lung metastasis formation. Furthermore, CD-31 staining revealed that QC-56-treated tumors exhibited a significant reduction in vascularization.

VII Discussion

HO-1 Inhibitors as Neuroprotective Compounds

VII.I Oxidative Stress, Iron Deposition and Mitochondrial Insufficiency in AD Brain Oxidative stress and mitochondrial deficits have been consistently implicated in the pathogenesis of sporadic AD (Youdim, M., *Inorganic neurotoxins in neurodegenerative disorders without primary dementia*. Neurodegenerative Diseases, ed. D. B. Calne. 1994: Saunders, W. B. 251-276; Klausner, R. D., T. A. Rouault, and J. B. Harford, *Regulating the fate of mRNA: the control of cellular iron metabolism*. Cell, 1993. 72(1): 19-28; Richardson, D. R. and P. Ponka, *The molecular mechanisms of the metabolism and transport of iron in normal and neoplastic cells*. Biochim Biophys Acta, 1997. 1331 (1):1-40). Mitochondrial insufficiency in AD brain is evidenced by: (i) deficits in pyruvate dehydrogenase, α-ketoglutarate dehydrogenase and cytochrome c oxidase protein or activity (Theil, E. C., *Regulation of ferritin and transferrin receptor mRNAs*. J Biol Chem, 1990. 265(9):4771-4); (ii) the presence of excessive mtDNA deletion and mis-sense mutations (Aschner, M., *Neuron-astrocyte interactions: implications for cellular energetics and antioxidant levels*. Neurotoxicology, 2000. 21(6): 1101-7; Ouyang, Y. B. and R. G. Giffard, *Bcl-XL maintains mitochondrial function in murine astrocytes deprived of glucose*. J Cereb Blood Flow Metab, 2003. 23(3): 275-9) which, in one report, correlated with the level of free radical damage (Schipper, H. M., *Astrocytes, brain aging, and neurodegeneration*. Neurobiol Aging, 1996. 17(3): 467-80); and (iii) suppressed cerebral metabolism (glucose utilization) in positron emission tomography studies (Schipper, H., et al., *Role of the gonads in* the histologic aging of the hypothalamic arcuate nucleus. Biol Reprod, 1981. 25(2): 413-9; Schipper, H. M., *Glial HO-1 expression, iron deposition and oxidative stress in neurodegenerative diseases.* Neurotox Res, 1999. 1(1): 57-70). Potential sources of oxidative stress in the AD brain include baseline ROS generation by senescent mitochondria, accelerated β-amyloid deposition (Schipper, N. M., et al., *Astrocyte mitochondria: a substrate for iron deposition in the aging rat substantia nigra.* Exp Neurol, 1998. 152(2): 188-96), production of pro-inflammatory cytokines (TNE-α, IL-1β) and nitric oxide (NO) by activated microglia (Schipper, H. M., et al., *Gomori-positive astrocytes in primary culture: effects of in vitro age and cysteamine exposure.* Brain Res Dev Brain Res, 1990. 54(1): 71-9), and excessive sequestration of redox-active iron in the basal forebrain and association cortices (McLaren, J., J. R. Brawer, and H. M. Schipper, *Iron content correlates with peroxidase activity in cysteamine-induced astroglial organelles.* J Histochem Cytochem, 1992. 40(12):1887-97; Brawer, J. R., et al., *The origin and composition of peroxidase-positive granules in cysteaminetreated astrocytes in culture.* Brain Res, 1994. 633 (1-2): 9-20). Abnormally high levels of tissue iron have been consistently reported in the cerebral cortex and hippocampus of AD subjects. These pathological iron stores may serve as a major generator of reactive oxygen species (ROS) in this condition by reducing $H_2O_2$ to hydroxyl radical. The excessive iron appears to be predominantly deposited within astrocytes, microglia, macrophages and microvessels. Increased expression of tissue ferritin, the major intracellular iron storage protein, parallels the distribution of the excess iron and largely implicates non-neuronal (glial) cellular compartments (Janetzky, B., et al., *Iron and oxidative damage in neurodegenerative disease.* Mitochondria and Free Radicals in Neurodegenerative Diseases, ed. M. F. Beal, N. Howell, and I. Bodis-Wollner. 1997, New York: Wiley-Liss. 407-421; Youdim, M., *Inorganic neurotoxins in neurodegenerative disorders without primary dementia.* Neurodegenerative Diseases, ed. D. B. Calne. 1994: Saunders, W. B. 251-276). The extracellular transport of ferric iron and its delivery to virtually all mammalian tissues is mediated by a second iron-binding protein, transferrin. To maintain normal tissue iron homeostasis, plasma membrane transferrin receptor densities and intracellular ferritin concentrations are tightly regulated at transcriptional and post-transcriptional levels by iron bioavailability and intracellular iron stores (Klausner, R. D., T. A. Rouault, and J. B. Harford, *Regulating the fate of mRNVA: the control of cellular iron metabolism.* Cell, 1993. 72(1): 19-28; Richardson, D. R. and P. Ponka, *The molecular mechanisms of the metabolism and transport of iron in normal and neoplastic cells.* Biochim Biophys Acta, 1997. 1331(1): p. 1-40; Theil, E. C., *Regulation of ferritin and transferrin receptor mRNAs.* J Biol Chem, 1990. 265(9): 4771-4). In normal rat and human brain tissues, there appears to be an overt mismatch between local brain iron concentrations and the densities of cell surface transferrin binding sites. A glial mitochondriopathy may directly or indirectly perpetuate neural injury in the AD brain by (i) accelerating free radical production within damaged components of the ETC, (ii) suppression of cellular ATP levels and critical ATP-dependent processes such as de novo glutathione biosynthesis and uptake of excitotoxic neurotransmitters (glutamate), and (iii) release of cytochrome c and other pro-apoptotic factors.

As described herein, the present inventors and others have investigated a cascade of biochemical and structural changes that occur in aging subcortical astrocytes and in oxidatively-challenged astroglial cultures that has yielded important factors concerning the subcellular pathways of aberrant brain iron sequestration and bioenergetic failure that may prevail in AD subjects.

VII.II Peroxidase-Positive Astrocytes: A Senescent Glial Phenotype

In aging rats, humans, and other vertebrates, a sub-population of subcortical astrocytes progressively accumulates unique cytoplasmic inclusions that exhibit an affinity for Gomori stains, orange-red autofluorescence, and non-enzymatic (pseudo-) peroxidase activity mediated by ferrous iron. Using dissociated fetal or neonatal rat brain cell cultures, the present inventors have observed that exposure to the sulfhydryl agent, cysteamine (CSH; 2-mercaptoethylamine) induces a massive accumulation of peroxidase-positive astrocytic inclusions that are structurally and histochemically identical to those that naturally accumulate in subcortical astroglia of the intact aging brain. Elemental iron is readily detected in the inclusions by electron microprobe analysis, and the presence and concentration of the metal correlates closely with the presence and intensity of DAB (peroxidase) staining. Within 24-72 hours of CSH exposure, many astroglial mitochondria exhibit progressive swelling, rearrangement or dissolution of their cristae, subcompartmental sequestration of redox-active iron and fusion with lysosomes or cisternae of the endoplasmic reticulum (Brawer, J. R., et al., *The origin and composition of peroxidase-positive granules in cysteaminetreated astrocytes in culture.* Brain Res, 1994. 633(1-2): p. 9-20; Chopra, V. S., et al., *A cellular stress model for the differential expression of glial lysosoma cathepsins in the aging nervous system.* Exp Neurol, 1997. 147(2): 221-8). In young adult rats, subcutaneous CSH injections (150-300 mg/kg twice weekly for 3 weeks) induce 2-3 fold increases in numbers of peroxidase positive astrocyte granules in the basal ganglia, hippocampus and other brain regions (Schipper, H. M., M. B. Mydlarski, and X. Wang, *Cysteamine gliopathy in situ: a cellular stress model for the biogenesis of astrocytic inclusions.* J Neuropathol Exp Neurol, 1993. 52(4):399-410). As in the case of the CSH treated cultures, peroxidase-positive glial granules in the intact rat and human brain invariably exhibit mitochondrial epitopes (as well as identical profiles of heat shock protein expression) in immunohistochemical preparations (Brawer, J. R., et al., *Composition of Gomori-positive inclusions in astrocytes of the hypothalamic arcuate nucleus.* Anat Rec, 1994. 240(3): 407-15; Schipper, H. M. and S. Cissé, *Mitochondrial constituents of corpora amylacea and autofluorescent astrocytic inclusions in senescent human brain.* Glia, 1995. 14(1):55-64). Further studies indicated that intracellular oxidative stress may be responsible for the transformation of normal astrocyte mitochondria to peroxidase-positive inclusions and corpora amylacea in vitro and in the intact aging brain (Manganaro, F., et al., *Redox perturbations in cysteamine-stressed astroglia: implications for inclusion formation and gliosis in the aging brain.* Free Radic Biol Med, 1995. 19(6): p. 823-35; Sahlas, D. J., A. Liberman, and H. M. Schipper, *Role of heme oxygenase-1 in the biogenesis of corpora amylacea.* Biogerontology, 2002. 3(4): p. 223-31; Schipper, H. M., *Brain iron deposition and the free radical-mitochondrial theory of ageing.* Ageing Res Rev, 2004. 3:265-301; Srebro, Z., *Periventricular Gomori-positive glia in brains of X-irradiated rats.* Brain Res, 1971. 35(2): 463-8). The latter are glycoproteinaceous inclusions characteristic of aging and AD-affected neural tissues.

VII.III Iron Sequestration in 'Stressed' Astroglia

It has been shown that CSH (880 μM), dopamine (0.1-1.0 μM), β-amyloid (15 μM), TNFα (20 ng/mL) or IL-β (20 ng/mL) significantly augment the incorporation of $^{59}$Fe (or $^{55}$Fe) into astroglial mitochondria without affecting transfer of the metal into whole-cell and lysosomal compartments (Wang, X., F. Manganaro, and H. M. Schipper, *A cellular stress model for the sequestration of redox-active glial iron in the aging and degenerating nervous system*. J Neurochem, 1995. 64(4): 1868-77; Ham, D. and H. M. Schipper, *Heme oxygenase-1 induction and mitochondrial iron sequestration in astroglia exposed to amyloid peptides*. Cell Mol Biol Noisy-le-grand), 2000. 46(3): p. 587-96; Mehindate, K., et al., *Proinflammatory cytokines promote glial heme oxygenase-1 expression and mitochondrial iron deposition: implications for multiple sclerosis*. J Neurochem, 2001. 77(5): 1386-95; Schipper, H. M., et al., *Mitochondrial iron sequestration in dopamine-challenged astroglia: role of heme oxygenase-1 and the permeability transition pore*. J Neurochem, 1999. 72(5):1802-11). These effects were only demonstrable when inorganic $^{59}$FeCl$_3$, but not $^{59}$Fe-diferric transferrin, served as the metal donor (ibid). These in vitro data are also commensurate with the fact that a) pathological iron accumulation appears to be a transferrin-independent process (see section 1.2) and b) mitochondrial insufficiency is an invariant feature of AD brain tissues exhibiting iron overload.

Herein the present inventors and others have presented evidence implicating glial heme oxygenase-1 (HO-1) expression is a 'common pathway' leading to pathological iron deposition and oxidative mitochondrial damage in the brains of AD subjects.

VII.IV Glial HO-1 Expression and Mitochondrial Iron Sequestration

Cysteamine (CSH; 880 µM), β-amyloid, and TH1 cytokines implicated in the pathogenesis of AD, viz., tumour necrosis factor-α (TNFα; 20 ng/mL) and interleukin-1β (IL-1β; 20 ng/mL), upregulate HO-1 mRNA, protein and/or activity levels in cultured neonatal rat astroglia within 3-12 hours of treatment.

Within 3-6 days of exposure to these stimuli, sequestration of non-transferrin-derived $^{59}$Fe (or $^{55}$Fe) by the mitochondrial compartment is significantly augmented in these cells (Schipper, H. M., *Glial HO-1 expression, iron deposition and oxidative stress in neurodegenerative diseases*. Neurotox Res, 1999. 1(1): 57-70; Mehindate, K., et al., *Proinflammatory cytokines promote glial heme oxygenase-1 expression and mitochondrial iron deposition: implications for multiple sclerosis*. J Neurochem, 2001. 77(5): 1386-95). Using various pharmacological approaches, it has been determined that oxidative stress is a likely common mechanism mediating glial ho-1 gene induction under these experimental conditions (Schipper, H. M., et al., *Mitochondrial iron sequestration in dopamine-challenged astroglia: role of heme oxygenase-1 and the permeability transition pore*. J Neurochem, 1999. 72(5):1802-11; Mydlarski, M. B., J. J. Liang, and H. M. Schipper, *Role of the cellular stress response in the biogenesis of cysteamine-induced astrocytic inclusions in primary culture*. J Neurochem, 1993. 61(5): 1755-65).

VII.V Role of HO-1 in Mitochondrial Iron Trapping

Administration of dexamethasone (DEX; 50 µg/mL), a transcriptional suppressor of the ho-1 gene, significantly attenuated mitochondrial iron sequestration in cultured astrocytes exposed to β-amyloid, TNFα or IL-11 (Mehindate, K., et al., *Proinflammatory cytokines promote glial heme oxygenase-1 expression and mitochondrial iron deposition: implications for multiple sclerosis*. J Neurochem, 2001. 77(5): 1386-95). Similarly, administration of SaMP or DEX abolished the pathological accumulation of mitochondrial $^{55}$Fe observed in rat astroglia engineered to over-express the human ho-1 gene by transient transfection (Ham, D. and H. M. Schipper, *Heme oxygenase-1 induction and mitochondrial iron sequestration in astroglia exposed to amyloid peptides*. Cell Mol Biol (Noisy-le-grand), 2000. 46(3):587-96; Mehindate, K., et al., *Proinflammatory cytokines promote glial heme oxygenase-1 expression and mitochondrial iron deposition: implications for multiple sclerosis*. J Neurochem, 2001. 77(5): 1386-95). These findings indicate that up-regulation of HO-1 is a critical event in the cascade leading to excessive mitochondrial iron deposition in oxidatively-challenged astroglia.

VII.VI HO-1, Intracellular OS and the Mitochondrial Permeability Transition Pore.

In astrocytes, up-regulation of HO-1 promotes intracellular OS as evidenced by observations that a) treatment with SnMP or antioxidants (ascorbate, melatonin or resveratrol) blocked the compensatory induction of the MnSOD gene in astrocytes challenged with dopamine or transiently transfected with human (h) HO-1 cDNA (Frankel, D., K. Mehindate, and H. M. Schipper, *Role of heme oxygenase-1 in the regulation of manganese superoxide dismutase gene expression in oxidatively-challenged astroglia*. J Cell Physiol, 2000. 185(1): 80-6) and b) levels of protein carbonyls (protein oxidation), 8-epiPGF2α (lipid peroxidation), 8-OHdG (nucleic acid oxidation) and a synthetic redox reporter molecule were significantly increased in glial mitochondrial fractions after 3-4 days of hHO-1 transfection relative to sham-transfected controls and HO-1-transfected cells receiving SnMP (Song, W., et al., *Over-expression of heme oxygenase-1 promotes oxidative mitochondrial damage in rat astroglia*. J Cell Physiol, 2006. 206(3):655-63; Vaya, J., et al., *Effects of heme oxygenase-1 expression on sterol homeostasis in rat astroglia*. Free Radic Biol Med, 2007. 42(6): p. 864-71).

Treatment with cyclosporin A, a potent inhibitor of the mitochondrial permeability transition pore, also curtailed mitochondrial iron trapping in hHO-1 transfected glia and cells exposed to β-amyloid, TNFα or IL-1β (Mehindate, K., et al., *Proinflammatory cytokines promote glial heme oxygenase-1 expression and mitochondrial iron deposition: implications for multiple sclerosis*. J Neurochem, 2001. 77(5): 1386-95; Schipper, H. M., et al., *Mitochondrial iron sequestration in dopamine-challenged astroglia: role of heme oxygenase-1 and the permeability transition pore*. J Neurochem, 1999. 72(5) 1802-11). Conceivably, intracellular oxidative stress accruing from HO-1 activity promotes pore opening (Petronilli, V., et al., *Physiological effectors modify voltage sensing by the cyclosporin Asensitive permeability transition pore of mitochondria*. J Biol Chem, 1993. 268(29):21939-45; Bernardi, P., *The permeability transition pore. Control points of a cyclosporin A-sensitive mitochondrial channel involved in cell death*. Biochim Biophys Acta, 1996. 1275(1-2):5-9) and influx of cytosolic iron to the mitochondrial matrix.

VII.VII Glial HO-1 Expression in MCI and AD Brain

Numbers of neuroglia immunoreactive for HO-1 in cortical and subcortical regions of the normal human brain increase progressively with advancing age (Hirose, W., K. Ikematsu, and R. Tsuda, *Age-associated increases in heme oxygenase-1 and ferritin immunoreactivity in the autopsied brain*. Leg Med (Tokyo), 2003. 5 Suppl: S360-6). More recently it has been shown that glial HO-1 expression in the temporal cortex and hippocampus of patients with mild cognitive impairment (MCI) was significantly greater than in the nondemented group and did not differ from AD values. Astroglial HO-1 expression in the temporal cortex was associated with decreased scores for global cognition, episodic memory, semantic memory and working memory. Hippocampal astroglial HO-1 expression was associated with lower scores for global cognition, semantic memory and perceptual speed.

Glial HO-1 immunoreactivity in the temporal cortex, but not hippocampus, correlated with the burden of neurofibrillary pathology. The MCI findings indicate that cortical and hippocampal oxidative stress and glial HO-1 hyperexpression are very early events in the pathogenesis of sporadic AD.

It is thus proposed by the present inventors that suppression of glial HO-1 activity is a rational and effective neurotherapeutic intervention in AD and related neurodegenerative disorders.

VII.VIII Selective HO-1 Inhibition

The rate-limiting enzyme in heme degradation is heme oxygenase (HO), for which the two active isoenzymes include the inducible HO-1, and the constitutively-active HO-2. Normally, HO-1 is barely detectable in the brain, and HO-2 accounts for most of the HO activity in this organ. It has been reported that HO-2 is neuroprotective by detoxifying excess heme in the brain. Currently available metalloporphyrin inhibitors of HO activity are relatively non-specific for HO isoforms (HO-1, HO-2) and other enzymes (e.g. nitric oxide synthase), exhibit limited penetration of the blood-brain barrier and engender photosensitization and other toxicity with chronic administration. Thus, a specific HO-1 inhibitor as described herein, such as QC-56, would be highly desirable.

As a non-limiting example, the present inventors have shown herein that QC-56 is a specific and potent inhibitor of HO-1 based on $IC_{50}$ val ues for HO-1 inhibition (rat spleen) and HO-2 inhibition (rat brain) of 1.9±0.2 and 100 μM respectively.

VII.IX Effect of QC-56 on Oxidative Whole Cell & Mitochondrial Damage

The present inventors have shown that in primary rat astroglial cultures, transient transfection of hHO-1 significantly augmented the content of protein carbonyls in mitochondrial and whole cell compartments. Administration of 6.5 μM QC-56 significantly attenuated oxidative protein damage accruing from hHO-1 transfection in primary rat astroglial cultures. QC-56 produced significant dose-dependant attenuations of oxidative protein damage in whole cell and mitochondrial compartments in the transiently transfected rat astroglial cultures.

Based on the above discussion, and the evidence of HO-1 selective inhibition presented herein for the compounds of the present invention, including but not limited to QC-56, there exists strong support for the usefulness of the compounds of the invention in effectively treating AD and related neurodegenerative disorders.

VIII. Anti-Angiogenic and Anti-Metastatic Activity of QC-56

VIII.I Material and Methods
VIII.I (i) Test Agents

QC-56 was stored at −80° C. protected against light. Stock solutions were prepared freshly and stored at −80° C. Each solution was used for two->three consecutive administrations. In this case, tubes were thawed at room temperature before administration. Taxol™ was purchased from the Oncology Pharmacy at the Jewish General Hospital, Montreal, QC, Canada, and stored at 4° C.

VIII.I (i) Bioassay
VIII.I (i)(a) Mouse Strain
Species and strain: Mouse (*Mus musculus*), male SCID
Age: 6-8 weeks old.
Supplier: Charles River Laboratories, Inc., St-Constant, Quebec, Canada.
Acclimation: Mice were acclimated to laboratory conditions for approximately 1 week prior to tumor cell inoculation.
Identification: Mice were identified by ear punch combination.
Housing: Mice were housed in groups of 3-5 in a designated animal facility with a temperature of 22° C., a relative humidity of 40-50%, and a 12 hr light/dark cycle. Mice were fed pellets (Purina Mills, Inc. Certified Diet® #5001) and autoclaved tap water ad libitum.
Environment: Temp. 22° C., Relative humidity 40-50%, light/dark cycles, 12 h VIII.I (ii)(b) Tumor Cells PC-3 & PC-3M (human prostate carcinoma). The PC-3 human prostate cancer cell line was originally obtained from the American Type Culture Collection (Rockville, Md.). The PC-3M cell line was kindly provided by Dr. Issac (MD Anderson Cancer Center). This cell variant was derived from a liver metastasis produced by the parental PC-3 cells growing in the spleen of a nude mouse [Pettaway C A, Pathak S, Greene G, et al. Selection of highly metastatic variants of different human prostate carcinomas utilizing orthotopic implantation in nude mice. Clin Cancer Res 1996; 2:1627-36].

Both PC-3 parental and PC-3M lines were maintained as monolayer cultures in RPMI-1640 supplemented with 10% fetal bovine serum, sodium pyruvate, nonessential amino acids, L-glutamine, a two-fold vitamin solution (Gibco, Grand Island, N.Y.), and penicillin-streptomycin (Flow Laboratories, Rockville, Md.). Cell cultures were maintained in 5% $CO_2$/95% air at 37° C. SKMEL-V (human melanoma cells). SKMEL-V cells were derived from SKMEL-24 cells (ATCC) by overexpression of mouse VEGF. Early passage cells (tested free of mycoplasma) were grown to 60% confluence in RPMI-1640 medium supplemented with 10% fetal calf serum, and antibiotics. Cell harvesting was performed using trypsin-EDTA solution. Cells were centrifuged and washed twice with phosphate buffered saline solution and were re-suspended at a dilution of $1 \times 10^6$ cells/0.1 mL.

VIII.I (ii)(c) Tissue Preparation and Immunohistochemistry for CD31

Tumors were either snap frozen in liquid nitrogen or fixed in 10% buffered formalin and embedded in paraffin. The antibody used for immunohistochemistry are rat monoclonal anti-mouse CD31 (Mec 13.3; BD PharMingen, San Diego, Calif.). For CD31 staining, 7-μm cryosections of tumors were air-dried and fixed in −20° C. acetone for 10 min. Sections were rehydrated in PBS and then blocked with 5% normal goat serum for 1 h. The sections were then incubated overnight at 4° C. with CD31 antibody diluted 1:25 in 3% BSA-PBS. After several PBS rinses, sections were incubated for 30 min with a biotinylated secondary anti-rat antibody (BD PharMingen), followed by a 30-min incubation with avidin-biotin-horseradish peroxidase complex, and then developed with DAB kit (Vector Laboratories, Burlingame, Calif.). Paraffin-embedded material was used for Harris' hematoxylin. Microvessel density was quantified using a method described by Weidner et al (Weidner N, Semple J P, Welch W R, and Folkman J. N Engl. J. Med, 1991; 324:1-8). Briefly, randomly vascularized areas were selected (hot spots) under 40× field and 100× fields. Then a 400× field was used to count microvessels in each of these areas. Single endothelial cells or clusters of endothelial cells with or without lumen were considered to be individual vessels. The mean value of 10× field counts per tumor (total of 30 fields per group) was recorded as mean vascular density of the section. All slides were examined blindly with no prior knowledge of the treatment status.

VIII.I (ii)(d) Orthotopic Implantation of PC-3/PC-3M into the Prostate.

Male SCID mice were housed in laminar flow under specific pathogen-free conditions and used at 8-9 weeks of age.

Animals were maintained in the LDI facilities approved by the Laboratory Animal Care in accordance with current Canadian regulations and standards for the use of animals for research.

Exponentially growing cells were harvested using a brief exposure to 0.25% trypsins:0.1% EDTA solution (w/v). Cells were centrifuged and washed twice with phosphate buffered saline solution and were re-suspended at a dilution of $1-2\times10^6$ cells/0.1 mL. Cell viability was confirmed by trypan blue staining. Only those cells in single-cell suspensions with >95% viability and "normal" morphology were used for in-vivo.

Mice were anesthesized with isofluorane given by inhalation and placed in a supine position. Betadine and 75% Ethanol was used to clean the skin of abdomen. A low midline incision was made and the prostate was exposed. Fifty microliters of HBSS containing $1\times10^6$ cells was injected into a lateral lobe of the prostate. The wound was closed with surgical metal clips in two layers, the muscle layer first and then the skin layer using stainless steel clips (autoclips: 9 mm; Clay Adams Inc., Parsippany, N.J.). All animals were inoculated at the same site. Buprenorphine was administered post-operation at a dose of 0.1 mg/kg/sc. One week after implantation, mice were then blindly randomized to various experimental groups (based on the experimental plan) and treatment was initiated immediately after. Mice were subjected to general examination on daily basis. QC-56 was given ip, iv, or oral at the indicated schedules. Control groups received the vehicle alone. Taxol™ was given either ip or iv as indicated. Body weights were monitored every third to fifth day. Animals experiencing signs of discomfort were sacrificed immediately (in some cases they were replaced by spared mice).

VIII.I (ii)(e) Necropsy and Pathology

At the end of study, mice were sacrificed by cervical dislocation and immediately subjected to full autopsy. When applicable, lungs were fixed in 10% Bouin's fixative, and lung surface metastases were counted using a stereomicroscope. Primary tumors in the prostate were excised, measured, and weighed. When applicable, immunohistochemistry and H&E staining were conducted on one part of the tumor, fixed in formalin and embedded in paraffin or OCT compound (Miles Inc., Elkhart, Ind.); the later was rapidly frozen in liquid nitrogen, and stored at −70° C. Macroscopically enlarged regional lymph nodes were harvested and the presence of metastatic disease was confirmed by histology.

VIII.I (ii)(f) Statistics

The in vivo data was analyzed using the Mann-Whitney U test.

VIII.I (iii) Results

VIII.I (iii)(a) Anti-Angiogenic Activity of QC-56

Figure 36:
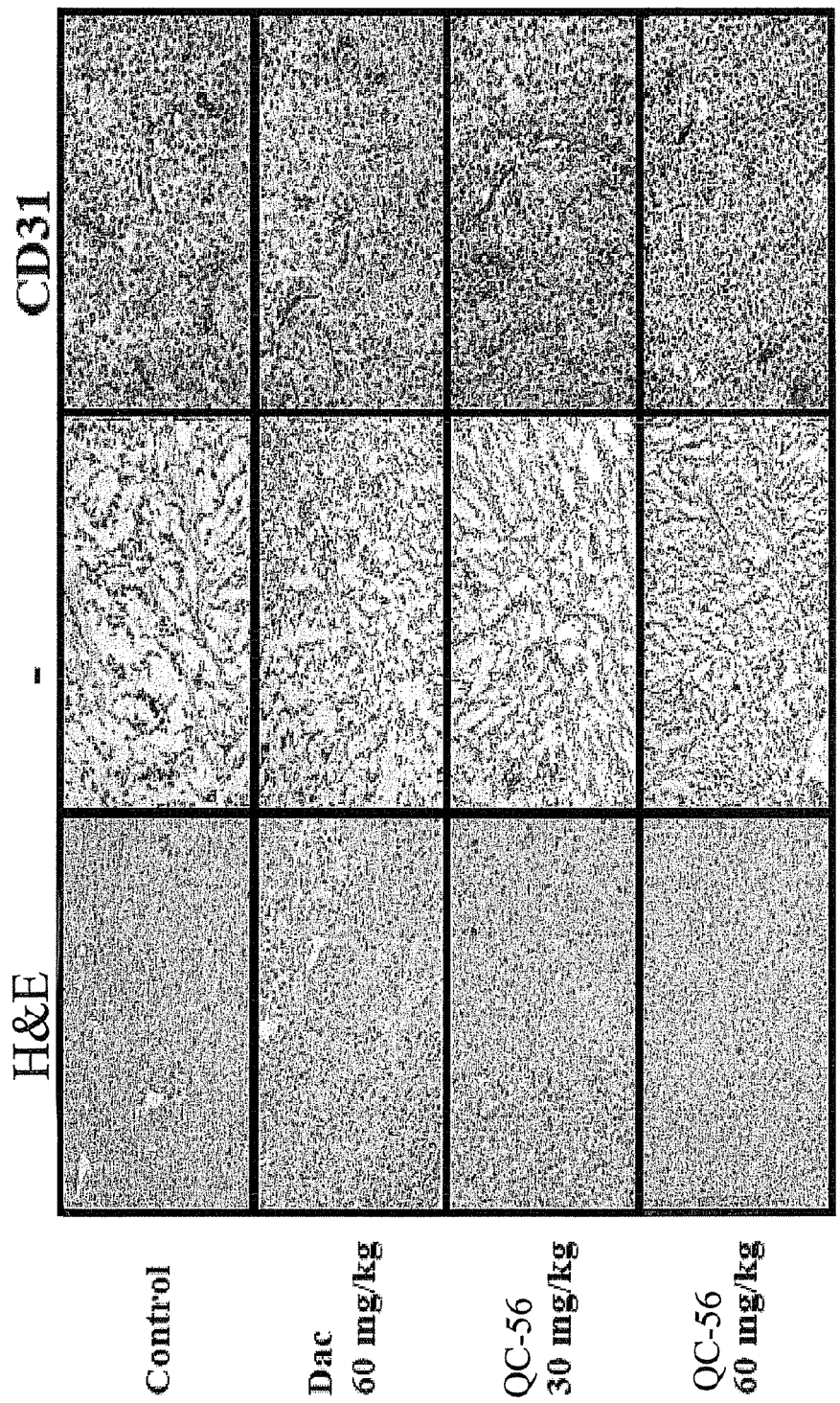
FIG. 36 shows H&E staining, unstained and rat monoclonal anti mouse CD31 antibody stained images of SKMEL-V+ tumors from mice treated with vehicle alone, Dacarbazine, QC-56 and Dacarbazine+QC-56. Compared to the control group and the group treated with Dacarbazine, there is a significant decrease in the size and number of blood vessels in tumors in mice treated with QC-56. (H&E: H stands for Hematoxylin stain and E stands for Eosin stain; CD31: also known as PECAM-1 or Platelet Endothelial Cell Adhesion Molecule-1, is a 130 kDa integral membrane protein, a member of the immunoglobulin super family that mediates cell-to-cell adhesion, is expressed constitutively on the surface of adult and embryonic endothelial cells and is weakly expressed on many peripheral leukocytes and platelets. CD31 mediates endothelial cell-cell interactions and is used as a marker of endothelial cells).
Figure 37:
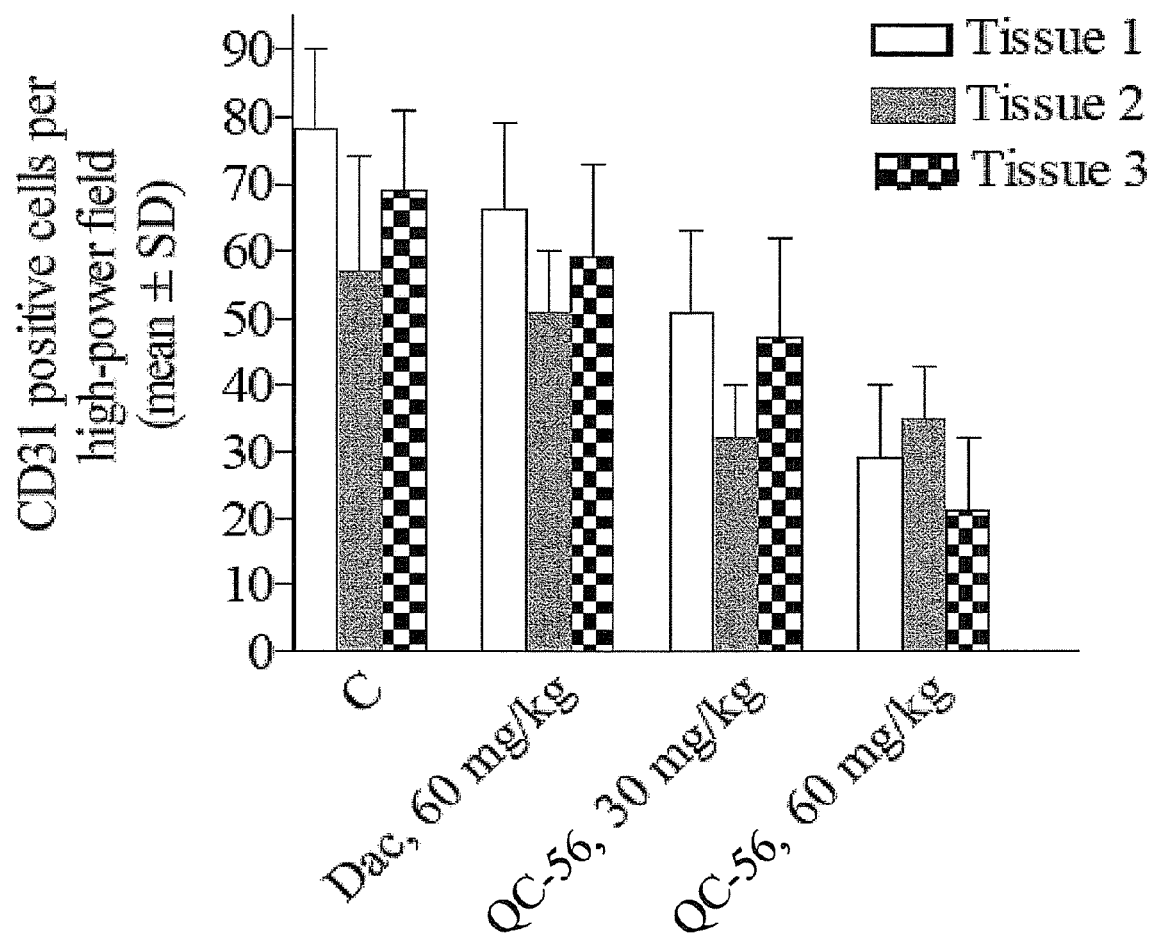
FIG. 37 shows the results of measuring CD31 positive cells in SKMEL-V+ tumors from mice treated with vehicle alone, Dacarbazine, QC-56 and Dacarbazine+QC-56.

As shown in FIG. 36, extensive vascularization was observed in control tumors from mice treated with the vehicle alone. Control slides treated in the same way except anti-CD31 showed minimal background staining. Most of the CD31-positive vessels appeared to be well formed and well demarcated from the surrounding connective tissues and some contained a clear lumen; vessels with no lumen are believed to be proliferating endothelial cells sprouted from the larger microvessels. We noted that few microvessels are seen in the peripheral areas compared to central area from the core of tumors. This would suggest that hypoxia generated in central areas may contribute to enhanced vessel formation as has been documented in several previous studies. Treatment with Dacarbazine had a minor effect on vessel count (FIG. 37) and morphology (FIG. 36) but a decrease was seen with QC-56, particularly at 60 mg/kg. We noted that in this group vessels are smaller and have a small lumen and less sprouted compared to control sections. These morphological features clearly indicate that the anti-tumor effect of QC-56 is associated with reduced tumor vascularization. This can be due to a direct anti-angiogenenic property of QC-56.

VIII.I (iii)(b) Anti-Metastatic Activity of QC-56

PC-3M: Although we noticed that lungs from untreated and Taxol™-treated animals present macroscopic lesions, a pathology examination of tissue sections by a prostate pathologist revealed only collapsed areas in the lungs with no or very few metastases. Lung sections from QC-56–Taxol™ treated mice were clear with no apparent lesions.

Figure 38:
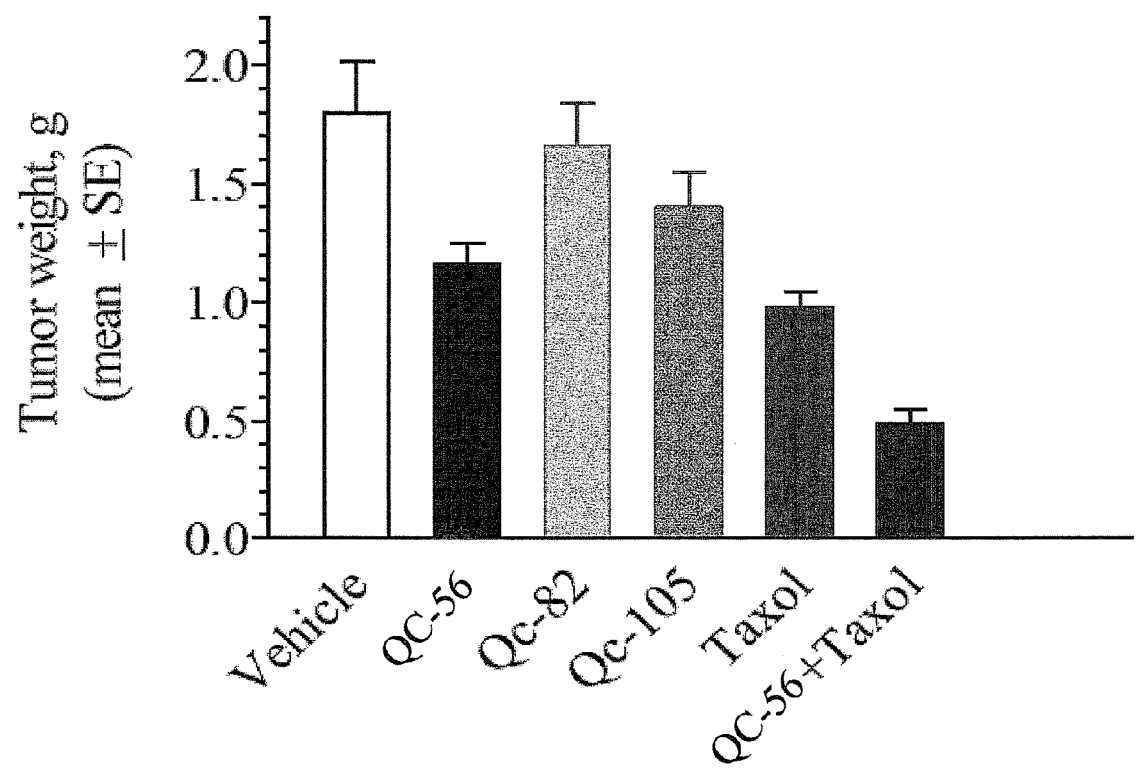
FIG. 38 shows results from a pre-clinical study involving a total of 32 SCID male mice implanted orthotopically with human metastatic prostate cancer PC-3M cells in the mouse prostate, in which QC-56, QC-82, QC-105, Taxol™ and QC-56+Taxol™ are tested for effect on primary tumor weights.
Figure 39:
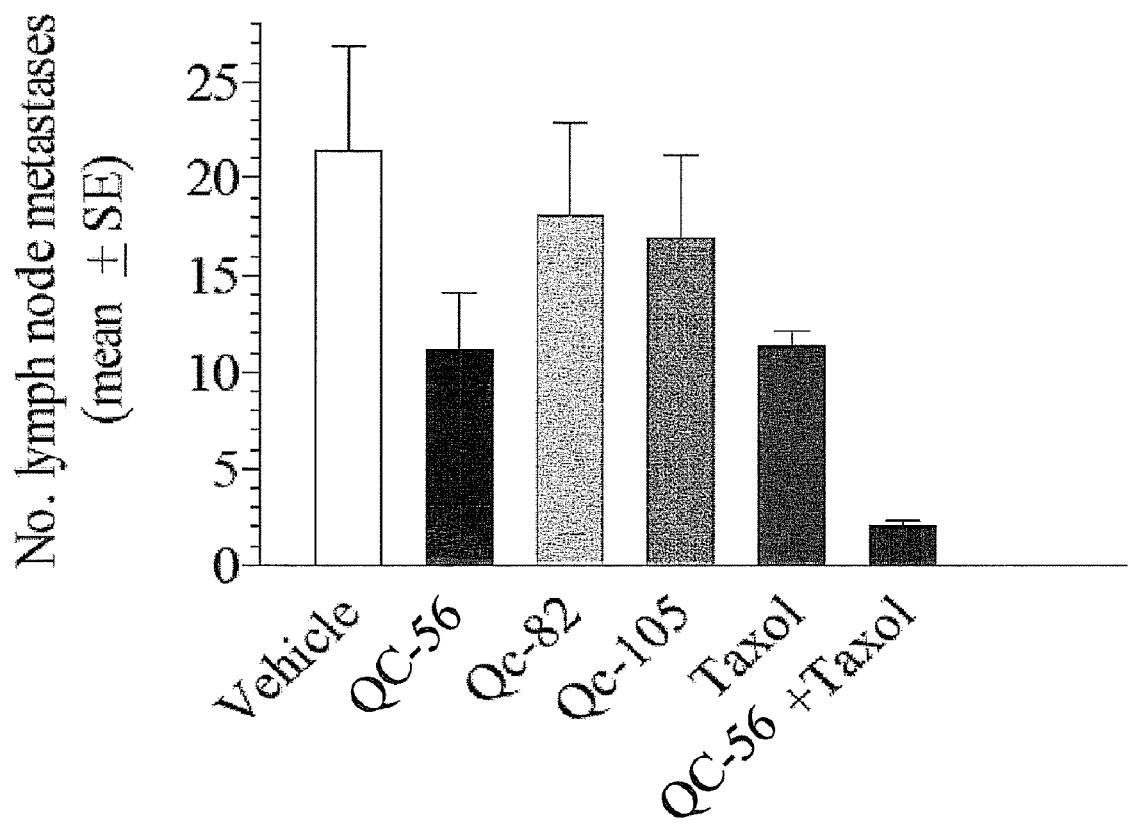
FIG. 39 shows results from a pre-clinical study involving a total of 32 SCID male mice implanted orthotopically with human metastatic prostate cancer PC-3M cells in the mouse prostate, in which QC-56, QC-82, QC-105, Taxol™ and QC-56+Taxol™ are tested for effect on number of lymph node metastases.

In a pre-clinical study involving a total of 32 SCID male mice implanted with human metastatic prostate cancer PC-3M cells in the mouse prostate, the tumor volumes (FIG. 38) were found to be statistically significantly smaller in mice treated with QC-56 at 40 mg/kg daily for 24 days (35% inhibition) compared to untreated mice. The inhibition in tumor growth in mice treated with QC-56 was slightly lower than those treated with Taxol™ (10 mg/kg, 4 cycles, 3 administrations per cycle; 45% inhibition). Remarkably, QC-56 at 40 mg/kg given daily for 24 days in combination with Taxol™ at 10 mg/kg administered for 4 cycles (3 days per cycle), led to a 73% inhibition in tumor growth and a significant increase in the body weights of mice compared to the mice treated with Taxol™ alone. In addition, there was a complete inhibition in the formation of macroscopic lymph node metastases and the reduction in microscopic lymph node metastases in mice (FIG. 39) treated with QC-56 alone (48%) was comparable to that seen in mice treated with Taxol™ alone (47%). However, mice treated with a combination of QC-56 and Taxol™ showed a remarkable reduction in prostate microscopic lymph node metastasis (>90%) and a complete inhibition of metastasis in kidneys and liver. These results clearly indicate that QC-56 makes Taxol™ significantly more effective and significantly improves its safety profile.

Figure 40:
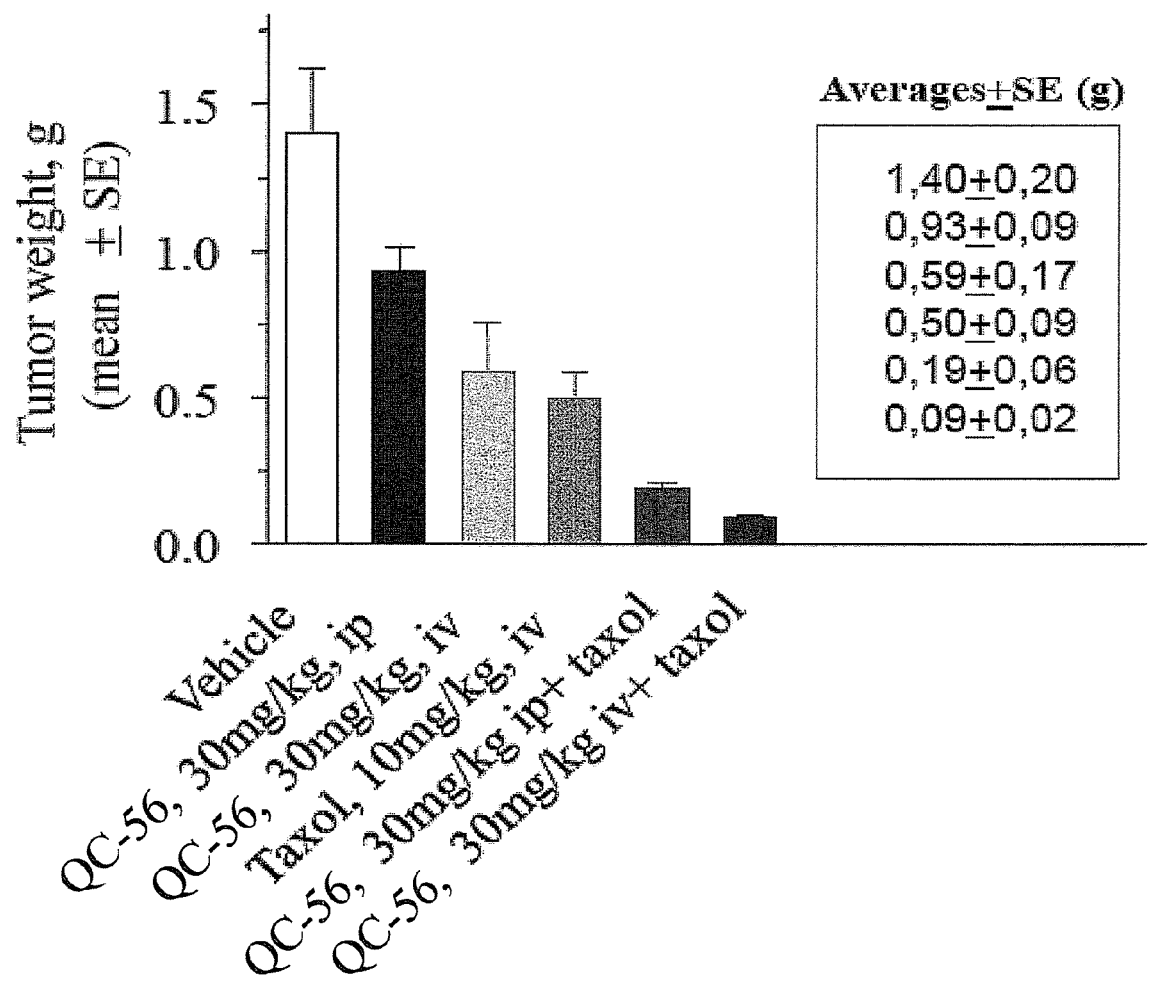
FIG. 40 shows anti-tumor activity of QC-56 and QC-56+Taxol™ given intravenously vs. intraperitoneally using the orthotopic PC-3M model.

In another pre-clinical study involving a total of 48 SCID male mice implanted with human metastatic prostate cancer PC-3M cells in the mouse prostate, the tumor volumes (FIG. 40) were found to be statistically significantly smaller in mice treated intravenously with QC-56 at 30 mg/kg daily for 12 days (58% inhibition) compared to untreated mice and compared to mice treated intraperitonially with QC-56 at 30 mg/kg daily for 12 days (34%). Remarkably, QC-56 at 30 mg/kg given intraperitonially daily for 12 days in combination with Taxol™ at 10 mg/kg administered intraperitonially for 3 cycles (3 days per cycle), led to a 86% inhibition in tumor growth a compared to the mice treated with Taxol™ alone (64%). Also, QC-56 at 30 mg/kg given intravenously daily for 12 days in combination with Taxol™ at 10 mg/kg administered intraperitonially for 3 cycles (3 days per cycle), led to a 94% inhibition in tumor growth compared to the mice treated with Taxol™ alone (64%).

Figure 41:
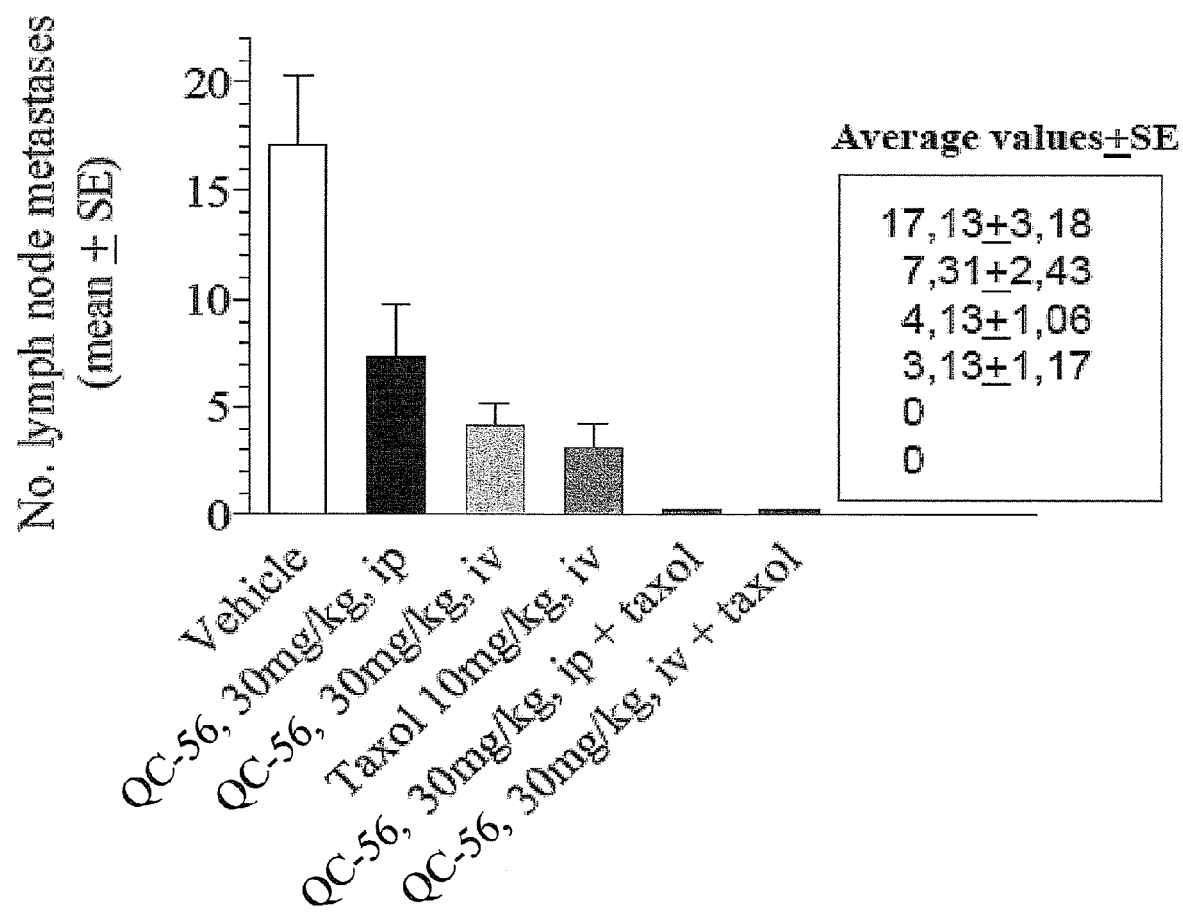
FIG. 41 shows anti-metastatic activity of QC-56 and QC-56+Taxol™ given intravenously vs. intraperitoneally using the orthotopic PC-3M model.

Particularly important was the observation of a complete inhibition in the formation of both macroscopic and microscopic lymph node metasteses (FIG. 41) in mice treated with QC-56 at 30 mg/kg given intraperitonially or intravenously daily for 12 days in combination with Taxol™ at 10 mg/kg administered intraperitonially for 3 cycles (3 days per cycle), compared to a 82% reduction in microscopic lymph node metastases in mice treated with Taxol™ alone at 10 mg/kg administered intraperitonially for 3 cycles (3 days per cycle). The reduction in microscopic lymph node metastases in mice treated with QC-56 alone at 30 mg/kg given intraperitonially daily for 12 days was 59% compared to a reduction of 76% in microscopic lymph node metastases in mice treated with QC-56 alone at 30 mg/kg given intravenously daily for 12 days. These results clearly indicate that QC-56 synergizes with Taxol™ by making this major chemotherapeutic agent significantly more effective.

VIII.I (iv) Discussion and Summary

The synergy between QC-56 and Taxol™ in terms of increased efficacy and reduced toxicity of Taxol™ is particularly interesting in view of a recent publication of Choi et al. (B.-M. Choi et al. *Biochemical and Biophysical Research Communications*, 2004, 321:132-137). Choi et al. demonstrated that exposure of vascular smooth muscle cells (VSMC) to paclitaxel (Taxol™) leads to a dose and time dependent increase in HO-1 expression and activity. Without wishing to be bound by any theory, this finding in VSMC could potentially provide an explanation as to why there exists such a synergy between an HO-1 inhibitor such as QC-56 and Taxol™ provided the tumor cells treated with Taxol™ also lead to an increase in HO-1 expression and activity. Inhibiting HO-1 expression in tumors treated with Taxol™ in that case, would significantly enhance the antitumor activity of Taxol™. Similar synergy would also exist with other anti-cancer drugs that give rise to an increase in HO-1 expression in tumors.

Although this invention is described in detail with reference to preferred embodiments thereof, these embodiments are offered to illustrate but not to limit the invention. It is possible to make other embodiments that employ the principles of the invention and that fall within its scope as defined by the claims appended hereto. All scientific and patent publications cited herein are hereby incorporated in their entirety by reference.

REFERENCES

1. Ackrell, J.; Franco, F.; Greenhouse, R.; Guzman, A.; Muchowski, J. M. *J. Heterocycl. Chem.* (1980) 17, 1081.
2. Appleton, S. D.; Chretien, M. L.; McLaughlin, B. E.; Vreman, H. J.; Stevenson, D. K.; Brien, J. F.; Nakatsu, K.; Maurice, D. H.; Marks, G. S. *Drug Metab. Dispos.,* 1999, 27, 1214.
3. Baranano D. E. and Snyder S. H. (2001) *Proc Natl Acad Sci USA* 98, 10996-11002.
4. Barlin, G. B.; Davies, L. P.; Ireland, S. J.; Zhang, J. *Aust. J. Chem.* (1992) 45, 1281.
5. Berberat, P. O., Dambrauskas Z., Gulbinas A., Giese T., Giese N., Kunzli B., Autschbach F., Meuer S., Buchler M. W. and Friess H. (2005) *Clin Cancer Res* 11(10) 3790-3798.
6. Berthiol, F.; Doucet H.; Santelli, M. *Tetrahedron* (2006) 62, 4372.
7. Boatman, S.; Harris, T. M.; Hauser, C. R. *J. Org. Chem.* (1965) 60, 3321.
8. Braggins, P. E.; Trakshel, G. M.; Kutty, R. K.; Maines, M. D. (1986) *Biochem. Biophys. Res. Commun.,* 141, 528-533.
9. Buss H., Chan T. P., Sluis K. B., Domigan N. M. and Winterbourn C. C. (1997) *Free Radic Biol Med* 23, 361-366.
10. Chopra V. S., Chalifour L. E. and Schipper H. M. (1995) *Brain Res Mol Brain Res* 31, 173-184.
11. Cook, M. N.; Nakatsu, K.; Marks, G. S.; McLaughlin, B. E.; Vreman, H. J.; Stevenson, D. K. *Can. J. Physiol. Pharmacol.,* 1995, 73, 515.
12. Cuevas-Yañez, E.; Serrano, J. M.; Huerta, G.; Muchowski, J. M.; Cruz-Almanza, R. *Tetrahedron* (2004) 60, 9391.
13. Dennery P. A. (2000) *Curr Top Cell Regul* 36, 181-199.
14. Dore S., Takahashi M., Ferris C. D., Zakhary R., Hester L. D., Guastella D. and Snyder S. H. (1999) *Proc Natl Acad Sci USA* 96, 2445-2450.
15. Droge W. (2002) *Physiol Rev* 82, 47-95.
16. Ewing J. F. and Maines M. D. (1995) *Brain Res* 672, 29-41.
17. Fang J., Akaike T. and Maeda H. (2004) *Apoptosis* 9, 27-35.
18. Fleming, I.; Newton, T. W.; Sabin, V.; Zammatio, F. *Tetrahedron* (1992) 48, 7793.
19. Frankel D., Mehindate K. and Schipper H. M. (2000) *J Cell Physiol* 185, 80-86.
20. Gaudry, M.; Marquet, A. *Tetrahedron* (1970) 26, 5611.
21. Gottlieb, H. E.; Kotlyar, V.; Nudelman, A. *J. Org. Chem.* (1997) 62, 7512-7515.
22. Harris, M. C.; Huang, X.; Buchwald, S. L. *Org. Lett.* (2002) 4, 2885.
23. Kinobe, R. T.; Vlahakis, J. Z.; Vreman, H. J.; Stevenson, D. K.; Brien, J. F.; Szarek, W. A.; Nakatsu, K. *British Journal of Pharmacology* (2006) 147: 307-315.
24. Laemmli, U. K. (1970) *Nature,* 277, 680-685.
25. Lash, G. E.; McLaughlin, B. E.; MacDonald-Goodfellow, S. K.; Smith, G. N.; Brien, J. F.; Marks, G. S.; Nakatsu, K.; Graham, C. H. (2003) *Am. J. Physiol Heart Circ. Physiol.,* 284, 160-167.
26. Llesuy S. F. and Tomaro M. L. (1994) *Biochim Biophys Acta* 1223, 9-14.
27. Maines, M. D. (1997) *Ann. Rev. Pharmacol. Toxicol.,* 37, 517-554.
28. Matsuoka Y., Kitamura Y., Okazaki M., Kakimura J., Tooyama I., Kimura H. and Taniguchi T. (1998) *Neuroscience* 85, 1223-1233.
29. Mayerhofer, M., Florian, S., Krauth, M.-T., Aichberger, K. J., Bilban, M., Marculescu, M., Printz, D., Fritsch, G., Wagner, O., Selzer, E., Sperr, W. R., Valent, P., Sillaber, C. (2004) *Cancer Research,* 64, 3148-3154.
30. Murphy, J. A.; Commeureuc, A. G. J.; Snaddon, T. N.; McGuire, T. M.; Khan, T. A.; Hisler, K.; Dewis, M. L.; Carling, R. *Org. Lett,* (2005) 7, 1427.
31. Nakagami T., Toyomura K., Kinoshita T. and Morisawa S. (1993) *Biochim Biophys Acta* 1158, 189-193.
32. Ponka P., Wilczynska A. and Schulman H. M. (1982) *Biochim Biophys Acta* 720, 96-105.
33. Ryter S. W. and Tyrrell R. M. (2000) *Free Radic Biol Med* 28, 289-309.
34. Ryter S. W., Kvam E. and Tyrrell R. M. (2000) *Methods Mol Biol* 99, 369-391.
35. Schipper H. M. (2000) *Exp Gerontol* 35, 821-830.
36. Schipper H. M. (2004) in *Redox-active Metals in Neurological Disorders*, Vol. 1012 (S. LeVine, Connor J. R. and Schipper H. M., eds), pp 84-93. Ann NY Acad Sci, New York.
37. Schipper H. M., fernier L., Mehindate K. and Frankel D. (1999) *J Neurochem* 72, 1802-1811.
38. Song W, Su H, Song S, Schipper H M. (2006) *J Cell Physiol* 206: 655-663.
39. Stocker R., Yamamoto Y., McDonagh A. F., Glazer A. N. and Ames B. N. (1987) *Science* 235, 1043-1046.
40. Trakshel, G. M.; Kutty, R. K.; Maines, M. D. (1988) *Arch. Biochem. Biophys.,* 260, 732-739.
41. Vlahakis, J. Z.; Kinobe, R. T.; Bowers, R. J.; Brien, J. F.; Nakatsu, K.; Szarek, W. A. Bioorg. Med. Chem. Lett. 2005, 15, 1457-1461.
42. Vlahakis, J. Z.; Kinobe, R. T.; Bowers, R. J.; Brien, J. F.; Nakatsu, K.; Szarek, W. A. *J. Med. Chem.* (2006) 49, 4437-4441.

43. Vreman, H. J.; Stevenson, D. K. *Anal. Biochem.*, 1988, 168, 31.
44. Vreman, H. J.; Stevenson, D. K., Unit 9.2. In: *Current Protocols in Toxicology*, Maines, M. D., Costa, L. G., Reed, D. J., Sassa, S., Sipes, I. G. (eds) John Wiley & Sons, Inc.: New York, 1999, pp 9.2.1-9.2.10.
45. Walker, K. A. M.; Braemer, A. C.; Hitt, S.; Jones, R. E.; Matthews, T. R. *J. Med. Chem.* (1978) 21, 840.
46. Walker, K. A. M. (1982) U.S. Pat. No. 4,359,475.
47. Walker, K. A. M.; Burton, P. M.; Swinney, D. C., Eur. Patent 0 492 474 B1, Mar. 5, 1997.
48. Winterbourn C. C. and Buss I. H. (1999) *Methods Enzymol* 300, 106-111.
49. Zhang J. and Piantadosi C. A. (1992) *J Clin Invest* 90, 1193-1199.

1,3-dithianyl, wherein the C is optionally contained as part of the ring structure, the ring structure optionally substituted with the group:

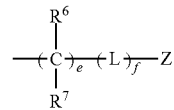

where e and f are independently 0, 1, 2, 3, 4, 5, or 6;

L is O, $CR^{19}R^{20}$, $OSO_2$, SO, OSO, $NR^{21}$, NHCO, CONH, OCO, COO, CO, OP(O)(OR)O, or OP(OR)O, wherein R is hydrogen, alkyl, aryl, or arylalkyl;

We claim:

1. A method of treating and/or mitigating prostate cancer, ovarian cancer, melanoma, colorectal cancer, breast cancer or lung cancer, comprising administering to an individual in need thereof a pharmaceutical composition comprising a pharmaceutically acceptable carrier and a compound of formula (I):

where
T is phenyl optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are unsubstituted and are independently hydrogen, alkyl, perfluoroalkyl, alkyloxy, alkenyl, alkynyl, cycloalkyl, aryl, aryloxy, arylalkyl or mercaptoalkyl;
n is 1 to 6:
C represents carbon, at least one C of $(C)_n$ is substituted with a ring structure selected from the group consisting of 1,3-dioxolanyl, 1,3-dioxanyl, 1,3-dithiolanyl, and Z, $R^6$, $R^7$, $R^{19}$, $R^{20}$ and $R^{21}$ are independently hydrogen, alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above, wherein Z is optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above; and D is imidazolyl;

or a pharmaceutically acceptable salt or ester of said compound.

2. The method of claim 1, wherein n is 1 to 4.
3. The method of claim 1, wherein n is 4.
4. The method of claim 1, wherein T is selected from the group consisting of: 4-chlorophenyl, 3-methoxyphenyl, 2-amino-4-chlorophenyl, 4-methoxyphenyl, phenyl, 4-fluorophenyl, 4-bromophenyl, 4-iodophenyl, 2-hydroxyphenyl, 4-nitrophenyl, 4-methylphenyl, biphenyl-4-yl, 3,4-dichlorophenyl, 4-isopropylphenyl, 4-tert-butylphenyl, 4-hydroxyphenyl, 4-(trifluoromethyl)phenyl, and 4-benzoylphenyl.

5. The method of claim 1, wherein said compound is selected from the group consisting of:

(2S,4S)-2-[2-(4-chlorophenyl)ethyl]-2-[(1H-imidazol-1-yl)methyl]-4-[(p-toluenesulfonyloxy)methyl]-1,3-dioxolane hydrochloride (QC-4); (2S,4S)-2-[2-(4-chlorophenyl)ethyl]-2-[(1H-imidazol-1-yl)methyl]-4-[(p-toluenesulfonyloxy)methyl]-1,3-dioxolane (QC-6); (2S,4S)-2-[2-4-chlorophenyl)ethyl]-2-[(1H-imidazol-1-yl)methyl]-4- [(4-methoxyphenyloxy)methyl]-1,3-dioxolane hydrochloride (QC-8); (2R,4R) -2-[2-(4-chlorophenyl)ethyl]-2-[(1H-imidazol-1-yl)methyl]-4-methyl-1,3-dioxolane hydrochloride (QC-13); 2[2(4-chlorophenyl)ethyl]-2-[(1H-imidazol-1-yl)methyl]-1,3-dioxolane hydrochloride (QC-15); (2R,4S)-2-[2-(4-chlorophenyl)ethyl]-2-[(1H-imidazol-1-yl)methyl]-4-[(p -toluenesulfonyloxy)methyl]-1,3-dioxolane (QC-16); (2S,4R)-2-[2-(4-chlorophenyl)ethyl]-2-[(1H-imidazol-1-yl)methyl]-4-[(p-toluenesulfonyloxy)methyl]-1,3-dioxolane (QC-17); (2R,4R)-2-[2-(4-chlorophenyl)ethyl]-2-[(1H-imidazol-1-yl)methyl]-4-[(p-toluenesulfonyloxy)methyl]-1,3-dioxolane (QC-21); (2R,4S) -2-[2-(4-chlorophenyl)ethyl]-2-[1H-imidazol-1-yl)methyl[-4-methyl-1,3-dioxolane hydrochloride (QC-25); (2S,4S)-2-[2-(4-chlorophenyl)ethyl]-2-[(1H-imidazol-1-yl)methyl]-4-methyl-1,3-dioxolane hydrochloride (QC-26); (2S,4R)-2-[2-(4-chlorophenyl)ethyl]-2-[(1H-imidazol-1-yl)methyl]-4-methyl-1,3-dioxolane hydrochloride (QC-27); (2R,4R)-2-[2-(4-phenyl)ethyl]-2-[(1H-imidazol-1-yl)methyl]-4-methyl-1,3-dioxolane hydrochloride (QC-35); (2R,4R)-2-[2-(4-chlorophenyl)ethyl]-2-[(1H-imidazol-1-yl)methyl]-4-(hydroxymethyl)-1,3-dioxolane hydrochloride (QC-38); (2R,4S)-2-[2-(4chlorophenyl)ethyl]-2-[(1H-imidazol-1-yl)methyl]-4-[(4-aminophenyloxy)methyl]-1,3-dioxolane dihydrochloride (QC-39); 2-[2-(4-chlorophenyl)ethyl]-2-[(1H-imidazol-1-yl)methyl]-1,3-dithiolane hydrochloride (QC-42); (2R, 4S)-2-[2-(4-chlorophenyl)ethyl]-2-[(1H- imidazol-1-yl)methyl]-4-[(4-hydroxyphenyloxy)methyl]-1,3-dioxolane hydrochloride (QC-46); (2R,4S)-2-[2-(4-chlorophenyl)ethyl]-2-[(1H-imidazol-1-yl)methyl]-4-(fluoromethyl)-1,3-dioxolane hydrochloride (QC-47); (2R,4R)-2-[2-(4-chlorophenyl)ethyl]-2-[(1H-imidazol-1-yl)methyl]-4-[(1H-imidazol-1-yl)methyl]-1,3-dioxolane dihydrochloride (QC-51); 2-[2-(4-fluorophenyl)ethyl]-2-[(1H-imidazol-1-yl)methyl]-1,3-dioxolane hydrochloride (QC-55); 2-[2-(4-bromophenyl)ethyl]-2-[(1H-imidazol-1-yl)methyl]-1,3-dioxolane hydrochloride (QC-56); 2-[2-phenylethyl]-2-[(1H-imidazol-1-yl)methyl]-1,3-dioxolane hydrochloride (QC-57); 2-[2-(4-chlorophenyl)ethyl]-2-[(1H-imidazol-1-yl)methyl]-1,3-dioxane hydrochloride (QC-70); 2[2(4-iodophenyl)ethyl]-2-[(1H-imidazol-1-yl)methyl]-1,3-dioxolane hydrochloride (QC-78); 1{4-chloromethyl-2[2-(4-chloro-phenyl)-ethyl-[1,3]dioxolan-2-ylmethyl}-1H-imidazole hydrochloride (QC-108); 1-{2-[2-(4-chloro-phenyl) -ethyl]-4-phenoxymethyl-[1,3]dioxolan-2-ylmethyl}-1H-imidazole hydrochloride (QC-116); 1-{[4-(4-bromo-phenoxymethyl)-2-[2-4-chloro-phenyl)-ethyl]-[1,3]dioxolan-2-ylmethyl}-1H -imidazole hydrochloride (QC-119); 1-[2-[2-(4-chloro-phenyl)-ethyl]-4-(4-fluoro-phenoxymethyl)-[1,3]dioxolan-2-ylmethyl]-1H-imidazole hydrochloride (QC-120); 1(2phenyl-[1,3]dioxolan-2-ylmethyl)-1H-imidazole hydrochloride (QC-246); and pharmaceutically acceptable salts thereof.

6. The method of claim 1, wherein said compound is selected from the group consisting of: (2R, 4S)- 2-(2-(4-chlorophenyl)ethyl)- 2(1H-imidazol-1-yl)methyl)- 4-(fluoromethyl)- 1,3-dioxolane hydrochloride (QC-47); 2-(2-(4-bromophenyl)ethyl)-2-((1H-imidazol-1-yl)methyl)- 1,3-dioxolane hydrochloride (QC-56); and pharmaceutically acceptable salts thereof.

7. The method of claim 1, wherein said cancer is selected from prostate cancer, ovarian cancer, melanoma and lung cancer.

8. A method of suppressing tumor growth in prostate cancer, ovarian cancer, melanoma, colorectal cancer, breast cancer or lung cancer, comprising administering to an individual in need thereof a pharmaceutical composition comprising a pharmaceutically acceptable carrier and a compound of formula (I):

where
T is phenyl optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are unsubstituted and are independently hydrogen, alkyl, perfluoroalkyl, alkyloxy, alkenyl, alkynyl, cycloalkyl, aryl, aryloxy, arylalkyl or mercaptoalkyl;
n is 1 to 6:
C represents carbon, at least one C of $(C)_n$ is substituted with a ring structure selected from the group consisting of 1,3-dioxolanyl, 1,3-dioxanyl, 1,3-dithiolanyl, and 1,3-dithianyl, wherein the C is optionally contained as part of the ring structure, the ring structure optionally substituted with the group:

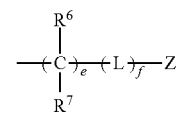

where e and f are independently 0, 1, 2, 3, 4, 5, or 6;
L is O, $CR^{19}R^{20}$, $OSO_2$, SO, OSO, $NR^{21}$, NHCO, OCO, COO, CO, OP(O)(OR)O, or OP(OR)O, wherein R is hydrogen, alkyl, aryl, or arylalkyl;
Z, $R^6$, $R^7$, $R^{19}R^{20}$ and $R^{21}$ are independently hydrogen, alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above, wherein Z is optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and are as defined above; and
D is imidazolyl;
or a pharmaceutically acceptable salt or ester of said compound.

9. The method of claim 8, wherein n is 1 to 4.

10. The method of claim 8, wherein n is 4.

11. The method of claim 8, wherein T is selected from the group consisting of: 4-chlorophenyl, 3-methoxyphenyl, 2-amino-4-chlorophenyl, 4-methoxyphenyl, phenyl, 4-fluorophenyl, 4-bromophenyl, 4-iodophenyl, 2-hydroxyphenyl, 4-nitrophenyl, 4-methylphenyl, biphenyl-4-yl, 3,4-dichlorophenyl, 4-isopropylphenyl, 4-tert-butylphenyl, 4-hydroxyphenyl, 4-(trifluoromethyl)phenyl, and 4-benzoylphenyl.

12. The method of claim 8, wherein said compound is selected from the group consisting of: (2S,4S)-2-[2-(4-chlorophenyl)ethyl]-2-[(1H-imidazol-1-yl)methyl]-4-[p-toluenesulfonyloxy)methyl]-1,3-dioxolane hydrochloride (QC-4); (2S,4S)-2]2-(4-chlorophenyl)ethyl]-2-[(1H-imidazol-1-yl)methyl]-4-[(p-toluenesulfonyloxy)methyl]-1,3-dioxolane (QC-6); (2S,4S)-2-[2-(4-chlorophenyl)ethyl]-2-[(1H-imidazol-1-yl)methyl]-4-[(4-methoxyphenyloxy)methyl]-1,3-dioxolane hydrochloride (QC-8) (2R,4R) -2-[2-(4-chlorophenyl)ethyl]-2-[(1H-imidazol-1-yl)methyl]-4-methyl-1,3-dioxolane hydrochloride (QC-13); 2[2(4-chlorophenyl)ethyl]-2-[(1H-imidazol-1-yl)methyl]-1,3-dioxolane hydrochloride (QC-15); (2R,4S)-2-[2-(4-chlorophenyl)ethyl]-2-[(1H-imidazol-1-yl)methyl]-4-[(p-toluenesulfonyloxy)methyl]-1,3-dioxolane (QC-16); (2S,4R)-2-[2-(4-chlorophenyl)ethyl]-2-[(1H-imidazol-1-yl)methyl]-4-[(p-toluenesulfonyloxy)methyl]-1,3-dioxolane (QC-17); (2R,4R)-2-[2-(4-chlorophenyl)ethyl]-2-[(1H-imidazol-1-yl)methyl]-4-[(p-toluenesulfonyloxy)methyl]-1,3-dioxolane (QC-21); (2R,4S) -2-[2-(4-chlorophenyl)ethyl]-2-[(1H-imidazol-1-yl)methyl]-4-methyl-1,3-dioxolane hydrochloride (QC-25); (2S,4S)-2-[2-(4-chlorophenyl)ethyl]-2-[(1H-imidazol-1-yl)methyl]-4-methyl-1,3-dioxolane hydrochloride (QC-26); (2S,4R)-2-[2-(4-chlorophenyl)ethyl]-2[(1H -imidazol-1-yl)methyl]-4-methyl-1,3-dioxolane hydrochloride (QC-27); (2R,4R)-2-[2-(4-phenyl)ethyl]-2-[(1H-imidazol-1-yl)methyl]-4-methyl-1,3-dioxolane hydrochloride (QC-35); (2R,4R)-2-[2-(4-chlorophenyl)ethyl]-2-[(1H-imidazol-1-yl)methyl]-4-(hydroxymethyl)-1,3-dioxolane hydrochloride (QC-38); (2R,4S)-2-[2-(4-chlorophenyl)ethyl]-2-[(1H-imidazol-1-yl)methyl]-4-[(4-aminophenyloxy)methyl]-1,3-dioxolane dihydrochloride (QC-39); 2[2-(4-chlorophenyl)ethyl]-2-[(1H-imidazol-1-yl)methyl]-1,3-dithiolane hydrochloride (QC-42); (2R,4S)-2-[2-(4-chlorophenyl)ethyl]-2-[(1H-imidazol-1-yl)methyl]-4-[(4-hydroxyphenyloxy)methyl]-1,3-dioxolane hydrochloride (QC-46); (2R, 4S)-2-[2-(4-chlorophenyl)ethyl]-2-[(1H-imidazol-1-yl)methyl]-4-(fluoromethyl)-1,3-dioxolane hydrochloride (QC-47); (2R,4R)-2-[2-(4-chlorophenyl)ethyl]-2-[(1H-imidazol-1-yl)methyl]-4-[(1H-imidazol-1-yl)methyl]-1,3-dioxolane dihydrochloride (QC-51); 2-[2-(4-fluorophenypethyl]-2-[(1H-imidazol-1-yl)methyl]-1,3-dioxolane hydrochloride (QC-55); 2-[2-(4-bromophenyl)ethyl]-2-[(1H-imidazol-1-yemethyl]-1,3-dioxolane hydrochloride (QC-56); 2-[2-phenylethyl]-2-[(1H-imidazol-1-yemethyl]-1,3-dioxolane hydrochloride (QC-57); 2-(4-chlorophenyl)ethyl]-2-[(1H-imidazol-1-yl)methyl]-1,3-dioxane hydrochloride (QC-70); 2-[2-(4-iodophenyl)ethyl]-2-[(1H-imidazol-1-yl)methyl]-1,3-dioxolane hydrochloride (QC-78); 1-{4-chloromethyl-2[-2-(4-chloro-phenyl)-ethyl]-[1,3]dioxolan-2-ylmethyl}-1H-imidazole hydrochloride (QC-108); 1-{2-[2-(4-chlorophenyl)-ethyl]-4-phenoxymethyl-[1,3]dioxolan-2-ylmethyl}-1H-imidazole hydrochloride (QC-116); 1-{4-(4-bromo-phenoxymethyl)-2-[2-(4-chloro-phenyl)-ethyl]-[1,3]dioxolan-2-ylmethyl}-1H-imidazole hydrochloride (QC-119); 1-[2-[2-(4-chloro-phenyl)-ethyl]-4-(4-fluoro-phenoxymethyl)[1,3]dioxolan-2-ylmethyl]1H-imidazole hydrochloride (QC-120); 1-(2-phenyl-1,3]dioxolan-2-ylmethyl)-1H-imidazole hydrochloride (QC-246); and pharmaceutically acceptable salts thereof.

13. The method of claim 8, wherein said compound is selected from the group consisting of: (2R, 4S)-2-(2-(4-chloropheny)ethyl)-2-((1H-imidazol-1-yl)methyl)-4-(fluoromethyl)-1,3-dioxolane hydrochloride (QC-47); 2-(2-(4-bromophenyl)ethyl)-2-((1H-imidazol-1-yl)methyl)- 1,3-dioxolane hydrochloride (QC-56); and pharmaceutically acceptable salts thereof.

14. The method of claim 8, wherein said tumor is selected from prostate tumors, ovarian tumors, melanoma and lung tumors.

15. A method of treating and/or mitigating prostate cancer, ovarian cancer, melanoma, colorectal cancer, breast cancer or lung cancer, comprising administering a pharmaceutical combination to an individual in need thereof in amounts effective to treat and/or mitigate said cancer, the pharmaceutical combination comprising at least one antineoplastic agent and a compound of formula (I):

where
T is phenyl optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are unsubstituted and are independently hydrogen, alkyl, perfluoroalkyl, alkyloxy, alkenyl, alkynyl, cycloalkyl, aryl, aryloxy, arylalkyl or mercaptoalkyl;
n is 1 to 6:
C represents carbon, at least one C of $(C)_n$ is substituted with a ring structure selected from the group consisting of 1,3-dioxolanyl, 1,3-dioxanyl, 1,3-dithiolanyl, and 1,3-dithianyl, wherein the C is optionally contained as part of the ring structure, the ring structure optionally substituted with the group:

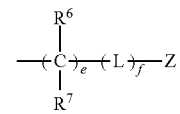

where e and f are independently 0, 1, 2, 3, 4, 5, or 6;
L is O, $CR^{19}R^{20}$, $OSO_2$, SO, OSO, $NR^{21}$, NHCO, CONH, OCO, COO, CO, OP(O)(OR)O, or OP(OR)O, wherein R is hydrogen, alkyl, aryl, or arylalkyl;
Z, $R^6$, $R^7$, $R^{19}$, $R^{20}$ and $R^{21}$ are independently hydrogen, alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above, wherein Z is optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above; and
D is imidazolyl;
or a pharmaceutically acceptable salt or ester of said compound.

16. The method of claim 15, wherein said antineoplastic agent and said compound or pharmaceutically acceptable salt or ester of said compound are administered in effective amounts either separately or combined.

17. The method of claim 15, wherein the antineoplastic agent is selected from the group consisting of signal transduction inhibitors, apoptosis inducers, angiogenesis inhibitors, monoclonal antibodies, cancer vaccines, gene therapy agents, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products, colony stimulating growth factors, adjuncts, erythropoetin, alkylating antineoplastic agents, anti-metabolites and combinations thereof.

18. The method of claim 15, wherein the antineoplastic agent is selected from the group consisting of dacarbazine, paclitaxel, cisplatin, and fluorouracil.

19. The method of claim 15, wherein n is 1 to 4.

20. The method of claim 15, wherein n is 4.

21. The method of claim 15, wherein T is selected from the group consisting of: 4-chlorophenyl, 3-methoxyphenyl, 2-amino-4-chlorophenyl, 4-methoxyphenyl, phenyl, 4-fluorophenyl, 4-bromophenyl, 4-iodophenyl, 2-hydroxyphenyl, 4-nitrophenyl, 4-methylphenyl, biphenyl-4-yl, 3,4-dichlorophenyl, 4-isopropylphenyl, 4-tert-butylphenyl, 4-hydroxyphenyl, 4-(trifluoromethyl)phenyl, and 4-benzoylphenyl.

22. The method of claim 15, wherein said compound is selected from the group consisting of: (2S, 4S)-2-[2-(4-chlorophenyl)ethyl]-2-(1H-imidazol-1-yl)methyl]-4-[(p-toluenesulfonyloxy)methyl]-1,3-dioxolane hydrochloride (QC-4); (2S, 4S)- 2-[2-(4-chlorophenyl)ethyl]-2-[(1H-imidazol-1-yl)methyl]-4-[(p-toluenesulfonyloxy)methyl]-1,3-dioxolane (QC-6); (2S, 4S)- 2-[2-(4-chlorophenyl)ethyl]-2-[(1H-imidazol-1-yl)methyl]-4- [(4-methoxyphenyloxy)methyl]-1,3-dioxolane hydrochloride (QC-8) (2R, 4R)-2-[2-(4-chlorophenyl)ethyl]-2-[(1H-imidazol-1-yl)methyl]-4-methyl-1,3-dioxolane hydrochloride (QC-13); 2-[2-(4-chlorophenyl)ethyl]-2-[(1H-imidazol-1-yl)methyl]-1,3-dioxolane hydrochloride (QC-15); (2R, 4S)-2-[2-(4-chlorophenyl)ethyl]-2-[(1H-imidazol-1-yl)methyl]-4-[(p-toluenesulfonyloxy)methyl]-1,3-dioxolane (QC-16); (2S, 4R)-2-[2-(4-chlorophenyl)ethyl]-2-[(1H-imidazol-1-yl)methyl]-4-[(p-toluenesulfonyloxy)methyl]-1,3-dioxolane (QC-17); (2R,4R)-2-[2-(4-chlorophenyl)ethyl]-2-[(1H-imidazol-1-yl)methyl]-4-[(p-toluenesulfonyloxy)methyl]-1,3-dioxolane (QC-21); (2R, 4S)-2-[2-(4-chlorophenyl)ethyl]-2-[(1H-imidazol-1-yl)methyl]-4-methyl-1,3-dioxolane hydrochloride (QC-25); (2S, 4S)-2-[2-(4-chlorophenyl)ethyl]-2-[(1H-imidazol-1-yl)methyl]-4-methyl-1,3-dioxolane hydrochloride (QC-26); (2S, 4R)-2-[2-(4-chlorophenyl)ethyl]-2-[(1H-imidazol-1-yl)methyl]-4-methyl-1,3-dioxolane hydrochloride (QC-27); (2R,4R)-2-[2-(4-phenypethyl)-2-[(1H-imidazol-1-yl)methyl]-4-methyl-1,3-dioxolane hydrochloride (QC-35); (2R, 4R)-2-[2-(4-chlorophenypethyl]-2-[(1H-imidazol-1-yl)methyl]-4-(hydroxymethyl)-1,3-dioxolane hydrochloride (QC-38); (2R, 4S)-2-[2-(4-chlorophenyl)ethyl]-2-[(1H-imidazol-1-yl) methyl]-4-[(4-aminophenyloxy)methyl]-1,3-dioxolane dihydrochloride (QC-39); 2-[2-(4-chlorophenyl)ethyl]-2-[(1H-imidazol-1-yl)methyl]-1,3-dithiolane hydrochloride (QC-42); (2R, 4S)- 2-[2-(4-chlorophenyl)ethyl]-2-[(1H-imidazol-1-yl)methyl]-4-[(4-hydroxyphenyloxy)methyl]-1,3-dioxolane hydrochloride (QC-46); (2R, 4S)-2-[2-(4-chlorophenypethyl]-2- [(1H-imidazol-1-yl)methyl]-4- (fluoromethyl)- 1,3-dioxolane hydrochloride (QC-47); (2R, 4R)- 2-[2-(4-chlorophenyl)ethyl]-2-[(1H-imidazol-1-yl)methyl]-4-[(1H-imidazol-1-yl)methyl]-1,3-dioxolane dihydrochloride (QC-51); 2-[2-(4-fluorophenyl)ethyl]-2-[(1H-imidazol-1-yl)methyl]-1,3-dioxolane hydrochloride (QC-55); 2-[2-(4-bromophenyl)ethyl]-2-[(1H-imidazol-1-yl)methyl]-1,3-dioxolane hydrochloride (QC-56); 2-[2-phenylethyl]-2- [(1H-imidazol-1-yl)methyl]-1,3-dioxolane hydrochloride (QC-57); 2-[2-(4-chlorophenyl)ethyl]-2-[(1H-imidazol-1-yl)methyl]-1,3-dioxane hydrochloride (QC-70); 2-[2-(4-iodophenyl)ethyl]-2-[(1H-imidazol-1-yl)methyl]-1,3-dioxolane hydrochloride (QC-78); 1-{4-chloromethyl-2-[2-(4-chloro-phenyl)-ethyl]-[1,3]dioxolan-2-ylmethyl)-1H-imidazole hydrochloride (QC-108); 1-{2-[2-(4-chlorophenyl)-ethyl]-4-phenoxymethyl-[1,3]dioxolan-2-ylmethyl}1H-imidazole hydrochloride (QC-116); 1-{4-(4-bromo-phenoxymethyl)-2-[2-(4-chloro-phenyl)-ethyl)[1,3]dioxolan-2-ylmethyl-1H-imidazole hydrochloride (QC-119); 1-[2-[2-(4-chloro-phenyl)-ethyl]-4-(4-fluoro-phenoxymethyl)-[1,3]dioxolan-2-ylmethyl]-1H-imidazole hydrochloride (QC-120); 1-(2-phenyl-[1,3]dioxolan-2-ylmethyl)- 1H-imidazole hydrochloride (QC-246); and pharmaceutically acceptable salts thereof.

23. The method of claim 15, wherein said compound is selected from the group consisting of: (2R, 4S)-2-(2-(4-chlorophenyl)ethyl)-2-((1H-imidazol-1-yl)methyl)-4-(fluoromethyl)-1,3-dioxolane hydrochloride (QC-47); 2-(2-(4-bromophenyl)ethyl)-2-((1H-imidazol-1-yl)methyl)- 1,3-dioxolane hydrochloride (QC-56); and pharmaceutically acceptable salts thereof.

24. The method of claim 15, wherein said cancer is selected from prostate cancer, ovarian cancer, melanoma and lung cancer.

25. A method of suppressing tumor growth in prostate cancer, ovarian cancer, melanoma, colorectal cancer, breast cancer or lung cancer, comprising administering a pharmaceutical combination to an individual in need thereof in amounts effective to suppress tumor growth, the pharmaceutical combination comprising at least one antineoplastic agent and a compound of formula (I):

where
T is phenyl optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are unsubstituted and are independently hydrogen, alkyl, perfluoroalkyl, alkyloxy, alkenyl, alkynyl, cycloalkyl, aryl, aryloxy, arylalkyl or mercaptoalkyl;
n is 1 to 6:
C represents carbon, at least one C of $(C)_n$ is substituted with a ring structure selected from the group consisting of 1,3-dioxolanyl, 1,3-dioxanyl, 1,3-dithiolanyl, and 1,3-dithianyl, wherein the C is optionally contained as part of the ring structure, the ring structure optionally substituted with the group:

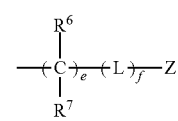

where e and f are independently 0, 1, 2, 3, 4, 5, or 6;
L is O, $CR^{19}R^{20}$, $OSO_2$, SO, OSO, $NR^{21}$, NHCO, CONH, OCO, COO, CO, OP(O)(OR)O, or OP(OR)O, wherein R is hydrogen, alkyl, aryl, or arylalkyl;

Z, $R^6$, $R^7$, $R^{19}$, $R^{20}$ and $R^{21}$ are independently hydrogen, alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above, wherein Z is optionally substituted with alkyl, perfluoroalkyl, alkyloxy, alkenyl, alkynyl, cycloalkyl, aryl, aryloxy, arylalkyl, mercaptoalkyl, or a moiety selected from the group consisting of F, Cl, Br, I, OH, SH, CN, $NR^8R^9$, $NO_2$, $CO_2R^{10}$ and CHO, wherein $R^8$, $R^9$ and $R^{10}$ are as defined above; and D is imidazolyl;

or a pharmaceutically acceptable salt or ester of said compound.

26. The method of claim 25, wherein said antineoplastic agent and said compound or pharmaceutically acceptable salt or ester of said compound are administered in effective amounts either separately or combined.

27. The method of claim 25, wherein the antineoplastic agent is selected from the group consisting of signal transduction inhibitors, apoptosis inducers, angiogenesis inhibitors, monoclonal antibodies, cancer vaccines, gene therapy agents, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products, colony stimulating growth factors, adjuncts, erythropoetin, alkylating antineoplastic agents, anti-metabolites and combinations thereof 28. The method of claim 25, wherein the antineoplastic agent is selected from the group consisting of dacarbazine, paclitaxel, cisplatin, and fluorouracil.

29. The method of claim 25, wherein n is 1 to 4.

30. The method of claim 25, wherein n is 4.

31. The method of claim 25, wherein T is selected from the group consisting of: 4-chlorophenyl, 3-methoxyphenyl, 2-amino-4-chlorophenyl, 4-methoxyphenyl, phenyl, 4-fluorophenyl, 4-bromophenyl, 4-iodophenyl, 2-hydroxyphenyl, 4-nitrophenyl, 4-methylphenyl, biphenyl-4-yl, 3,4-dichlorophenyl, 4-isopropylphenyl, 4-tert-butylphenyl, 4-hydroxyphenyl, 4-(trifluoromethyl)phenyl, and 4-benzoylphenyl.

32. The method of claim 25, wherein said compound is selected from the group consisting of: (2S,4S)-2-[2-(4-chlorophenyl)ethyl]-2-[(1H-imidazol-1-yl)methyl]-4-[(p-toluenesulfonyloxy)methyl]-1,3-dioxolane hydrochloride (QC-4); (2S,4S)-2-[2-(4-chlorophenyl)ethyl]-2-[(1H-imidazol-1-yl)methyl]-4-[(p-toluenesulfonyloxy)methyl]-1,3-dioxolane (QC-6); (2S,4S)-2-[2-(4-chlorophenyl)ethyl]-2-[(1H-imidazol-1-yl)methyl]-4-[(4-methoxyphenyloxy)methyl]-1,3dioxolane hydrochloride (QC-8); (2R,4R)-2-[2-(4-chlorophenyl)ethyl]-2-[(1H-imidazol-1-yl)methyl]-4-methyl-1,3-dioxolane hydrochloride (QC-13); 2-[2-(4-chlorophenyl)ethyl]-2-[(1H-imidazol-1-yl)methyl]-1,3-dioxolane hydrochloride (QC-15); (2R,4S)-2-[2-(4-chlorophenyl)ethyl]-2-[(1H-imidazol-1-yl)methyl]-4-[(p-toluenesulfonyloxy)methyl]-1,3-dioxolane (QC-16); (2S,4R)-2-[2-(4-chlorophenyl)ethyl]-2-[(1H-imidazol-1-yl)methyl]-4-[(p-toluenesulfonyloxy)methyl]-1,3-dioxolane (QC-17); (2R,4R)-2-[2-(4-chlorophenyl)ethyl]-2-[(1H-imidazol-1-yl)methyl]-4-[(p-toluenesulfonyloxy)methyl]-1,3-dioxolane (QC-21); (2R,4S)-2-[2-(4-chlorophenyl)ethyl]-2-[(1H-imidazol-1-yl)methyl]-4-methyl-1,3-dioxolane hydrochloride (QC-25); (2S,4S)-2-[2-(4-chlorophenyl)ethyl]-2-[(1H-imidazol-1-yl)methyl]-4-methyl-1,3-dioxolane hydrochloride (QC-26); (2S,4R)-2-[2-(4-chlorophenyl)ethyl]-2-[(1H-imidazol-1-yl)methyl]-4-methyl-1,3-dioxolane hydrochloride (QC-27); (2R,4R)-2[2-(4-phenyl)ethyl]-2-[(1H-imidazol-1-yl)methyl]-4-methyl-1,3-dioxolane hydrochloride (QC-35); (2R,4R)-2-[2-(4-chlorophenyl)ethyl]-2-[(1H-imidazol-1-yl)methyl]-4-(hydroxymethyl)-1,3-dioxolane hydrochloride (QC-38); (2R,4S)-2-[2-(4-Chlorophenyl)ethyl]-2-[(1H-imidazol-1-yl)methyl]-4-[(4-aminophenyloxy)methyl]-1,3-dioxolane dihydrochloride (QC-39); 2[2-(4-chlorophenyl)ethyl]-2-[(1H-imidazol-1-yl)methyl]-1,3-dithiolane hydrochloride (QC-42); (2R,4S)-2-[2-(4-chlorophenyl)ethyl]-2-[(1H-imidazol-1-yl)methyl]-4-[(4-hydroxyphenyloxy)methyl]-1,3-dioxolane hydrochloride (QC-46); (2R,4S)-2-[2-(4-chlorophenyl)ethyl]-2-[(1H-imidazol-1-yl)methyl]-4-(fluoromethyl)-1,3-dioxolane hydrochloride (QC-47); (2R,4R)-2[2-(4-chlorophenyl)ethyl]-2-[(1H-imidazol-1-yl)methyl]-4-[(1H-imidazol-1-yl)methyl]-1,3-dioxolane dihydrochloride (QC-51); 2-[2-(4-fluorophenyl)ethyl]-2-[(1H-imidazol-1-yl)methyl]-1,3-dioxolane hydrochloride (QC-55); 2-[2-(4-bromophenyl)ethyl]-2-[(1H-imidazol-1-yl)methyl]-1,3-dioxolane hydrochloride (QC-56); 2-[2-phenylethyl]-2-[(1H-imidazol-1-yl)methyl]-1,3-dioxolane hydrochloride (QC-57); 2-[2-(4-chlorophenyl)ethyl]-2-[(1H-imidazol-1-yl)methyl]-1,3-dioxane hydrochloride (QC-70); 2-[2-(4-iodophenyl)ethyl]-2-[(1H-imidazol-1-yl)methyl]-1,3-dioxolane hydrochloride (QC-78); 1{4-chloromethyl-2[2-(4-chloro-phenyl)-ethyl]-[1,3]dioxolan-2-ylmethyl}-1H-imidazole hydrochloride (QC-108); 1-{2-[2-(4-chloro-phenyl)-ethyl]-4-phenoxymethyl-[1,3]dioxolan-2-ylmethyl}-1H-imidazole hydrochloride (QC-116); 1-{4-(4-bromo-phenoxymethyl)-2-[2-(4-chloro-phenyl)-ethyl]-[1,3]dioxolan-2-ylmethyl}-1H-imidazole hydrochloride (QC-119); 1-[2-[2-(4-chloro-phenyl)-ethyl]-4-(4-fluoro-phenoxymethyl)-[1,3]dioxolan-2-ylmethyl]-1H-imidazole hydrochloride (QC-120); 1-(2-phenyl-[1,3]dioxolan-2-ylmethyl)-1H-imidazole hydrochloride (QC-246); and pharmaceutically acceptable salts thereof.

33. The method of claim 25, wherein said compound is selected from the group consisting of: (2R,4S)-2-(2-(4-chlorophenyl)ethyl)-3-((1H-imidazol-1-yl)methyl)-4-(fluoromethyl)-1,3-dioxolane hydrochloride (QC-47); 2-(2-(4-bromophenyl)ethyl) -2-((1H-imidazol-1-yl)methyl)-1,3-dioxolane hydrochloride (QC-56); and pharmaceutically acceptable salts thereof.

34. The method of claim 25, wherein said tumor is selected from prostate tumors, ovarian tumors, melanoma and lung tumors.

35. The method of claim 1, wherein the moiety that substitutes T is Br.

36. The method of claim 1, wherein the moiety that substitutes T is selected from the group consisting of F, Cl, Br and I.

37. The method of claim 1, wherein the moiety that substitutes T is selected from the group consisting of F, Cl, Br, I, OH, SH, CN, $NO_2$, $CO_2R^{10}$ and CHO, wherein $R^{10}$ is unsubstituted and is independently hydrogen, alkyl, perfluoroalkyl, alkyloxy, alkenyl, alkynyl, cycloalkyl, aryl, aryloxy, arylalkyl or mercaptoalkyl.

38. The method of claim 1, wherein L is O.

39. The method of claim 8, wherein the moiety that substitutes T is Br.

40. The method of claim 8, wherein the moiety that substitutes T is selected from the group consisting of F, Cl, Br and I.

41. The method of claim 8, wherein the moiety that substitutes T is selected from the group consisting of F, Cl, Br, I, OH, SH, CN, $NO_2$, $CO_2R^{10}$ and CHO, wherein $R^{10}$ is unsubstituted and is independently hydrogen, alkyl, perfluoroalkyl, alkyloxy, alkenyl, alkynyl, cycloalkyl, aryl, aryloxy, arylalkyl or mercaptoalkyl.

42. The method of claim 8, wherein L is O.

43. The method of claim 15, wherein the moiety that substitutes T is Br.

44. The method of claim 15, wherein the moiety that substitutes T is selected from the group consisting of F, Cl, Br and I.

45. The method of claim 15, wherein the moiety that substitutes T is selected from the group consisting of F, Cl, Br, I, OH, SH, CN, $NO_2$, $CO_2R^{10}$ and CHO, wherein $R^{10}$ is unsubstituted and is independently hydrogen, alkyl, perfluoroalkyl, alkyloxy, alkenyl, alkynyl, cycloalkyl, aryl, aryloxy, arylalkyl or mercaptoalkyl.

46. The method of claim 15, wherein L is O.

47. The method of claim 25, wherein the moiety that substitutes T is Br.

48. The method of claim 25, wherein the moiety that substitutes T is selected from the group consisting of F, Cl, Br and I.

49. The method of claim 25, wherein the moiety that substitutes T is selected from the group consisting of F, Cl, Br, I, OH, SH, CN, $NO_2$, $CO_2R^{10}$ and CHO, wherein $R^{10}$ is unsubstituted and is independently hydrogen, alkyl, perfluoroalkyl, alkyloxy, alkenyl, alkynyl, cycloalkyl, aryl, aryloxy, arylalkyl or mercaptoalkyl.

50. The method of claim 25, wherein L is O.

51. The method of claim 1, wherein the treating and/or mitigating is for prostate cancer.

52. The method of claim 1, wherein the treating and/or mitigating is for ovarian cancer.

53. The method of claim 1, wherein the treating and/or mitigating is for melanoma.

54. The method of claim 1, wherein the treating and/or mitigating is for colorectal cancer.

55. The method of claim 1, wherein the treating and/or mitigating is for breast cancer.

56. The method of claim 1, wherein the treating and/or mitigating is for lung cancer.

57. The method of claim 1, wherein T is unsubstituted.

58. The method of claim 8, wherein T is unsubstituted.

59. The method of claim 15, wherein T is unsubstituted.

60. The method of claim 25, wherein T is unsubstituted.

61. The method of claim 1, wherein said compound is 2-(2-(4-bromophenyl)ethyl)-2-((1H-imidazol-1-yl)methyl)-1,3-dioxolane hydrochloride (QC-56) or a pharmaceutically acceptable salt thereof.

62. The method of claim 1, wherein the ring structure that substitutes at least one C of $C_n$ is unsubstituted.

63. The method of claim 8, wherein the ring structure that substitutes at least one C of $C_n$ is unsubstituted.

64. The method of claim 15, wherein the ring structure that substitutes at least one C of $C_n$ is unsubstituted.

65. The method of claim 25, wherein the ring structure that substitutes at least one C of $C_n$ is unsubstituted.

66. A method of treating and/or mitigating prostate cancer, ovarian cancer, melanoma, colorectal cancer, breast cancer or lung cancer, comprising administering to an individual in need thereof a pharmaceutical composition comprising a pharmaceutically acceptable carrier and a compound selected from the group consisting of 1-{2-[2-(4-chloro -phenyl)-ethyl[-hexahydro-benzo[1,3]dioxol-2-ylmethyl}-1H-imidazole (QC-71) and 1-{4-azidomethyl-2-[2-(4-chloro-phenyl)-ethyl]-[1,3]dioxolan-2-ylmethyl}-1H-imidazole hydrochloride (QC-112), or a pharmaceutically acceptable salt of said compound.

67. The method of claim 66, wherein said cancer is selected from prostate cancer, ovarian cancer, melanoma and lung cancer.

68. A method of suppressing tumor growth in prostate cancer, ovarian cancer, melanoma, colorectal cancer, breast cancer or lung cancer, comprising administering to an individual in need thereof a pharmaceutical composition comprising a pharmaceutically acceptable carrier and a compound selected from the group consisting of 1-{2-[2-(4-chloro -phenyl)-ethyl[-hexahydro-benzo[1,3]dioxol-2-ylmethyl}-1H-imidazole (QC-71) and 1-{4-azidomethyl-2-[2-(4-chloro-phenyl)-ethyl]-[1,3]dioxolan-2-ylmethyl}-1H-imidazole hydrochloride (QC-112), or a pharmaceutically acceptable salt of said compound.

69. The method of claim 68, wherein said tumor is selected from prostate tumors, ovarian tumors, melanoma and lung tumors.

70. A method of treating and/or mitigating prostate cancer, ovarian cancer, melanoma, colorectal cancer, breast cancer or lung cancer, comprising administering a pharmaceutical combination to an individual in need thereof in amounts effective to treat and/or mitigate said cancer, the pharmaceutical combination comprising at least one antineoplastic agent and a compound selected from the group consisting of 1-{2-[2-(4-chloro-phenyl)-ethyl]-hexahydro-benzo[1,3]dioxol-2-ylmethyl}-1H-imidazole (QC-71) and 1-{4-azidomethyl-2-[2-(4-chloro-phenyl)-ethyl]-[1,3]dioxolan-2-ylmethyl}-1H-imidazole hydrochloride (QC-112), or a pharmaceutically acceptable salt of said compound.

71. The method of claim 70, wherein said antineoplastic agent and said compound or pharmaceutically acceptable salt of said compound are administered in effective amounts either separately or combined.

72. The method of claim 70, wherein the antineoplastic agent is selected from the group consisting of signal transduction inhibitors, apoptosis inducers, angiogenesis inhibitors, monoclonal antibodies, cancer vaccines, gene therapy agents, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products, colony stimulating growth factors, adjuncts, erythropoetin, alkylating antineoplastic agents, anti-metabolites and combinations thereof.

73. The method of claim 70, wherein the antineoplastic agent is selected from the group consisting of dacarbazine, paclitaxel, cisplatin, and fluorouracil.

74. The method of claim 70, wherein said cancer is selected from prostate cancer, ovarian cancer, melanoma and lung cancer.

75. A method of suppressing tumor growth in prostate cancer, ovarian cancer, melanoma, colorectal cancer, breast cancer or lung cancer, comprising administering a pharmaceutical combination to an individual in need thereof in amounts effective to suppress tumor growth, the pharmaceutical combination comprising at least one antineoplastic agent and a compound selected from the group consisting of 1-{2 [2-(4-chloro-phenyl)-ethyl]-hexahydro -benzo[1,3]dioxol-2-ylmethyl}-1H-imidazole (QC-71) and 1-{4-azidomethyl-2-[2-(4-chloro-phenyl)-ethyl]-[1,3]dioxolan-2-ylmethyl}-1H-imidazole hydrochloride (QC-112), or a pharmaceutically acceptable salt of said compound.

76. The method of claim 75, wherein said antineoplastic agent and said compound or pharmaceutically acceptable salt of said compound are administered in effective amounts either separately or combined.

77. The method of claim 75, wherein the antineoplastic agent is selected from the group consisting of signal transduction inhibitors, apoptosis inducers, angiogenesis inhibitors, monoclonal antibodies, cancer vaccines, gene therapy agents, anti-sense compounds, H2 receptor antagonists, interferon, GnRH antagonists, macrophage stimulators, small molecule cytotoxics, MMP inhibitors, cytostatic polyamine inhibitors, recombinant adenoviruses targeting oncogenes, interleukins, hormonal drugs, natural antineoplastic products, colony stimulating growth factors, adjuncts, erythropoetin, alkylating antineoplastic agents, anti-metabolites and combinations thereof.

78. The method of claim 75, wherein the antineoplastic agent is selected from the group consisting of dacarbazine, paclitaxel, cisplatin, and fluorouracil.

79. The method of claim 75, wherein said tumor is selected from prostate tumors, ovarian tumors, melanoma and lung tumors.

* * * * *